US012465640B2

(12) United States Patent
Hubbell et al.

(10) Patent No.: US 12,465,640 B2
(45) Date of Patent: Nov. 11, 2025

(54) METHODS AND COMPOSITIONS FOR TREATING INFLAMMATORY AND AUTOIMMUNE CONDITIONS WITH ECM-AFFINITY PEPTIDES LINKED TO ANTI-INFLAMMATORY AGENTS

(71) Applicant: The University of Chicago, Chicago, IL (US)

(72) Inventors: Jeffrey A. Hubbell, Chicago, IL (US); Kiyomitsu Katsumata, Chicago, IL (US); Ako Ishihara, Chicago, IL (US); Jun Ishihara, Chicago, IL (US); Aslan Mansurov, Chicago, IL (US)

(73) Assignee: The University of Chicago, Chicago, IL (US)

( * ) Notice: Subject to any disclaimer, the term of this patent is extended or adjusted under 35 U.S.C. 154(b) by 805 days.

(21) Appl. No.: 17/310,802

(22) PCT Filed: Feb. 25, 2020

(86) PCT No.: PCT/US2020/019668
§ 371 (c)(1),
(2) Date: Aug. 25, 2021

(87) PCT Pub. No.: WO2020/176478
PCT Pub. Date: Sep. 3, 2020

(65) Prior Publication Data

US 2022/0118089 A1 Apr. 21, 2022

Related U.S. Application Data

(60) Provisional application No. 62/809,988, filed on Feb. 25, 2019.

(51) Int. Cl.

| | |
|---|---|
| ***A61K 38/20*** | (2006.01) |
| ***A61K 38/17*** | (2006.01) |
| ***A61K 38/18*** | (2006.01) |
| ***A61K 38/19*** | (2006.01) |
| ***A61K 38/21*** | (2006.01) |
| ***A61K 39/44*** | (2006.01) |
| ***A61K 47/64*** | (2017.01) |
| ***A61P 37/06*** | (2006.01) |

(52) U.S. Cl.
CPC .......... *A61K 39/44* (2013.01); *A61K 38/1709* (2013.01); *A61K 38/1774* (2013.01); *A61K 38/1841* (2013.01); *A61K 38/191* (2013.01); *A61K 38/20* (2013.01); *A61K 38/2006* (2013.01); *A61K 38/2026* (2013.01); *A61K 38/2033* (2013.01); *A61K 38/2066* (2013.01); *A61K 38/2073* (2013.01); *A61K 38/215* (2013.01); *A61K 47/643* (2017.08); *A61P 37/06* (2018.01)

(58) Field of Classification Search
CPC .................................................. A61K 38/2066
See application file for complete search history.

(56) References Cited

U.S. PATENT DOCUMENTS

| | | | |
|---|---|---|---|
| 6,358,524 | B1 | 3/2002 | Sedlacek et al. |
| 6,617,135 | B1 | 9/2003 | Gillies et al. |
| 7,018,626 | B2 | 3/2006 | Strom et al. |
| 7,081,354 | B2 | 7/2006 | Fleer et al. |
| 7,166,577 | B2 | 1/2007 | Otagiri et al. |
| 7,253,259 | B2 | 8/2007 | Otagiri et al. |
| 7,556,816 | B2 | 7/2009 | Walker et al. |
| 7,867,491 | B2 | 1/2011 | Yang et al. |
| 7,927,596 | B2 | 4/2011 | Grant et al. |
| 7,939,056 | B2 | 5/2011 | Horwitz et al. |
| 8,246,960 | B2 | 8/2012 | Chang et al. |
| 8,558,048 | B2 | 10/2013 | Margolin et al. |
| 8,685,406 | B2 | 4/2014 | Walker et al. |
| 8,734,774 | B2 | 5/2014 | Frelinger et al. |
| 8,859,209 | B2 | 10/2014 | Larsen |
| 8,889,130 | B2 | 11/2014 | Kamath |
| 8,921,528 | B2 | 12/2014 | Holt et al. |
| 8,927,694 | B2 | 1/2015 | McDonagh et al. |
| 9,074,010 | B2 | 7/2015 | Sheffer et al. |
| 9,120,875 | B2 | 9/2015 | Gao et al. |

(Continued)

FOREIGN PATENT DOCUMENTS

| | | |
|---|---|---|
| CN | 109553684 | 4/2019 |
| JP | H11-501506 | 2/1999 |

(Continued)

OTHER PUBLICATIONS

English translation of Office Communication issued in Japanese Patent Application No. 2021-549595, dated Feb. 22, 2024.

(Continued)

*Primary Examiner* — Prema M Mertz

(74) *Attorney, Agent, or Firm* — Norton Rose Fulbright US LLP

(57) ABSTRACT

The disclosure relates to the engineering of collagen-binding modification of anti-inflammatory agents using collagen-binding peptide (CBP) and vWF A3 to achieve targeted therapy for inflammatory diseases. Accordingly, embodiments of the disclosure relate to a composition comprising an anti-inflammatory agent operatively linked to an extra-cellular matrix (ECM)-affinity peptide. Also disclosed are cytokines and anti-inflammatory agents, such as CD200, linked to a serum protein and/or an ECM-affinity peptide. Further aspects of the disclosure relate to a method for treating an autoimmune or inflammatory condition in a subject comprising administering a composition of the disclosure to the subject.

15 Claims, 45 Drawing Sheets

Specification includes a Sequence Listing.

(56) References Cited

U.S. PATENT DOCUMENTS

| | | | |
|---|---|---|---|
| 9,133,265 | B2 | 9/2015 | Sleep |
| 9,376,495 | B2 | 6/2016 | Bonvini et al. |
| 9,394,374 | B2 | 7/2016 | Hamblin et al. |
| 9,493,564 | B2 | 11/2016 | Thompson et al. |
| 9,675,672 | B2 | 6/2017 | Tagaya et al. |
| 9,714,281 | B2 | 7/2017 | Dasgupta et al. |
| 9,775,912 | B2 | 10/2017 | Steiner et al. |
| 9,879,077 | B2 | 1/2018 | Cha |
| 10,118,949 | B2 | 11/2018 | Abrahmsen et al. |
| 10,143,726 | B2 | 12/2018 | Oft |
| 10,233,228 | B2 | 3/2019 | Plumridge et al. |
| 10,245,298 | B2 | 4/2019 | Murali et al. |
| 10,293,043 | B2 | 5/2019 | Mumm et al. |
| 10,364,419 | B2 | 7/2019 | Buller et al. |
| 10,457,748 | B2 | 10/2019 | Dave et al. |
| 10,711,050 | B2 | 7/2020 | Schmidt et al. |
| 10,934,341 | B2 | 3/2021 | Cameron et al. |
| 10,934,572 | B2 | 3/2021 | Gosselin et al. |
| 11,028,166 | B2 | 6/2021 | Cini et al. |
| 11,046,767 | B2 | 6/2021 | Roobrouck et al. |
| 11,096,997 | B2 | 8/2021 | Mooney et al. |
| 2001/0056075 | A1 | 12/2001 | Gyuris et al. |
| 2006/0025573 | A1 | 2/2006 | Gillies et al. |
| 2007/0041987 | A1 | 2/2007 | Carter |
| 2013/0123199 | A1 | 5/2013 | Lee |
| 2013/0288372 | A1 | 10/2013 | Dasgupta et al. |
| 2015/0038678 | A1 | 2/2015 | Eaton et al. |
| 2015/0283073 | A1 | 10/2015 | Tang |
| 2016/0068583 | A1 | 3/2016 | Van Vlasselaer et al. |
| 2016/0106858 | A1 | 4/2016 | Hall et al. |
| 2017/0096472 | A1 | 4/2017 | Rosen et al. |
| 2018/0000962 | A1 | 1/2018 | Eigenbrot, Jr. et al. |
| 2018/0009869 | A1 | 1/2018 | Lu et al. |
| 2018/0028679 | A1 | 2/2018 | Kratz et al. |
| 2018/0280524 | A1 | 10/2018 | Hubbell et al. |
| 2018/0326080 | A1 | 11/2018 | Deng |
| 2018/0333464 | A1 | 11/2018 | Mumm et al. |
| 2019/0070263 | A1 | 3/2019 | Azimi |
| 2019/0099485 | A1 | 4/2019 | Swartz et al. |
| 2019/0099487 | A1 | 4/2019 | Mumm et al. |
| 2019/0127489 | A1 | 5/2019 | Humphreys et al. |
| 2019/0144529 | A1 | 5/2019 | Adams et al. |
| 2019/0183992 | A1 | 6/2019 | Sands et al. |
| 2019/0184012 | A1 | 6/2019 | Qu et al. |
| 2019/0216898 | A1 | 7/2019 | Wang et al. |
| 2019/0282692 | A1 | 9/2019 | Bredehorst et al. |
| 2019/0290688 | A1 | 9/2019 | Bar-Sagi et al. |
| 2019/0307849 | A1 | 10/2019 | Oft |
| 2019/0352335 | A1 | 11/2019 | Jeong et al. |
| 2019/0365819 | A1 | 12/2019 | Jones et al. |
| 2019/0375799 | A1 | 12/2019 | Ekblad et al. |
| 2019/0375823 | A1 | 12/2019 | Dixit et al. |
| 2020/0048325 | A1 | 2/2020 | Zhan et al. |
| 2020/0055947 | A1 | 2/2020 | Khalil et al. |
| 2020/0069814 | A1 | 3/2020 | Zhao et al. |
| 2020/0102368 | A1 | 4/2020 | Andersen et al. |
| 2020/0102370 | A1 | 4/2020 | Wittrup et al. |
| 2020/0123228 | A1 | 4/2020 | Hubbell et al. |
| 2020/0148733 | A1 | 5/2020 | Hinner et al. |
| 2020/0172480 | A1 | 6/2020 | Zhao et al. |
| 2020/0179283 | A1 | 6/2020 | Fahmy et al. |
| 2020/0230250 | A1 | 7/2020 | Park et al. |
| 2020/0255512 | A1 | 8/2020 | Fuh et al. |
| 2020/0268884 | A1 | 8/2020 | Markovic et al. |
| 2020/0276261 | A1 | 9/2020 | Zhao et al. |
| 2020/0281994 | A1 | 9/2020 | Irvine et al. |
| 2020/0317749 | A1 | 10/2020 | Dennis et al. |
| 2020/0339696 | A1 | 10/2020 | Gerstam et al. |
| 2020/0385442 | A1 | 12/2020 | Sleep et al. |
| 2020/0390861 | A1 | 12/2020 | Merchant |
| 2020/0392206 | A1 | 12/2020 | Finnis et al. |
| 2020/0405850 | A1 | 12/2020 | Irvine et al. |
| 2021/0009659 | A1 | 1/2021 | Dixit et al. |
| 2021/0017247 | A1 | 1/2021 | Jones et al. |
| 2021/0040179 | A1 | 2/2021 | Hubbell et al. |
| 2021/0046189 | A1 | 2/2021 | Jung et al. |
| 2021/0070839 | A1 | 3/2021 | Delahay et al. |
| 2021/0094995 | A1 | 4/2021 | Hubbell et al. |
| 2021/0115102 | A1 | 4/2021 | Winston et al. |
| 2021/0121533 | A1 | 4/2021 | Jones et al. |
| 2021/0139560 | A1 | 5/2021 | Larson et al. |
| 2021/0163565 | A1 | 6/2021 | Zhong et al. |
| 2021/0163599 | A1 | 6/2021 | Basran et al. |
| 2021/0171642 | A1 | 6/2021 | Hubbell et al. |
| 2021/0188963 | A1 | 6/2021 | Rommelaere et al. |
| 2021/0188967 | A1 | 6/2021 | Buyse |
| 2021/0230242 | A1 | 7/2021 | Zhong et al. |
| 2021/0230285 | A1 | 7/2021 | Cha |
| 2021/0244812 | A1 | 8/2021 | Hubbell et al. |

FOREIGN PATENT DOCUMENTS

| | | |
|---|---|---|
| JP | 2010503396 | 2/2010 |
| JP | 2010-534060 | 11/2010 |
| JP | 5178513 | 4/2013 |
| JP | 2017537141 | 12/2017 |
| JP | 2019123719 | 7/2019 |
| JP | 2019523653 | 8/2019 |
| JP | 2020515252 | 5/2020 |
| JP | 2020535264 | 12/2020 |
| JP | 2021006563 | 1/2021 |
| JP | 2021501221 | 1/2021 |
| JP | 6827411 | 2/2021 |
| JP | 2021073291 | 5/2021 |
| JP | 2021515599 | 6/2021 |
| KR | 101286721 | 7/2013 |
| KR | 1010774150 | 9/2017 |
| WO | WO 96/18412 | 6/1996 |
| WO | WO 2009/004339 | 1/2009 |
| WO | WO 2009/013461 | 1/2009 |
| WO | WO 2012/054929 | 4/2012 |
| WO | WO 2012/112690 | 8/2012 |
| WO | WO 2014/139468 | 9/2014 |
| WO | WO 2014/176284 | 10/2014 |
| WO | WO 2016/174575 | 11/2016 |
| WO | WO 2018/069467 | 4/2018 |
| WO | WO 2018/112394 | 6/2018 |
| WO | WO 2018/184003 | 10/2018 |
| WO | WO 2018/195386 | 10/2018 |
| WO | WO 2019/173289 | 9/2019 |
| WO | WO 2019/209965 | 10/2019 |
| WO | WO 2019/222294 | 11/2019 |
| WO | WO 2020/041758 | 2/2020 |
| WO | WO 2020/108426 | 6/2020 |
| WO | WO 2020/176478 | 9/2020 |
| WO | WO 2020/247973 | 12/2020 |
| WO | WO 2021/016640 | 1/2021 |
| WO | WO 2021/091986 | 5/2021 |
| WO | WO 2021/158938 | 8/2021 |

OTHER PUBLICATIONS

Extended European Search Report issued in corresponding European Application No. 20762257.2, dated Feb. 6, 2023.

Addi et al., "Design and use of chimeric proteins containing a collagen-binding domain for wound healing and bone regeneration" *Tissue Eng. Part B. Rev.* 2017, 23, 163-182.

Chaudhury et al., "The major histocompatibility complex-related Fc receptor for IgG (FcRn) binds albumin and prolongs its lifespan." *J. Exp. Med.* 2003, 197, 315-322.

Garamszegi et al. "Extracellular matrix-induced transforming growth factor-β receptor signaling dynamics" *Oncogene* 2010, 29(16), 2368-2380.

Green et al., "Abraxane®, a novel Cremophor®-free, albumin-bound particle form of paclitaxel for the treatment of advanced non-small-cell lung cancer" *Annals of Oncology* 2006, 17: 1263-1268.

Hummel et al., "Synthetic Deletion of the Interleukin 23 Receptor (IL-23R) Stalk Region Led to Autonomous IL-23R Homodimerization and Activation" *Molecular and Cellular Biology* 2017, 37(17), 1-19.

(56) References Cited

OTHER PUBLICATIONS

International Search Report and Written Opinion issued in Corresponding PCT Application No. PCT/US2020/070308, dated Nov. 5, 2020.
International Search Report and Written Opinion issued in Corresponding PCT Application No. PCT/US2020/019668, dated Jun. 9, 2020.
International Search Report and Written Opinion issued in Corresponding PCT Application No. PCT/US2020/70113, dated Sep. 10, 2020.
Ishihara et al., "Prolonged residence of an albumin-IL-4 fusion protein in secondary lymphoid organs ameliorates experimental autoimmune encephalomyelitis" *Nat Biomed Eng* 2021, 5, 387-398.
Ishihara et al., "Targeted antibody and cytokine cancer immunotherapies through collagen affinity" *Sci. Transl. Med.* 2019, 11(487).
Katsumata et al., "Targeting inflammatory sites through collagen affinity enhances the therapeutic efficacy of anti-inflammatory antibodies" *Sci. Adv.* 2019, 5:eaay1971, 1-9.
Kratz et al., "Probing the cysteine-34 position of endogenous serum albumin with thiol-binding doxorubicin derivatives. Improved efficacy of an acid-sensitive doxorubicin derivative with specific albumin-binding properties compared to that of the parent compound." *J. Med. Chem.* 2002, 45, 5523-5533.
Kratz, F. "Albumin as a drug carrier: design of prodrugs, drug conjugates and nanoparticles." *J. Control. Release* 2008, 132, 171-183.
Puskas et al., "Development of an attenuated interleukin-2 fusion protein that can be activated by tumour-expressed proteases" *Immunology* 2011, 133(2), 206-220.
Sasaki et al., "Engineered collagen-binding serum albumin as a drug conjugate carrier for cancer therapy." *Sci. Adv.* 2019, 5:eaaw6081, 12 pages.
Temming et al., "Evaluation of RGD-targeted albumin carriers for specific delivery of auristatin E to tumor blood vessels" *Bioconjug. Chem.* 2006, 17, 1385-1394.
You et al. "The Extracellular Matrix and Remyelination Strategies in Multiple Sclerosis" *eNeuro* 2018, 5(1), 1-4.
Yuba et al., "Suppression of Rheumatoid Arthritis by Enhanced Lymph Node Trafficking of Engineered Interleukin-10 in Murine Models" *Arthritis and Rheumatology* 2021, 73(5), 769-778.
Zhong et al., "710 Development of IL-33 as a novel immunotherapy of cancer" *Journal for Immuno Therapy of Cancer* 2020; 8(Suppl 3): A426.
Zorzi et al., "Non-covalent albumin-binding ligands for extending the circulating half-life of small biotherapeutics" *Medchemcomm.* 2019, 10(7):1068-1081.

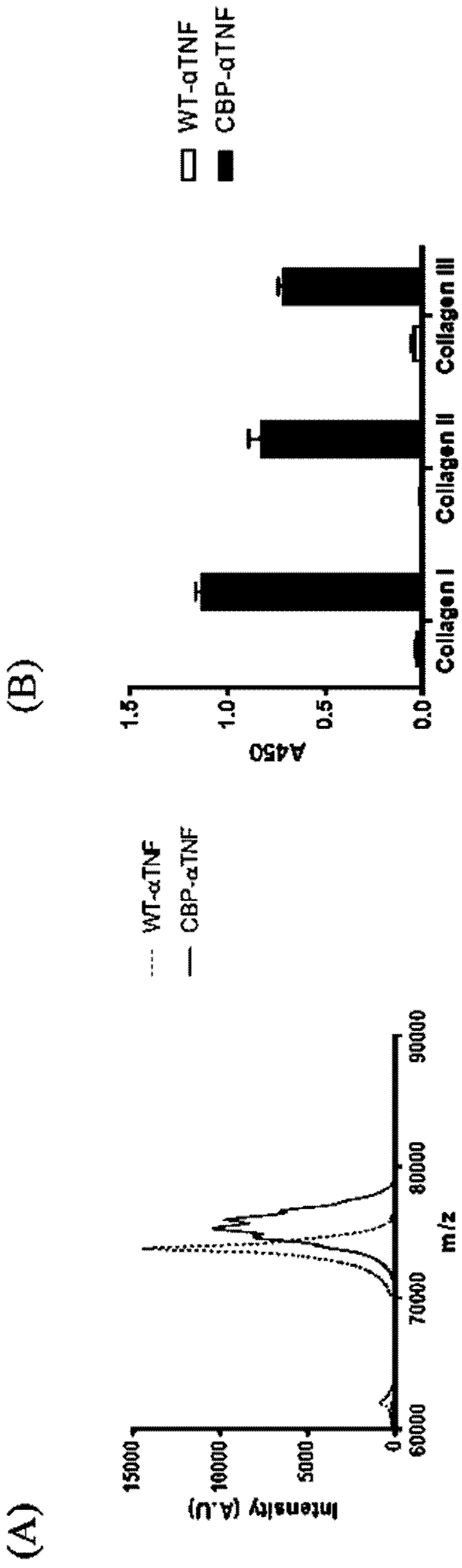
FIG. 1A-B

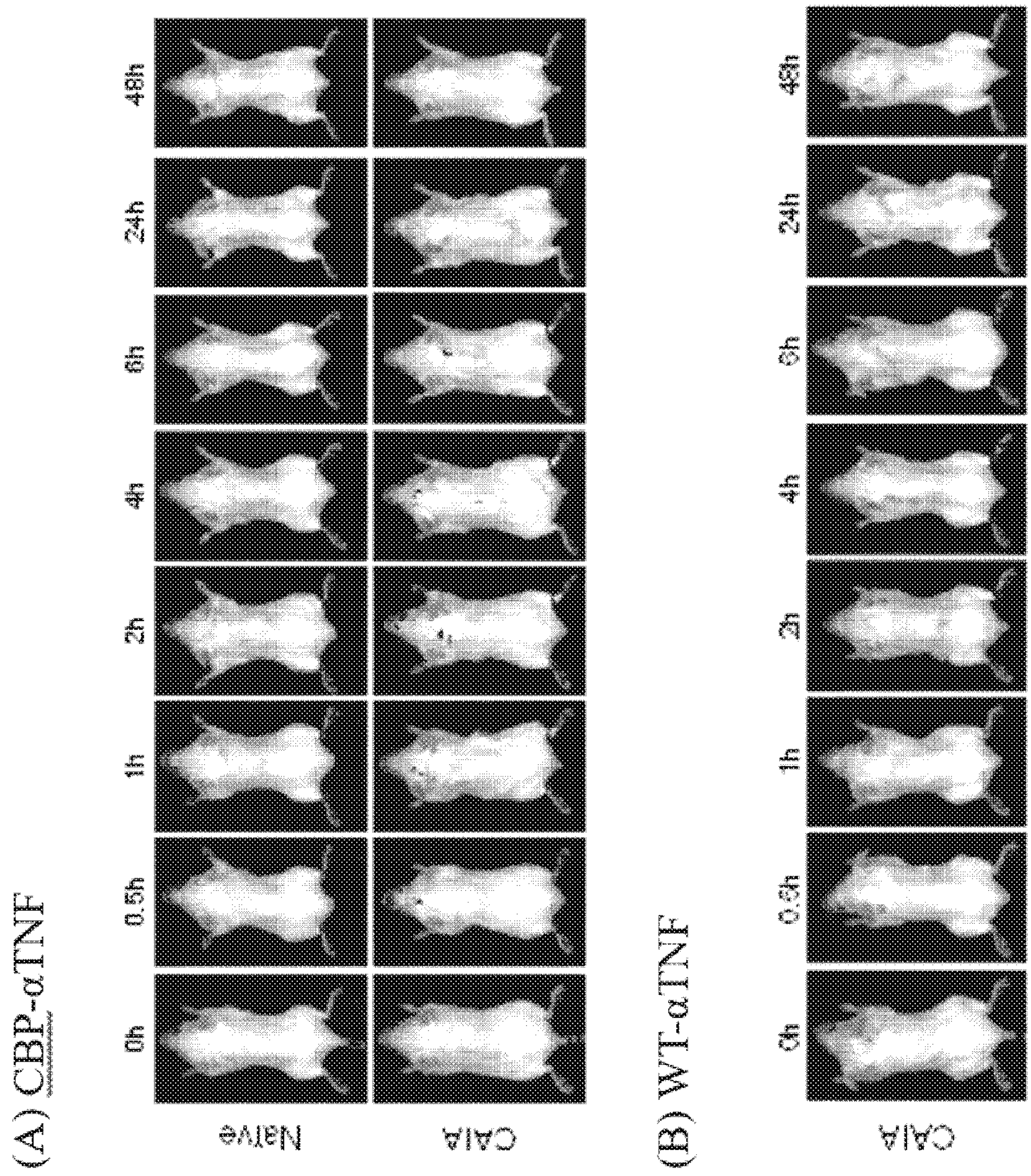
FIG. 2A-B

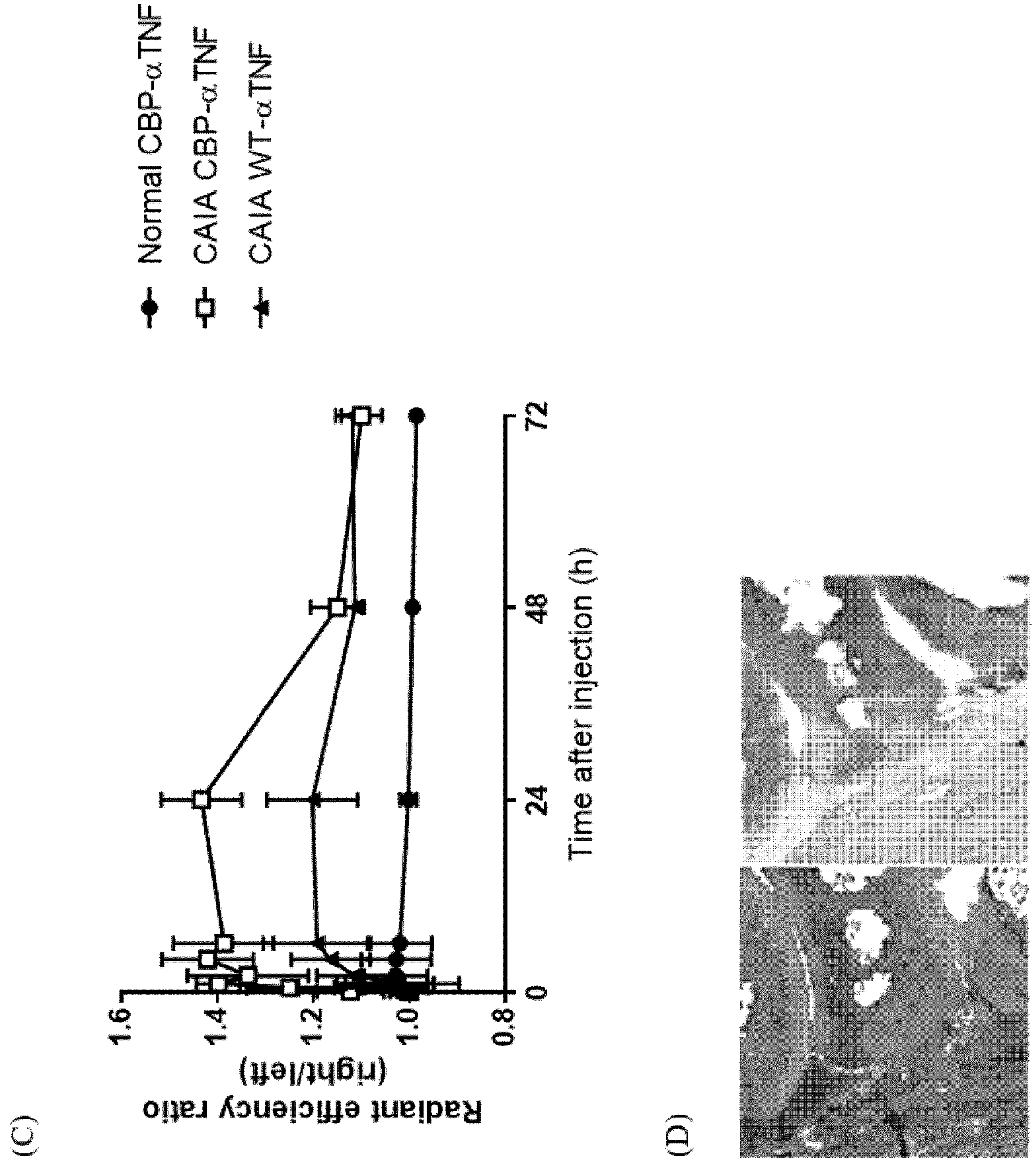
FIG. 2C-D

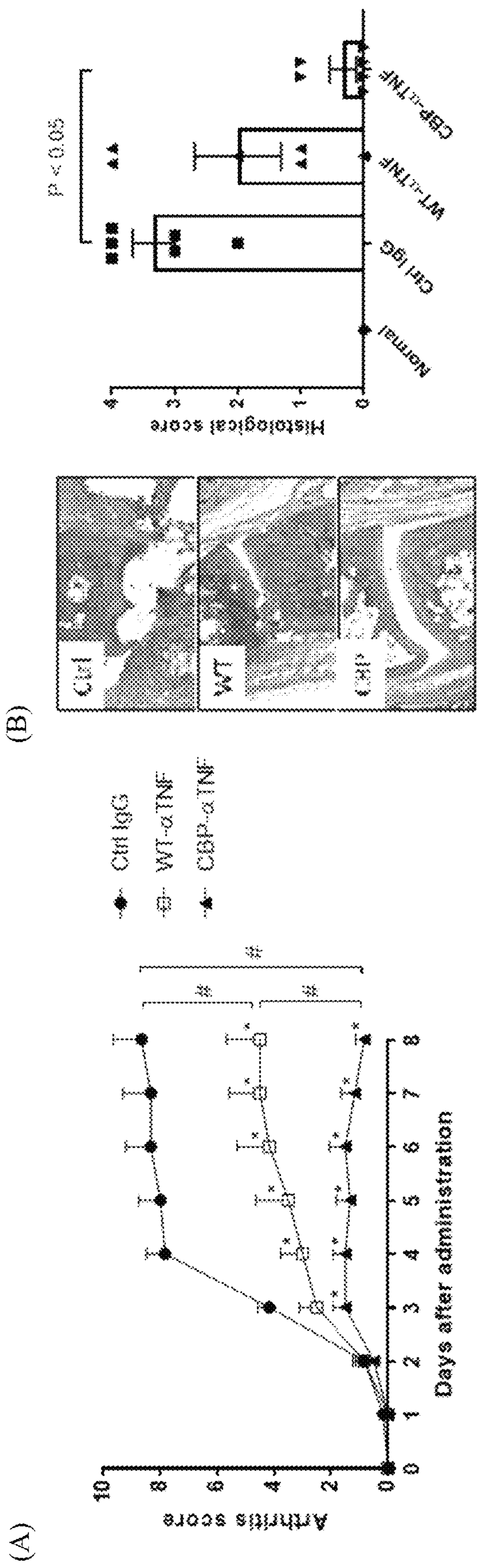
FIG. 3A-B

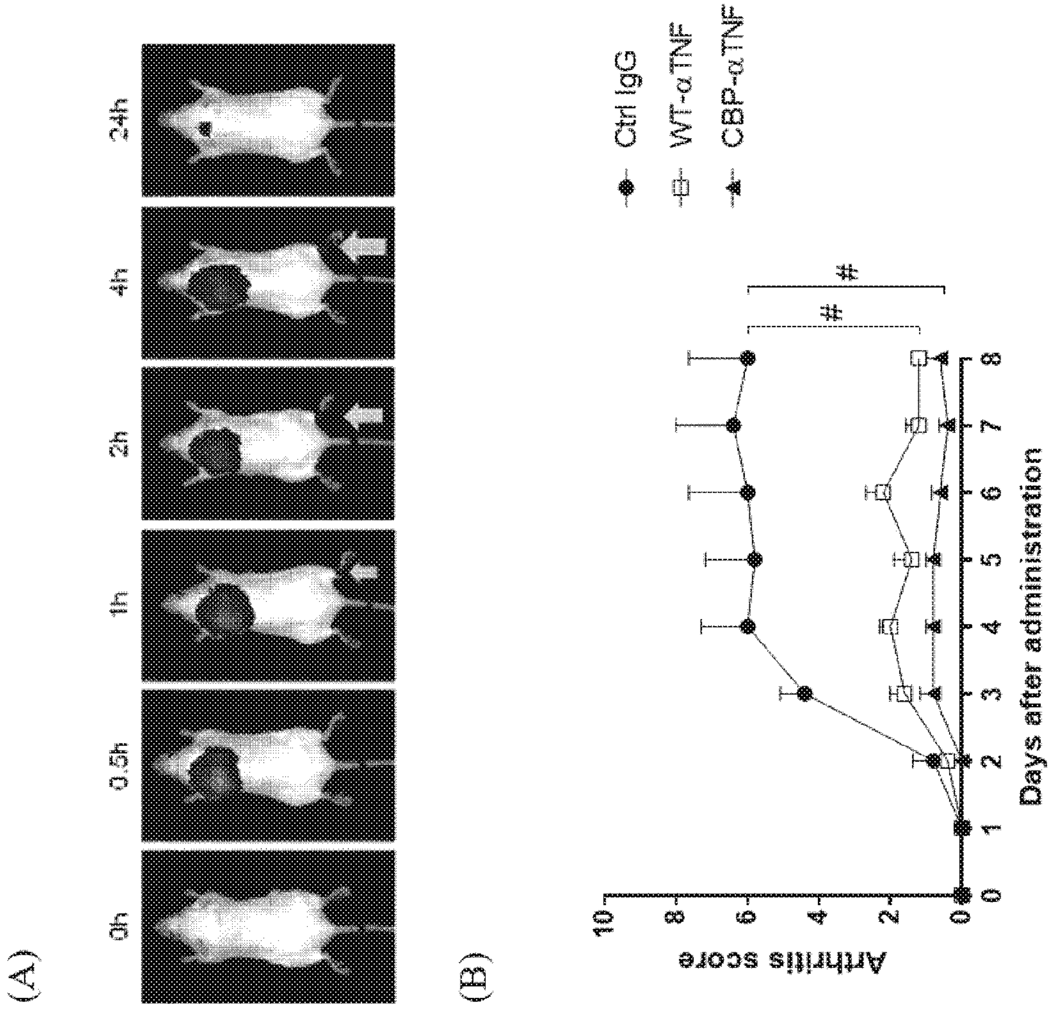
FIG. 4A-B

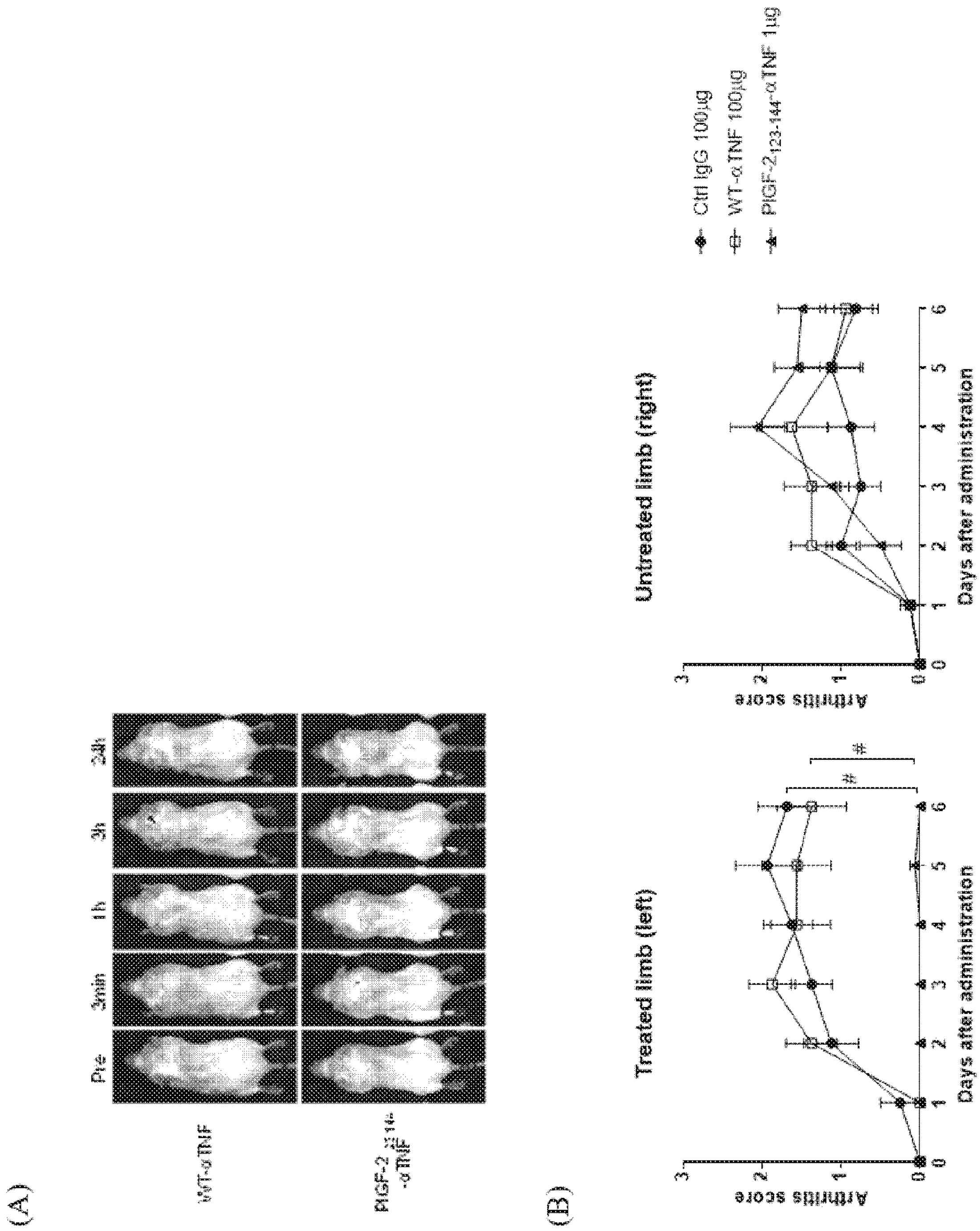
FIG. 5A-B

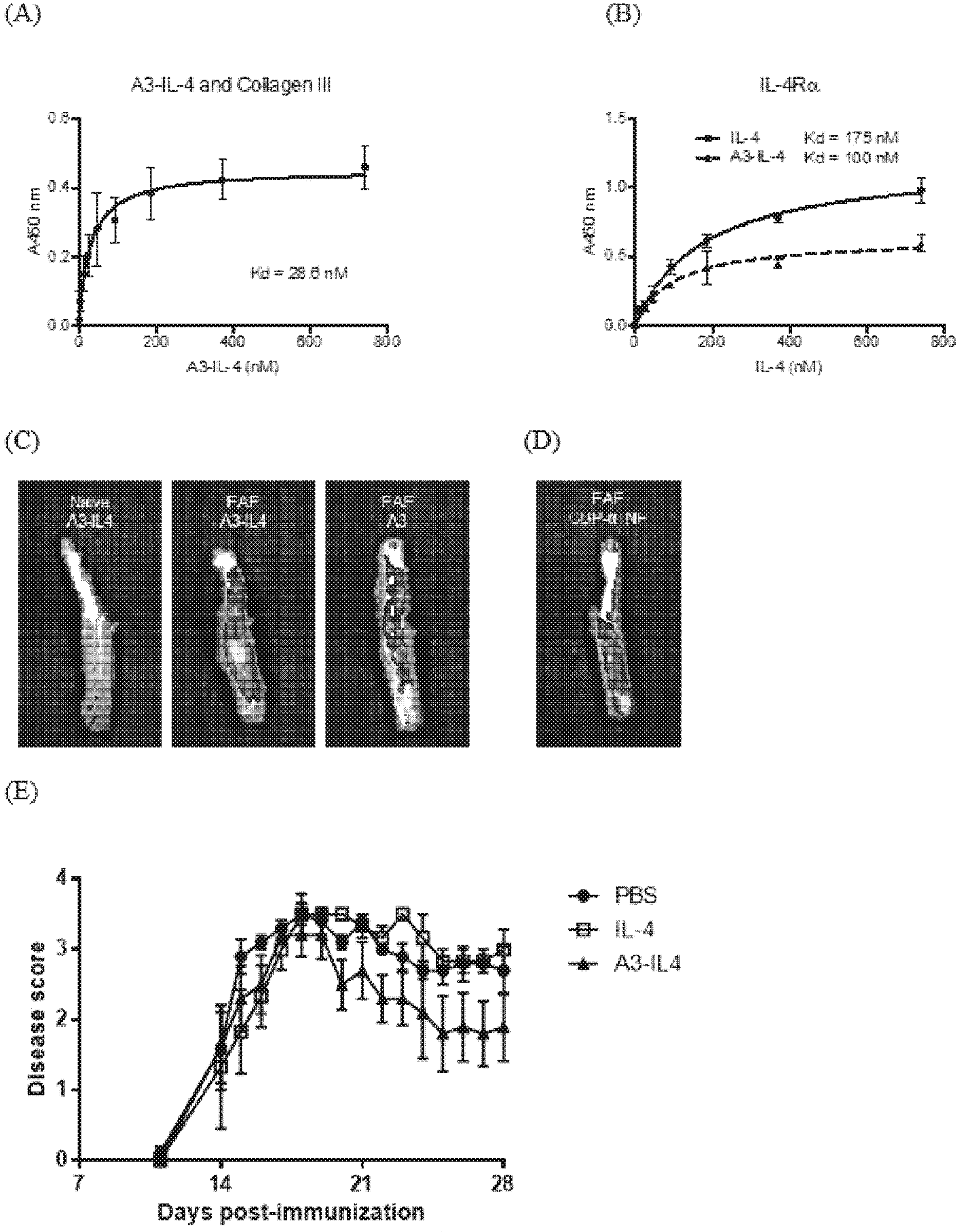
FIG. 6A-E (A) IBD
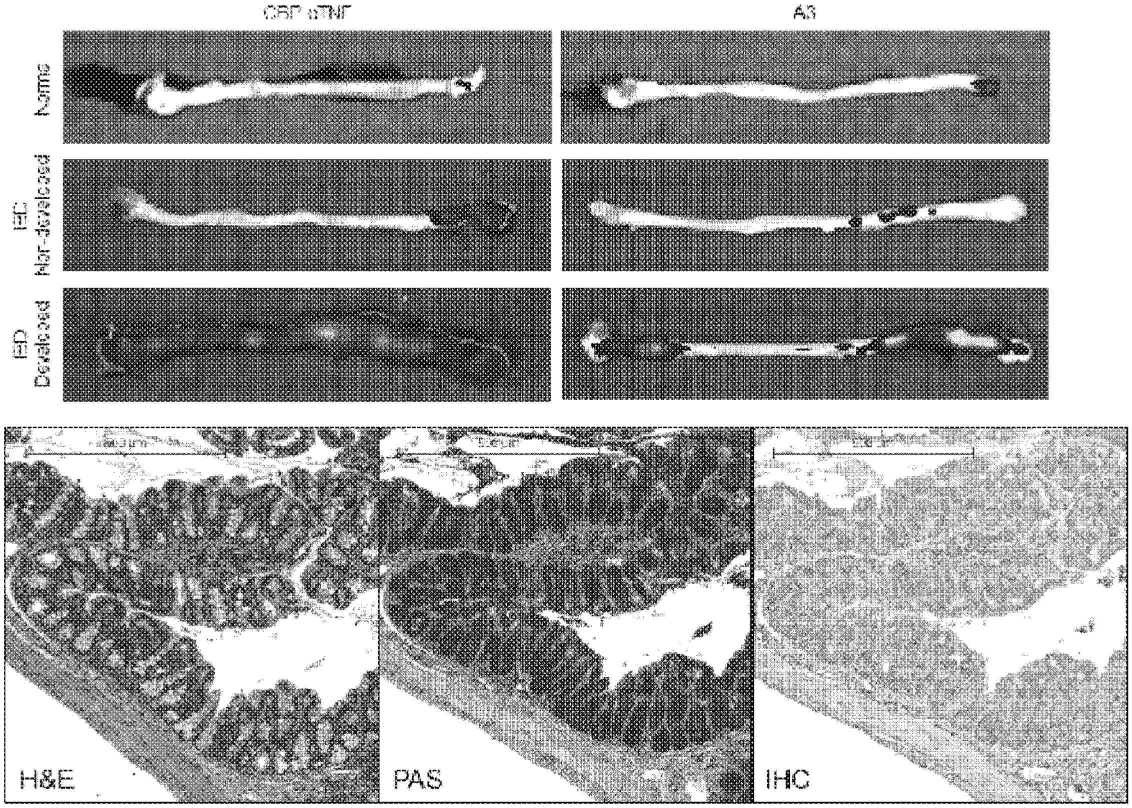
(B) IPF
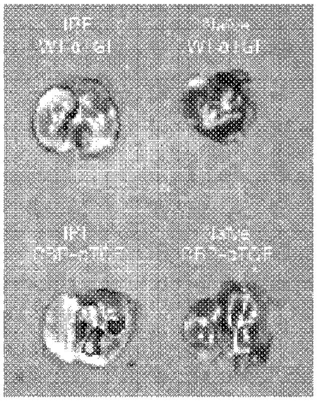
(C) T1D
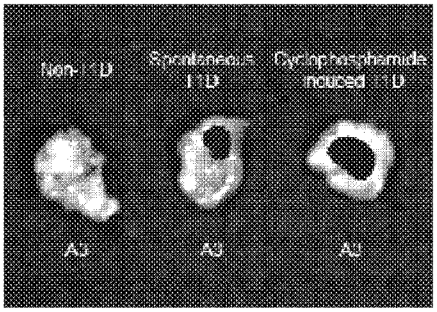
FIG. 7A-C

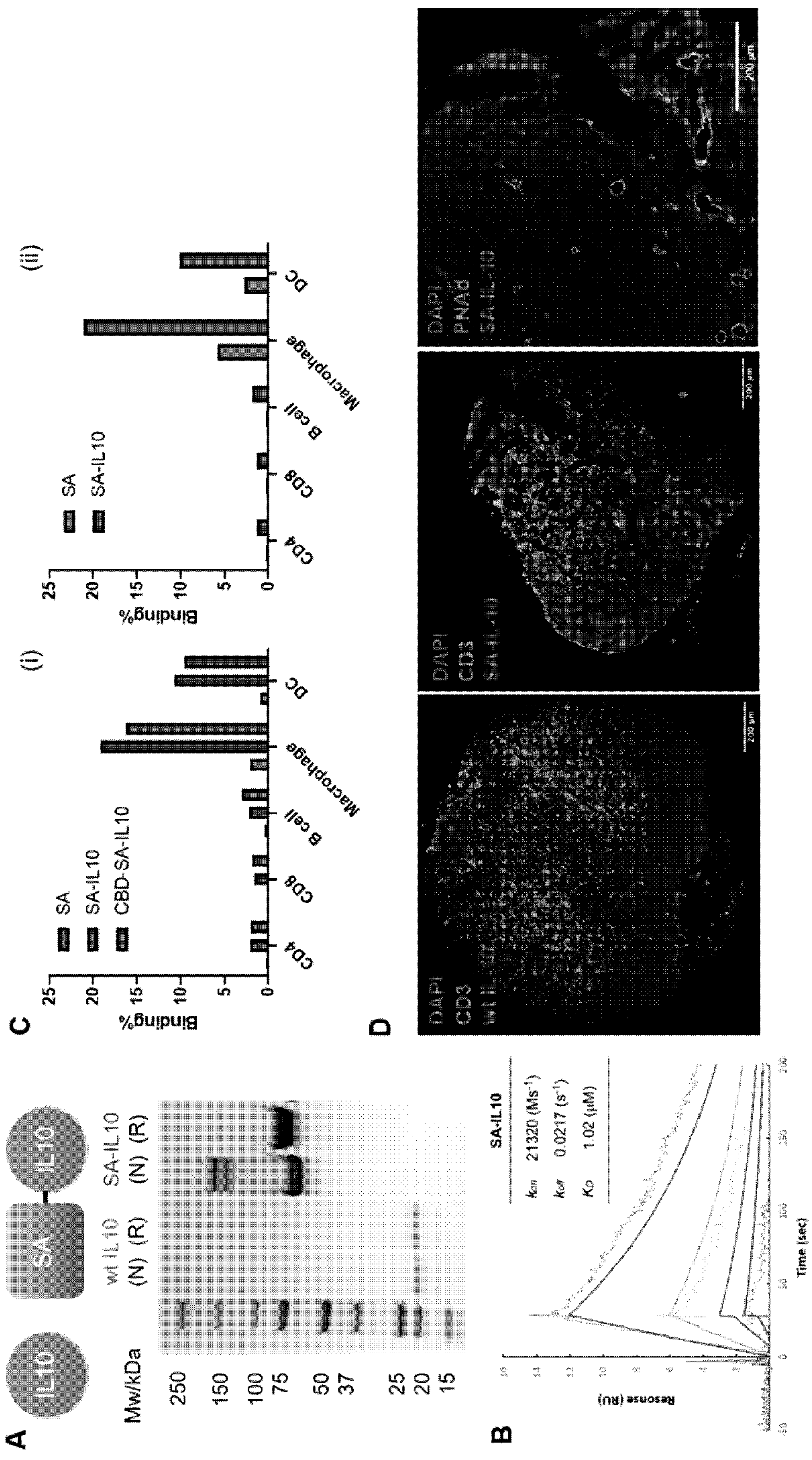
FIG. 8A-D

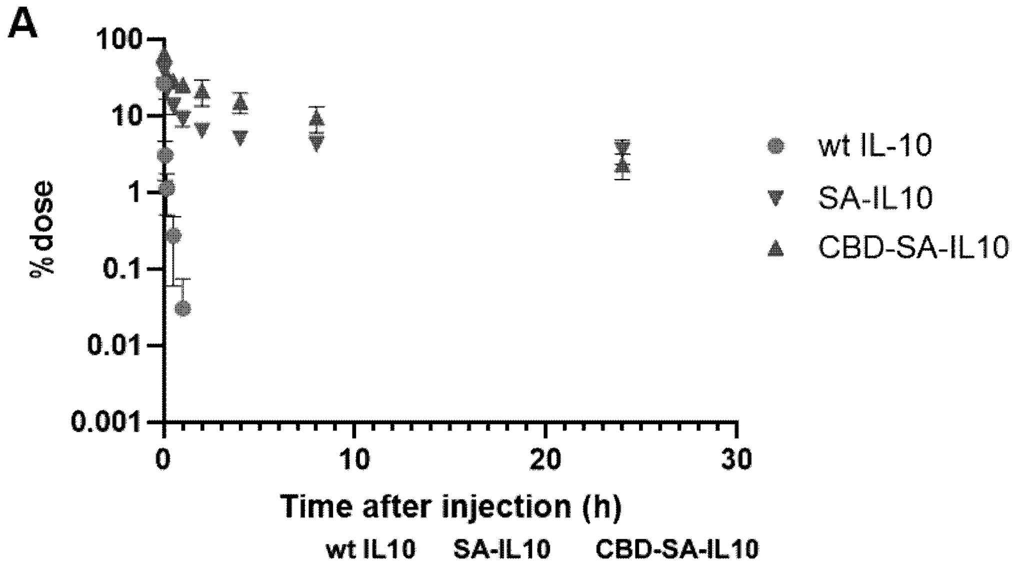
| | wt IL10 | SA-IL10 | CBD-SA-IL10 |
|---|---|---|---|
| $t_{1/2,}\ \alpha$ (min) | 0.997 | 4.77 | 2.87 |
| $t_{1/2,}\ \beta$ (min) | 10.05 | 43.97 | 228.1 |
| AUC (%dose・h) | 1.497 | 116.8 | 236.4 |
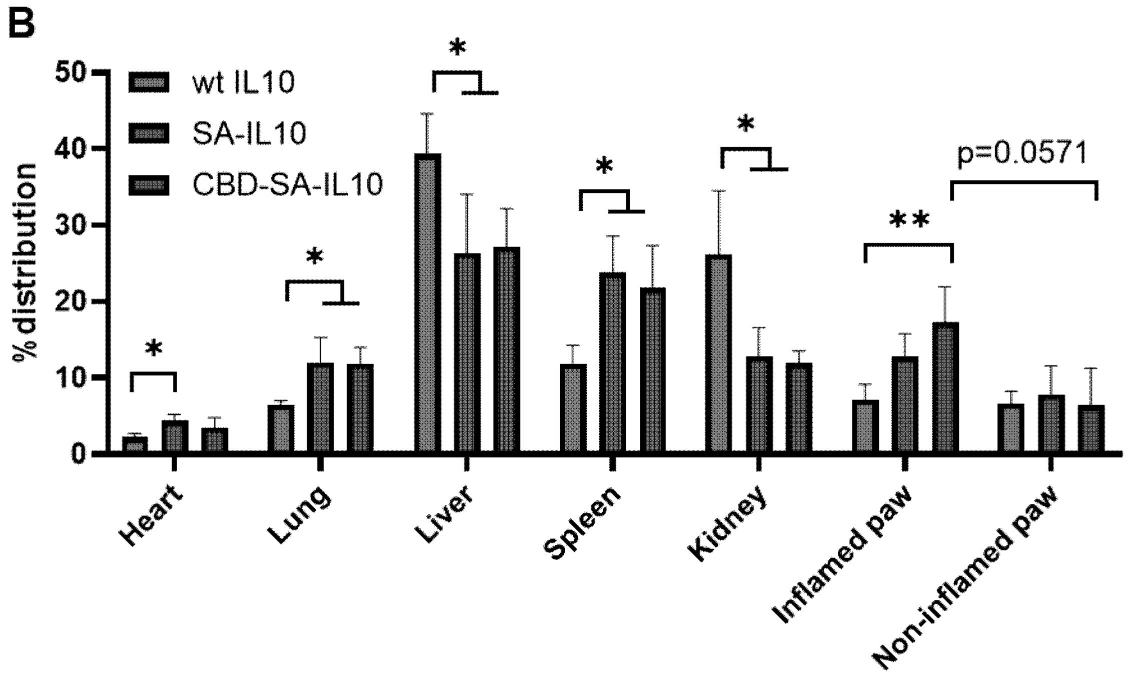
FIG. 9A-B

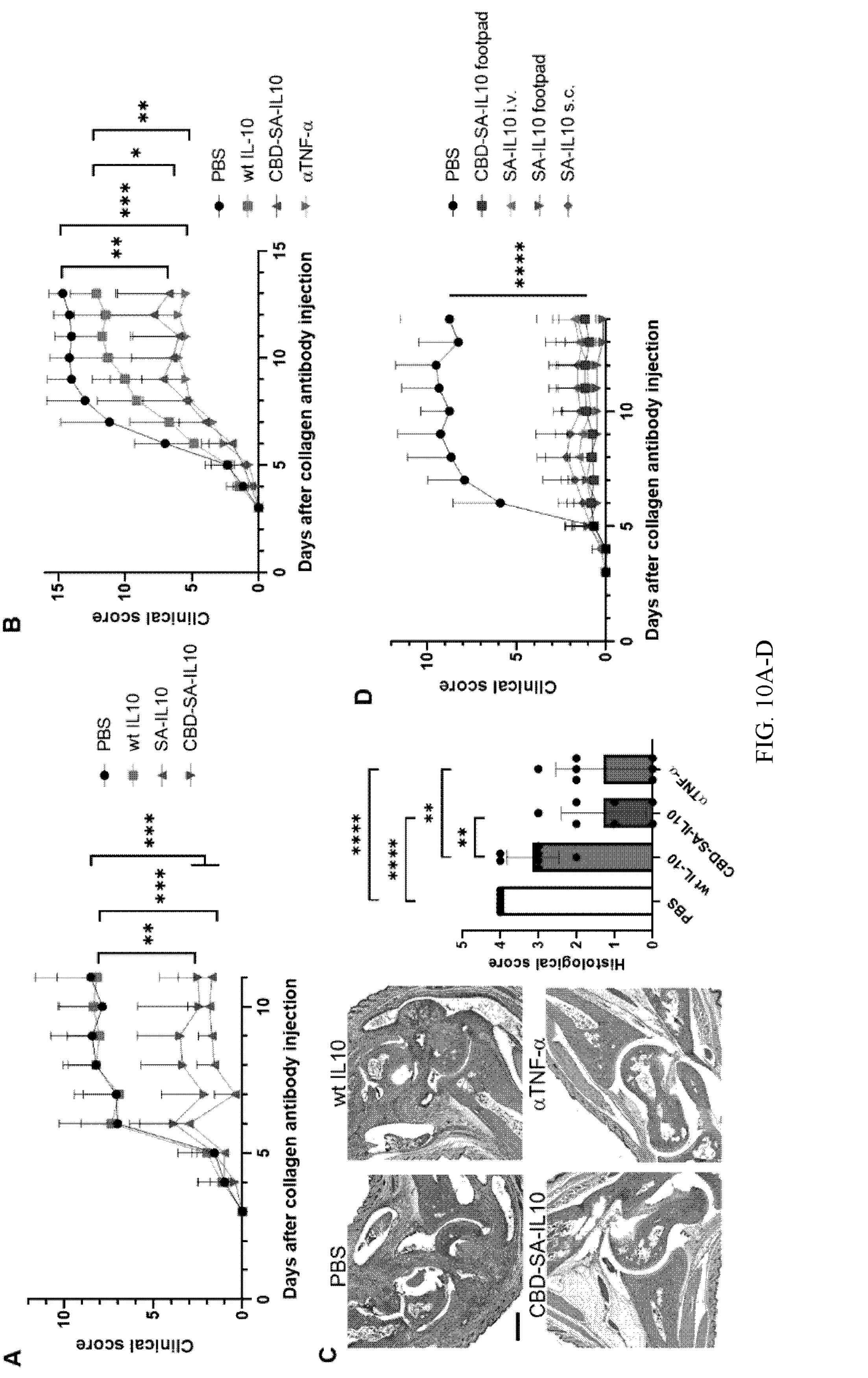
FIG. 10A-D

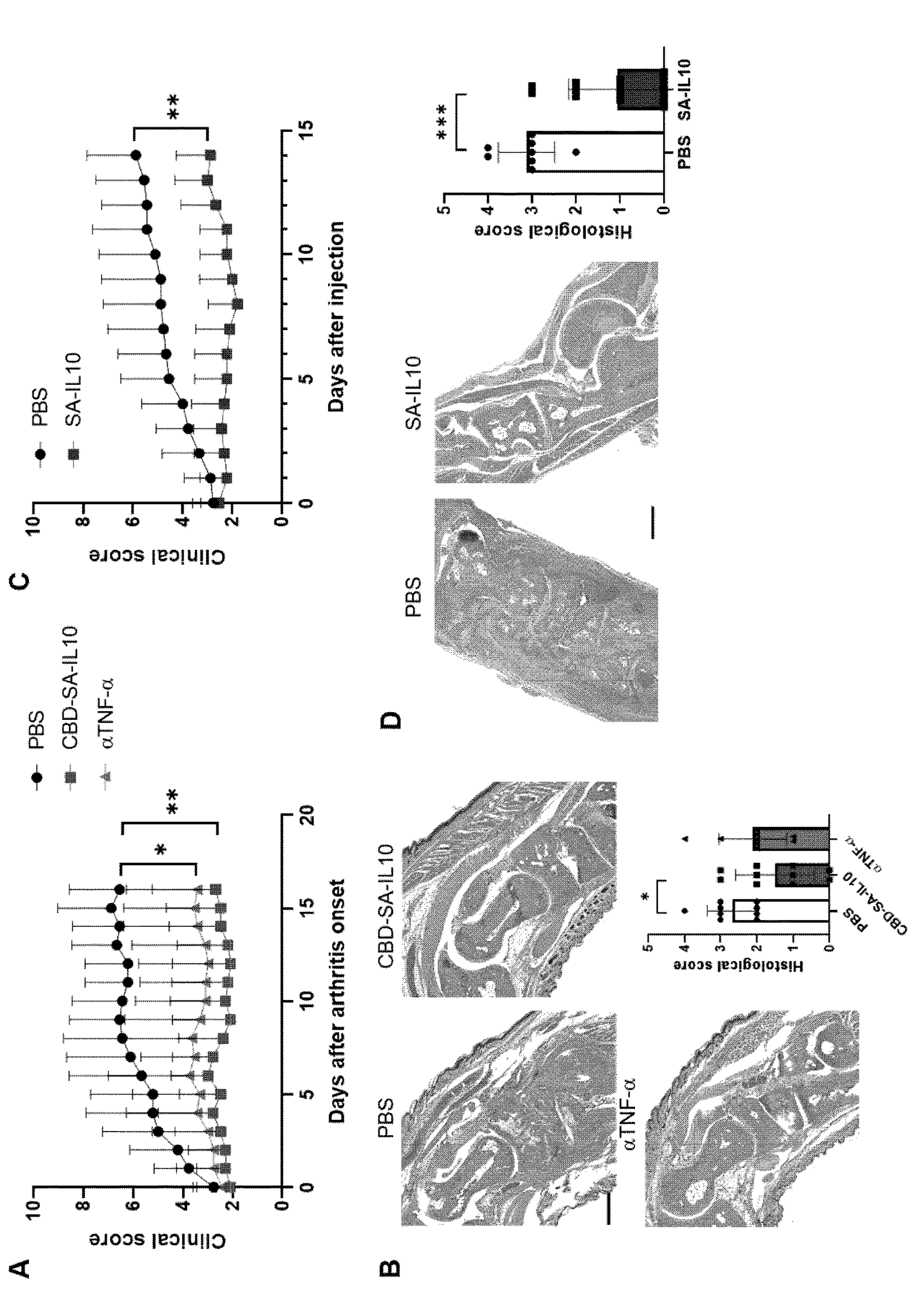
FIG. 11A-D

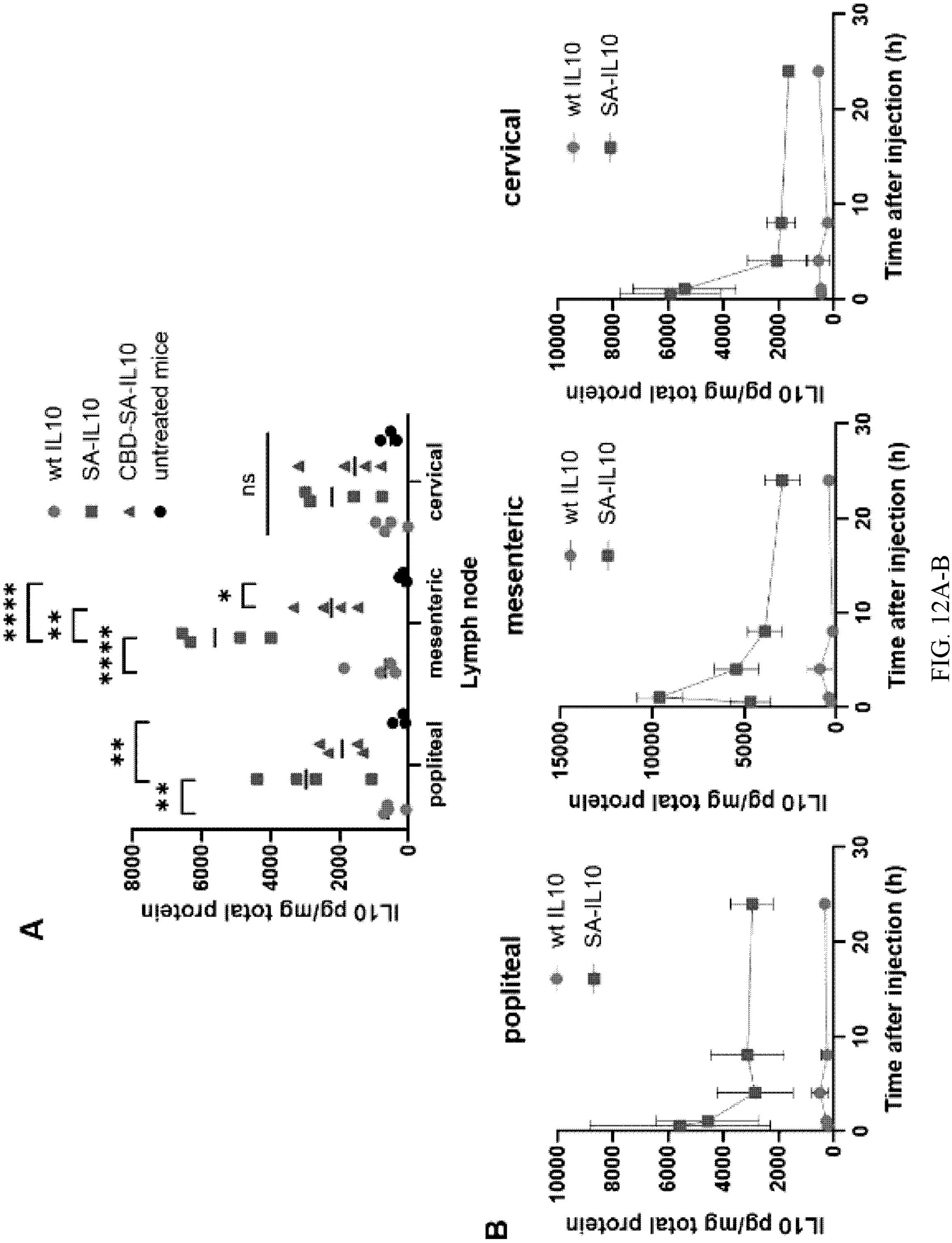
FIG. 12A-B

C
| Lymph node | AUC (IL10 pg · h/mg protein) wt IL10 | SA-IL10 |
|---|---|---|
| Popliteal | 7227 | 74177 |
| Mesenteric | 9586 | 99438 |
| Cervical | 9488 | 50127 |
D
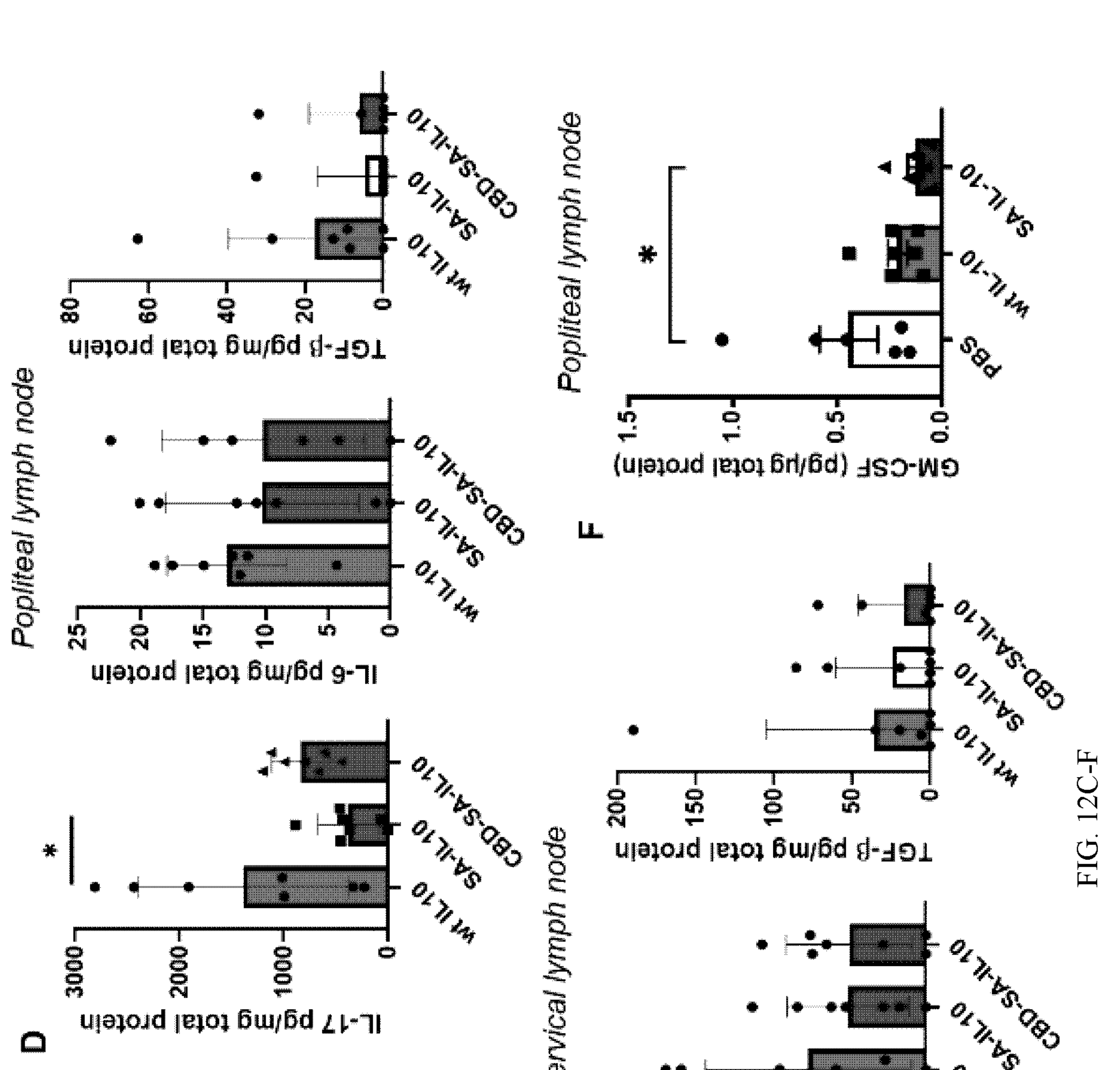
E
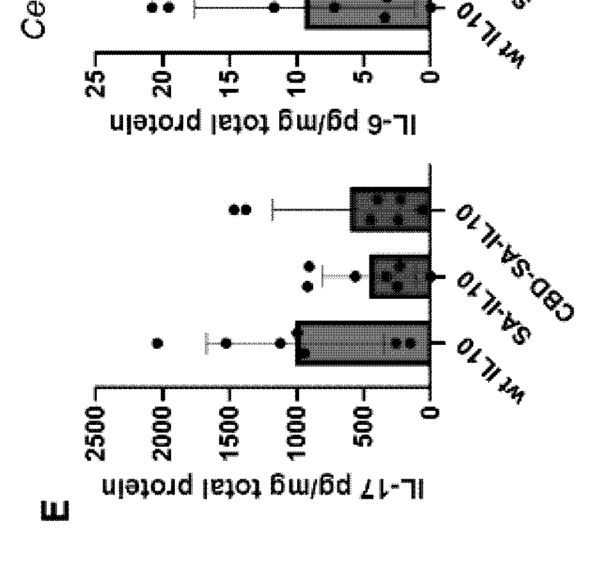
FIG. 12C-F

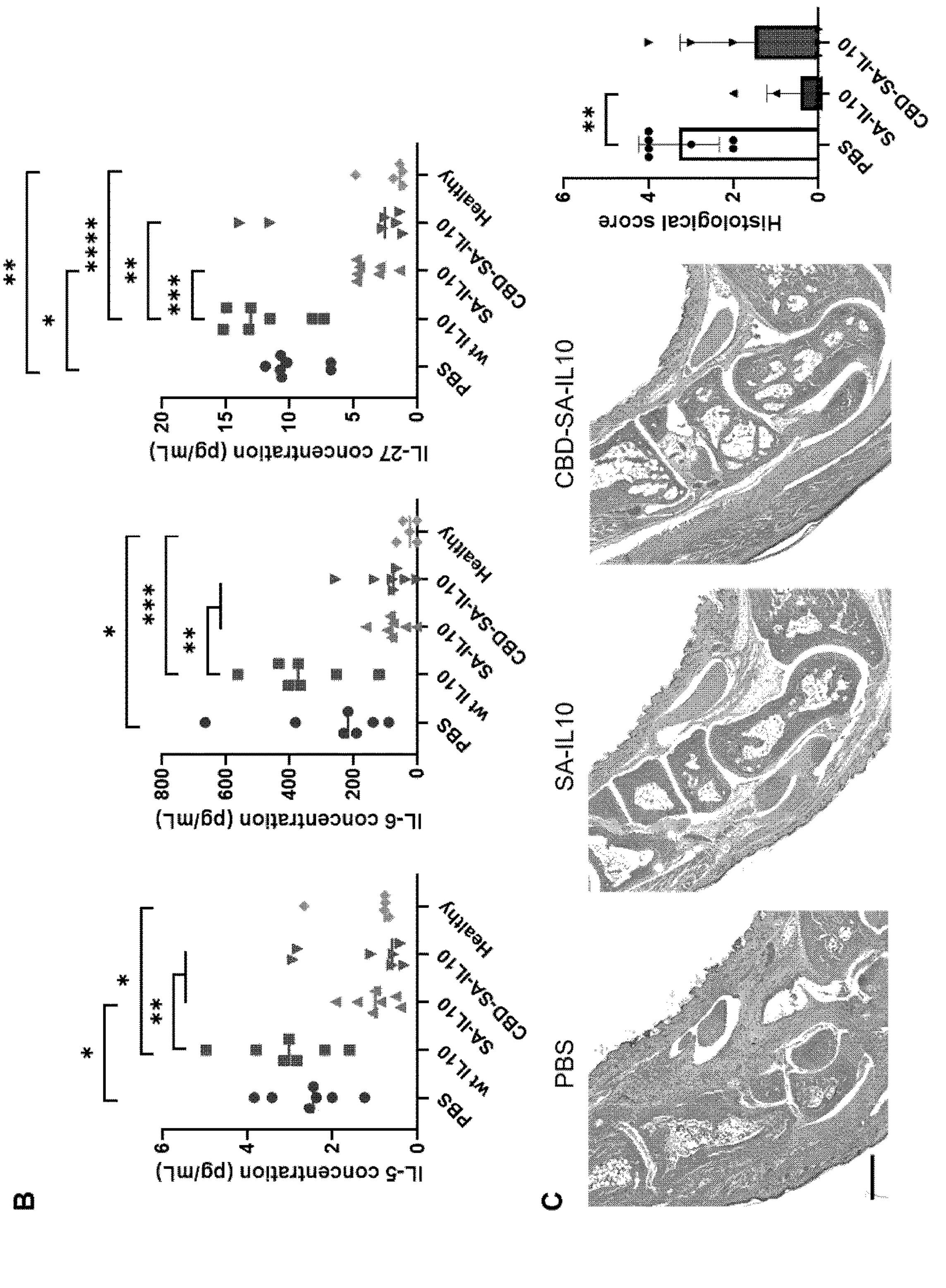
FIG. 13B-C

B
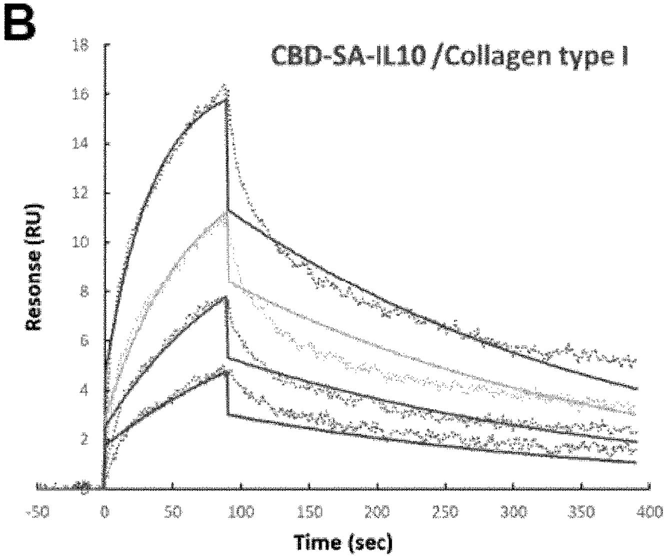
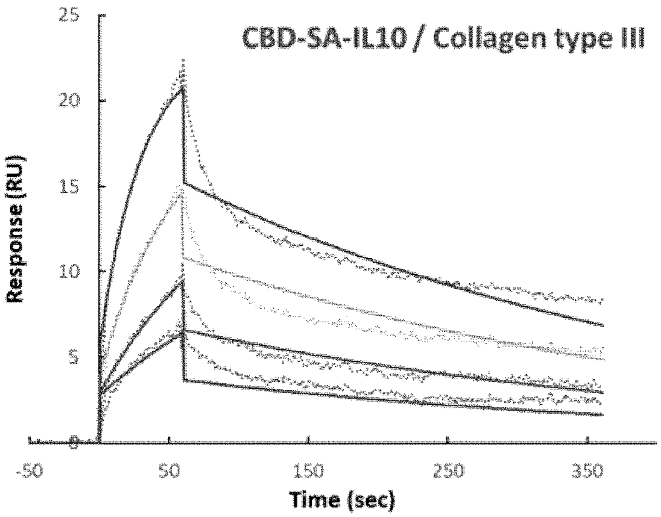
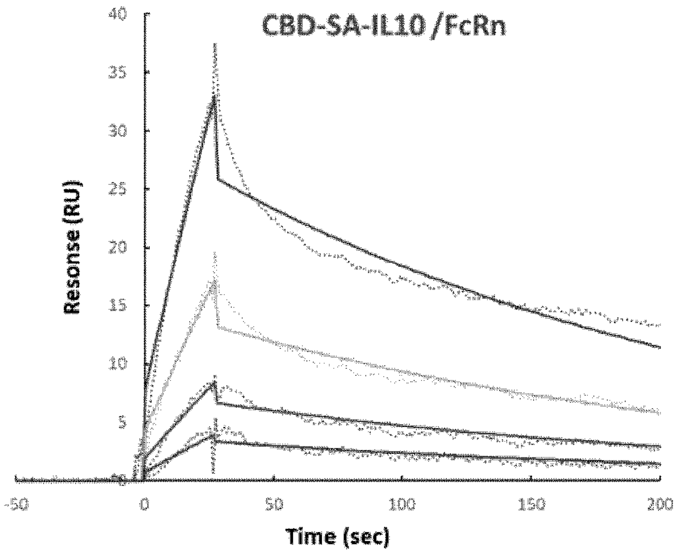
CBD-SA-IL10
| | Collagen I | Collagen III | FcRn |
|---|---|---|---|
| $k_{on}$ ($Ms^{-1}$) | 27500 | 33100 | 5213 |
| $k_{off}$ ($s^{-1}$) | 0.0034 | 0.0026 | 0.0084 |
| $K_D$ (nM) | 12.4 | 8.0 | 1600 |
FIG. 14B

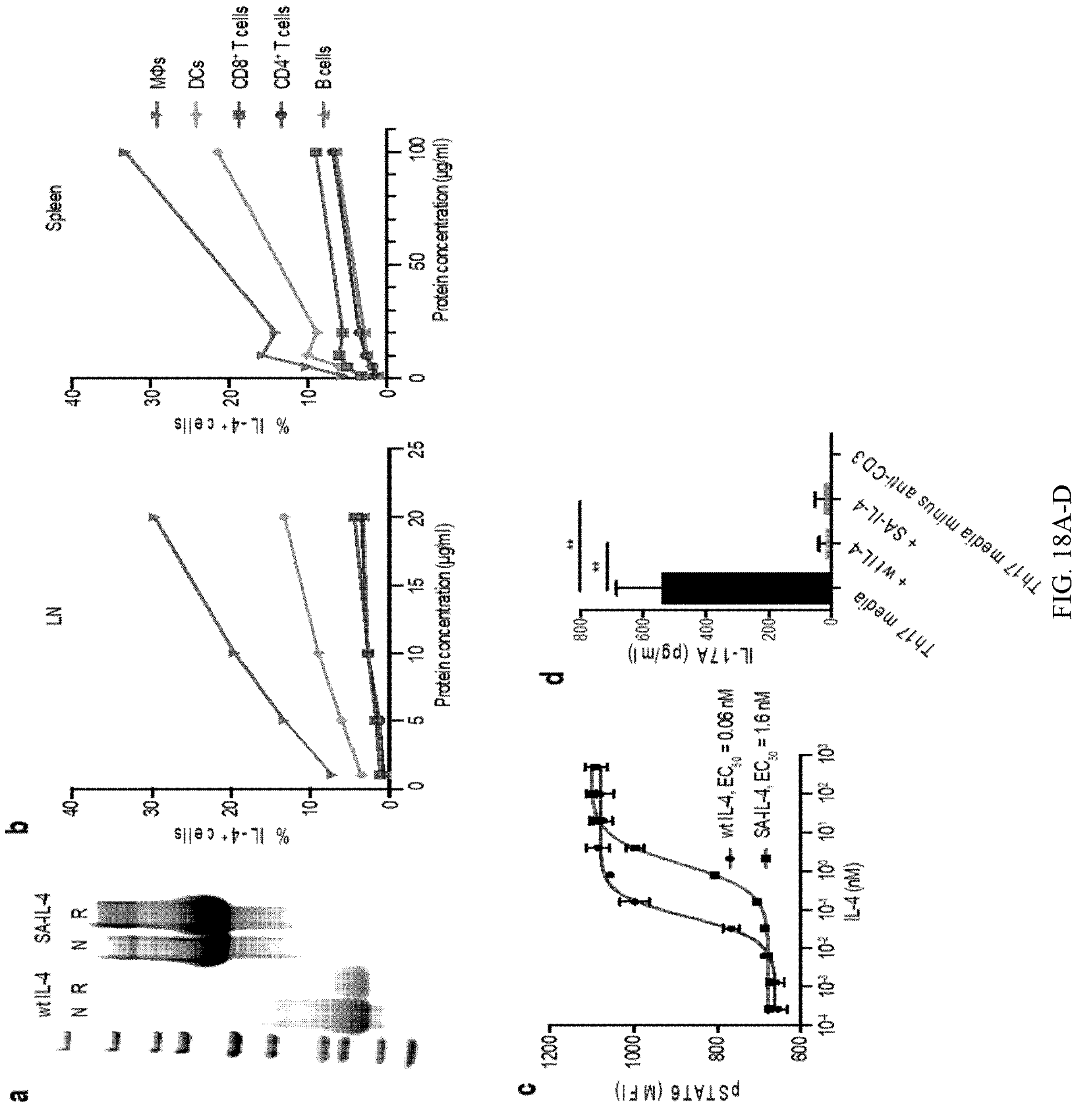
FIG. 18A-D

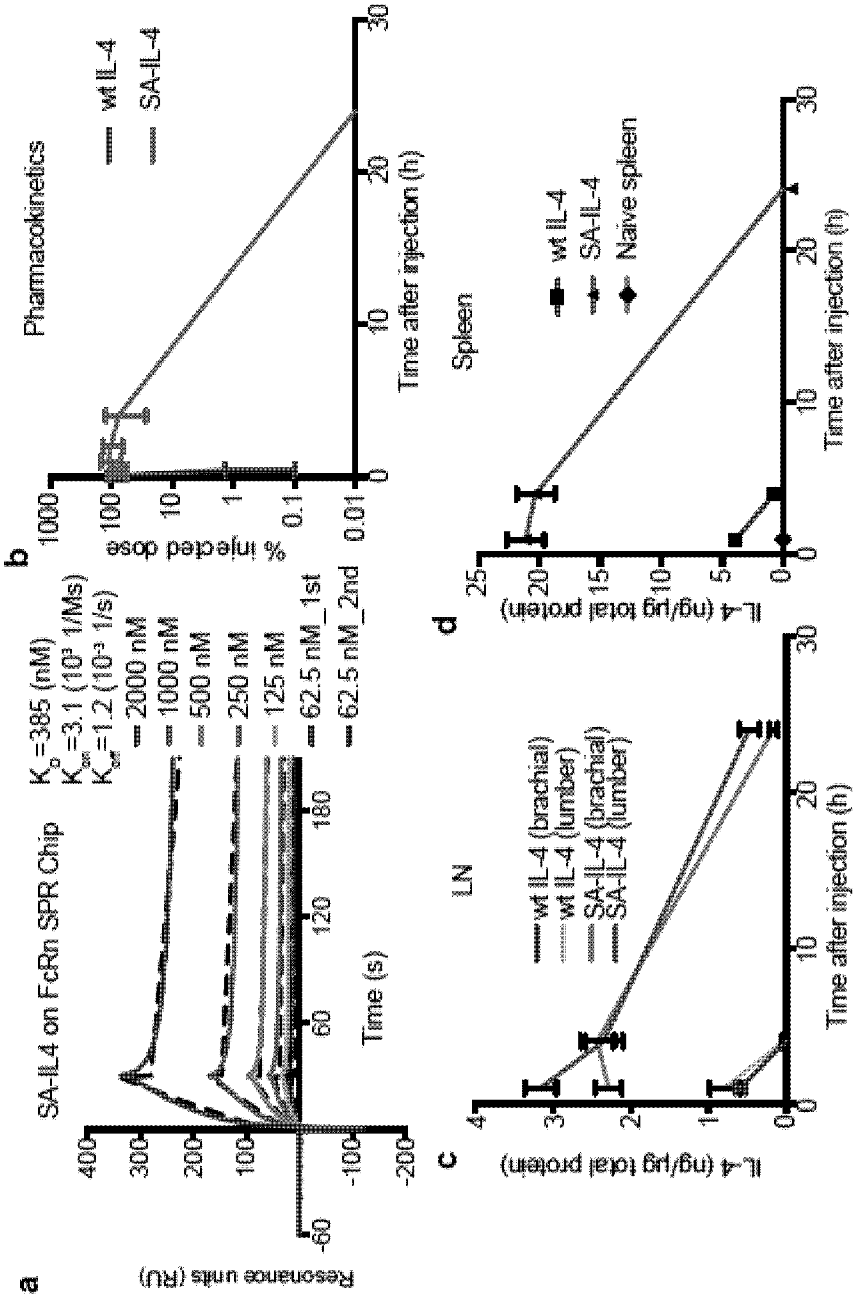
FIG. 19A-D

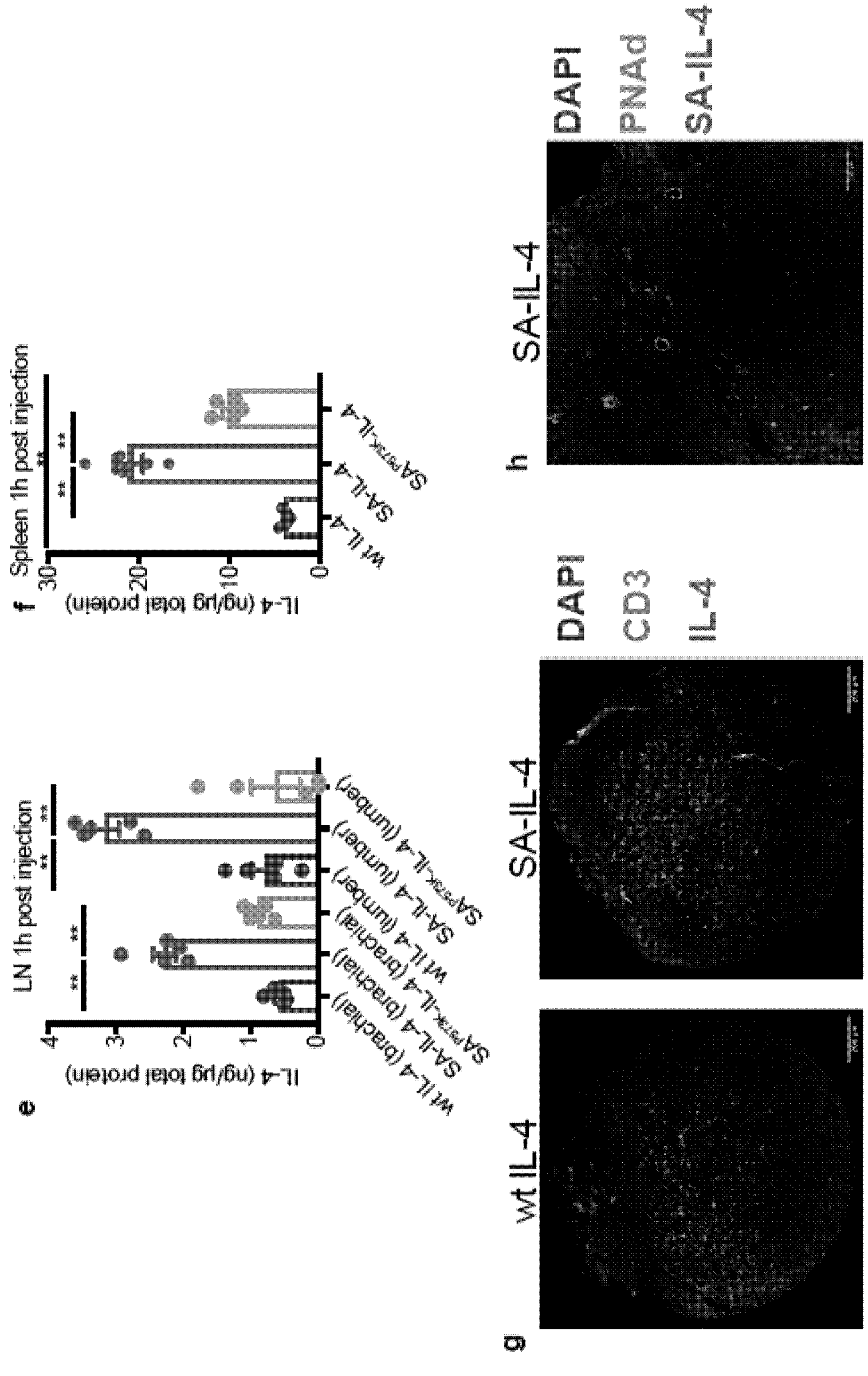
FIG. 19E-H a
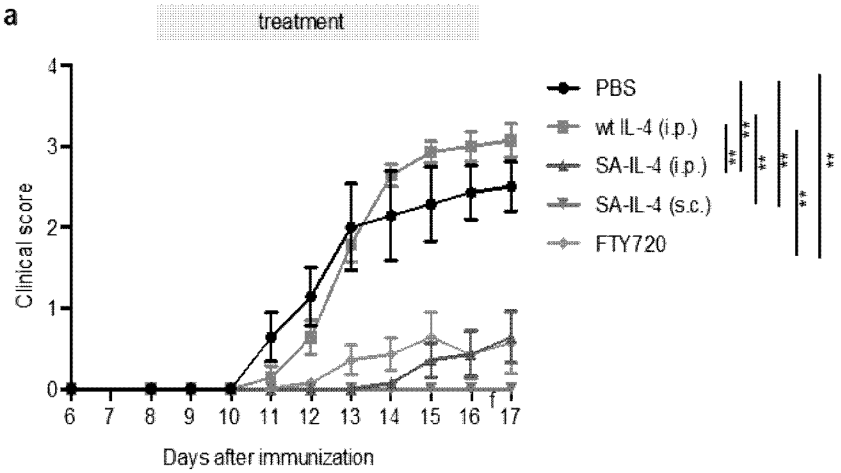
b
| Treatment | Disease incidence |
|---|---|
| PBS | 7/7 |
| wt IL-4 (i.p.) | 7/7 |
| SA-IL-4 (i.p.) | 3/7 |
| SA-IL-4 (s.c.) | 0/7 |
| FTY720 | 3/7 |
c
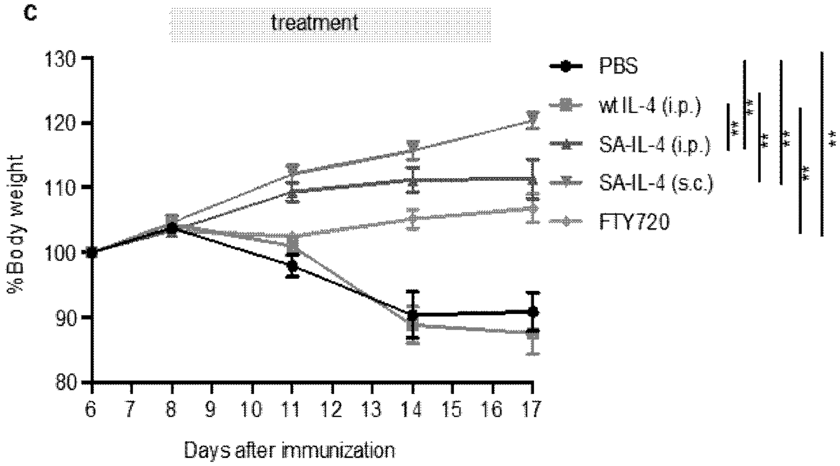
FIG. 20A-C

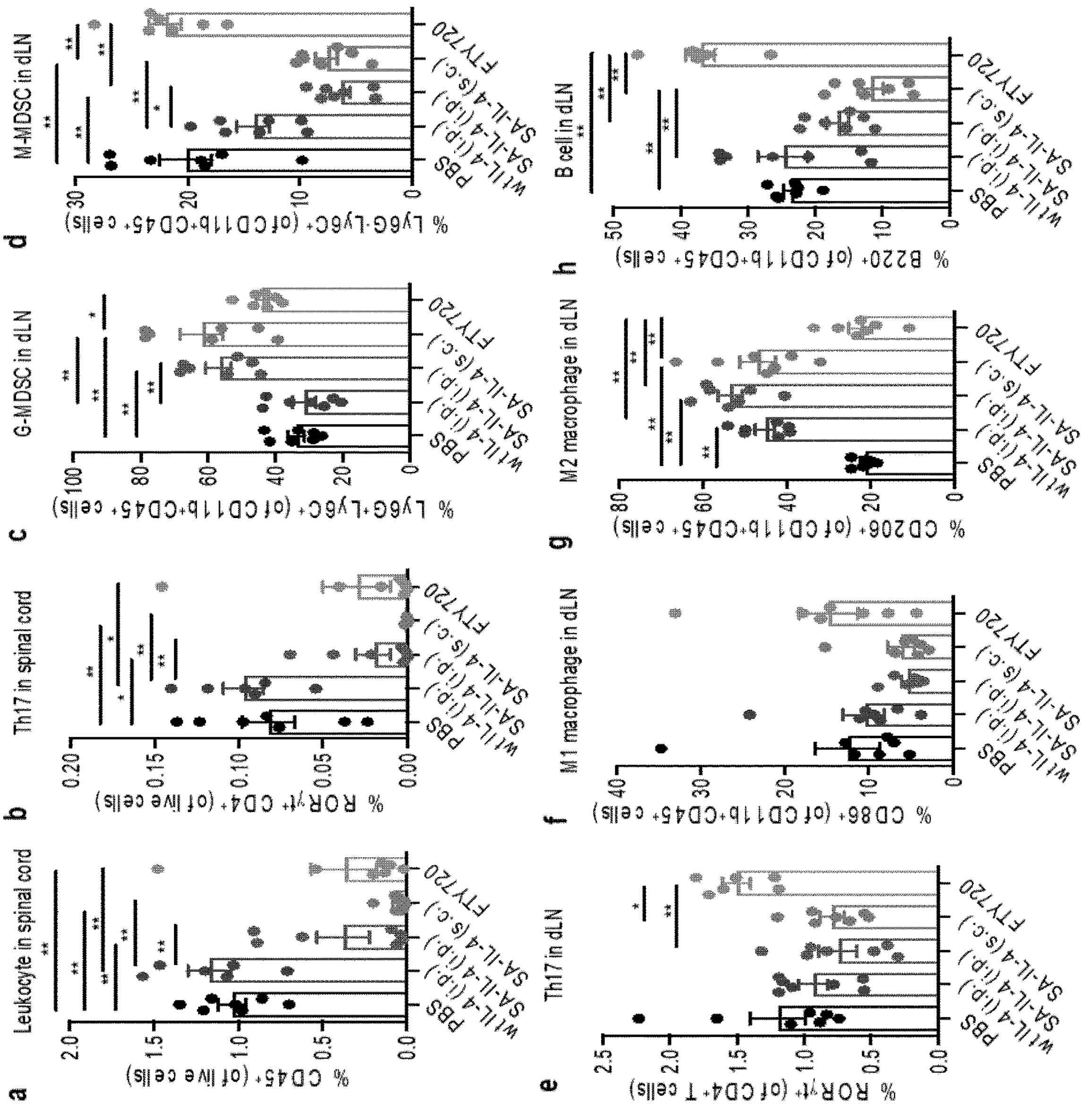
FIG. 21A-H

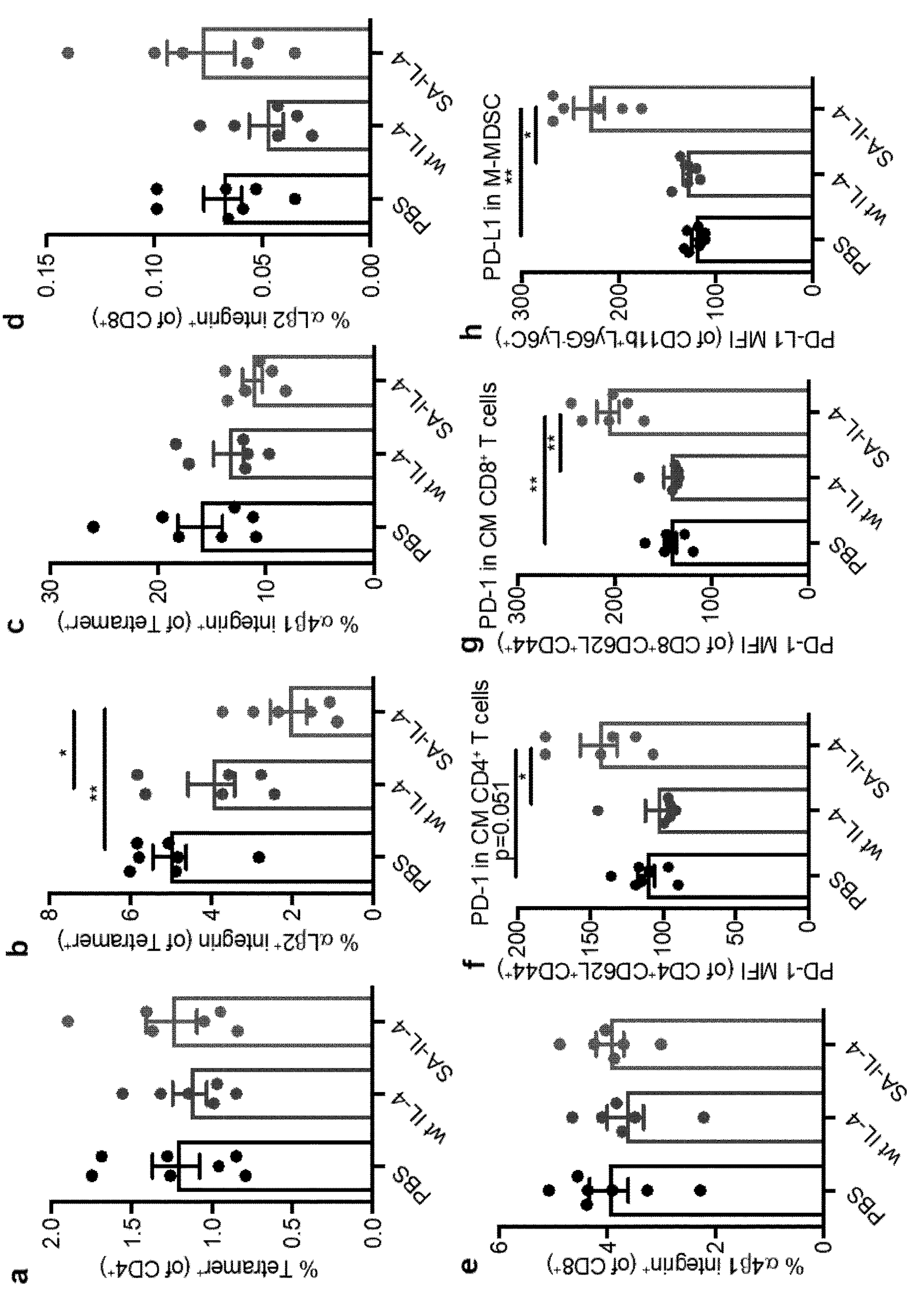
FIG. 22A-H

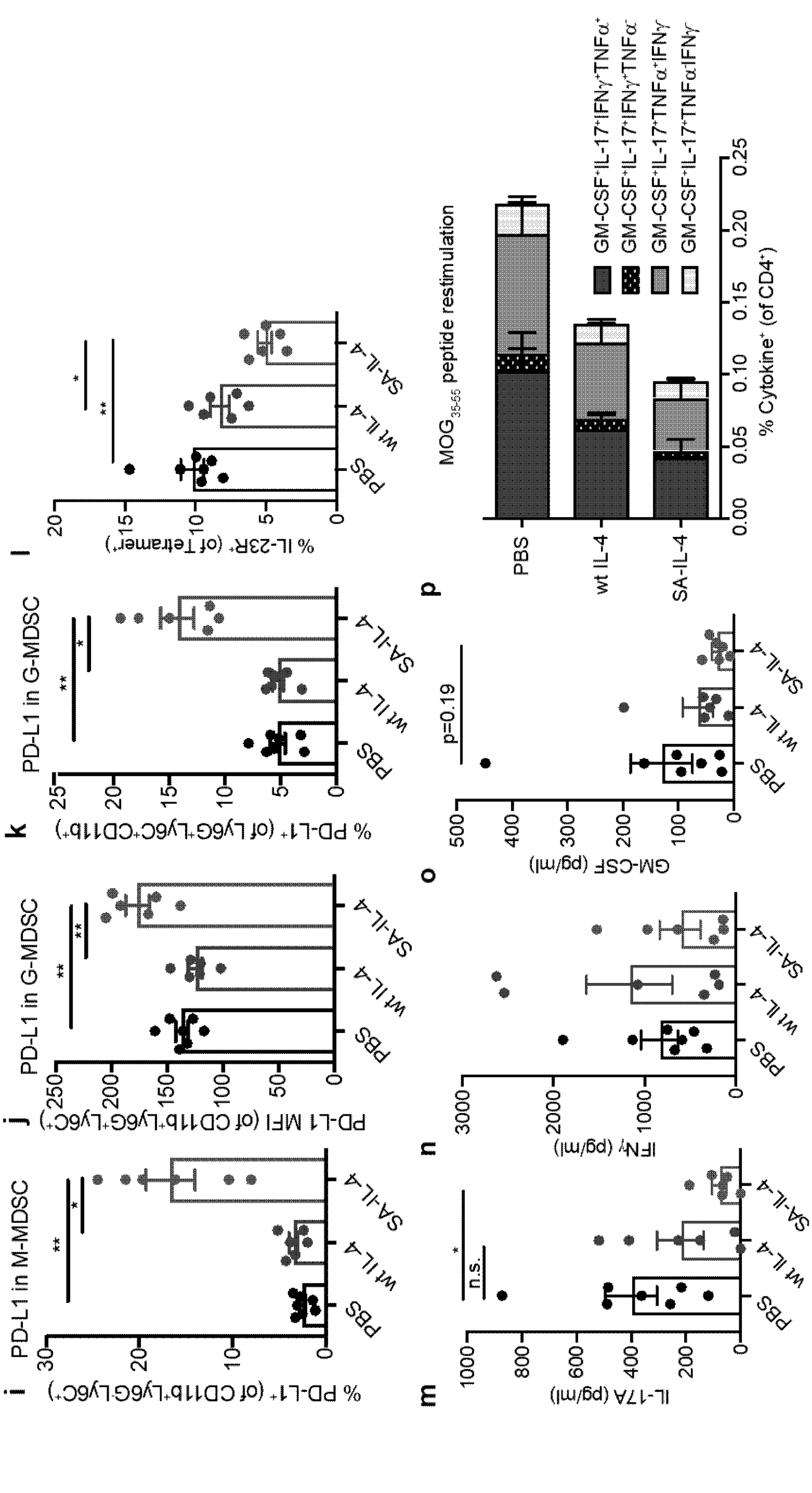
FIG. 22I-P

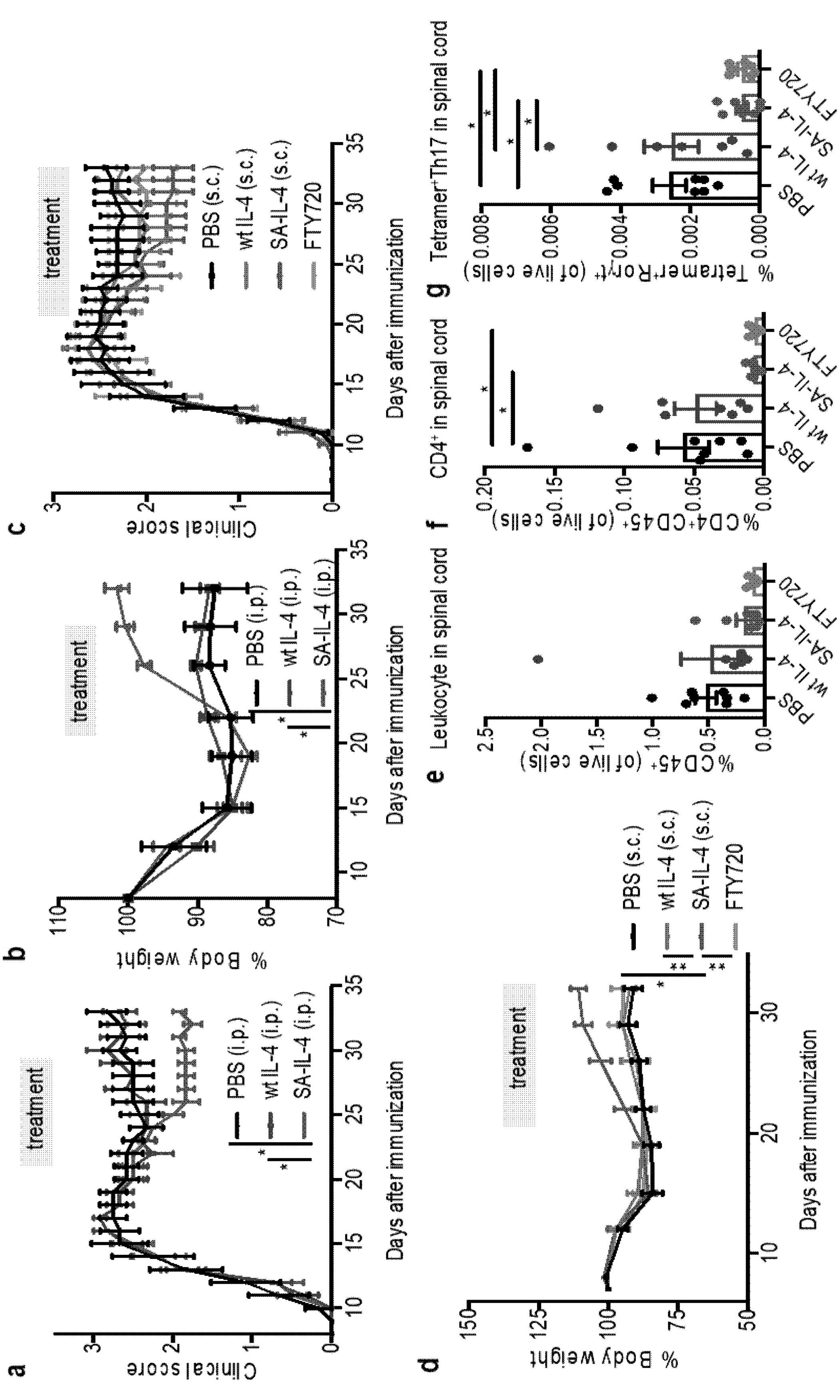
FIG. 23A-G

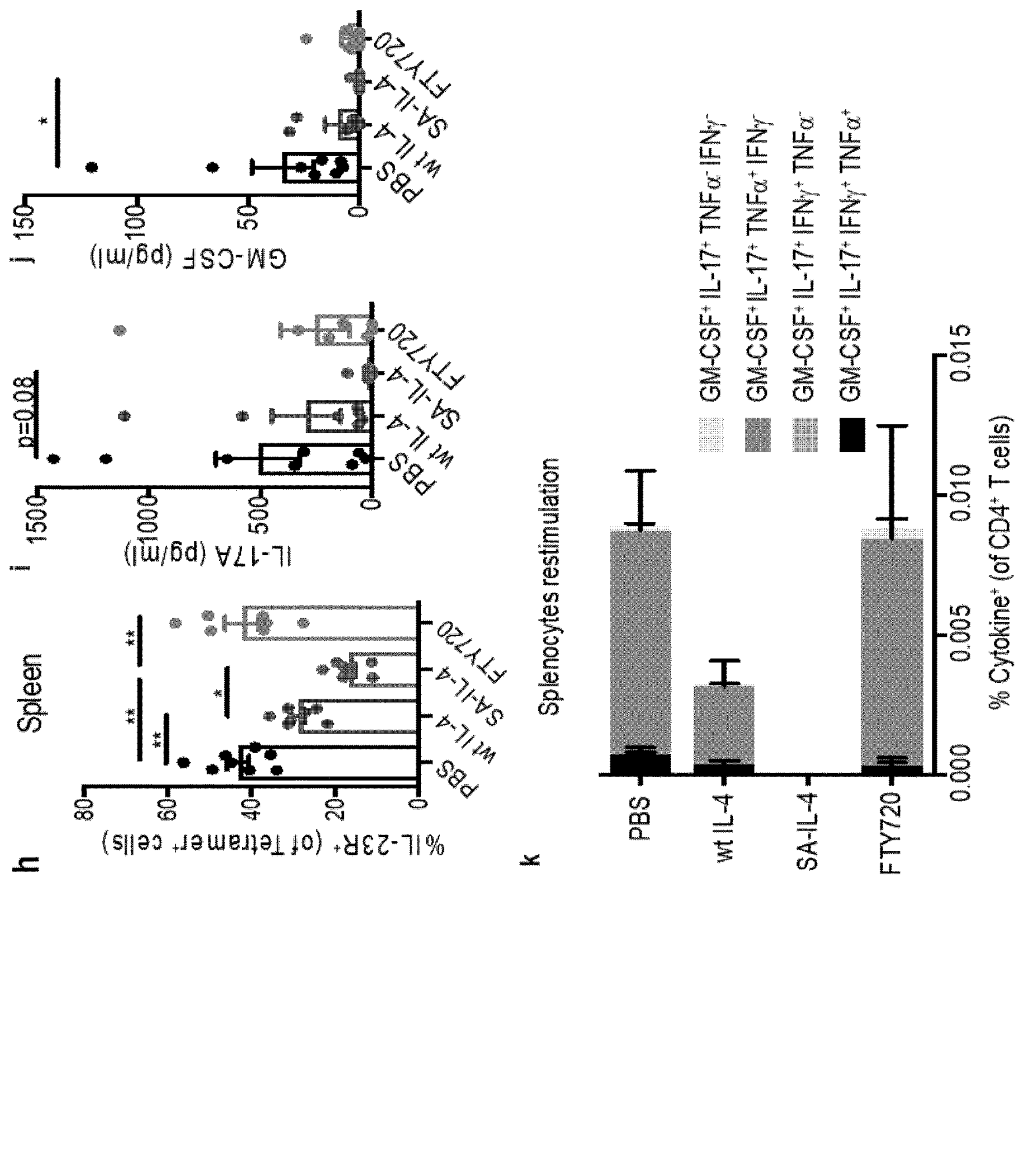
FIG. 23H-K

FIG. 25A-B

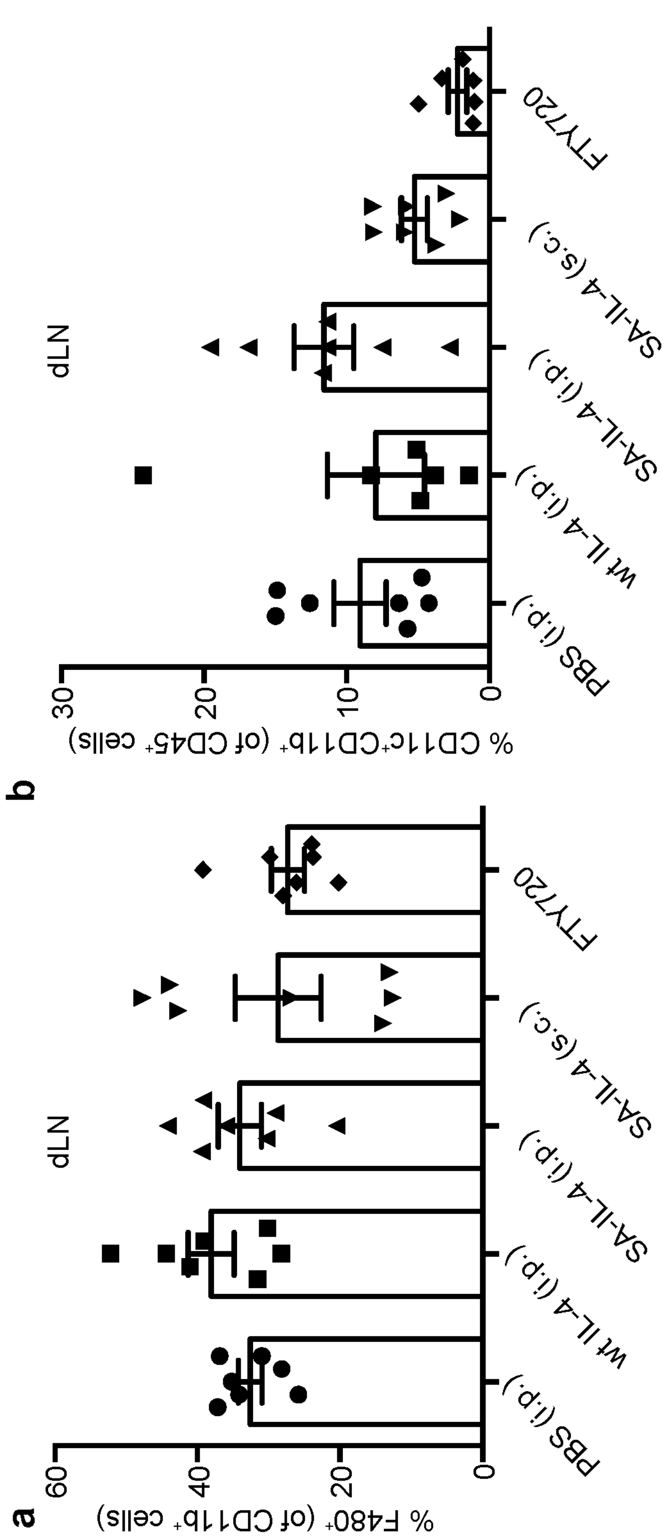
FIG. 28A-B

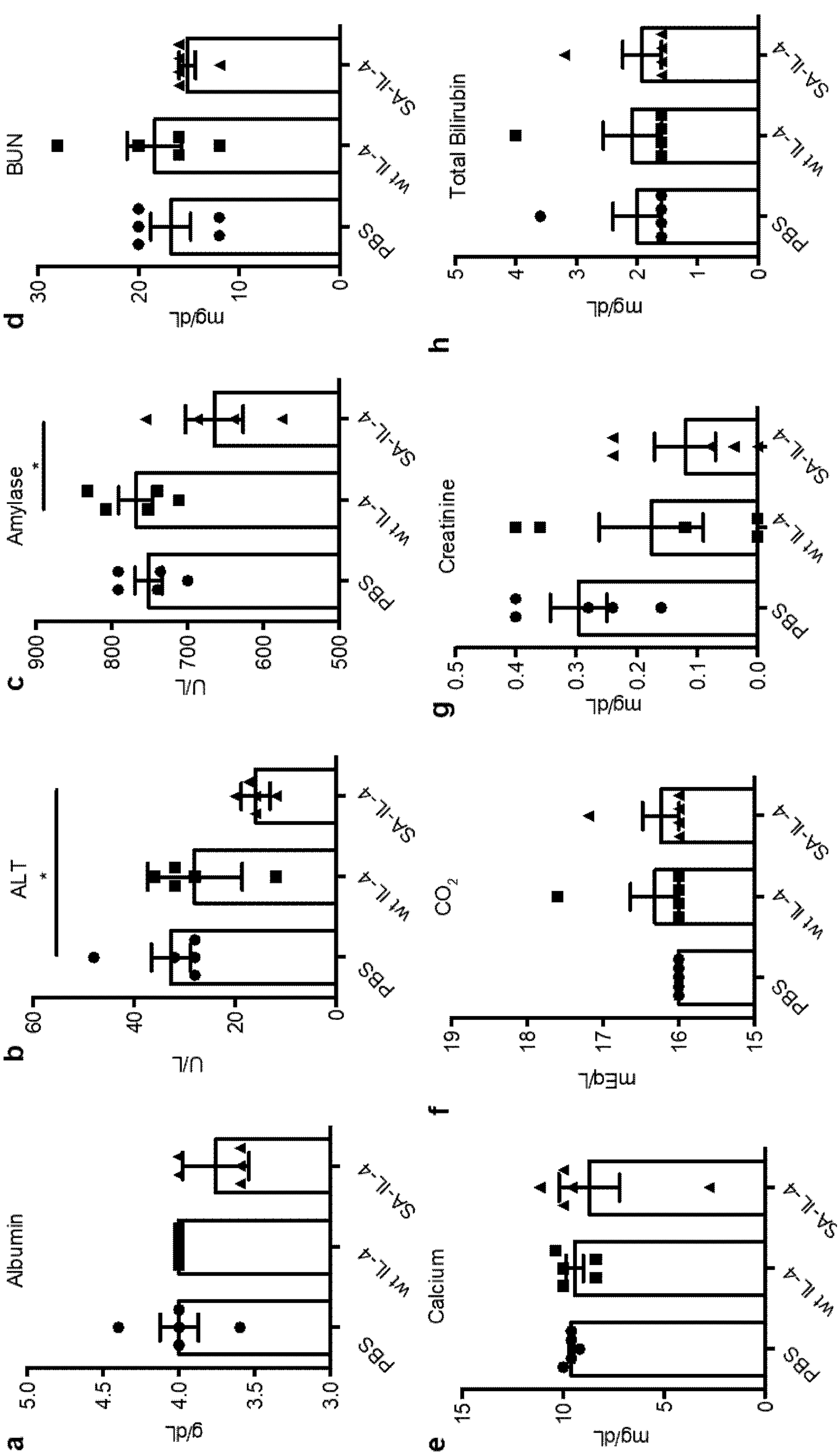
FIG. 29A-H

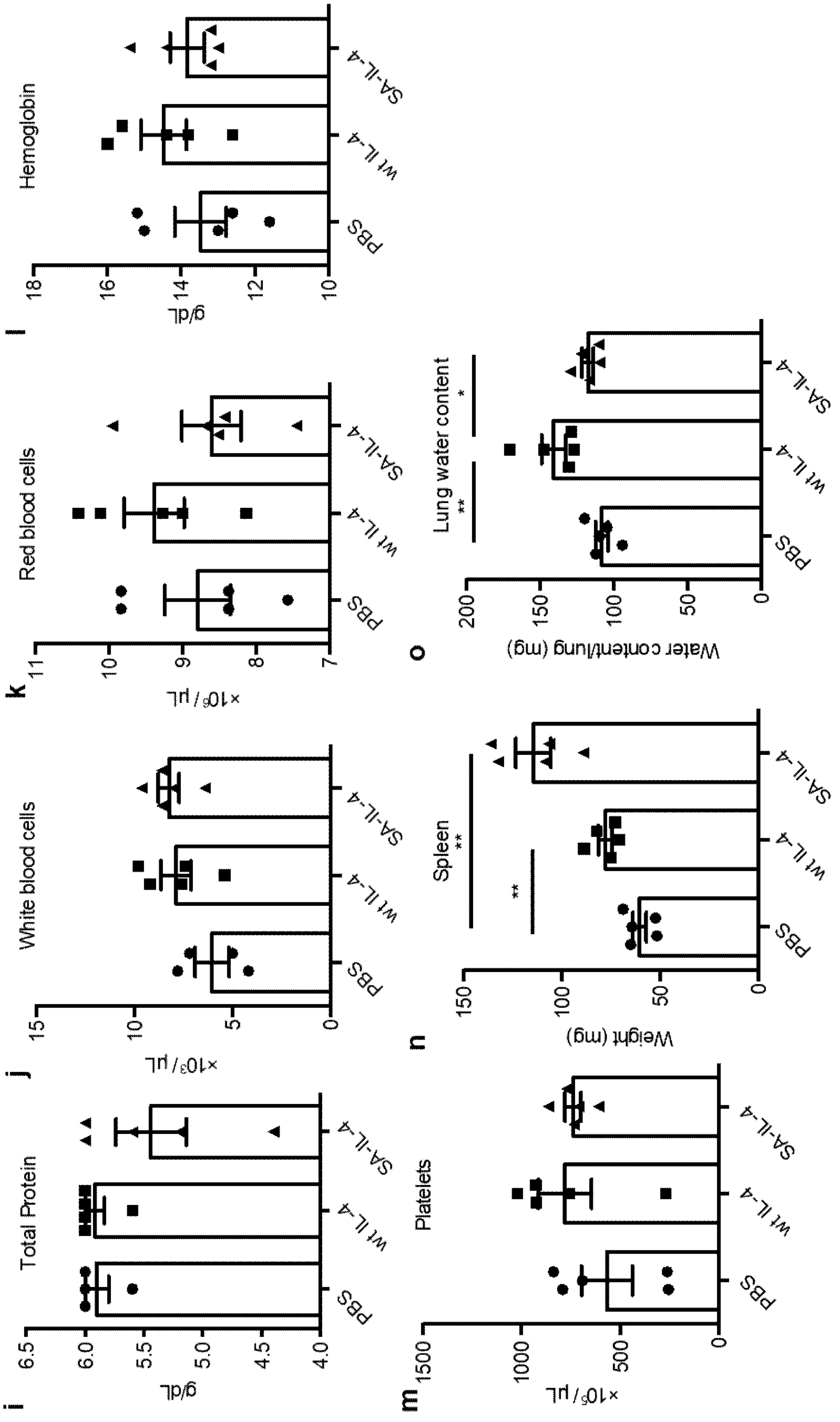
FIG. 29I-O

SEQUENCE LISTING

<160> NUMBER OF SEQ ID NOS: 69

<210> SEQ ID NO 1
<211> LENGTH: 10
<212> TYPE: PRT
<213> ORGANISM: Bos sp.

<400> SEQUENCE: 1

Leu Arg Glu Leu His Leu Asn Asn Asn Cys
1 5 10

<210> SEQ ID NO 2
<211> LENGTH: 10
<212> TYPE: PRT
<213> ORGANISM: Homo sapiens

<400> SEQUENCE: 2

Leu Arg Glu Leu His Leu Asp Asn Asn Cys
1 5 10

<210> SEQ ID NO 3
<211> LENGTH: 344
<212> TYPE: PRT
<213> ORGANISM: Homo sapiens

<400> SEQUENCE: 3

Cys Gly Pro Phe Gln Gln Arg Gly Leu Phe Asp Phe Met Leu Glu Asp
1 5 10 15

Glu Ala Ser Gly Ile Gly Pro Glu Val Pro Asp Asp Arg Asp Phe Glu
20 25 30

Pro Ser Leu Gly Pro Val Cys Pro Phe Arg Cys Gln Cys His Leu Arg
35 40 45

Val Val Gln Cys Ser Asp Leu Gly Leu Asp Lys Val Pro Lys Asp Leu
50 55 60

Pro Pro Asp Thr Thr Leu Leu Asp Leu Gln Asn Asn Lys Ile Thr Glu
65 70 75 80

Ile Lys Asp Gly Asp Phe Lys Asn Leu Lys Asn Leu His Ala Leu Ile
85 90 95

Leu Val Asn Asn Lys Ile Ser Lys Val Ser Pro Gly Ala Phe Thr Pro
100 105 110

Leu Val Lys Leu Glu Arg Leu Tyr Leu Ser Lys Asn Gln Leu Lys Glu
115 120 125

Leu Pro Glu Lys Met Pro Lys Thr Leu Gln Glu Leu Arg Ala His Glu
130 135 140

Asn Glu Ile Thr Lys Val Arg Lys Val Thr Phe Asn Gly Leu Asn Gln
145 150 155 160

Met Ile Val Ile Glu Leu Gly Thr Asn Pro Leu Lys Ser Ser Gly Ile
165 170 175

Glu Asn Gly Ala Phe Gln Gly Met Lys Lys Leu Ser Tyr Ile Arg Ile
180 185 190

Ala Asp Thr Asn Ile Thr Ser Ile Pro Gln Gly Leu Pro Pro Ser Leu
195 200 205

Thr Glu Leu His Leu Asp Gly Asn Lys Ile Ser Arg Val Asp Ala Ala

```
    210                 215                 220

Ser Leu Lys Gly Leu Asn Asn Leu Ala Lys Leu Gly Leu Ser Phe Asn
225                 230                 235                 240

Ser Ile Ser Ala Val Asp Asn Gly Ser Leu Ala Asn Thr Pro His Leu
                245                 250                 255

Arg Glu Leu His Leu Asp Asn Asn Lys Leu Thr Arg Val Pro Gly Gly
            260                 265                 270

Leu Ala Glu His Lys Tyr Ile Gln Val Val Tyr Leu His Asn Asn Asn
        275                 280                 285

Ile Ser Val Val Gly Ser Ser Asp Phe Cys Pro Pro Gly His Asn Thr
    290                 295                 300

Lys Lys Ala Ser Tyr Ser Gly Val Ser Leu Phe Ser Asn Pro Val Gln
305                 310                 315                 320

Tyr Trp Glu Ile Gln Pro Ser Thr Phe Arg Cys Val Tyr Val Arg Ser
                325                 330                 335

Ala Ile Gln Leu Gly Asn Tyr Lys
            340


<210> SEQ ID NO 4
<211> LENGTH: 222
<212> TYPE: PRT
<213> ORGANISM: Homo sapiens

<400> SEQUENCE: 4

Cys Gln Glu Pro Gly Gly Leu Val Val Pro Pro Thr Asp Ala Pro Val
1               5                   10                  15

Ser Pro Thr Thr Leu Tyr Val Glu Asp Ile Ser Glu Pro Pro Leu His
            20                  25                  30

Asp Phe Tyr Cys Ser Arg Leu Leu Asp Leu Val Phe Leu Leu Asp Gly
        35                  40                  45

Ser Ser Arg Leu Ser Glu Ala Glu Phe Glu Val Leu Lys Ala Phe Val
    50                  55                  60

Val Asp Met Met Glu Arg Leu Arg Ile Ser Gln Lys Trp Val Arg Val
65                  70                  75                  80

Ala Val Val Glu Tyr His Asp Gly Ser His Ala Tyr Ile Gly Leu Lys
                85                  90                  95

Asp Arg Lys Arg Pro Ser Glu Leu Arg Arg Ile Ala Ser Gln Val Lys
            100                 105                 110

Tyr Ala Gly Ser Gln Val Ala Ser Thr Ser Glu Val Leu Lys Tyr Thr
        115                 120                 125

Leu Phe Gln Ile Phe Ser Lys Ile Asp Arg Pro Glu Ala Ser Arg Ile
    130                 135                 140

Thr Leu Leu Leu Met Ala Ser Gln Glu Pro Gln Arg Met Ser Arg Asn
145                 150                 155                 160

Phe Val Arg Tyr Val Gln Gly Leu Lys Lys Lys Lys Val Ile Val Ile
                165                 170                 175

Pro Val Gly Ile Gly Pro His Ala Asn Leu Lys Gln Ile Arg Leu Ile
            180                 185                 190

Glu Lys Gln Ala Pro Glu Asn Lys Ala Phe Val Leu Ser Ser Val Asp
        195                 200                 205

Glu Leu Glu Gln Gln Arg Asp Glu Ile Val Ser Tyr Leu Cys
    210                 215                 220


<210> SEQ ID NO 5
<211> LENGTH: 196
```

<212> TYPE: PRT
<213> ORGANISM: Unknown
<220> FEATURE:
<223> OTHER INFORMATION: Description of Unknown:
vWF A3 sequence

<400> SEQUENCE: 5

Cys Ser Gln Pro Leu Asp Val Ile Leu Leu Leu Asp Gly Ser Ser Ser
1 5 10 15

Phe Pro Ala Ser Tyr Phe Asp Glu Met Lys Ser Phe Ala Lys Ala Phe
20 25 30

Ile Ser Lys Ala Asn Ile Gly Pro Arg Leu Thr Gln Val Ser Val Leu
35 40 45

Gln Tyr Gly Ser Ile Thr Thr Ile Asp Val Pro Trp Asn Val Val Pro
50 55 60

Glu Lys Ala His Leu Leu Ser Leu Val Asp Val Met Gln Arg Glu Gly
65 70 75 80

Gly Pro Ser Gln Ile Gly Asp Ala Leu Gly Phe Ala Val Arg Tyr Leu
85 90 95

Thr Ser Glu Met His Gly Ala Arg Pro Gly Ala Ser Lys Ala Val Val
100 105 110

Ile Leu Val Thr Asp Val Ser Val Asp Ser Val Asp Ala Ala Ala Asp
115 120 125

Ala Ala Arg Ser Asn Arg Val Thr Val Phe Pro Ile Gly Ile Gly Asp
130 135 140

Arg Tyr Asp Ala Ala Gln Leu Arg Ile Leu Ala Gly Pro Ala Gly Asp
145 150 155 160

Ser Asn Val Val Lys Leu Gln Arg Ile Glu Asp Leu Pro Thr Met Val
165 170 175

Thr Leu Gly Asn Ser Phe Leu His Lys Leu Cys Ser Gly Phe Val Arg
180 185 190

Ile Cys Thr Gly
195

<210> SEQ ID NO 6
<211> LENGTH: 2813
<212> TYPE: PRT
<213> ORGANISM: Homo sapiens

<400> SEQUENCE: 6

Met Ile Pro Ala Arg Phe Ala Gly Val Leu Leu Ala Leu Ala Leu Ile
1 5 10 15

Leu Pro Gly Thr Leu Cys Ala Glu Gly Thr Arg Gly Arg Ser Ser Thr
20 25 30

Ala Arg Cys Ser Leu Phe Gly Ser Asp Phe Val Asn Thr Phe Asp Gly
35 40 45

Ser Met Tyr Ser Phe Ala Gly Tyr Cys Ser Tyr Leu Leu Ala Gly Gly
50 55 60

Cys Gln Lys Arg Ser Phe Ser Ile Ile Gly Asp Phe Gln Asn Gly Lys
65 70 75 80

Arg Val Ser Leu Ser Val Tyr Leu Gly Glu Phe Phe Asp Ile His Leu
85 90 95

Phe Val Asn Gly Thr Val Thr Gln Gly Asp Gln Arg Val Ser Met Pro
100 105 110

Tyr Ala Ser Lys Gly Leu Tyr Leu Glu Thr Glu Ala Gly Tyr Tyr Lys
115 120 125

```
Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
```

```
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975
```

```
His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                 1005

Ser Ser  Asn Leu Gln Val Glu  Glu Asp Pro Val Asp  Phe Gly Asn
    1010                 1015                 1020

Ser Trp  Lys Val Ser Ser Gln  Cys Ala Asp Thr Arg  Lys Val Pro
    1025                 1030                 1035

Leu Asp  Ser Ser Pro Ala Thr  Cys His Asn Asn Ile  Met Lys Gln
    1040                 1045                 1050

Thr Met  Val Asp Ser Ser Cys  Arg Ile Leu Thr Ser  Asp Val Phe
    1055                 1060                 1065

Gln Asp  Cys Asn Lys Leu Val  Asp Pro Glu Pro Tyr  Leu Asp Val
    1070                 1075                 1080

Cys Ile  Tyr Asp Thr Cys Ser  Cys Glu Ser Ile Gly  Asp Cys Ala
    1085                 1090                 1095

Cys Phe  Cys Asp Thr Ile Ala  Ala Tyr Ala His Val  Cys Ala Gln
    1100                 1105                 1110

His Gly  Lys Val Val Thr Trp  Arg Thr Ala Thr Leu  Cys Pro Gln
    1115                 1120                 1125

Ser Cys  Glu Glu Arg Asn Leu  Arg Glu Asn Gly Tyr  Glu Cys Glu
    1130                 1135                 1140

Trp Arg  Tyr Asn Ser Cys Ala  Pro Ala Cys Gln Val  Thr Cys Gln
    1145                 1150                 1155

His Pro  Glu Pro Leu Ala Cys  Pro Val Gln Cys Val  Glu Gly Cys
    1160                 1165                 1170

His Ala  His Cys Pro Pro Gly  Lys Ile Leu Asp Glu  Leu Leu Gln
    1175                 1180                 1185

Thr Cys  Val Asp Pro Glu Asp  Cys Pro Val Cys Glu  Val Ala Gly
    1190                 1195                 1200

Arg Arg  Phe Ala Ser Gly Lys  Lys Val Thr Leu Asn  Pro Ser Asp
    1205                 1210                 1215

Pro Glu  His Cys Gln Ile Cys  His Cys Asp Val Val  Asn Leu Thr
    1220                 1225                 1230

Cys Glu  Ala Cys Gln Glu Pro  Gly Gly Leu Val Val  Pro Pro Thr
    1235                 1240                 1245

Asp Ala  Pro Val Ser Pro Thr  Thr Leu Tyr Val Glu  Asp Ile Ser
    1250                 1255                 1260

Glu Pro  Pro Leu His Asp Phe  Tyr Cys Ser Arg Leu  Leu Asp Leu
    1265                 1270                 1275

Val Phe  Leu Leu Asp Gly Ser  Ser Arg Leu Ser Glu  Ala Glu Phe
    1280                 1285                 1290

Glu Val  Leu Lys Ala Phe Val  Val Asp Met Met Glu  Arg Leu Arg
    1295                 1300                 1305

Ile Ser  Gln Lys Trp Val Arg  Val Ala Val Val Glu  Tyr His Asp
    1310                 1315                 1320

Gly Ser  His Ala Tyr Ile Gly  Leu Lys Asp Arg Lys  Arg Pro Ser
    1325                 1330                 1335

Glu Leu  Arg Arg Ile Ala Ser  Gln Val Lys Tyr Ala  Gly Ser Gln
    1340                 1345                 1350

Val Ala  Ser Thr Ser Glu Val  Leu Lys Tyr Thr Leu  Phe Gln Ile
    1355                 1360                 1365
```

```
Phe Ser  Lys Ile Asp Arg Pro  Glu Ala Ser Arg Ile  Thr Leu Leu
    1370                 1375                 1380

Leu Met  Ala Ser Gln Glu Pro  Gln Arg Met Ser Arg  Asn Phe Val
    1385                 1390                 1395

Arg Tyr  Val Gln Gly Leu Lys  Lys Lys Lys Val Ile  Val Ile Pro
    1400                 1405                 1410

Val Gly  Ile Gly Pro His Ala  Asn Leu Lys Gln Ile  Arg Leu Ile
    1415                 1420                 1425

Glu Lys  Gln Ala Pro Glu Asn  Lys Ala Phe Val Leu  Ser Ser Val
    1430                 1435                 1440

Asp Glu  Leu Glu Gln Gln Arg  Asp Glu Ile Val Ser  Tyr Leu Cys
    1445                 1450                 1455

Asp Leu  Ala Pro Glu Ala Pro  Pro Pro Thr Leu Pro  Pro Asp Met
    1460                 1465                 1470

Ala Gln  Val Thr Val Gly Pro  Gly Leu Leu Gly Val  Ser Thr Leu
    1475                 1480                 1485

Gly Pro  Lys Arg Asn Ser Met  Val Leu Asp Val Ala  Phe Val Leu
    1490                 1495                 1500

Glu Gly  Ser Asp Lys Ile Gly  Glu Ala Asp Phe Asn  Arg Ser Lys
    1505                 1510                 1515

Glu Phe  Met Glu Glu Val Ile  Gln Arg Met Asp Val  Gly Gln Asp
    1520                 1525                 1530

Ser Ile  His Val Thr Val Leu  Gln Tyr Ser Tyr Met  Val Thr Val
    1535                 1540                 1545

Glu Tyr  Pro Phe Ser Glu Ala  Gln Ser Lys Gly Asp  Ile Leu Gln
    1550                 1555                 1560

Arg Val  Arg Glu Ile Arg Tyr  Gln Gly Gly Asn Arg  Thr Asn Thr
    1565                 1570                 1575

Gly Leu  Ala Leu Arg Tyr Leu  Ser Asp His Ser Phe  Leu Val Ser
    1580                 1585                 1590

Gln Gly  Asp Arg Glu Gln Ala  Pro Asn Leu Val Tyr  Met Val Thr
    1595                 1600                 1605

Gly Asn  Pro Ala Ser Asp Glu  Ile Lys Arg Leu Pro  Gly Asp Ile
    1610                 1615                 1620

Gln Val  Val Pro Ile Gly Val  Gly Pro Asn Ala Asn  Val Gln Glu
    1625                 1630                 1635

Leu Glu  Arg Ile Gly Trp Pro  Asn Ala Pro Ile Leu  Ile Gln Asp
    1640                 1645                 1650

Phe Glu  Thr Leu Pro Arg Glu  Ala Pro Asp Leu Val  Leu Gln Arg
    1655                 1660                 1665

Cys Cys  Ser Gly Glu Gly Leu  Gln Ile Pro Thr Leu  Ser Pro Ala
    1670                 1675                 1680

Pro Asp  Cys Ser Gln Pro Leu  Asp Val Ile Leu Leu  Leu Asp Gly
    1685                 1690                 1695

Ser Ser  Ser Phe Pro Ala Ser  Tyr Phe Asp Glu Met  Lys Ser Phe
    1700                 1705                 1710

Ala Lys  Ala Phe Ile Ser Lys  Ala Asn Ile Gly Pro  Arg Leu Thr
    1715                 1720                 1725

Gln Val  Ser Val Leu Gln Tyr  Gly Ser Ile Thr Thr  Ile Asp Val
    1730                 1735                 1740

Pro Trp  Asn Val Val Pro Glu  Lys Ala His Leu Leu  Ser Leu Val
    1745                 1750                 1755

Asp Val  Met Gln Arg Glu Gly  Gly Pro Ser Gln Ile  Gly Asp Ala
```

```
    1760                1765                1770

Leu Gly  Phe Ala Val Arg Tyr  Leu Thr Ser Glu Met  His Gly Ala
    1775                1780                1785

Arg Pro  Gly Ala Ser Lys Ala  Val Val Ile Leu Val  Thr Asp Val
    1790                1795                1800

Ser Val  Asp Ser Val Asp Ala  Ala Ala Asp Ala Ala  Arg Ser Asn
    1805                1810                1815

Arg Val  Thr Val Phe Pro Ile  Gly Ile Gly Asp Arg  Tyr Asp Ala
    1820                1825                1830

Ala Gln  Leu Arg Ile Leu Ala  Gly Pro Ala Gly Asp  Ser Asn Val
    1835                1840                1845

Val Lys  Leu Gln Arg Ile Glu  Asp Leu Pro Thr Met  Val Thr Leu
    1850                1855                1860

Gly Asn  Ser Phe Leu His Lys  Leu Cys Ser Gly Phe  Val Arg Ile
    1865                1870                1875

Cys Met  Asp Glu Asp Gly Asn  Glu Lys Arg Pro Gly  Asp Val Trp
    1880                1885                1890

Thr Leu  Pro Asp Gln Cys His  Thr Val Thr Cys Gln  Pro Asp Gly
    1895                1900                1905

Gln Thr  Leu Leu Lys Ser His  Arg Val Asn Cys Asp  Arg Gly Leu
    1910                1915                1920

Arg Pro  Ser Cys Pro Asn Ser  Gln Ser Pro Val Lys  Val Glu Glu
    1925                1930                1935

Thr Cys  Gly Cys Arg Trp Thr  Cys Pro Cys Val Cys  Thr Gly Ser
    1940                1945                1950

Ser Thr  Arg His Ile Val Thr  Phe Asp Gly Gln Asn  Phe Lys Leu
    1955                1960                1965

Thr Gly  Ser Cys Ser Tyr Val  Leu Phe Gln Asn Lys  Glu Gln Asp
    1970                1975                1980

Leu Glu  Val Ile Leu His Asn  Gly Ala Cys Ser Pro  Gly Ala Arg
    1985                1990                1995

Gln Gly  Cys Met Lys Ser Ile  Glu Val Lys His Ser  Ala Leu Ser
    2000                2005                2010

Val Glu  Leu His Ser Asp Met  Glu Val Thr Val Asn  Gly Arg Leu
    2015                2020                2025

Val Ser  Val Pro Tyr Val Gly  Gly Asn Met Glu Val  Asn Val Tyr
    2030                2035                2040

Gly Ala  Ile Met His Glu Val  Arg Phe Asn His Leu  Gly His Ile
    2045                2050                2055

Phe Thr  Phe Thr Pro Gln Asn  Asn Glu Phe Gln Leu  Gln Leu Ser
    2060                2065                2070

Pro Lys  Thr Phe Ala Ser Lys  Thr Tyr Gly Leu Cys  Gly Ile Cys
    2075                2080                2085

Asp Glu  Asn Gly Ala Asn Asp  Phe Met Leu Arg Asp  Gly Thr Val
    2090                2095                2100

Thr Thr  Asp Trp Lys Thr Leu  Val Gln Glu Trp Thr  Val Gln Arg
    2105                2110                2115

Pro Gly  Gln Thr Cys Gln Pro  Ile Leu Glu Glu Gln  Cys Leu Val
    2120                2125                2130

Pro Asp  Ser Ser His Cys Gln  Val Leu Leu Leu Pro  Leu Phe Ala
    2135                2140                2145

Glu Cys  His Lys Val Leu Ala  Pro Ala Thr Phe Tyr  Ala Ile Cys
    2150                2155                2160
```

```
Gln Gln  Asp Ser Cys His Gln  Glu Gln Val Cys Glu  Val Ile Ala
    2165                 2170                 2175

Ser Tyr  Ala His Leu Cys Arg  Thr Asn Gly Val Cys  Val Asp Trp
    2180                 2185                 2190

Arg Thr  Pro Asp Phe Cys Ala  Met Ser Cys Pro Pro  Ser Leu Val
    2195                 2200                 2205

Tyr Asn  His Cys Glu His Gly  Cys Pro Arg His Cys  Asp Gly Asn
    2210                 2215                 2220

Val Ser  Ser Cys Gly Asp His  Pro Ser Glu Gly Cys  Phe Cys Pro
    2225                 2230                 2235

Pro Asp  Lys Val Met Leu Glu  Gly Ser Cys Val Pro  Glu Glu Ala
    2240                 2245                 2250

Cys Thr  Gln Cys Ile Gly Glu  Asp Gly Val Gln His  Gln Phe Leu
    2255                 2260                 2265

Glu Ala  Trp Val Pro Asp His  Gln Pro Cys Gln Ile  Cys Thr Cys
    2270                 2275                 2280

Leu Ser  Gly Arg Lys Val Asn  Cys Thr Thr Gln Pro  Cys Pro Thr
    2285                 2290                 2295

Ala Lys  Ala Pro Thr Cys Gly  Leu Cys Glu Val Ala  Arg Leu Arg
    2300                 2305                 2310

Gln Asn  Ala Asp Gln Cys Cys  Pro Glu Tyr Glu Cys  Val Cys Asp
    2315                 2320                 2325

Pro Val  Ser Cys Asp Leu Pro  Pro Val Pro His Cys  Glu Arg Gly
    2330                 2335                 2340

Leu Gln  Pro Thr Leu Thr Asn  Pro Gly Glu Cys Arg  Pro Asn Phe
    2345                 2350                 2355

Thr Cys  Ala Cys Arg Lys Glu  Glu Cys Lys Arg Val  Ser Pro Pro
    2360                 2365                 2370

Ser Cys  Pro Pro His Arg Leu  Pro Thr Leu Arg Lys  Thr Gln Cys
    2375                 2380                 2385

Cys Asp  Glu Tyr Glu Cys Ala  Cys Asn Cys Val Asn  Ser Thr Val
    2390                 2395                 2400

Ser Cys  Pro Leu Gly Tyr Leu  Ala Ser Thr Ala Thr  Asn Asp Cys
    2405                 2410                 2415

Gly Cys  Thr Thr Thr Thr Cys  Leu Pro Asp Lys Val  Cys Val His
    2420                 2425                 2430

Arg Ser  Thr Ile Tyr Pro Val  Gly Gln Phe Trp Glu  Glu Gly Cys
    2435                 2440                 2445

Asp Val  Cys Thr Cys Thr Asp  Met Glu Asp Ala Val  Met Gly Leu
    2450                 2455                 2460

Arg Val  Ala Gln Cys Ser Gln  Lys Pro Cys Glu Asp  Ser Cys Arg
    2465                 2470                 2475

Ser Gly  Phe Thr Tyr Val Leu  His Glu Gly Glu Cys  Cys Gly Arg
    2480                 2485                 2490

Cys Leu  Pro Ser Ala Cys Glu  Val Val Thr Gly Ser  Pro Arg Gly
    2495                 2500                 2505

Asp Ser  Gln Ser Ser Trp Lys  Ser Val Gly Ser Gln  Trp Ala Ser
    2510                 2515                 2520

Pro Glu  Asn Pro Cys Leu Ile  Asn Glu Cys Val Arg  Val Lys Glu
    2525                 2530                 2535

Glu Val  Phe Ile Gln Gln Arg  Asn Val Ser Cys Pro  Gln Leu Glu
    2540                 2545                 2550
```

```
Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810


<210> SEQ ID NO 7
<211> LENGTH: 205
<212> TYPE: PRT
<213> ORGANISM: Homo sapiens

<400> SEQUENCE: 7

Cys Ser Gly Glu Gly Leu Gln Ile Pro Thr Leu Ser Pro Ala Pro Asp
1               5                   10                  15

Cys Ser Gln Pro Leu Asp Val Ile Leu Leu Leu Asp Gly Ser Ser Ser
            20                  25                  30

Phe Pro Ala Ser Tyr Phe Asp Glu Met Lys Ser Phe Ala Lys Ala Phe
        35                  40                  45

Ile Ser Lys Ala Asn Ile Gly Pro Arg Leu Thr Gln Val Ser Val Leu
    50                  55                  60

Gln Tyr Gly Ser Ile Thr Thr Ile Asp Val Pro Trp Asn Val Val Pro
65                  70                  75                  80

Glu Lys Ala His Leu Leu Ser Leu Val Asp Val Met Gln Arg Glu Gly
                85                  90                  95
```

```
Gly Pro Ser Gln Ile Gly Asp Ala Leu Gly Phe Ala Val Arg Tyr Leu
            100                 105                 110

Thr Ser Glu Met His Gly Ala Arg Pro Gly Ala Ser Lys Ala Val Val
        115                 120                 125

Ile Leu Val Thr Asp Val Ser Val Asp Ser Val Asp Ala Ala Ala Asp
    130                 135                 140

Ala Ala Arg Ser Asn Arg Val Thr Val Phe Pro Ile Gly Ile Gly Asp
145                 150                 155                 160

Arg Tyr Asp Ala Ala Gln Leu Arg Ile Leu Ala Gly Pro Ala Gly Asp
                165                 170                 175

Ser Asn Val Val Lys Leu Gln Arg Ile Glu Asp Leu Pro Thr Met Val
            180                 185                 190

Thr Leu Gly Asn Ser Phe Leu His Lys Leu Cys Ser Gly
        195                 200                 205


<210> SEQ ID NO 8
<211> LENGTH: 170
<212> TYPE: PRT
<213> ORGANISM: Unknown
<220> FEATURE:
<223> OTHER INFORMATION: Description of Unknown:
      PlGF-2 sequence

<400> SEQUENCE: 8

Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Val Pro Phe Gln Glu Val Trp Gly
        35                  40                  45

Arg Ser Tyr Cys Arg Ala Leu Glu Arg Leu Val Asp Val Val Ser Glu
    50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg Pro Leu Arg Glu Lys Met Lys Pro Glu Arg Arg Arg Pro
    130                 135                 140

Lys Gly Arg Gly Lys Arg Arg Arg Glu Lys Gln Arg Pro Thr Asp Cys
145                 150                 155                 160

His Leu Cys Gly Asp Ala Val Pro Arg Arg
                165                 170


<210> SEQ ID NO 9
<211> LENGTH: 30
<212> TYPE: PRT
<213> ORGANISM: Unknown
<220> FEATURE:
<223> OTHER INFORMATION: Description of Unknown:
      PlGF-2 sequence

<400> SEQUENCE: 9

Arg Arg Arg Pro Lys Gly Arg Gly Lys Arg Arg Arg Glu Lys Gln Arg
1               5                   10                  15
```

```
Pro Thr Asp Cys His Leu Cys Gly Asp Ala Val Pro Arg Arg
            20                  25                  30


<210> SEQ ID NO 10
<211> LENGTH: 22
<212> TYPE: PRT
<213> ORGANISM: Unknown
<220> FEATURE:
<223> OTHER INFORMATION: Description of Unknown:
      PlGF-2 sequence

<400> SEQUENCE: 10

Arg Arg Arg Pro Lys Gly Arg Gly Lys Arg Arg Arg Glu Lys Gln Arg
1               5                   10                  15

Pro Thr Asp Cys His Leu
            20


<210> SEQ ID NO 11
<211> LENGTH: 18
<212> TYPE: PRT
<213> ORGANISM: Unknown
<220> FEATURE:
<223> OTHER INFORMATION: Description of Unknown:
      PlGF-2 sequence

<400> SEQUENCE: 11

Arg Arg Pro Lys Gly Arg Gly Lys Arg Arg Arg Glu Lys Gln Arg Pro
1               5                   10                  15

Thr Asp


<210> SEQ ID NO 12
<211> LENGTH: 15
<212> TYPE: PRT
<213> ORGANISM: Unknown
<220> FEATURE:
<223> OTHER INFORMATION: Description of Unknown:
      PlGF-2 sequence

<400> SEQUENCE: 12

Arg Arg Arg Pro Lys Gly Arg Gly Lys Arg Arg Arg Glu Lys Gln
1               5                   10                  15


<210> SEQ ID NO 13
<211> LENGTH: 8
<212> TYPE: PRT
<213> ORGANISM: Unknown
<220> FEATURE:
<223> OTHER INFORMATION: Description of Unknown:
      PlGF-2 sequence

<400> SEQUENCE: 13

Gly Lys Arg Arg Arg Glu Lys Gln
1               5


<210> SEQ ID NO 14
<211> LENGTH: 8
<212> TYPE: PRT
<213> ORGANISM: Unknown
<220> FEATURE:
<223> OTHER INFORMATION: Description of Unknown:
      PlGF-2 sequence

<400> SEQUENCE: 14

Arg Arg Arg Pro Lys Gly Arg Gly
1               5
```

<210> SEQ ID NO 15
<211> LENGTH: 21
<212> TYPE: PRT
<213> ORGANISM: Unknown
<220> FEATURE:
<223> OTHER INFORMATION: Description of Unknown:
PlGF-2 sequence

<400> SEQUENCE: 15

```
Arg Arg Lys Thr Lys Gly Lys Arg Lys Arg Ser Arg Asn Ser Gln Thr
1               5                   10                  15

Glu Glu Pro His Pro
            20
```

<210> SEQ ID NO 16
<211> LENGTH: 98
<212> TYPE: PRT
<213> ORGANISM: Unknown
<220> FEATURE:
<223> OTHER INFORMATION: Description of Unknown:
CXCL-12gamma sequence

<400> SEQUENCE: 16

```
Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Gly Arg Arg Glu Glu Lys Val Gly Lys Lys Glu Lys
65                  70                  75                  80

Ile Gly Lys Lys Lys Arg Gln Lys Lys Arg Lys Ala Ala Gln Lys Arg
                85                  90                  95

Lys Asn
```

<210> SEQ ID NO 17
<211> LENGTH: 30
<212> TYPE: PRT
<213> ORGANISM: Unknown
<220> FEATURE:
<223> OTHER INFORMATION: Description of Unknown:
CXCL-12gamma sequence

<400> SEQUENCE: 17

```
Gly Arg Arg Glu Glu Lys Val Gly Lys Lys Glu Lys Ile Gly Lys Lys
1               5                   10                  15

Lys Arg Gln Lys Lys Arg Lys Ala Ala Gln Lys Arg Lys Asn
            20                  25                  30
```

<210> SEQ ID NO 18
<211> LENGTH: 152
<212> TYPE: PRT
<213> ORGANISM: Homo sapiens

<400> SEQUENCE: 18

```
Arg Pro Ser Gly Arg Lys Ser Ser Lys Met Gln Ala Phe Arg Ile Trp
1               5                   10                  15

Asp Val Asn Gln Lys Thr Phe Tyr Leu Arg Asn Asn Gln Leu Val Ala
            20                  25                  30
```

Gly Tyr Leu Gln Gly Pro Asn Val Asn Leu Glu Glu Lys Ile Asp Val
        35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp Glu
145                 150

<210> SEQ ID NO 19
<211> LENGTH: 152
<212> TYPE: PRT
<213> ORGANISM: Mus sp.

<400> SEQUENCE: 19

Arg Pro Ser Gly Lys Arg Pro Cys Lys Met Gln Ala Phe Arg Ile Trp
1               5                   10                  15

Asp Thr Asn Gln Lys Thr Phe Tyr Leu Arg Asn Asn Gln Leu Ile Ala
            20                  25                  30

Gly Tyr Leu Gln Gly Pro Asn Ile Lys Leu Glu Glu Lys Ile Asp Met
        35                  40                  45

Val Pro Ile Asp Leu His Ser Val Phe Leu Gly Ile His Gly Gly Lys
    50                  55                  60

Leu Cys Leu Ser Cys Ala Lys Ser Gly Asp Asp Ile Lys Leu Gln Leu
65                  70                  75                  80

Glu Glu Val Asn Ile Thr Asp Leu Ser Lys Asn Lys Glu Glu Asp Lys
                85                  90                  95

Arg Phe Thr Phe Ile Arg Ser Glu Lys Gly Pro Thr Thr Ser Phe Glu
            100                 105                 110

Ser Ala Ala Cys Pro Gly Trp Phe Leu Cys Thr Thr Leu Glu Ala Asp
        115                 120                 125

Arg Pro Val Ser Leu Thr Asn Thr Pro Glu Glu Pro Leu Ile Val Thr
    130                 135                 140

Lys Phe Tyr Phe Gln Glu Asp Gln
145                 150

<210> SEQ ID NO 20
<211> LENGTH: 129
<212> TYPE: PRT
<213> ORGANISM: Homo sapiens

<400> SEQUENCE: 20

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 21
<211> LENGTH: 120
<212> TYPE: PRT
<213> ORGANISM: Mus sp.

<400> SEQUENCE: 21

His Ile His Gly Cys Asp Lys Asn His Leu Arg Glu Ile Ile Gly Ile
1               5                   10                  15

Leu Asn Glu Val Thr Gly Glu Gly Thr Pro Cys Thr Glu Met Asp Val
            20                  25                  30

Pro Asn Val Leu Thr Ala Thr Lys Asn Thr Thr Glu Ser Glu Leu Val
        35                  40                  45

Cys Arg Ala Ser Lys Val Leu Arg Ile Phe Tyr Leu Lys His Gly Lys
    50                  55                  60

Thr Pro Cys Leu Lys Lys Asn Ser Ser Val Leu Met Glu Leu Gln Arg
65                  70                  75                  80

Leu Phe Arg Ala Phe Arg Cys Leu Asp Ser Ser Ile Ser Cys Thr Met
                85                  90                  95

Asn Glu Ser Lys Ser Thr Ser Leu Lys Asp Phe Leu Glu Ser Leu Lys
            100                 105                 110

Ser Ile Met Gln Met Asp Tyr Ser
        115                 120

<210> SEQ ID NO 22
<211> LENGTH: 115
<212> TYPE: PRT
<213> ORGANISM: Homo sapiens

<400> SEQUENCE: 22

Ile Pro Thr Glu Ile Pro Thr Ser Ala Leu Val Lys Glu Thr Leu Ala
1               5                   10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
65                  70                  75                  80

Gly Gln Lys Lys Lys Cys Gly Glu Glu Arg Arg Arg Val Asn Gln Phe
                85                  90                  95

Leu Asp Tyr Leu Gln Glu Phe Leu Gly Val Met Asn Thr Glu Trp Ile
            100                 105                 110

Ile Glu Ser

115

<210> SEQ ID NO 23
<211> LENGTH: 112
<212> TYPE: PRT
<213> ORGANISM: Mus sp.

<400> SEQUENCE: 23

Glu Ile Pro Met Ser Thr Val Val Lys Glu Thr Leu Thr Gln Leu Ser
1 5 10 15

Ala His Arg Ala Leu Leu Thr Ser Asn Glu Thr Met Arg Leu Pro Val
20 25 30

Pro Thr His Lys Asn His Gln Leu Cys Ile Gly Glu Ile Phe Gln Gly
35 40 45

Leu Asp Ile Leu Lys Asn Gln Thr Val Arg Gly Gly Thr Val Glu Met
50 55 60

Leu Phe Gln Asn Leu Ser Leu Ile Lys Lys Tyr Ile Asp Arg Gln Lys
65 70 75 80

Glu Lys Cys Gly Glu Glu Arg Arg Arg Thr Arg Gln Phe Leu Asp Tyr
85 90 95

Leu Gln Glu Phe Leu Gly Val Met Ser Thr Glu Trp Ala Met Glu Gly
100 105 110

<210> SEQ ID NO 24
<211> LENGTH: 160
<212> TYPE: PRT
<213> ORGANISM: Homo sapiens

<400> SEQUENCE: 24

Ser Pro Gly Gln Gly Thr Gln Ser Glu Asn Ser Cys Thr His Phe Pro
1 5 10 15

Gly Asn Leu Pro Asn Met Leu Arg Asp Leu Arg Asp Ala Phe Ser Arg
20 25 30

Val Lys Thr Phe Phe Gln Met Lys Asp Gln Leu Asp Asn Leu Leu Leu
35 40 45

Lys Glu Ser Leu Leu Glu Asp Phe Lys Gly Tyr Leu Gly Cys Gln Ala
50 55 60

Leu Ser Glu Met Ile Gln Phe Tyr Leu Glu Glu Val Met Pro Gln Ala
65 70 75 80

Glu Asn Gln Asp Pro Asp Ile Lys Ala His Val Asn Ser Leu Gly Glu
85 90 95

Asn Leu Lys Thr Leu Arg Leu Arg Leu Arg Arg Cys His Arg Phe Leu
100 105 110

Pro Cys Glu Asn Lys Ser Lys Ala Val Glu Gln Val Lys Asn Ala Phe
115 120 125

Asn Lys Leu Gln Glu Lys Gly Ile Tyr Lys Ala Met Ser Glu Phe Asp
130 135 140

Ile Phe Ile Asn Tyr Ile Glu Ala Tyr Met Thr Met Lys Ile Arg Asn
145 150 155 160

<210> SEQ ID NO 25
<211> LENGTH: 101
<212> TYPE: PRT
<213> ORGANISM: Mus sp.

<400> SEQUENCE: 25

Leu Gly Cys Gln Ala Leu Ser Glu Met Ile Gln Phe Tyr Leu Val Glu
1 5 10 15

Val Met Pro Gln Ala Glu Lys His Gly Pro Glu Ile Lys Glu His Leu
20 25 30

Asn Ser Leu Gly Gln Lys Leu Lys Thr Leu Arg Met Arg Leu Arg Arg
35 40 45

Cys His Arg Phe Leu Pro Cys Glu Asn Lys Ser Lys Ala Val Glu Gln
50 55 60

Val Lys Ser Asp Phe Asn Lys Leu Glu Asp Gln Gly Val Tyr Lys Ala
65 70 75 80

Met Asn Glu Phe Asp Ile Phe Ile Asn Cys Ile Glu Ala Tyr Met Met
85 90 95

Ile Lys Met Lys Ser
100

<210> SEQ ID NO 26
<211> LENGTH: 178
<212> TYPE: PRT
<213> ORGANISM: Homo sapiens

<400> SEQUENCE: 26

Pro Gly Pro Pro Pro Gly Pro Pro Arg Val Ser Pro Asp Pro Arg Ala
1 5 10 15

Glu Leu Asp Ser Thr Val Leu Leu Thr Arg Ser Leu Leu Ala Asp Thr
20 25 30

Arg Gln Leu Ala Ala Gln Leu Arg Asp Lys Phe Pro Ala Asp Gly Asp
35 40 45

His Asn Leu Asp Ser Leu Pro Thr Leu Ala Met Ser Ala Gly Ala Leu
50 55 60

Gly Ala Leu Gln Leu Pro Gly Val Leu Thr Arg Leu Arg Ala Asp Leu
65 70 75 80

Leu Ser Tyr Leu Arg His Val Gln Trp Leu Arg Arg Ala Gly Gly Ser
85 90 95

Ser Leu Lys Thr Leu Glu Pro Glu Leu Gly Thr Leu Gln Ala Arg Leu
100 105 110

Asp Arg Leu Leu Arg Arg Leu Gln Leu Leu Met Ser Arg Leu Ala Leu
115 120 125

Pro Gln Pro Pro Pro Asp Pro Pro Ala Pro Pro Leu Ala Pro Pro Ser
130 135 140

Ser Ala Trp Gly Gly Ile Arg Ala Ala His Ala Ile Leu Gly Gly Leu
145 150 155 160

His Leu Thr Leu Asp Trp Ala Val Arg Gly Leu Leu Leu Leu Lys Thr
165 170 175

Arg Leu

<210> SEQ ID NO 27
<211> LENGTH: 179
<212> TYPE: PRT
<213> ORGANISM: Mus sp.

<400> SEQUENCE: 27

Met Pro Gly Pro Pro Ala Gly Ser Pro Arg Val Ser Ser Asp Pro Arg
1 5 10 15

Ala Asp Leu Asp Ser Ala Val Leu Leu Thr Arg Ser Leu Leu Ala Asp
20 25 30

Thr Arg Gln Leu Ala Ala Gln Met Arg Asp Lys Phe Pro Ala Asp Gly
35 40 45

```
Asp His Ser Leu Asp Ser Leu Pro Thr Leu Ala Met Ser Ala Gly Thr
    50                  55                  60

Leu Gly Ser Leu Gln Leu Pro Gly Val Leu Thr Arg Leu Arg Val Asp
65                  70                  75                  80

Leu Met Ser Tyr Leu Arg His Val Gln Trp Leu Arg Arg Ala Gly Gly
                85                  90                  95

Pro Ser Leu Lys Thr Leu Glu Pro Glu Leu Gly Ala Leu Gln Ala Arg
            100                 105                 110

Leu Glu Arg Leu Leu Arg Arg Leu Gln Leu Leu Met Ser Arg Leu Ala
        115                 120                 125

Leu Pro Gln Ala Ala Pro Asp Gln Pro Val Ile Pro Leu Gly Pro Pro
    130                 135                 140

Ala Ser Ala Trp Gly Ser Ile Arg Ala Ala His Ala Ile Leu Gly Gly
145                 150                 155                 160

Leu His Leu Thr Leu Asp Trp Ala Val Arg Gly Leu Leu Leu Leu Lys
                165                 170                 175

Thr Arg Leu


<210> SEQ ID NO 28
<211> LENGTH: 170
<212> TYPE: PRT
<213> ORGANISM: Homo sapiens

<400> SEQUENCE: 28

Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
            20                  25                  30

Gly His Met Asp Leu Arg Glu Glu Gly Asp Glu Glu Thr Thr Asn Asp
        35                  40                  45

Val Pro His Ile Gln Cys Gly Asp Gly Cys Asp Pro Gln Gly Leu Arg
    50                  55                  60

Asp Asn Ser Gln Phe Cys Leu Gln Arg Ile His Gln Gly Leu Ile Phe
65                  70                  75                  80

Tyr Glu Lys Leu Leu Gly Ser Asp Ile Phe Thr Gly Glu Pro Ser Leu
                85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                165                 170


<210> SEQ ID NO 29
<211> LENGTH: 306
<212> TYPE: PRT
<213> ORGANISM: Homo sapiens

<400> SEQUENCE: 29

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
```

```
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305


<210> SEQ ID NO 30
<211> LENGTH: 197
<212> TYPE: PRT
<213> ORGANISM: Homo sapiens

<400> SEQUENCE: 30

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80
```

Ser Phe Ile Thr Asn Gly Ser Cys Leu Ala Ser Arg Lys Thr Ser Phe
85 90 95

Met Met Ala Leu Cys Leu Ser Ser Ile Tyr Glu Asp Leu Lys Met Tyr
100 105 110

Gln Val Glu Phe Lys Thr Met Asn Ala Lys Leu Leu Met Asp Pro Lys
115 120 125

Arg Gln Ile Phe Leu Asp Gln Asn Met Leu Ala Val Ile Asp Glu Leu
130 135 140

Met Gln Ala Leu Asn Phe Asn Ser Glu Thr Val Pro Gln Lys Ser Ser
145 150 155 160

Leu Glu Glu Pro Asp Phe Tyr Lys Thr Lys Ile Lys Leu Cys Ile Leu
165 170 175

Leu His Ala Phe Arg Ile Arg Ala Val Thr Ile Asp Arg Val Met Ser
180 185 190

Tyr Leu Asn Ala Ser
195

<210> SEQ ID NO 31
<211> LENGTH: 209
<212> TYPE: PRT
<213> ORGANISM: Homo sapiens

<400> SEQUENCE: 31

Arg Lys Gly Pro Pro Ala Ala Leu Thr Leu Pro Arg Val Gln Cys Arg
1 5 10 15

Ala Ser Arg Tyr Pro Ile Ala Val Asp Cys Ser Trp Thr Leu Pro Pro
20 25 30

Ala Pro Asn Ser Thr Ser Pro Val Ser Phe Ile Ala Thr Tyr Arg Leu
35 40 45

Gly Met Ala Ala Arg Gly His Ser Trp Pro Cys Leu Gln Gln Thr Pro
50 55 60

Thr Ser Thr Ser Cys Thr Ile Thr Asp Val Gln Leu Phe Ser Met Ala
65 70 75 80

Pro Tyr Val Leu Asn Val Thr Ala Val His Pro Trp Gly Ser Ser Ser
85 90 95

Ser Phe Val Pro Phe Ile Thr Glu His Ile Ile Lys Pro Asp Pro Pro
100 105 110

Glu Gly Val Arg Leu Ser Pro Leu Ala Glu Arg Gln Leu Gln Val Gln
115 120 125

Trp Glu Pro Pro Gly Ser Trp Pro Phe Pro Glu Ile Phe Ser Leu Lys
130 135 140

Tyr Trp Ile Arg Tyr Lys Arg Gln Gly Ala Ala Arg Phe His Arg Val
145 150 155 160

Gly Pro Ile Glu Ala Thr Ser Phe Ile Leu Arg Ala Val Arg Pro Arg
165 170 175

Ala Arg Tyr Tyr Val Gln Val Ala Ala Gln Asp Leu Thr Asp Tyr Gly
180 185 190

Glu Leu Ser Asp Trp Ser Leu Pro Ala Thr Ala Thr Met Ser Leu Gly
195 200 205

Lys

<210> SEQ ID NO 32
<211> LENGTH: 193
<212> TYPE: PRT
<213> ORGANISM: Mus sp.

<400> SEQUENCE: 32

```
Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125

Leu Asp Lys Gly Met Leu Val Ala Ile Asp Glu Leu Met Gln Ser Leu
    130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala
```

<210> SEQ ID NO 33
<211> LENGTH: 206
<212> TYPE: PRT
<213> ORGANISM: Mus sp.

<400> SEQUENCE: 33

```
Ala Leu Val Ala Leu Ser Gln Pro Arg Val Gln Cys His Ala Ser Arg
1               5                   10                  15

Tyr Pro Val Ala Val Asp Cys Ser Trp Thr Pro Leu Gln Ala Pro Asn
            20                  25                  30

Ser Thr Arg Ser Thr Ser Phe Ile Ala Thr Tyr Arg Leu Gly Val Ala
        35                  40                  45

Thr Gln Gln Gln Ser Gln Pro Cys Leu Gln Arg Ser Pro Gln Ala Ser
    50                  55                  60

Arg Cys Thr Ile Pro Asp Val His Leu Phe Ser Thr Val Pro Tyr Met
65                  70                  75                  80

Leu Asn Val Thr Ala Val His Pro Gly Gly Ala Ser Ser Ser Leu Leu
                85                  90                  95

Ala Phe Val Ala Glu Arg Ile Ile Lys Pro Asp Pro Pro Glu Gly Val
            100                 105                 110

Arg Leu Arg Thr Ala Gly Gln Arg Leu Gln Val Leu Trp His Pro Pro
        115                 120                 125

Ala Ser Trp Pro Phe Pro Asp Ile Phe Ser Leu Lys Tyr Arg Leu Arg
    130                 135                 140

Tyr Arg Arg Arg Gly Ala Ser His Phe Arg Gln Val Gly Pro Ile Glu
145                 150                 155                 160

Ala Thr Thr Phe Thr Leu Arg Asn Ser Lys Pro His Ala Lys Tyr Cys
```

```
                165                 170                 175

Ile Gln Val Ser Ala Gln Asp Leu Thr Asp Tyr Gly Lys Pro Ser Asp
            180                 185                 190

Trp Ser Leu Pro Gly Gln Val Glu Ser Ala Pro His Lys Pro
        195                 200                 205


<210> SEQ ID NO 34
<211> LENGTH: 154
<212> TYPE: PRT
<213> ORGANISM: Homo sapiens

<400> SEQUENCE: 34

Val Leu Ser Gly Ala Leu Cys Phe Arg Met Lys Asp Ser Ala Leu Lys
1               5                   10                  15

Val Leu Tyr Leu His Asn Asn Gln Leu Leu Ala Gly Gly Leu His Ala
            20                  25                  30

Gly Lys Val Ile Lys Gly Glu Glu Ile Ser Val Val Pro Asn Arg Trp
        35                  40                  45

Leu Asp Ala Ser Leu Ser Pro Val Ile Leu Gly Val Gln Gly Gly Ser
    50                  55                  60

Gln Cys Leu Ser Cys Gly Val Gly Gln Glu Pro Thr Leu Thr Leu Glu
65                  70                  75                  80

Pro Val Asn Ile Met Glu Leu Tyr Leu Gly Ala Lys Glu Ser Lys Ser
                85                  90                  95

Phe Thr Phe Tyr Arg Arg Asp Met Gly Leu Thr Ser Ser Phe Glu Ser
            100                 105                 110

Ala Ala Tyr Pro Gly Trp Phe Leu Cys Thr Val Pro Glu Ala Asp Gln
        115                 120                 125

Pro Val Arg Leu Thr Gln Leu Pro Glu Asn Gly Gly Trp Asn Ala Pro
    130                 135                 140

Ile Thr Asp Phe Tyr Phe Gln Gln Cys Asp
145                 150


<210> SEQ ID NO 35
<211> LENGTH: 154
<212> TYPE: PRT
<213> ORGANISM: Mus sp.

<400> SEQUENCE: 35

Val Leu Ser Gly Ala Leu Cys Phe Arg Met Lys Asp Ser Ala Leu Lys
1               5                   10                  15

Val Leu Tyr Leu His Asn Asn Gln Leu Leu Ala Gly Gly Leu His Ala
            20                  25                  30

Glu Lys Val Ile Lys Gly Glu Glu Ile Ser Val Val Pro Asn Arg Ala
        35                  40                  45

Leu Asp Ala Ser Leu Ser Pro Val Ile Leu Gly Val Gln Gly Gly Ser
    50                  55                  60

Gln Cys Leu Ser Cys Gly Thr Glu Lys Gly Pro Ile Leu Lys Leu Glu
65                  70                  75                  80

Pro Val Asn Ile Met Glu Leu Tyr Leu Gly Ala Lys Glu Ser Lys Ser
                85                  90                  95

Phe Thr Phe Tyr Arg Arg Asp Met Gly Leu Thr Ser Ser Phe Glu Ser
            100                 105                 110

Ala Ala Tyr Pro Gly Trp Phe Leu Cys Thr Ser Pro Glu Ala Asp Gln
        115                 120                 125

Pro Val Arg Leu Thr Gln Ile Pro Glu Asp Pro Ala Trp Asp Ala Pro
```

```
    130                 135                 140

Ile Thr Asp Phe Tyr Phe Gln Gln Cys Asp
145                 150


<210> SEQ ID NO 36
<211> LENGTH: 173
<212> TYPE: PRT
<213> ORGANISM: Homo sapiens

<400> SEQUENCE: 36

Val His Thr Ser Pro Lys Val Lys Asn Leu Asn Pro Lys Lys Phe Ser
1               5                   10                  15

Ile His Asp Gln Asp His Lys Val Leu Val Leu Asp Ser Gly Asn Leu
            20                  25                  30

Ile Ala Val Pro Asp Lys Asn Tyr Ile Arg Pro Glu Ile Phe Phe Ala
        35                  40                  45

Leu Ala Ser Ser Leu Ser Ser Ala Ser Ala Glu Lys Gly Ser Pro Ile
    50                  55                  60

Leu Leu Gly Val Ser Lys Gly Glu Phe Cys Leu Tyr Cys Asp Lys Asp
65                  70                  75                  80

Lys Gly Gln Ser His Pro Ser Leu Gln Leu Lys Lys Glu Lys Leu Met
                85                  90                  95

Lys Leu Ala Ala Gln Lys Glu Ser Ala Arg Arg Pro Phe Ile Phe Tyr
            100                 105                 110

Arg Ala Gln Val Gly Ser Trp Asn Met Leu Glu Ser Ala Ala His Pro
        115                 120                 125

Gly Trp Phe Ile Cys Thr Ser Cys Asn Cys Asn Glu Pro Val Gly Val
    130                 135                 140

Thr Asp Lys Phe Glu Asn Arg Lys His Ile Glu Phe Ser Phe Gln Pro
145                 150                 155                 160

Val Cys Lys Ala Glu Met Ser Pro Ser Glu Val Ser Asp
                165                 170


<210> SEQ ID NO 37
<211> LENGTH: 171
<212> TYPE: PRT
<213> ORGANISM: Mus sp.

<400> SEQUENCE: 37

Val Pro Ser Ser Ala Lys Val Asn Ala Arg Ala Pro Glu Lys Phe Ser
1               5                   10                  15

Ile Arg Asp Gln Asp Gln Lys Val Leu Val Leu Ser Asp Glu Thr Leu
            20                  25                  30

Ile Ala Val Pro Asn Lys Pro Tyr Thr Val Pro Glu Thr Phe Phe Val
        35                  40                  45

Leu Ala Ser His Thr Ser Ser Ser His Glu Gly Ser Pro Ile Leu Leu
    50                  55                  60

Ala Val Ser Lys Gly Glu Leu Cys Leu Cys Cys Asp Lys Asp Glu Glu
65                  70                  75                  80

Gln Ser Lys Pro Ser Leu Gln Leu Lys Lys Asn Glu Leu Met Lys Leu
                85                  90                  95

Ala Thr Gln Lys Glu Lys Val Arg Leu Pro Phe Val Phe Tyr Arg Ala
            100                 105                 110

Gln Val Gly Ser Cys Cys Thr Leu Glu Ser Ala Ala His Pro Gly Trp
        115                 120                 125

Phe Val Cys Thr Ser Arg Asn Ser Gly Ala Pro Val Glu Val Thr Asp
```

130 135 140

Thr Ser Gly Glu Gly Lys Leu Met Glu Phe Ser Phe Gln Gln Val Ser
145 150 155 160

Glu Thr Glu Met Ser Pro Ser Glu Val Ser Ile
165 170

<210> SEQ ID NO 38
<211> LENGTH: 165
<212> TYPE: PRT
<213> ORGANISM: Homo sapiens

<400> SEQUENCE: 38

Ser Tyr Asn Leu Leu Gly Phe Leu Gln Arg Ser Ser Asn Phe Gln Cys
1 5 10 15

Gln Lys Leu Leu Trp Gln Leu Asn Gly Arg Leu Glu Tyr Cys Leu Lys
20 25 30

Asp Arg Met Asn Phe Asp Ile Pro Glu Glu Ile Lys Gln Leu Gln Gln
35 40 45

Phe Gln Lys Glu Asp Ala Ala Leu Thr Ile Tyr Glu Met Leu Gln Asn
50 55 60

Ile Phe Ala Ile Phe Arg Gln Asp Ser Ser Ser Thr Gly Trp Asn Glu
65 70 75 80

Thr Ile Val Glu Asn Leu Leu Ala Asn Val Tyr His Gln Ile Asn His
85 90 95

Leu Lys Thr Val Leu Glu Glu Lys Leu Glu Lys Glu Asp Phe Thr Arg
100 105 110

Gly Lys Leu Met Ser Ser Leu His Leu Lys Arg Tyr Tyr Gly Arg Ile
115 120 125

Leu His Tyr Leu Lys Ala Lys Glu Tyr Ser His Cys Ala Trp Thr Ile
130 135 140

Val Arg Val Glu Ile Leu Arg Asn Phe Tyr Phe Ile Asn Arg Leu Thr
145 150 155 160

Gly Tyr Leu Arg Asn
165

<210> SEQ ID NO 39
<211> LENGTH: 161
<212> TYPE: PRT
<213> ORGANISM: Mus sp.

<400> SEQUENCE: 39

Ile Asn Tyr Lys Gln Leu Gln Leu Gln Glu Arg Thr Asn Ile Arg Lys
1 5 10 15

Cys Gln Glu Leu Leu Glu Gln Leu Asn Gly Lys Ile Asn Leu Thr Tyr
20 25 30

Arg Ala Asp Phe Lys Ile Pro Met Glu Met Thr Glu Lys Met Gln Lys
35 40 45

Ser Tyr Thr Ala Phe Ala Ile Gln Glu Met Leu Gln Asn Val Phe Leu
50 55 60

Val Phe Arg Asn Asn Phe Ser Ser Thr Gly Trp Asn Glu Thr Ile Val
65 70 75 80

Val Arg Leu Leu Asp Glu Leu His Gln Gln Thr Val Phe Leu Lys Thr
85 90 95

Val Leu Glu Glu Lys Gln Glu Glu Arg Leu Thr Trp Glu Met Ser Ser
100 105 110

Thr Ala Leu His Leu Lys Ser Tyr Tyr Trp Arg Val Gln Arg Tyr Leu

```
        115                 120                 125

Lys Leu Met Lys Tyr Asn Ser Tyr Ala Trp Met Val Val Arg Ala Glu
    130                 135                 140

Ile Phe Arg Asn Phe Leu Ile Ile Arg Arg Leu Thr Arg Asn Phe Gln
145                 150                 155                 160

Asn


<210> SEQ ID NO 40
<211> LENGTH: 112
<212> TYPE: PRT
<213> ORGANISM: Homo sapiens

<400> SEQUENCE: 40

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110


<210> SEQ ID NO 41
<211> LENGTH: 112
<212> TYPE: PRT
<213> ORGANISM: Mus sp.

<400> SEQUENCE: 41

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ser Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110


<210> SEQ ID NO 42
<211> LENGTH: 161
<212> TYPE: PRT
<213> ORGANISM: Homo sapiens

<400> SEQUENCE: 42

Asp Ser Val Cys Pro Gln Gly Lys Tyr Ile His Pro Gln Asn Asn Ser
1               5                   10                  15
```

Ile Cys Cys Thr Lys Cys His Lys Gly Thr Tyr Leu Tyr Asn Asp Cys
20 25 30

Pro Gly Pro Gly Gln Asp Thr Asp Cys Arg Glu Cys Glu Ser Gly Ser
35 40 45

Phe Thr Ala Ser Glu Asn His Leu Arg His Cys Leu Ser Cys Ser Lys
50 55 60

Cys Arg Lys Glu Met Gly Gln Val Glu Ile Ser Ser Cys Thr Val Asp
65 70 75 80

Arg Asp Thr Val Cys Gly Cys Arg Lys Asn Gln Tyr Arg His Tyr Trp
85 90 95

Ser Glu Asn Leu Phe Gln Cys Phe Asn Cys Ser Leu Cys Leu Asn Gly
100 105 110

Thr Val His Leu Ser Cys Gln Glu Lys Gln Asn Thr Val Cys Thr Cys
115 120 125

His Ala Gly Phe Phe Leu Arg Glu Asn Glu Cys Val Ser Cys Ser Asn
130 135 140

Cys Lys Lys Ser Leu Glu Cys Thr Lys Leu Cys Leu Pro Gln Ile Glu
145 150 155 160

Asn

<210> SEQ ID NO 43
<211> LENGTH: 439
<212> TYPE: PRT
<213> ORGANISM: Homo sapiens

<400> SEQUENCE: 43

Leu Pro Ala Gln Val Ala Phe Thr Pro Tyr Ala Pro Glu Pro Gly Ser
1 5 10 15

Thr Cys Arg Leu Arg Glu Tyr Tyr Asp Gln Thr Ala Gln Met Cys Cys
20 25 30

Ser Lys Cys Ser Pro Gly Gln His Ala Lys Val Phe Cys Thr Lys Thr
35 40 45

Ser Asp Thr Val Cys Asp Ser Cys Glu Asp Ser Thr Tyr Thr Gln Leu
50 55 60

Trp Asn Trp Val Pro Glu Cys Leu Ser Cys Gly Ser Arg Cys Ser Ser
65 70 75 80

Asp Gln Val Glu Thr Gln Ala Cys Thr Arg Glu Gln Asn Arg Ile Cys
85 90 95

Thr Cys Arg Pro Gly Trp Tyr Cys Ala Leu Ser Lys Gln Glu Gly Cys
100 105 110

Arg Leu Cys Ala Pro Leu Arg Lys Cys Arg Pro Gly Phe Gly Val Ala
115 120 125

Arg Pro Gly Thr Glu Thr Ser Asp Val Val Cys Lys Pro Cys Ala Pro
130 135 140

Gly Thr Phe Ser Asn Thr Thr Ser Ser Thr Asp Ile Cys Arg Pro His
145 150 155 160

Gln Ile Cys Asn Val Val Ala Ile Pro Gly Asn Ala Ser Met Asp Ala
165 170 175

Val Cys Thr Ser Thr Ser Pro Thr Arg Ser Met Ala Pro Gly Ala Val
180 185 190

His Leu Pro Gln Pro Val Ser Thr Arg Ser Gln His Thr Gln Pro Thr
195 200 205

Pro Glu Pro Ser Thr Ala Pro Ser Thr Ser Phe Leu Leu Pro Met Gly
210 215 220

```
Pro Ser Pro Pro Ala Glu Gly Ser Thr Gly Asp Phe Ala Leu Pro Val
225                 230                 235                 240

Gly Leu Ile Val Gly Val Thr Ala Leu Gly Leu Leu Ile Ile Gly Val
                245                 250                 255

Val Asn Cys Val Ile Met Thr Gln Val Lys Lys Lys Pro Leu Cys Leu
            260                 265                 270

Gln Arg Glu Ala Lys Val Pro His Leu Pro Ala Asp Lys Ala Arg Gly
        275                 280                 285

Thr Gln Gly Pro Glu Gln Gln His Leu Leu Ile Thr Ala Pro Ser Ser
    290                 295                 300

Ser Ser Ser Ser Leu Glu Ser Ser Ala Ser Ala Leu Asp Arg Arg Ala
305                 310                 315                 320

Pro Thr Arg Asn Gln Pro Gln Ala Pro Gly Val Glu Ala Ser Gly Ala
                325                 330                 335

Gly Glu Ala Arg Ala Ser Thr Gly Ser Ser Asp Ser Ser Pro Gly Gly
            340                 345                 350

His Gly Thr Gln Val Asn Val Thr Cys Ile Val Asn Val Cys Ser Ser
        355                 360                 365

Ser Asp His Ser Ser Gln Cys Ser Ser Gln Ala Ser Ser Thr Met Gly
    370                 375                 380

Asp Thr Asp Ser Ser Pro Ser Glu Ser Pro Lys Asp Glu Gln Val Pro
385                 390                 395                 400

Phe Ser Lys Glu Glu Cys Ala Phe Arg Ser Gln Leu Glu Thr Pro Glu
                405                 410                 415

Thr Leu Leu Gly Ser Thr Glu Glu Lys Pro Leu Pro Leu Gly Val Pro
            420                 425                 430

Asp Ala Gly Met Lys Pro Ser
        435
```

<210> SEQ ID NO 44
<211> LENGTH: 236
<212> TYPE: PRT
<213> ORGANISM: Mus sp.

<400> SEQUENCE: 44

```
Val Pro Ala Gln Val Val Leu Thr Pro Tyr Lys Pro Glu Pro Gly Tyr
1               5                   10                  15

Glu Cys Gln Ile Ser Gln Glu Tyr Tyr Asp Arg Lys Ala Gln Met Cys
            20                  25                  30

Cys Ala Lys Cys Pro Pro Gly Gln Tyr Val Lys His Phe Cys Asn Lys
        35                  40                  45

Thr Ser Asp Thr Val Cys Ala Asp Cys Glu Ala Ser Met Tyr Thr Gln
    50                  55                  60

Val Trp Asn Gln Phe Arg Thr Cys Leu Ser Cys Ser Ser Ser Cys Thr
65                  70                  75                  80

Thr Asp Gln Val Glu Ile Arg Ala Cys Thr Lys Gln Gln Asn Arg Val
                85                  90                  95

Cys Ala Cys Glu Ala Gly Arg Tyr Cys Ala Leu Lys Thr His Ser Gly
            100                 105                 110

Ser Cys Arg Gln Cys Met Arg Leu Ser Lys Cys Gly Pro Gly Phe Gly
        115                 120                 125

Val Ala Ser Ser Arg Ala Pro Asn Gly Asn Val Leu Cys Lys Ala Cys
    130                 135                 140

Ala Pro Gly Thr Phe Ser Asp Thr Thr Ser Ser Thr Asp Val Cys Arg
145                 150                 155                 160
```

Pro His Arg Ile Cys Ser Ile Leu Ala Ile Pro Gly Asn Ala Ser Thr
165 170 175

Asp Ala Val Cys Ala Pro Glu Ser Pro Thr Leu Ser Ala Ile Pro Arg
180 185 190

Thr Leu Tyr Val Ser Gln Pro Glu Pro Thr Arg Ser Gln Pro Leu Asp
195 200 205

Gln Glu Pro Gly Pro Ser Gln Thr Pro Ser Ile Leu Thr Ser Leu Gly
210 215 220

Ser Thr Pro Ile Ile Glu Gln Ser Thr Lys Gly Gly
225 230 235

<210> SEQ ID NO 45
<211> LENGTH: 608
<212> TYPE: PRT
<213> ORGANISM: Homo sapiens

<400> SEQUENCE: 45

Lys Trp Val Thr Phe Ile Ser Leu Leu Phe Leu Phe Ser Ser Ala Tyr
1 5 10 15

Ser Arg Gly Val Phe Arg Arg Asp Ala His Lys Ser Glu Val Ala His
20 25 30

Arg Phe Lys Asp Leu Gly Glu Glu Asn Phe Lys Ala Leu Val Leu Ile
35 40 45

Ala Phe Ala Gln Tyr Leu Gln Gln Cys Pro Phe Glu Asp His Val Lys
50 55 60

Leu Val Asn Glu Val Thr Glu Phe Ala Lys Thr Cys Val Ala Asp Glu
65 70 75 80

Ser Ala Glu Asn Cys Asp Lys Ser Leu His Thr Leu Phe Gly Asp Lys
85 90 95

Leu Cys Thr Val Ala Thr Leu Arg Glu Thr Tyr Gly Glu Met Ala Asp
100 105 110

Cys Cys Ala Lys Gln Glu Pro Glu Arg Asn Glu Cys Phe Leu Gln His
115 120 125

Lys Asp Asp Asn Pro Asn Leu Pro Arg Leu Val Arg Pro Glu Val Asp
130 135 140

Val Met Cys Thr Ala Phe His Asp Asn Glu Glu Thr Phe Leu Lys Lys
145 150 155 160

Tyr Leu Tyr Glu Ile Ala Arg Arg His Pro Tyr Phe Tyr Ala Pro Glu
165 170 175

Leu Leu Phe Phe Ala Lys Arg Tyr Lys Ala Ala Phe Thr Glu Cys Cys
180 185 190

Gln Ala Ala Asp Lys Ala Ala Cys Leu Leu Pro Lys Leu Asp Glu Leu
195 200 205

Arg Asp Glu Gly Lys Ala Ser Ser Ala Lys Gln Arg Leu Lys Cys Ala
210 215 220

Ser Leu Gln Lys Phe Gly Glu Arg Ala Phe Lys Ala Trp Ala Val Ala
225 230 235 240

Arg Leu Ser Gln Arg Phe Pro Lys Ala Glu Phe Ala Glu Val Ser Lys
245 250 255

Leu Val Thr Asp Leu Thr Lys Val His Thr Glu Cys Cys His Gly Asp
260 265 270

Leu Leu Glu Cys Ala Asp Asp Arg Ala Asp Leu Ala Lys Tyr Ile Cys
275 280 285

Glu Asn Gln Asp Ser Ile Ser Ser Lys Leu Lys Glu Cys Cys Glu Lys

```
    290                 295                 300

Pro Leu Leu Glu Lys Ser His Cys Ile Ala Glu Val Glu Asn Asp Glu
305                 310                 315                 320

Met Pro Ala Asp Leu Pro Ser Leu Ala Ala Asp Phe Val Glu Ser Lys
                325                 330                 335

Asp Val Cys Lys Asn Tyr Ala Glu Ala Lys Asp Val Phe Leu Gly Met
            340                 345                 350

Phe Leu Tyr Glu Tyr Ala Arg Arg His Pro Asp Tyr Ser Val Val Leu
        355                 360                 365

Leu Leu Arg Leu Ala Lys Thr Tyr Glu Thr Thr Leu Glu Lys Cys Cys
    370                 375                 380

Ala Ala Ala Asp Pro His Glu Cys Tyr Ala Lys Val Phe Asp Glu Phe
385                 390                 395                 400

Lys Pro Leu Val Glu Glu Pro Gln Asn Leu Ile Lys Gln Asn Cys Glu
                405                 410                 415

Leu Phe Glu Gln Leu Gly Glu Tyr Lys Phe Gln Asn Ala Leu Leu Val
            420                 425                 430

Arg Tyr Thr Lys Lys Val Pro Gln Val Ser Thr Pro Thr Leu Val Glu
        435                 440                 445

Val Ser Arg Asn Leu Gly Lys Val Gly Ser Lys Cys Cys Lys His Pro
    450                 455                 460

Glu Ala Lys Arg Met Pro Cys Ala Glu Asp Tyr Leu Ser Val Val Leu
465                 470                 475                 480

Asn Gln Leu Cys Val Leu His Glu Lys Thr Pro Val Ser Asp Arg Val
                485                 490                 495

Thr Lys Cys Cys Thr Glu Ser Leu Val Asn Arg Arg Pro Cys Phe Ser
            500                 505                 510

Ala Leu Glu Val Asp Glu Thr Tyr Val Pro Lys Glu Phe Asn Ala Glu
        515                 520                 525

Thr Phe Thr Phe His Ala Asp Ile Cys Thr Leu Ser Glu Lys Glu Arg
    530                 535                 540

Gln Ile Lys Lys Gln Thr Ala Leu Val Glu Leu Val Lys His Lys Pro
545                 550                 555                 560

Lys Ala Thr Lys Glu Gln Leu Lys Ala Val Met Asp Asp Phe Ala Ala
                565                 570                 575

Phe Val Glu Lys Cys Cys Lys Ala Asp Asp Lys Glu Thr Cys Phe Ala
            580                 585                 590

Glu Glu Gly Lys Lys Leu Val Ala Ala Ser Gln Ala Ala Leu Gly Leu
        595                 600                 605


<210> SEQ ID NO 46
<211> LENGTH: 584
<212> TYPE: PRT
<213> ORGANISM: Mus sp.

<400> SEQUENCE: 46

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60
```

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
    290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
    370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
    450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr

```
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
    530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala
            580


<210> SEQ ID NO 47
<211> LENGTH: 193
<212> TYPE: PRT
<213> ORGANISM: Unknown
<220> FEATURE:
<223> OTHER INFORMATION: Description of Unknown:
      vWF A3 sequence

<400> SEQUENCE: 47

Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
            20                  25                  30

Ile Ser Lys Ala Asn Ile Gly Pro Arg Leu Thr Gln Val Ser Val Leu
        35                  40                  45

Gln Tyr Gly Ser Ile Thr Thr Ile Asp Val Pro Trp Asn Val Val Pro
    50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
            100                 105                 110

Ile Leu Val Thr Asp Val Ser Val Asp Ser Val Asp Ala Ala Ala Asp
        115                 120                 125

Ala Ala Arg Ser Asn Arg Val Thr Val Phe Pro Ile Gly Ile Gly Asp
    130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190

Ile


<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48
```

```
Gly Gly Gly Ser Gly Gly Gly Ser
1               5


<210> SEQ ID NO 49
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly
      Ser" repeating units
<220> FEATURE:
<223> OTHER INFORMATION: See specification as filed for detailed
      description of substitutions and preferred embodiments

<400> SEQUENCE: 49

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40


<210> SEQ ID NO 50
<211> LENGTH: 785
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
            20                  25                  30

Ile Ser Lys Ala Asn Ile Gly Pro Arg Leu Thr Gln Val Ser Val Leu
        35                  40                  45

Gln Tyr Gly Ser Ile Thr Thr Ile Asp Val Pro Trp Asn Val Val Pro
    50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
            100                 105                 110

Ile Leu Val Thr Asp Val Ser Val Asp Ser Val Asp Ala Ala Ala Asp
        115                 120                 125

Ala Ala Arg Ser Asn Arg Val Thr Val Phe Pro Ile Gly Ile Gly Asp
    130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175

Thr Leu Gly Asn Ser Phe Leu His Lys Leu Cys Ser Gly Phe Val Arg
            180                 185                 190
```

```
Ile Gly Gly Gly Ser Gly Gly Gly Ser Glu Ala His Lys Ser Glu Ile
        195                 200                 205

Ala His Arg Tyr Asn Asp Leu Gly Glu Gln His Phe Lys Gly Leu Val
    210                 215                 220

Leu Ile Ala Phe Ser Gln Tyr Leu Gln Lys Cys Ser Tyr Asp Glu His
225                 230                 235                 240

Ala Lys Leu Val Gln Glu Val Thr Asp Phe Ala Lys Thr Cys Val Ala
                245                 250                 255

Asp Glu Ser Ala Ala Asn Cys Asp Lys Ser Leu His Thr Leu Phe Gly
            260                 265                 270

Asp Lys Leu Cys Ala Ile Pro Asn Leu Arg Glu Asn Tyr Gly Glu Leu
        275                 280                 285

Ala Asp Cys Cys Thr Lys Gln Glu Pro Glu Arg Asn Glu Cys Phe Leu
    290                 295                 300

Gln His Lys Asp Asp Asn Pro Ser Leu Pro Pro Phe Glu Arg Pro Glu
305                 310                 315                 320

Ala Glu Ala Met Cys Thr Ser Phe Lys Glu Asn Pro Thr Thr Phe Met
                325                 330                 335

Gly His Tyr Leu His Glu Val Ala Arg Arg His Pro Tyr Phe Tyr Ala
            340                 345                 350

Pro Glu Leu Leu Tyr Tyr Ala Glu Gln Tyr Asn Glu Ile Leu Thr Gln
        355                 360                 365

Cys Cys Ala Glu Ala Asp Lys Glu Ser Cys Leu Thr Pro Lys Leu Asp
    370                 375                 380

Gly Val Lys Glu Lys Ala Leu Val Ser Ser Val Arg Gln Arg Met Lys
385                 390                 395                 400

Cys Ser Ser Met Gln Lys Phe Gly Glu Arg Ala Phe Lys Ala Trp Ala
                405                 410                 415

Val Ala Arg Leu Ser Gln Thr Phe Pro Asn Ala Asp Phe Ala Glu Ile
            420                 425                 430

Thr Lys Leu Ala Thr Asp Leu Thr Lys Val Asn Lys Glu Cys Cys His
        435                 440                 445

Gly Asp Leu Leu Glu Cys Ala Asp Asp Arg Ala Glu Leu Ala Lys Tyr
    450                 455                 460

Met Cys Glu Asn Gln Ala Thr Ile Ser Ser Lys Leu Gln Thr Cys Cys
465                 470                 475                 480

Asp Lys Pro Leu Leu Lys Lys Ala His Cys Leu Ser Glu Val Glu His
                485                 490                 495

Asp Thr Met Pro Ala Asp Leu Pro Ala Ile Ala Ala Asp Phe Val Glu
            500                 505                 510

Asp Gln Glu Val Cys Lys Asn Tyr Ala Glu Ala Lys Asp Val Phe Leu
        515                 520                 525

Gly Thr Phe Leu Tyr Glu Tyr Ser Arg Arg His Pro Asp Tyr Ser Val
    530                 535                 540

Ser Leu Leu Leu Arg Leu Ala Lys Lys Tyr Glu Ala Thr Leu Glu Lys
545                 550                 555                 560

Cys Cys Ala Glu Ala Asn Pro Pro Ala Cys Tyr Gly Thr Val Leu Ala
                565                 570                 575

Glu Phe Gln Pro Leu Val Glu Glu Pro Lys Asn Leu Val Lys Thr Asn
            580                 585                 590

Cys Asp Leu Tyr Glu Lys Leu Gly Glu Tyr Gly Phe Gln Asn Ala Ile
        595                 600                 605

Leu Val Arg Tyr Thr Gln Lys Ala Pro Gln Val Ser Thr Pro Thr Leu
```

```
    610                 615                 620

Val Glu Ala Ala Arg Asn Leu Gly Arg Val Gly Thr Lys Cys Cys Thr
625                 630                 635                 640

Leu Pro Glu Asp Gln Arg Leu Pro Cys Val Glu Asp Tyr Leu Ser Ala
                645                 650                 655

Ile Leu Asn Arg Val Cys Leu Leu His Glu Lys Thr Pro Val Ser Glu
            660                 665                 670

His Val Thr Lys Cys Cys Ser Gly Ser Leu Val Glu Arg Arg Pro Cys
        675                 680                 685

Phe Ser Ala Leu Thr Val Asp Glu Thr Tyr Val Pro Lys Glu Phe Lys
    690                 695                 700

Ala Glu Thr Phe Thr Phe His Ser Asp Ile Cys Thr Leu Pro Glu Lys
705                 710                 715                 720

Glu Lys Gln Ile Lys Lys Gln Thr Ala Leu Ala Glu Leu Val Lys His
                725                 730                 735

Lys Pro Lys Ala Thr Ala Glu Gln Leu Lys Thr Val Met Asp Asp Phe
            740                 745                 750

Ala Gln Phe Leu Asp Thr Cys Cys Lys Ala Ala Asp Lys Asp Thr Cys
        755                 760                 765

Phe Ser Thr Glu Gly Pro Asn Leu Val Thr Arg Cys Lys Asp Ala Leu
    770                 775                 780

Ala
785
```

<210> SEQ ID NO 51
<211> LENGTH: 809
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Cys Ser Gln Pro Leu Asp Val Ile Leu Leu Leu Asp Gly Ser Ser Ser
1               5                   10                  15

Phe Pro Ala Ser Tyr Phe Asp Glu Met Lys Ser Phe Ala Lys Ala Phe
            20                  25                  30

Ile Ser Lys Ala Asn Ile Gly Pro Arg Leu Thr Gln Val Ser Val Leu
        35                  40                  45

Gln Tyr Gly Ser Ile Thr Thr Ile Asp Val Pro Trp Asn Val Val Pro
    50                  55                  60

Glu Lys Ala His Leu Leu Ser Leu Val Asp Val Met Gln Arg Glu Gly
65                  70                  75                  80

Gly Pro Ser Gln Ile Gly Asp Ala Leu Gly Phe Ala Val Arg Tyr Leu
                85                  90                  95

Thr Ser Glu Met His Gly Ala Arg Pro Gly Ala Ser Lys Ala Val Val
            100                 105                 110

Ile Leu Val Thr Asp Val Ser Val Asp Ser Val Asp Ala Ala Ala Asp
        115                 120                 125

Ala Ala Arg Ser Asn Arg Val Thr Val Phe Pro Ile Gly Ile Gly Asp
    130                 135                 140

Arg Tyr Asp Ala Ala Gln Leu Arg Ile Leu Ala Gly Pro Ala Gly Asp
145                 150                 155                 160

Ser Asn Val Val Lys Leu Gln Arg Ile Glu Asp Leu Pro Thr Met Val
                165                 170                 175
```

```
Thr Leu Gly Asn Ser Phe Leu His Lys Leu Cys Ser Gly Phe Val Arg
            180                 185                 190

Ile Gly Gly Gly Ser Gly Gly Gly Ser Lys Trp Val Thr Phe Ile Ser
        195                 200                 205

Leu Leu Phe Leu Phe Ser Ser Ala Tyr Ser Arg Gly Val Phe Arg Arg
    210                 215                 220

Asp Ala His Lys Ser Glu Val Ala His Arg Phe Lys Asp Leu Gly Glu
225                 230                 235                 240

Glu Asn Phe Lys Ala Leu Val Leu Ile Ala Phe Ala Gln Tyr Leu Gln
                245                 250                 255

Gln Cys Pro Phe Glu Asp His Val Lys Leu Val Asn Glu Val Thr Glu
            260                 265                 270

Phe Ala Lys Thr Cys Val Ala Asp Glu Ser Ala Glu Asn Cys Asp Lys
        275                 280                 285

Ser Leu His Thr Leu Phe Gly Asp Lys Leu Cys Thr Val Ala Thr Leu
    290                 295                 300

Arg Glu Thr Tyr Gly Glu Met Ala Asp Cys Cys Ala Lys Gln Glu Pro
305                 310                 315                 320

Glu Arg Asn Glu Cys Phe Leu Gln His Lys Asp Asp Asn Pro Asn Leu
                325                 330                 335

Pro Arg Leu Val Arg Pro Glu Val Asp Val Met Cys Thr Ala Phe His
            340                 345                 350

Asp Asn Glu Glu Thr Phe Leu Lys Lys Tyr Leu Tyr Glu Ile Ala Arg
        355                 360                 365

Arg His Pro Tyr Phe Tyr Ala Pro Glu Leu Leu Phe Phe Ala Lys Arg
    370                 375                 380

Tyr Lys Ala Ala Phe Thr Glu Cys Cys Gln Ala Ala Asp Lys Ala Ala
385                 390                 395                 400

Cys Leu Leu Pro Lys Leu Asp Glu Leu Arg Asp Glu Gly Lys Ala Ser
                405                 410                 415

Ser Ala Lys Gln Arg Leu Lys Cys Ala Ser Leu Gln Lys Phe Gly Glu
            420                 425                 430

Arg Ala Phe Lys Ala Trp Ala Val Ala Arg Leu Ser Gln Arg Phe Pro
        435                 440                 445

Lys Ala Glu Phe Ala Glu Val Ser Lys Leu Val Thr Asp Leu Thr Lys
    450                 455                 460

Val His Thr Glu Cys Cys His Gly Asp Leu Leu Glu Cys Ala Asp Asp
465                 470                 475                 480

Arg Ala Asp Leu Ala Lys Tyr Ile Cys Glu Asn Gln Asp Ser Ile Ser
                485                 490                 495

Ser Lys Leu Lys Glu Cys Cys Glu Lys Pro Leu Leu Glu Lys Ser His
            500                 505                 510

Cys Ile Ala Glu Val Glu Asn Asp Glu Met Pro Ala Asp Leu Pro Ser
        515                 520                 525

Leu Ala Ala Asp Phe Val Glu Ser Lys Asp Val Cys Lys Asn Tyr Ala
    530                 535                 540

Glu Ala Lys Asp Val Phe Leu Gly Met Phe Leu Tyr Glu Tyr Ala Arg
545                 550                 555                 560

Arg His Pro Asp Tyr Ser Val Val Leu Leu Leu Arg Leu Ala Lys Thr
                565                 570                 575

Tyr Glu Thr Thr Leu Glu Lys Cys Cys Ala Ala Ala Asp Pro His Glu
            580                 585                 590

Cys Tyr Ala Lys Val Phe Asp Glu Phe Lys Pro Leu Val Glu Glu Pro
```

```
        595                 600                 605

Gln Asn Leu Ile Lys Gln Asn Cys Glu Leu Phe Glu Gln Leu Gly Glu
    610                 615                 620

Tyr Lys Phe Gln Asn Ala Leu Leu Val Arg Tyr Thr Lys Lys Val Pro
625                 630                 635                 640

Gln Val Ser Thr Pro Thr Leu Val Glu Val Ser Arg Asn Leu Gly Lys
                645                 650                 655

Val Gly Ser Lys Cys Cys Lys His Pro Glu Ala Lys Arg Met Pro Cys
            660                 665                 670

Ala Glu Asp Tyr Leu Ser Val Val Leu Asn Gln Leu Cys Val Leu His
        675                 680                 685

Glu Lys Thr Pro Val Ser Asp Arg Val Thr Lys Cys Cys Thr Glu Ser
    690                 695                 700

Leu Val Asn Arg Arg Pro Cys Phe Ser Ala Leu Glu Val Asp Glu Thr
705                 710                 715                 720

Tyr Val Pro Lys Glu Phe Asn Ala Glu Thr Phe Thr Phe His Ala Asp
                725                 730                 735

Ile Cys Thr Leu Ser Glu Lys Glu Arg Gln Ile Lys Lys Gln Thr Ala
            740                 745                 750

Leu Val Glu Leu Val Lys His Lys Pro Lys Ala Thr Lys Glu Gln Leu
        755                 760                 765

Lys Ala Val Met Asp Asp Phe Ala Ala Phe Val Glu Lys Cys Cys Lys
    770                 775                 780

Ala Asp Asp Lys Glu Thr Cys Phe Ala Glu Glu Gly Lys Lys Leu Val
785                 790                 795                 800

Ala Ala Ser Gln Ala Ala Leu Gly Leu
                805


<210> SEQ ID NO 52
<211> LENGTH: 193
<212> TYPE: PRT
<213> ORGANISM: Unknown
<220> FEATURE:
<223> OTHER INFORMATION: Description of Unknown:
      vWF A3 sequence

<400> SEQUENCE: 52

Cys Ser Gln Pro Leu Asp Val Val Leu Leu Leu Asp Gly Ser Ser Ser
1               5                   10                  15

Leu Pro Glu Ser Ser Phe Asp Lys Met Lys Ser Phe Ala Lys Ala Phe
            20                  25                  30

Ile Ser Lys Ala Asn Ile Gly Pro His Leu Thr Gln Val Ser Val Ile
        35                  40                  45

Gln Tyr Gly Ser Ile Asn Thr Ile Asp Val Pro Trp Asn Val Val Gln
    50                  55                  60

Glu Lys Ala His Leu Gln Ser Leu Val Asp Leu Met Gln Gln Glu Gly
65                  70                  75                  80

Gly Pro Ser Gln Ile Gly Asp Ala Leu Ala Phe Ala Val Arg Tyr Val
                85                  90                  95

Thr Ser Gln Ile His Gly Ala Arg Pro Gly Ala Ser Lys Ala Val Val
            100                 105                 110

Ile Ile Ile Met Asp Thr Ser Leu Asp Pro Val Asp Thr Ala Ala Asp
        115                 120                 125

Ala Ala Arg Ser Asn Arg Val Ala Val Phe Pro Val Gly Val Gly Asp
    130                 135                 140
```

Arg Tyr Asp Glu Ala Gln Leu Arg Ile Leu Ala Gly Pro Gly Ala Ser
145 150 155 160

Ser Asn Val Val Lys Leu Gln Gln Val Glu Asp Leu Ser Thr Met Ala
165 170 175

Thr Leu Gly Asn Ser Phe Phe His Lys Leu Cys Ser Gly Phe Ser Gly
180 185 190

Val

<210> SEQ ID NO 53
<211> LENGTH: 165
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

Arg Gly Gln Tyr Ser Arg Glu Asp Asn Asn Cys Thr His Phe Pro Val
1 5 10 15

Gly Gln Ser His Met Leu Leu Glu Leu Arg Thr Ala Phe Ser Gln Val
20 25 30

Lys Thr Phe Phe Gln Thr Lys Asp Gln Leu Asp Asn Ile Leu Leu Thr
35 40 45

Asp Ser Leu Met Gln Asp Phe Lys Gly Tyr Leu Gly Cys Gln Ala Leu
50 55 60

Ser Glu Met Ile Gln Phe Tyr Leu Val Glu Val Met Pro Gln Ala Glu
65 70 75 80

Lys His Gly Pro Glu Ile Lys Glu His Leu Asn Ser Leu Gly Glu Lys
85 90 95

Leu Lys Thr Leu Arg Met Arg Leu Arg Arg Cys His Arg Phe Leu Pro
100 105 110

Cys Glu Asn Lys Ser Lys Ala Val Glu Gln Val Lys Ser Asp Phe Asn
115 120 125

Lys Leu Gln Asp Gln Gly Val Tyr Lys Ala Met Asn Glu Phe Asp Ile
130 135 140

Phe Ile Asn Cys Ile Glu Ala Tyr Met Met Ile Lys Met Lys Ser His
145 150 155 160

His His His His His
165

<210> SEQ ID NO 54
<211> LENGTH: 758
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

Glu Ala His Lys Ser Glu Ile Ala His Arg Tyr Asn Asp Leu Gly Glu
1 5 10 15

Gln His Phe Lys Gly Leu Val Leu Ile Ala Phe Ser Gln Tyr Leu Gln
20 25 30

Lys Cys Ser Tyr Asp Glu His Ala Lys Leu Val Gln Glu Val Thr Asp
35 40 45

Phe Ala Lys Thr Cys Val Ala Asp Glu Ser Ala Ala Asn Cys Asp Lys
50 55 60

Ser Leu His Thr Leu Phe Gly Asp Lys Leu Cys Ala Ile Pro Asn Leu

```
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
    290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
    370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
    450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495
```

```
Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
    530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala Gly Gly Gly Ser Gly Gly Gly Ser
            580                 585                 590

Ser Arg Gly Gln Tyr Ser Arg Glu Asp Asn Asn Cys Thr His Phe Pro
        595                 600                 605

Val Gly Gln Ser His Met Leu Leu Glu Leu Arg Thr Ala Phe Ser Gln
    610                 615                 620

Val Lys Thr Phe Phe Gln Thr Lys Asp Gln Leu Asp Asn Ile Leu Leu
625                 630                 635                 640

Thr Asp Ser Leu Met Gln Asp Phe Lys Gly Tyr Leu Gly Cys Gln Ala
                645                 650                 655

Leu Ser Glu Met Ile Gln Phe Tyr Leu Val Glu Val Met Pro Gln Ala
            660                 665                 670

Glu Lys His Gly Pro Glu Ile Lys Glu His Leu Asn Ser Leu Gly Glu
        675                 680                 685

Lys Leu Lys Thr Leu Arg Met Arg Leu Arg Arg Cys His Arg Phe Leu
    690                 695                 700

Pro Cys Glu Asn Lys Ser Lys Ala Val Glu Gln Val Lys Ser Asp Phe
705                 710                 715                 720

Asn Lys Leu Gln Asp Gln Gly Val Tyr Lys Ala Met Asn Glu Phe Asp
                725                 730                 735

Ile Phe Ile Asn Cys Ile Glu Ala Tyr Met Met Ile Lys Met Lys Ser
            740                 745                 750

His His His His His His
        755


<210> SEQ ID NO 55
<211> LENGTH: 959
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Cys Ser Gln Pro Leu Asp Val Val Leu Leu Leu Asp Gly Ser Ser Ser
1               5                   10                  15

Leu Pro Glu Ser Ser Phe Asp Lys Met Lys Ser Phe Ala Lys Ala Phe
            20                  25                  30

Ile Ser Lys Ala Asn Ile Gly Pro His Leu Thr Gln Val Ser Val Ile
        35                  40                  45

Gln Tyr Gly Ser Ile Asn Thr Ile Asp Val Pro Trp Asn Val Val Gln
    50                  55                  60

Glu Lys Ala His Leu Gln Ser Leu Val Asp Leu Met Gln Gln Glu Gly
65                  70                  75                  80

Gly Pro Ser Gln Ile Gly Asp Ala Leu Ala Phe Ala Val Arg Tyr Val
```

```
                85                  90                  95

Thr Ser Gln Ile His Gly Ala Arg Pro Gly Ala Ser Lys Ala Val Val
            100                 105                 110

Ile Ile Ile Met Asp Thr Ser Leu Asp Pro Val Asp Thr Ala Ala Asp
        115                 120                 125

Ala Ala Arg Ser Asn Arg Val Ala Val Phe Pro Val Gly Val Gly Asp
    130                 135                 140

Arg Tyr Asp Glu Ala Gln Leu Arg Ile Leu Ala Gly Pro Gly Ala Ser
145                 150                 155                 160

Ser Asn Val Val Lys Leu Gln Gln Val Glu Asp Leu Ser Thr Met Ala
                165                 170                 175

Thr Leu Gly Asn Ser Phe Phe His Lys Leu Cys Ser Gly Phe Ser Gly
            180                 185                 190

Val Gly Gly Gly Ser Gly Gly Gly Ser Glu Ala His Lys Ser Glu Ile
        195                 200                 205

Ala His Arg Tyr Asn Asp Leu Gly Glu Gln His Phe Lys Gly Leu Val
    210                 215                 220

Leu Ile Ala Phe Ser Gln Tyr Leu Gln Lys Cys Ser Tyr Asp Glu His
225                 230                 235                 240

Ala Lys Leu Val Gln Glu Val Thr Asp Phe Ala Lys Thr Cys Val Ala
                245                 250                 255

Asp Glu Ser Ala Ala Asn Cys Asp Lys Ser Leu His Thr Leu Phe Gly
            260                 265                 270

Asp Lys Leu Cys Ala Ile Pro Asn Leu Arg Glu Asn Tyr Gly Glu Leu
        275                 280                 285

Ala Asp Cys Cys Thr Lys Gln Glu Pro Glu Arg Asn Glu Cys Phe Leu
    290                 295                 300

Gln His Lys Asp Asp Asn Pro Ser Leu Pro Pro Phe Glu Arg Pro Glu
305                 310                 315                 320

Ala Glu Ala Met Cys Thr Ser Phe Lys Glu Asn Pro Thr Thr Phe Met
                325                 330                 335

Gly His Tyr Leu His Glu Val Ala Arg Arg His Pro Tyr Phe Tyr Ala
            340                 345                 350

Pro Glu Leu Leu Tyr Tyr Ala Glu Gln Tyr Asn Glu Ile Leu Thr Gln
        355                 360                 365

Cys Cys Ala Glu Ala Asp Lys Glu Ser Cys Leu Thr Pro Lys Leu Asp
    370                 375                 380

Gly Val Lys Glu Lys Ala Leu Val Ser Ser Val Arg Gln Arg Met Lys
385                 390                 395                 400

Cys Ser Ser Met Gln Lys Phe Gly Glu Arg Ala Phe Lys Ala Trp Ala
                405                 410                 415

Val Ala Arg Leu Ser Gln Thr Phe Pro Asn Ala Asp Phe Ala Glu Ile
            420                 425                 430

Thr Lys Leu Ala Thr Asp Leu Thr Lys Val Asn Lys Glu Cys Cys His
        435                 440                 445

Gly Asp Leu Leu Glu Cys Ala Asp Asp Arg Ala Glu Leu Ala Lys Tyr
    450                 455                 460

Met Cys Glu Asn Gln Ala Thr Ile Ser Ser Lys Leu Gln Thr Cys Cys
465                 470                 475                 480

Asp Lys Pro Leu Leu Lys Lys Ala His Cys Leu Ser Glu Val Glu His
                485                 490                 495

Asp Thr Met Pro Ala Asp Leu Pro Ala Ile Ala Ala Asp Phe Val Glu
            500                 505                 510
```

```
Asp Gln Glu Val Cys Lys Asn Tyr Ala Glu Ala Lys Asp Val Phe Leu
        515                 520                 525

Gly Thr Phe Leu Tyr Glu Tyr Ser Arg Arg His Pro Asp Tyr Ser Val
    530                 535                 540

Ser Leu Leu Leu Arg Leu Ala Lys Lys Tyr Glu Ala Thr Leu Glu Lys
545                 550                 555                 560

Cys Cys Ala Glu Ala Asn Pro Pro Ala Cys Tyr Gly Thr Val Leu Ala
                565                 570                 575

Glu Phe Gln Pro Leu Val Glu Glu Pro Lys Asn Leu Val Lys Thr Asn
            580                 585                 590

Cys Asp Leu Tyr Glu Lys Leu Gly Glu Tyr Gly Phe Gln Asn Ala Ile
        595                 600                 605

Leu Val Arg Tyr Thr Gln Lys Ala Pro Gln Val Ser Thr Pro Thr Leu
    610                 615                 620

Val Glu Ala Ala Arg Asn Leu Gly Arg Val Gly Thr Lys Cys Cys Thr
625                 630                 635                 640

Leu Pro Glu Asp Gln Arg Leu Pro Cys Val Glu Asp Tyr Leu Ser Ala
                645                 650                 655

Ile Leu Asn Arg Val Cys Leu Leu His Glu Lys Thr Pro Val Ser Glu
            660                 665                 670

His Val Thr Lys Cys Cys Ser Gly Ser Leu Val Glu Arg Arg Pro Cys
        675                 680                 685

Phe Ser Ala Leu Thr Val Asp Glu Thr Tyr Val Pro Lys Glu Phe Lys
    690                 695                 700

Ala Glu Thr Phe Thr Phe His Ser Asp Ile Cys Thr Leu Pro Glu Lys
705                 710                 715                 720

Glu Lys Gln Ile Lys Lys Gln Thr Ala Leu Ala Glu Leu Val Lys His
                725                 730                 735

Lys Pro Lys Ala Thr Ala Glu Gln Leu Lys Thr Val Met Asp Asp Phe
            740                 745                 750

Ala Gln Phe Leu Asp Thr Cys Cys Lys Ala Ala Asp Lys Asp Thr Cys
        755                 760                 765

Phe Ser Thr Glu Gly Pro Asn Leu Val Thr Arg Cys Lys Asp Ala Leu
    770                 775                 780

Ala Gly Gly Gly Ser Gly Gly Gly Ser Ser Arg Gly Gln Tyr Ser Arg
785                 790                 795                 800

Glu Asp Asn Asn Cys Thr His Phe Pro Val Gly Gln Ser His Met Leu
                805                 810                 815

Leu Glu Leu Arg Thr Ala Phe Ser Gln Val Lys Thr Phe Phe Gln Thr
            820                 825                 830

Lys Asp Gln Leu Asp Asn Ile Leu Leu Thr Asp Ser Leu Met Gln Asp
        835                 840                 845

Phe Lys Gly Tyr Leu Gly Cys Gln Ala Leu Ser Glu Met Ile Gln Phe
    850                 855                 860

Tyr Leu Val Glu Val Met Pro Gln Ala Glu Lys His Gly Pro Glu Ile
865                 870                 875                 880

Lys Glu His Leu Asn Ser Leu Gly Glu Lys Leu Lys Thr Leu Arg Met
                885                 890                 895

Arg Leu Arg Arg Cys His Arg Phe Leu Pro Cys Glu Asn Lys Ser Lys
            900                 905                 910

Ala Val Glu Gln Val Lys Ser Asp Phe Asn Lys Leu Gln Asp Gln Gly
        915                 920                 925
```

```
Val Tyr Lys Ala Met Asn Glu Phe Asp Ile Phe Ile Asn Cys Ile Glu
    930                 935                 940

Ala Tyr Met Met Ile Lys Met Lys Ser His His His His His His
945                 950                 955


<210> SEQ ID NO 56
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met His Ile His Gly Cys Asp Lys Asn His Leu Arg Glu Ile Ile Gly
1               5                   10                  15

Ile Leu Asn Glu Val Thr Gly Glu Gly Thr Pro Cys Thr Glu Met Asp
            20                  25                  30

Val Pro Asn Val Leu Thr Ala Thr Lys Asn Thr Thr Glu Ser Glu Leu
        35                  40                  45

Val Cys Arg Ala Ser Lys Val Leu Arg Ile Phe Tyr Leu Lys His Gly
    50                  55                  60

Lys Thr Pro Cys Leu Lys Lys Asn Ser Ser Val Leu Met Glu Leu Gln
65                  70                  75                  80

Arg Leu Phe Arg Ala Phe Arg Cys Leu Asp Ser Ser Ile Ser Cys Thr
                85                  90                  95

Met Asn Glu Ser Lys Ser Thr Ser Leu Lys Asp Phe Leu Glu Ser Leu
            100                 105                 110

Lys Ser Ile Met Gln Met Asp Tyr Ser His His His His His His
        115                 120                 125


<210> SEQ ID NO 57
<211> LENGTH: 720
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140
```

-continued

```
Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
    290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
    370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
    450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
    530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
```

```
                565                 570                 575

Thr Arg Cys Lys Asp Ala Leu Ala Gly Gly Gly Gly Ser Gly Gly Gly
            580                 585                 590

Ser Met His Ile His Gly Cys Asp Lys Asn His Leu Arg Glu Ile Ile
        595                 600                 605

Gly Ile Leu Asn Glu Val Thr Gly Glu Gly Thr Pro Cys Thr Glu Met
    610                 615                 620

Asp Val Pro Asn Val Leu Thr Ala Thr Lys Asn Thr Thr Glu Ser Glu
625                 630                 635                 640

Leu Val Cys Arg Ala Ser Lys Val Leu Arg Ile Phe Tyr Leu Lys His
                645                 650                 655

Gly Lys Thr Pro Cys Leu Lys Lys Asn Ser Ser Val Leu Met Glu Leu
            660                 665                 670

Gln Arg Leu Phe Arg Ala Phe Arg Cys Leu Asp Ser Ser Ile Ser Cys
        675                 680                 685

Thr Met Asn Glu Ser Lys Ser Thr Ser Leu Lys Asp Phe Leu Glu Ser
    690                 695                 700

Leu Lys Ser Ile Met Gln Met Asp Tyr Ser His His His His His His
705                 710                 715                 720


<210> SEQ ID NO 58
<211> LENGTH: 202
<212> TYPE: PRT
<213> ORGANISM: Mus sp.

<400> SEQUENCE: 58

Gln Val Glu Val Val Thr Gln Asp Glu Arg Lys Ala Leu His Thr Thr
1               5                   10                  15

Ala Ser Leu Arg Cys Ser Leu Lys Thr Ser Gln Glu Pro Leu Ile Val
            20                  25                  30

Thr Trp Gln Lys Lys Lys Ala Val Ser Pro Glu Asn Met Val Thr Tyr
        35                  40                  45

Ser Lys Thr His Gly Val Val Ile Gln Pro Ala Tyr Lys Asp Arg Ile
    50                  55                  60

Asn Val Thr Glu Leu Gly Leu Trp Asn Ser Ser Ile Thr Phe Trp Asn
65                  70                  75                  80

Thr Thr Leu Glu Asp Glu Gly Cys Tyr Met Cys Leu Phe Asn Thr Phe
                85                  90                  95

Gly Ser Gln Lys Val Ser Gly Thr Ala Cys Leu Thr Leu Tyr Val Gln
            100                 105                 110

Pro Ile Val His Leu His Tyr Asn Tyr Phe Glu Asp His Leu Asn Ile
        115                 120                 125

Thr Cys Ser Ala Thr Ala Arg Pro Ala Pro Ala Ile Ser Trp Lys Gly
    130                 135                 140

Thr Gly Thr Gly Ile Glu Asn Ser Thr Glu Ser His Phe His Ser Asn
145                 150                 155                 160

Gly Thr Thr Ser Val Thr Ser Ile Leu Arg Val Lys Asp Pro Lys Thr
                165                 170                 175

Gln Val Gly Lys Glu Val Ile Cys Gln Val Leu Tyr Leu Gly Asn Val
            180                 185                 190

Ile Asp Tyr Lys Gln Ser Leu Asp Lys Gly
        195                 200


<210> SEQ ID NO 59
<211> LENGTH: 202
```

<212> TYPE: PRT
<213> ORGANISM: Homo sapiens

<400> SEQUENCE: 59

```
Gln Val Gln Val Val Thr Gln Asp Glu Arg Glu Gln Leu Tyr Thr Pro
1               5                   10                  15

Ala Ser Leu Lys Cys Ser Leu Gln Asn Ala Gln Glu Ala Leu Ile Val
            20                  25                  30

Thr Trp Gln Lys Lys Lys Ala Val Ser Pro Glu Asn Met Val Thr Phe
        35                  40                  45

Ser Glu Asn His Gly Val Val Ile Gln Pro Ala Tyr Lys Asp Lys Ile
    50                  55                  60

Asn Ile Thr Gln Leu Gly Leu Gln Asn Ser Thr Ile Thr Phe Trp Asn
65                  70                  75                  80

Ile Thr Leu Glu Asp Glu Gly Cys Tyr Met Cys Leu Phe Asn Thr Phe
                85                  90                  95

Gly Phe Gly Lys Ile Ser Gly Thr Ala Cys Leu Thr Val Tyr Val Gln
            100                 105                 110

Pro Ile Val Ser Leu His Tyr Lys Phe Ser Glu Asp His Leu Asn Ile
        115                 120                 125

Thr Cys Ser Ala Thr Ala Arg Pro Ala Pro Met Val Phe Trp Lys Val
    130                 135                 140

Pro Arg Ser Gly Ile Glu Asn Ser Thr Val Thr Leu Ser His Pro Asn
145                 150                 155                 160

Gly Thr Thr Ser Val Thr Ser Ile Leu His Ile Lys Asp Pro Lys Asn
                165                 170                 175

Gln Val Gly Lys Glu Val Ile Cys Gln Val Leu His Leu Gly Thr Val
            180                 185                 190

Thr Asp Phe Lys Gln Thr Val Asn Lys Gly
        195                 200
```

<210> SEQ ID NO 60
<211> LENGTH: 585
<212> TYPE: PRT
<213> ORGANISM: Unknown
<220> FEATURE:
<223> OTHER INFORMATION: Description of Unknown:
serum albumin sequence

<400> SEQUENCE: 60

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125
```

```
Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
```

545 550 555 560

Ala Asp Asp Lys Glu Thr Cys Phe Ala Glu Glu Gly Lys Lys Leu Val
565 570 575

Ala Ala Ser Gln Ala Ala Leu Gly Leu
580 585

<210> SEQ ID NO 61
<211> LENGTH: 795
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

Gln Val Gln Val Val Thr Gln Asp Glu Arg Glu Gln Leu Tyr Thr Pro
1 5 10 15

Ala Ser Leu Lys Cys Ser Leu Gln Asn Ala Gln Glu Ala Leu Ile Val
20 25 30

Thr Trp Gln Lys Lys Lys Ala Val Ser Pro Glu Asn Met Val Thr Phe
35 40 45

Ser Glu Asn His Gly Val Val Ile Gln Pro Ala Tyr Lys Asp Lys Ile
50 55 60

Asn Ile Thr Gln Leu Gly Leu Gln Asn Ser Thr Ile Thr Phe Trp Asn
65 70 75 80

Ile Thr Leu Glu Asp Glu Gly Cys Tyr Met Cys Leu Phe Asn Thr Phe
85 90 95

Gly Phe Gly Lys Ile Ser Gly Thr Ala Cys Leu Thr Val Tyr Val Gln
100 105 110

Pro Ile Val Ser Leu His Tyr Lys Phe Ser Glu Asp His Leu Asn Ile
115 120 125

Thr Cys Ser Ala Thr Ala Arg Pro Ala Pro Met Val Phe Trp Lys Val
130 135 140

Pro Arg Ser Gly Ile Glu Asn Ser Thr Val Thr Leu Ser His Pro Asn
145 150 155 160

Gly Thr Thr Ser Val Thr Ser Ile Leu His Ile Lys Asp Pro Lys Asn
165 170 175

Gln Val Gly Lys Glu Val Ile Cys Gln Val Leu His Leu Gly Thr Val
180 185 190

Thr Asp Phe Lys Gln Thr Val Asn Lys Gly Gly Gly Gly Ser Gly Gly
195 200 205

Gly Ser Asp Ala His Lys Ser Glu Val Ala His Arg Phe Lys Asp Leu
210 215 220

Gly Glu Glu Asn Phe Lys Ala Leu Val Leu Ile Ala Phe Ala Gln Tyr
225 230 235 240

Leu Gln Gln Cys Pro Phe Glu Asp His Val Lys Leu Val Asn Glu Val
245 250 255

Thr Glu Phe Ala Lys Thr Cys Val Ala Asp Glu Ser Ala Glu Asn Cys
260 265 270

Asp Lys Ser Leu His Thr Leu Phe Gly Asp Lys Leu Cys Thr Val Ala
275 280 285

Thr Leu Arg Glu Thr Tyr Gly Glu Met Ala Asp Cys Cys Ala Lys Gln
290 295 300

Glu Pro Glu Arg Asn Glu Cys Phe Leu Gln His Lys Asp Asp Asn Pro
305 310 315 320

```
Asn Leu Pro Arg Leu Val Arg Pro Glu Val Asp Val Met Cys Thr Ala
                325                 330                 335

Phe His Asp Asn Glu Glu Thr Phe Leu Lys Lys Tyr Leu Tyr Glu Ile
            340                 345                 350

Ala Arg Arg His Pro Tyr Phe Tyr Ala Pro Glu Leu Leu Phe Phe Ala
        355                 360                 365

Lys Arg Tyr Lys Ala Ala Phe Thr Glu Cys Cys Gln Ala Ala Asp Lys
    370                 375                 380

Ala Ala Cys Leu Leu Pro Lys Leu Asp Glu Leu Arg Asp Glu Gly Lys
385                 390                 395                 400

Ala Ser Ser Ala Lys Gln Arg Leu Lys Cys Ala Ser Leu Gln Lys Phe
                405                 410                 415

Gly Glu Arg Ala Phe Lys Ala Trp Ala Val Ala Arg Leu Ser Gln Arg
            420                 425                 430

Phe Pro Lys Ala Glu Phe Ala Glu Val Ser Lys Leu Val Thr Asp Leu
        435                 440                 445

Thr Lys Val His Thr Glu Cys Cys His Gly Asp Leu Leu Glu Cys Ala
    450                 455                 460

Asp Asp Arg Ala Asp Leu Ala Lys Tyr Ile Cys Glu Asn Gln Asp Ser
465                 470                 475                 480

Ile Ser Ser Lys Leu Lys Glu Cys Cys Glu Lys Pro Leu Leu Glu Lys
                485                 490                 495

Ser His Cys Ile Ala Glu Val Glu Asn Asp Glu Met Pro Ala Asp Leu
            500                 505                 510

Pro Ser Leu Ala Ala Asp Phe Val Glu Ser Lys Asp Val Cys Lys Asn
        515                 520                 525

Tyr Ala Glu Ala Lys Asp Val Phe Leu Gly Met Phe Leu Tyr Glu Tyr
    530                 535                 540

Ala Arg Arg His Pro Asp Tyr Ser Val Val Leu Leu Leu Arg Leu Ala
545                 550                 555                 560

Lys Thr Tyr Glu Thr Thr Leu Glu Lys Cys Cys Ala Ala Ala Asp Pro
                565                 570                 575

His Glu Cys Tyr Ala Lys Val Phe Asp Glu Phe Lys Pro Leu Val Glu
            580                 585                 590

Glu Pro Gln Asn Leu Ile Lys Gln Asn Cys Glu Leu Phe Glu Gln Leu
        595                 600                 605

Gly Glu Tyr Lys Phe Gln Asn Ala Leu Leu Val Arg Tyr Thr Lys Lys
    610                 615                 620

Val Pro Gln Val Ser Thr Pro Thr Leu Val Glu Val Ser Arg Asn Leu
625                 630                 635                 640

Gly Lys Val Gly Ser Lys Cys Cys Lys His Pro Glu Ala Lys Arg Met
                645                 650                 655

Pro Cys Ala Glu Asp Tyr Leu Ser Val Val Leu Asn Gln Leu Cys Val
            660                 665                 670

Leu His Glu Lys Thr Pro Val Ser Asp Arg Val Thr Lys Cys Cys Thr
        675                 680                 685

Glu Ser Leu Val Asn Arg Arg Pro Cys Phe Ser Ala Leu Glu Val Asp
    690                 695                 700

Glu Thr Tyr Val Pro Lys Glu Phe Asn Ala Glu Thr Phe Thr Phe His
705                 710                 715                 720

Ala Asp Ile Cys Thr Leu Ser Glu Lys Glu Arg Gln Ile Lys Lys Gln
                725                 730                 735

Thr Ala Leu Val Glu Leu Val Lys His Lys Pro Lys Ala Thr Lys Glu
```

```
            740                 745                 750

Gln Leu Lys Ala Val Met Asp Asp Phe Ala Ala Phe Val Glu Lys Cys
        755                 760                 765

Cys Lys Ala Asp Asp Lys Glu Thr Cys Phe Ala Glu Glu Gly Lys Lys
    770                 775                 780

Leu Val Ala Ala Ser Gln Ala Ala Leu Gly Leu
785                 790                 795


<210> SEQ ID NO 62
<211> LENGTH: 403
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Glu Val Val Thr Gln Asp Glu Arg Lys Ala Leu His Thr Thr
1               5                   10                  15

Ala Ser Leu Arg Cys Ser Leu Lys Thr Ser Gln Glu Pro Leu Ile Val
            20                  25                  30

Thr Trp Gln Lys Lys Lys Ala Val Ser Pro Glu Asn Met Val Thr Tyr
        35                  40                  45

Ser Lys Thr His Gly Val Val Ile Gln Pro Ala Tyr Lys Asp Arg Ile
    50                  55                  60

Asn Val Thr Glu Leu Gly Leu Trp Asn Ser Ser Ile Thr Phe Trp Asn
65                  70                  75                  80

Thr Thr Leu Glu Asp Glu Gly Cys Tyr Met Cys Leu Phe Asn Thr Phe
                85                  90                  95

Gly Ser Gln Lys Val Ser Gly Thr Ala Cys Leu Thr Leu Tyr Val Gln
            100                 105                 110

Pro Ile Val His Leu His Tyr Asn Tyr Phe Glu Asp His Leu Asn Ile
        115                 120                 125

Thr Cys Ser Ala Thr Ala Arg Pro Ala Pro Ala Ile Ser Trp Lys Gly
    130                 135                 140

Thr Gly Thr Gly Ile Glu Asn Ser Thr Glu Ser His Phe His Ser Asn
145                 150                 155                 160

Gly Thr Thr Ser Val Thr Ser Ile Leu Arg Val Lys Asp Pro Lys Thr
                165                 170                 175

Gln Val Gly Lys Glu Val Ile Cys Gln Val Leu Tyr Leu Gly Asn Val
            180                 185                 190

Ile Asp Tyr Lys Gln Ser Leu Asp Lys Gly Gly Gly Gly Ser Gly Gly
        195                 200                 205

Gly Ser Cys Ser Gln Pro Leu Asp Val Ile Leu Leu Leu Asp Gly Ser
    210                 215                 220

Ser Ser Phe Pro Ala Ser Tyr Phe Asp Glu Met Lys Ser Phe Ala Lys
225                 230                 235                 240

Ala Phe Ile Ser Lys Ala Asn Ile Gly Pro Arg Leu Thr Gln Val Ser
                245                 250                 255

Val Leu Gln Tyr Gly Ser Ile Thr Thr Ile Asp Val Pro Trp Asn Val
            260                 265                 270

Val Pro Glu Lys Ala His Leu Leu Ser Leu Val Asp Val Met Gln Arg
        275                 280                 285

Glu Gly Gly Pro Ser Gln Ile Gly Asp Ala Leu Gly Phe Ala Val Arg
    290                 295                 300
```

Tyr Leu Thr Ser Glu Met His Gly Ala Arg Pro Gly Ala Ser Lys Ala
305 310 315 320

Val Val Ile Leu Val Thr Asp Val Ser Val Asp Ser Val Asp Ala Ala
325 330 335

Ala Asp Ala Ala Arg Ser Asn Arg Val Thr Val Phe Pro Ile Gly Ile
340 345 350

Gly Asp Arg Tyr Asp Ala Ala Gln Leu Arg Ile Leu Ala Gly Pro Ala
355 360 365

Gly Asp Ser Asn Val Val Lys Leu Gln Arg Ile Glu Asp Leu Pro Thr
370 375 380

Met Val Thr Leu Gly Asn Ser Phe Leu His Lys Leu Cys Ser Gly Phe
385 390 395 400

Val Arg Ile

<210> SEQ ID NO 63
<211> LENGTH: 403
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Gln Val Gln Val Val Thr Gln Asp Glu Arg Glu Gln Leu Tyr Thr Pro
1 5 10 15

Ala Ser Leu Lys Cys Ser Leu Gln Asn Ala Gln Glu Ala Leu Ile Val
20 25 30

Thr Trp Gln Lys Lys Lys Ala Val Ser Pro Glu Asn Met Val Thr Phe
35 40 45

Ser Glu Asn His Gly Val Val Ile Gln Pro Ala Tyr Lys Asp Lys Ile
50 55 60

Asn Ile Thr Gln Leu Gly Leu Gln Asn Ser Thr Ile Thr Phe Trp Asn
65 70 75 80

Ile Thr Leu Glu Asp Glu Gly Cys Tyr Met Cys Leu Phe Asn Thr Phe
85 90 95

Gly Phe Gly Lys Ile Ser Gly Thr Ala Cys Leu Thr Val Tyr Val Gln
100 105 110

Pro Ile Val Ser Leu His Tyr Lys Phe Ser Glu Asp His Leu Asn Ile
115 120 125

Thr Cys Ser Ala Thr Ala Arg Pro Ala Pro Met Val Phe Trp Lys Val
130 135 140

Pro Arg Ser Gly Ile Glu Asn Ser Thr Val Thr Leu Ser His Pro Asn
145 150 155 160

Gly Thr Thr Ser Val Thr Ser Ile Leu His Ile Lys Asp Pro Lys Asn
165 170 175

Gln Val Gly Lys Glu Val Ile Cys Gln Val Leu His Leu Gly Thr Val
180 185 190

Thr Asp Phe Lys Gln Thr Val Asn Lys Gly Gly Gly Gly Ser Gly Gly
195 200 205

Gly Ser Cys Ser Gln Pro Leu Asp Val Ile Leu Leu Leu Asp Gly Ser
210 215 220

Ser Ser Phe Pro Ala Ser Tyr Phe Asp Glu Met Lys Ser Phe Ala Lys
225 230 235 240

Ala Phe Ile Ser Lys Ala Asn Ile Gly Pro Arg Leu Thr Gln Val Ser
245 250 255

```
Val Leu Gln Tyr Gly Ser Ile Thr Thr Ile Asp Val Pro Trp Asn Val
            260                 265                 270

Val Pro Glu Lys Ala His Leu Leu Ser Leu Val Asp Val Met Gln Arg
        275                 280                 285

Glu Gly Gly Pro Ser Gln Ile Gly Asp Ala Leu Gly Phe Ala Val Arg
    290                 295                 300

Tyr Leu Thr Ser Glu Met His Gly Ala Arg Pro Gly Ala Ser Lys Ala
305                 310                 315                 320

Val Val Ile Leu Val Thr Asp Val Ser Val Asp Ser Val Asp Ala Ala
                325                 330                 335

Ala Asp Ala Ala Arg Ser Asn Arg Val Thr Val Phe Pro Ile Gly Ile
            340                 345                 350

Gly Asp Arg Tyr Asp Ala Ala Gln Leu Arg Ile Leu Ala Gly Pro Ala
        355                 360                 365

Gly Asp Ser Asn Val Val Lys Leu Gln Arg Ile Glu Asp Leu Pro Thr
    370                 375                 380

Met Val Thr Leu Gly Asn Ser Phe Leu His Lys Leu Cys Ser Gly Phe
385                 390                 395                 400

Val Arg Ile


<210> SEQ ID NO 64
<211> LENGTH: 995
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Glu Val Val Thr Gln Asp Glu Arg Lys Ala Leu His Thr Thr
1               5                   10                  15

Ala Ser Leu Arg Cys Ser Leu Lys Thr Ser Gln Glu Pro Leu Ile Val
            20                  25                  30

Thr Trp Gln Lys Lys Lys Ala Val Ser Pro Glu Asn Met Val Thr Tyr
        35                  40                  45

Ser Lys Thr His Gly Val Val Ile Gln Pro Ala Tyr Lys Asp Arg Ile
    50                  55                  60

Asn Val Thr Glu Leu Gly Leu Trp Asn Ser Ser Ile Thr Phe Trp Asn
65                  70                  75                  80

Thr Thr Leu Glu Asp Glu Gly Cys Tyr Met Cys Leu Phe Asn Thr Phe
                85                  90                  95

Gly Ser Gln Lys Val Ser Gly Thr Ala Cys Leu Thr Leu Tyr Val Gln
            100                 105                 110

Pro Ile Val His Leu His Tyr Asn Tyr Phe Glu Asp His Leu Asn Ile
        115                 120                 125

Thr Cys Ser Ala Thr Ala Arg Pro Ala Pro Ala Ile Ser Trp Lys Gly
    130                 135                 140

Thr Gly Thr Gly Ile Glu Asn Ser Thr Glu Ser His Phe His Ser Asn
145                 150                 155                 160

Gly Thr Thr Ser Val Thr Ser Ile Leu Arg Val Lys Asp Pro Lys Thr
                165                 170                 175

Gln Val Gly Lys Glu Val Ile Cys Gln Val Leu Tyr Leu Gly Asn Val
            180                 185                 190

Ile Asp Tyr Lys Gln Ser Leu Asp Lys Gly Gly Gly Gly Ser Gly Gly
        195                 200                 205
```

```
Gly Ser Glu Ala His Lys Ser Glu Ile Ala His Arg Tyr Asn Asp Leu
    210                 215                 220

Gly Glu Gln His Phe Lys Gly Leu Val Leu Ile Ala Phe Ser Gln Tyr
225                 230                 235                 240

Leu Gln Lys Cys Ser Tyr Asp Glu His Ala Lys Leu Val Gln Glu Val
                245                 250                 255

Thr Asp Phe Ala Lys Thr Cys Val Ala Asp Glu Ser Ala Ala Asn Cys
            260                 265                 270

Asp Lys Ser Leu His Thr Leu Phe Gly Asp Lys Leu Cys Ala Ile Pro
        275                 280                 285

Asn Leu Arg Glu Asn Tyr Gly Glu Leu Ala Asp Cys Cys Thr Lys Gln
    290                 295                 300

Glu Pro Glu Arg Asn Glu Cys Phe Leu Gln His Lys Asp Asp Asn Pro
305                 310                 315                 320

Ser Leu Pro Pro Phe Glu Arg Pro Glu Ala Glu Ala Met Cys Thr Ser
                325                 330                 335

Phe Lys Glu Asn Pro Thr Thr Phe Met Gly His Tyr Leu His Glu Val
            340                 345                 350

Ala Arg Arg His Pro Tyr Phe Tyr Ala Pro Glu Leu Leu Tyr Tyr Ala
        355                 360                 365

Glu Gln Tyr Asn Glu Ile Leu Thr Gln Cys Cys Ala Glu Ala Asp Lys
    370                 375                 380

Glu Ser Cys Leu Thr Pro Lys Leu Asp Gly Val Lys Glu Lys Ala Leu
385                 390                 395                 400

Val Ser Ser Val Arg Gln Arg Met Lys Cys Ser Ser Met Gln Lys Phe
                405                 410                 415

Gly Glu Arg Ala Phe Lys Ala Trp Ala Val Ala Arg Leu Ser Gln Thr
            420                 425                 430

Phe Pro Asn Ala Asp Phe Ala Glu Ile Thr Lys Leu Ala Thr Asp Leu
        435                 440                 445

Thr Lys Val Asn Lys Glu Cys Cys His Gly Asp Leu Leu Glu Cys Ala
    450                 455                 460

Asp Asp Arg Ala Glu Leu Ala Lys Tyr Met Cys Glu Asn Gln Ala Thr
465                 470                 475                 480

Ile Ser Ser Lys Leu Gln Thr Cys Cys Asp Lys Pro Leu Leu Lys Lys
                485                 490                 495

Ala His Cys Leu Ser Glu Val Glu His Asp Thr Met Pro Ala Asp Leu
            500                 505                 510

Pro Ala Ile Ala Ala Asp Phe Val Glu Asp Gln Glu Val Cys Lys Asn
        515                 520                 525

Tyr Ala Glu Ala Lys Asp Val Phe Leu Gly Thr Phe Leu Tyr Glu Tyr
    530                 535                 540

Ser Arg Arg His Pro Asp Tyr Ser Val Ser Leu Leu Leu Arg Leu Ala
545                 550                 555                 560

Lys Lys Tyr Glu Ala Thr Leu Glu Lys Cys Cys Ala Glu Ala Asn Pro
                565                 570                 575

Pro Ala Cys Tyr Gly Thr Val Leu Ala Glu Phe Gln Pro Leu Val Glu
            580                 585                 590

Glu Pro Lys Asn Leu Val Lys Thr Asn Cys Asp Leu Tyr Glu Lys Leu
        595                 600                 605

Gly Glu Tyr Gly Phe Gln Asn Ala Ile Leu Val Arg Tyr Thr Gln Lys
    610                 615                 620

Ala Pro Gln Val Ser Thr Pro Thr Leu Val Glu Ala Ala Arg Asn Leu
```

```
625                 630                 635                 640

Gly Arg Val Gly Thr Lys Cys Cys Thr Leu Pro Glu Asp Gln Arg Leu
                645                 650                 655

Pro Cys Val Glu Asp Tyr Leu Ser Ala Ile Leu Asn Arg Val Cys Leu
            660                 665                 670

Leu His Glu Lys Thr Pro Val Ser Glu His Val Thr Lys Cys Cys Ser
        675                 680                 685

Gly Ser Leu Val Glu Arg Arg Pro Cys Phe Ser Ala Leu Thr Val Asp
    690                 695                 700

Glu Thr Tyr Val Pro Lys Glu Phe Lys Ala Glu Thr Phe Thr Phe His
705                 710                 715                 720

Ser Asp Ile Cys Thr Leu Pro Glu Lys Glu Lys Gln Ile Lys Lys Gln
                725                 730                 735

Thr Ala Leu Ala Glu Leu Val Lys His Lys Pro Lys Ala Thr Ala Glu
            740                 745                 750

Gln Leu Lys Thr Val Met Asp Asp Phe Ala Gln Phe Leu Asp Thr Cys
        755                 760                 765

Cys Lys Ala Ala Asp Lys Asp Thr Cys Phe Ser Thr Glu Gly Pro Asn
    770                 775                 780

Leu Val Thr Arg Cys Lys Asp Ala Leu Ala Gly Gly Gly Ser Gly Gly
785                 790                 795                 800

Gly Ser Cys Ser Gln Pro Leu Asp Val Ile Leu Leu Leu Asp Gly Ser
                805                 810                 815

Ser Ser Phe Pro Ala Ser Tyr Phe Asp Glu Met Lys Ser Phe Ala Lys
            820                 825                 830

Ala Phe Ile Ser Lys Ala Asn Ile Gly Pro Arg Leu Thr Gln Val Ser
        835                 840                 845

Val Leu Gln Tyr Gly Ser Ile Thr Thr Ile Asp Val Pro Trp Asn Val
    850                 855                 860

Val Pro Glu Lys Ala His Leu Leu Ser Leu Val Asp Val Met Gln Arg
865                 870                 875                 880

Glu Gly Gly Pro Ser Gln Ile Gly Asp Ala Leu Gly Phe Ala Val Arg
                885                 890                 895

Tyr Leu Thr Ser Glu Met His Gly Ala Arg Pro Gly Ala Ser Lys Ala
            900                 905                 910

Val Val Ile Leu Val Thr Asp Val Ser Val Asp Ser Val Asp Ala Ala
        915                 920                 925

Ala Asp Ala Ala Arg Ser Asn Arg Val Thr Val Phe Pro Ile Gly Ile
    930                 935                 940

Gly Asp Arg Tyr Asp Ala Ala Gln Leu Arg Ile Leu Ala Gly Pro Ala
945                 950                 955                 960

Gly Asp Ser Asn Val Val Lys Leu Gln Arg Ile Glu Asp Leu Pro Thr
                965                 970                 975

Met Val Thr Leu Gly Asn Ser Phe Leu His Lys Leu Cys Ser Gly Phe
            980                 985                 990

Val Arg Ile
        995


<210> SEQ ID NO 65
<211> LENGTH: 996
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 65

Gln Val Gln Val Val Thr Gln Asp Glu Arg Glu Gln Leu Tyr Thr Pro
1               5                   10                  15

Ala Ser Leu Lys Cys Ser Leu Gln Asn Ala Gln Glu Ala Leu Ile Val
            20                  25                  30

Thr Trp Gln Lys Lys Lys Ala Val Ser Pro Glu Asn Met Val Thr Phe
        35                  40                  45

Ser Glu Asn His Gly Val Val Ile Gln Pro Ala Tyr Lys Asp Lys Ile
    50                  55                  60

Asn Ile Thr Gln Leu Gly Leu Gln Asn Ser Thr Ile Thr Phe Trp Asn
65                  70                  75                  80

Ile Thr Leu Glu Asp Glu Gly Cys Tyr Met Cys Leu Phe Asn Thr Phe
                85                  90                  95

Gly Phe Gly Lys Ile Ser Gly Thr Ala Cys Leu Thr Val Tyr Val Gln
            100                 105                 110

Pro Ile Val Ser Leu His Tyr Lys Phe Ser Glu Asp His Leu Asn Ile
        115                 120                 125

Thr Cys Ser Ala Thr Ala Arg Pro Ala Pro Met Val Phe Trp Lys Val
    130                 135                 140

Pro Arg Ser Gly Ile Glu Asn Ser Thr Val Thr Leu Ser His Pro Asn
145                 150                 155                 160

Gly Thr Thr Ser Val Thr Ser Ile Leu His Ile Lys Asp Pro Lys Asn
                165                 170                 175

Gln Val Gly Lys Glu Val Ile Cys Gln Val Leu His Leu Gly Thr Val
            180                 185                 190

Thr Asp Phe Lys Gln Thr Val Asn Lys Gly Gly Gly Gly Ser Gly Gly
        195                 200                 205

Gly Ser Asp Ala His Lys Ser Glu Val Ala His Arg Phe Lys Asp Leu
    210                 215                 220

Gly Glu Glu Asn Phe Lys Ala Leu Val Leu Ile Ala Phe Ala Gln Tyr
225                 230                 235                 240

Leu Gln Gln Cys Pro Phe Glu Asp His Val Lys Leu Val Asn Glu Val
                245                 250                 255

Thr Glu Phe Ala Lys Thr Cys Val Ala Asp Glu Ser Ala Glu Asn Cys
            260                 265                 270

Asp Lys Ser Leu His Thr Leu Phe Gly Asp Lys Leu Cys Thr Val Ala
        275                 280                 285

Thr Leu Arg Glu Thr Tyr Gly Glu Met Ala Asp Cys Cys Ala Lys Gln
    290                 295                 300

Glu Pro Glu Arg Asn Glu Cys Phe Leu Gln His Lys Asp Asp Asn Pro
305                 310                 315                 320

Asn Leu Pro Arg Leu Val Arg Pro Glu Val Asp Val Met Cys Thr Ala
                325                 330                 335

Phe His Asp Asn Glu Glu Thr Phe Leu Lys Lys Tyr Leu Tyr Glu Ile
            340                 345                 350

Ala Arg Arg His Pro Tyr Phe Tyr Ala Pro Glu Leu Leu Phe Phe Ala
        355                 360                 365

Lys Arg Tyr Lys Ala Ala Phe Thr Glu Cys Cys Gln Ala Ala Asp Lys
    370                 375                 380

Ala Ala Cys Leu Leu Pro Lys Leu Asp Glu Leu Arg Asp Glu Gly Lys
385                 390                 395                 400

Ala Ser Ser Ala Lys Gln Arg Leu Lys Cys Ala Ser Leu Gln Lys Phe

```
                405                 410                 415

Gly Glu Arg Ala Phe Lys Ala Trp Ala Val Ala Arg Leu Ser Gln Arg
            420                 425                 430

Phe Pro Lys Ala Glu Phe Ala Glu Val Ser Lys Leu Val Thr Asp Leu
        435                 440                 445

Thr Lys Val His Thr Glu Cys Cys His Gly Asp Leu Leu Glu Cys Ala
    450                 455                 460

Asp Asp Arg Ala Asp Leu Ala Lys Tyr Ile Cys Glu Asn Gln Asp Ser
465                 470                 475                 480

Ile Ser Ser Lys Leu Lys Glu Cys Cys Glu Lys Pro Leu Leu Glu Lys
                485                 490                 495

Ser His Cys Ile Ala Glu Val Glu Asn Asp Glu Met Pro Ala Asp Leu
            500                 505                 510

Pro Ser Leu Ala Ala Asp Phe Val Glu Ser Lys Asp Val Cys Lys Asn
        515                 520                 525

Tyr Ala Glu Ala Lys Asp Val Phe Leu Gly Met Phe Leu Tyr Glu Tyr
    530                 535                 540

Ala Arg Arg His Pro Asp Tyr Ser Val Val Leu Leu Leu Arg Leu Ala
545                 550                 555                 560

Lys Thr Tyr Glu Thr Thr Leu Glu Lys Cys Cys Ala Ala Ala Asp Pro
                565                 570                 575

His Glu Cys Tyr Ala Lys Val Phe Asp Glu Phe Lys Pro Leu Val Glu
            580                 585                 590

Glu Pro Gln Asn Leu Ile Lys Gln Asn Cys Glu Leu Phe Glu Gln Leu
        595                 600                 605

Gly Glu Tyr Lys Phe Gln Asn Ala Leu Leu Val Arg Tyr Thr Lys Lys
    610                 615                 620

Val Pro Gln Val Ser Thr Pro Thr Leu Val Glu Val Ser Arg Asn Leu
625                 630                 635                 640

Gly Lys Val Gly Ser Lys Cys Cys Lys His Pro Glu Ala Lys Arg Met
                645                 650                 655

Pro Cys Ala Glu Asp Tyr Leu Ser Val Val Leu Asn Gln Leu Cys Val
            660                 665                 670

Leu His Glu Lys Thr Pro Val Ser Asp Arg Val Thr Lys Cys Cys Thr
        675                 680                 685

Glu Ser Leu Val Asn Arg Arg Pro Cys Phe Ser Ala Leu Glu Val Asp
    690                 695                 700

Glu Thr Tyr Val Pro Lys Glu Phe Asn Ala Glu Thr Phe Thr Phe His
705                 710                 715                 720

Ala Asp Ile Cys Thr Leu Ser Glu Lys Glu Arg Gln Ile Lys Lys Gln
                725                 730                 735

Thr Ala Leu Val Glu Leu Val Lys His Lys Pro Lys Ala Thr Lys Glu
            740                 745                 750

Gln Leu Lys Ala Val Met Asp Asp Phe Ala Ala Phe Val Glu Lys Cys
        755                 760                 765

Cys Lys Ala Asp Asp Lys Glu Thr Cys Phe Ala Glu Glu Gly Lys Lys
    770                 775                 780

Leu Val Ala Ala Ser Gln Ala Ala Leu Gly Leu Gly Gly Gly Ser Gly
785                 790                 795                 800

Gly Gly Ser Cys Ser Gln Pro Leu Asp Val Ile Leu Leu Leu Asp Gly
                805                 810                 815

Ser Ser Ser Phe Pro Ala Ser Tyr Phe Asp Glu Met Lys Ser Phe Ala
            820                 825                 830
```

Lys Ala Phe Ile Ser Lys Ala Asn Ile Gly Pro Arg Leu Thr Gln Val
835 840 845

Ser Val Leu Gln Tyr Gly Ser Ile Thr Thr Ile Asp Val Pro Trp Asn
850 855 860

Val Val Pro Glu Lys Ala His Leu Leu Ser Leu Val Asp Val Met Gln
865 870 875 880

Arg Glu Gly Gly Pro Ser Gln Ile Gly Asp Ala Leu Gly Phe Ala Val
885 890 895

Arg Tyr Leu Thr Ser Glu Met His Gly Ala Arg Pro Gly Ala Ser Lys
900 905 910

Ala Val Val Ile Leu Val Thr Asp Val Ser Val Asp Ser Val Asp Ala
915 920 925

Ala Ala Asp Ala Ala Arg Ser Asn Arg Val Thr Val Phe Pro Ile Gly
930 935 940

Ile Gly Asp Arg Tyr Asp Ala Ala Gln Leu Arg Ile Leu Ala Gly Pro
945 950 955 960

Ala Gly Asp Ser Asn Val Val Lys Leu Gln Arg Ile Glu Asp Leu Pro
965 970 975

Thr Met Val Thr Leu Gly Asn Ser Phe Leu His Lys Leu Cys Ser Gly
980 985 990

Phe Val Arg Ile
995

<210> SEQ ID NO 66
<211> LENGTH: 794
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

Gln Val Glu Val Val Thr Gln Asp Glu Arg Lys Ala Leu His Thr Thr
1 5 10 15

Ala Ser Leu Arg Cys Ser Leu Lys Thr Ser Gln Glu Pro Leu Ile Val
20 25 30

Thr Trp Gln Lys Lys Lys Ala Val Ser Pro Glu Asn Met Val Thr Tyr
35 40 45

Ser Lys Thr His Gly Val Val Ile Gln Pro Ala Tyr Lys Asp Arg Ile
50 55 60

Asn Val Thr Glu Leu Gly Leu Trp Asn Ser Ser Ile Thr Phe Trp Asn
65 70 75 80

Thr Thr Leu Glu Asp Glu Gly Cys Tyr Met Cys Leu Phe Asn Thr Phe
85 90 95

Gly Ser Gln Lys Val Ser Gly Thr Ala Cys Leu Thr Leu Tyr Val Gln
100 105 110

Pro Ile Val His Leu His Tyr Asn Tyr Phe Glu Asp His Leu Asn Ile
115 120 125

Thr Cys Ser Ala Thr Ala Arg Pro Ala Pro Ala Ile Ser Trp Lys Gly
130 135 140

Thr Gly Thr Gly Ile Glu Asn Ser Thr Glu Ser His Phe His Ser Asn
145 150 155 160

Gly Thr Thr Ser Val Thr Ser Ile Leu Arg Val Lys Asp Pro Lys Thr
165 170 175

Gln Val Gly Lys Glu Val Ile Cys Gln Val Leu Tyr Leu Gly Asn Val

-continued

```
            180                 185                 190

Ile Asp Tyr Lys Gln Ser Leu Asp Lys Gly Gly Gly Gly Ser Gly Gly
        195                 200                 205

Gly Ser Glu Ala His Lys Ser Glu Ile Ala His Arg Tyr Asn Asp Leu
    210                 215                 220

Gly Glu Gln His Phe Lys Gly Leu Val Leu Ile Ala Phe Ser Gln Tyr
225                 230                 235                 240

Leu Gln Lys Cys Ser Tyr Asp Glu His Ala Lys Leu Val Gln Glu Val
                245                 250                 255

Thr Asp Phe Ala Lys Thr Cys Val Ala Asp Glu Ser Ala Ala Asn Cys
            260                 265                 270

Asp Lys Ser Leu His Thr Leu Phe Gly Asp Lys Leu Cys Ala Ile Pro
        275                 280                 285

Asn Leu Arg Glu Asn Tyr Gly Glu Leu Ala Asp Cys Cys Thr Lys Gln
    290                 295                 300

Glu Pro Glu Arg Asn Glu Cys Phe Leu Gln His Lys Asp Asp Asn Pro
305                 310                 315                 320

Ser Leu Pro Pro Phe Glu Arg Pro Glu Ala Glu Ala Met Cys Thr Ser
                325                 330                 335

Phe Lys Glu Asn Pro Thr Thr Phe Met Gly His Tyr Leu His Glu Val
            340                 345                 350

Ala Arg Arg His Pro Tyr Phe Tyr Ala Pro Glu Leu Leu Tyr Tyr Ala
        355                 360                 365

Glu Gln Tyr Asn Glu Ile Leu Thr Gln Cys Cys Ala Glu Ala Asp Lys
    370                 375                 380

Glu Ser Cys Leu Thr Pro Lys Leu Asp Gly Val Lys Glu Lys Ala Leu
385                 390                 395                 400

Val Ser Ser Val Arg Gln Arg Met Lys Cys Ser Ser Met Gln Lys Phe
                405                 410                 415

Gly Glu Arg Ala Phe Lys Ala Trp Ala Val Ala Arg Leu Ser Gln Thr
            420                 425                 430

Phe Pro Asn Ala Asp Phe Ala Glu Ile Thr Lys Leu Ala Thr Asp Leu
        435                 440                 445

Thr Lys Val Asn Lys Glu Cys Cys His Gly Asp Leu Leu Glu Cys Ala
    450                 455                 460

Asp Asp Arg Ala Glu Leu Ala Lys Tyr Met Cys Glu Asn Gln Ala Thr
465                 470                 475                 480

Ile Ser Ser Lys Leu Gln Thr Cys Cys Asp Lys Pro Leu Leu Lys Lys
                485                 490                 495

Ala His Cys Leu Ser Glu Val Glu His Asp Thr Met Pro Ala Asp Leu
            500                 505                 510

Pro Ala Ile Ala Ala Asp Phe Val Glu Asp Gln Glu Val Cys Lys Asn
        515                 520                 525

Tyr Ala Glu Ala Lys Asp Val Phe Leu Gly Thr Phe Leu Tyr Glu Tyr
    530                 535                 540

Ser Arg Arg His Pro Asp Tyr Ser Val Ser Leu Leu Leu Arg Leu Ala
545                 550                 555                 560

Lys Lys Tyr Glu Ala Thr Leu Glu Lys Cys Cys Ala Glu Ala Asn Pro
                565                 570                 575

Pro Ala Cys Tyr Gly Thr Val Leu Ala Glu Phe Gln Pro Leu Val Glu
            580                 585                 590

Glu Pro Lys Asn Leu Val Lys Thr Asn Cys Asp Leu Tyr Glu Lys Leu
        595                 600                 605
```

```
Gly Glu Tyr Gly Phe Gln Asn Ala Ile Leu Val Arg Tyr Thr Gln Lys
    610                 615                 620

Ala Pro Gln Val Ser Thr Pro Thr Leu Val Glu Ala Ala Arg Asn Leu
625                 630                 635                 640

Gly Arg Val Gly Thr Lys Cys Cys Thr Leu Pro Glu Asp Gln Arg Leu
                645                 650                 655

Pro Cys Val Glu Asp Tyr Leu Ser Ala Ile Leu Asn Arg Val Cys Leu
            660                 665                 670

Leu His Glu Lys Thr Pro Val Ser Glu His Val Thr Lys Cys Cys Ser
        675                 680                 685

Gly Ser Leu Val Glu Arg Arg Pro Cys Phe Ser Ala Leu Thr Val Asp
    690                 695                 700

Glu Thr Tyr Val Pro Lys Glu Phe Lys Ala Glu Thr Phe Thr Phe His
705                 710                 715                 720

Ser Asp Ile Cys Thr Leu Pro Glu Lys Glu Lys Gln Ile Lys Lys Gln
                725                 730                 735

Thr Ala Leu Ala Glu Leu Val Lys His Lys Pro Lys Ala Thr Ala Glu
            740                 745                 750

Gln Leu Lys Thr Val Met Asp Asp Phe Ala Gln Phe Leu Asp Thr Cys
        755                 760                 765

Cys Lys Ala Ala Asp Lys Asp Thr Cys Phe Ser Thr Glu Gly Pro Asn
    770                 775                 780

Leu Val Thr Arg Cys Lys Asp Ala Leu Ala
785                 790


<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 67

His His His His His His
1               5


<210> SEQ ID NO 68
<211> LENGTH: 11
<212> TYPE: PRT
<213> ORGANISM: Homo sapiens

<400> SEQUENCE: 68

Ser Tyr Ile Arg Ile Ala Asp Thr Asn Ile Thr
1               5                   10


<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Cy7 label

<400> SEQUENCE: 69

Leu Arg Glu Leu His Leu Asn Asn Asn Cys
1               5                   10
```

METHODS AND COMPOSITIONS FOR TREATING INFLAMMATORY AND AUTOIMMUNE CONDITIONS WITH ECM-AFFINITY PEPTIDES LINKED TO ANTI-INFLAMMATORY AGENTS

CROSS-REFERENCE TO RELATED APPLICATIONS

This application is a national phase application under 35 U.S.C. § 371 of International Application No. PCT/US2020/019668 filed Feb. 25, 2020, which claims the benefit of priority of U.S. Provisional Patent Application No. 62/809,988 filed Feb. 25, 2019, all of which are hereby incorporated by reference in their entirety.

BACKGROUND

I. Field of the Invention

The invention generally relates to the field of medicine. More particularly, it concerns compositions and methods involving nucleotide constructs and proteins—including engineered anti-inflammatory agents for targeting inflamed tissues.

II. Background

Therapies against cytokines and their receptors have dramatically altered outcomes for inflammatory and autoimmune diseases, especially in anti-TNF therapy for rheumatoid arthritis (RA) and inflammatory bowel disease (IBD) (1-5). However, currently approved medications do not completely cure most patients and possibly have significant side effects by suppressing systemic immunity (6-10). To enhance the therapeutic outcome and reduce systemic side effects, efficient drug delivery to the inflamed area is promising therapeutic strategies for such diseases. Inflammatory tissue releases a range of mediators that will induce the enhanced permeability and retention (EPR) effect (11-12). The EPR effect results from loose endothelial junctions allowing extravasation of macromolecules and nonfunctional lymphatics, resulting in prolonged retention of macromolecules within the solid tumors and inflamed tissues (11-15). Unlike tumor tissue, inflammatory tissue has functional lymphatic system to excrete agents from there (14-16). Currently, there is no effective way to target inflamed tissues of inflammatory and autoimmune diseases due to rapid clearance from the inflamed tissues. Therefore, there is a need in the art for therapies that directly target the inflamed tissues.

SUMMARY OF INVENTION

The disclosure relates to the engineering of collagen-binding modification of anti-inflammatory agents using collagen-binding peptide (CBP) and vWF A3 to achieve targeted therapy for inflammatory diseases. Accordingly, embodiments of the disclosure relate to a composition comprising an anti-inflammatory agent operatively linked to an extracellular matrix (ECM)-affinity peptide. Aspects of the disclosure also relate to an anti-inflammatory agent operatively linked to a serum protein and compositions containing an anti-inflammatory agent operatively linked to a serum protein. Further aspects of the disclosure relate to a method for treating an autoimmune or inflammatory condition in a subject comprising administering a composition of the disclosure to the subject.

Further aspects of the disclosure relate to a method for reducing inflammation in a subject comprising administering a composition comprising an anti-inflammatory agent operatively linked to an extracellular matrix (ECM)-affinity peptide to the subject. In some embodiments, the inflammation is due to and autoimmune or inflammatory condition and wherein the autoimmune or inflammatory condition comprises inflammatory bowel disease, idiopathic pulmonary fibrosis, multiple sclerosis, type 1 diabetes, or arthritis.

In some embodiments, the anti-inflammatory agent operatively linked to an ECM-affinity peptide comprises a collagen binding domain conjugated to anti-TNFα. In some embodiments, the anti-inflammatory agent operatively linked to an ECM-affinity peptide comprises vWF-A3 operatively linked to IL-4. In some embodiments, the anti-inflammatory agent operatively linked to an ECM-affinity peptide comprises a collagen binding domain conjugated to anti-TGF-β. In some embodiments, the composition is administered systemically. In some embodiments, the composition is administered locally. In some embodiments, the administered dose of the anti-inflammatory agent operatively linked to the ECM-affinity peptide is at least 20% less than the minimum effective dose of the anti-inflammatory agent administered locally without the peptide.

In some embodiments, the anti-inflammatory agent comprises an anti-inflammatory antibody. In some embodiments, the anti-inflammatory antibody comprises an antibody that is specific for TNF-α, IL-1, IL-5, IL-6, IL-6R, IL-12, IL-17A, IL-18, IFN-γ, GM-CSF, CD3, CD20, VLA-4, VLA-5, VCAM-1, TGFβ1, $\alpha_4$-integrin, $\alpha_4\beta_7$-integrin, connective tissue growth factor, platelet-derived growth factor, plasminogen activator inhibitor-1, or insulin-like growth factor-binding protein. In some embodiments, the antibody is an anti-TNF-α, anti-IL-1, anti-IL-5, anti-IL-6, anti-IL-6R, anti-IL-12, anti-IL-17A, anti-IL-18, anti-IFN-γ, anti-GM-CSF, anti-CD3, anti-CD20, anti-VLA-4, anti-VLA-5, anti-VCAM-1, anti-TGF-β1, anti-$\alpha_4$-integrin, anti-$\alpha_4\beta_7$-integrin, anti-connective tissue growth factor, anti-platelet-derived growth factor, anti-plasminogen activator inhibitor-1, or anti-insulin-like growth factor-binding protein antibody. In some embodiments, the anti-inflammatory antibody is a blocking antibody. In some embodiments, the anti-inflammatory antibody is a neutralizing antibody. In some embodiments, the anti-inflammatory antibody is an antagonistic antibody. One or more of these antibodies may be specifically excluded from an embodiment.

In some embodiments, the anti-inflammatory agent comprises an antigen-binding fragment of anti-TNF-α, anti-IL-1, anti-IL-5, anti-IL-6, anti-IL-6R, anti-IL-12, anti-IL-17A, anti-IL-18, anti-IFN-γ, anti-GM-CSF, anti-CD3, anti-CD20, anti-VLA-4, anti-VLA-5, anti-VCAM-1, anti-TGF-β1, anti-$\alpha_4$-integrin, anti-$\alpha_4\beta_7$-integrin, anti-connective tissue growth factor, anti-platelet-derived growth factor, anti-plasminogen activator inhibitor-1, or anti-insulin-like growth factor-binding protein antibody. The antigen binding fragment may comprise a variable light chain region comprising CDR1, CDR2, and CDR3 from an anti-TNF-α, anti-IL-1, anti-IL-5, anti-IL-6, anti-IL-6R, anti-IL-12, anti-IL-17A, anti-IL-18, anti-IFN-γ, anti-GM-CSF, anti-CD3, anti-CD20, anti-VLA-4, anti-VLA-5, anti-VCAM-1, anti-TGF-β1, anti-$\alpha_4$-integrin, anti-$\alpha_4\beta_7$-integrin, anti-connective tissue growth factor, anti-platelet-derived growth factor, anti-plasminogen activator inhibitor-1, or anti-insulin-like growth factor-binding protein antibody and/or a variable heavy chain region comprising CDR1, CDR2, and CDR3 from an anti-TNF-α, anti-IL-1, anti-IL-5, anti-IL-6, anti-IL-6R, anti-IL-12, anti-IL-17A, anti-IL-18, anti-IFN-γ, anti-GM-CSF, anti-CD3, anti-CD20, anti-VLA-4, anti-VLA-5, anti-VCAM-1, anti-TGF-β1, anti-$\alpha_4$-integrin, anti-$\alpha_4\beta_7$-integrin, anti-connective tissue growth factor, anti-platelet-derived growth factor, anti-plasminogen activator inhibitor-1, or anti-insulin-like growth factor-binding protein antibody. In some embodiments the antibody comprises adalimumab, certolizumab, infliximab, golimumab, tocilizumab, rituximab, ustekinumab, natalizumab, vedolizumab, secukinumab, or ixekizumab. In some embodiments, the anti-inflammatory agent comprises an antigen binding fragment derived from adalimumab, certolizumab, infliximab, golimumab, tocilizumab, rituximab, ustekinumab, natalizumab, vedolizumab, secukinumab, or ixekizumab. The antigen binding fragment may comprise a variable light chain region comprising CDR1, CDR2, and CDR3 from adalimumab, certolizumab, infliximab, golimumab, tocilizumab, rituximab, ustekinumab, natalizumab, vedolizumab, secukinumab, or ixekizumab and/or a variable heavy chain region comprising CDR1, CDR2, and CDR3 from adalimumab, certolizumab, infliximab, golimumab, tocilizumab, rituximab, ustekinumab, natalizumab, vedolizumab, secukinumab, or ixekizumab. Examples of antigen binding fragments derived from whole antibodies include minibodies, scFv, chimeric antigen receptors, and diabodies. Also contemplated are bivalent or multi specific constructs derived from one or more of an anti-TNF-α, anti-IL-1, anti-IL-5, anti-IL-6, anti-IL-6R, anti-IL-12, anti-IL-17A, anti-IL-18, anti-IFN-γ, anti-GM-CSF, anti-CD3, anti-CD20, anti-VLA-4, anti-VLA-5, anti-VCAM-1, anti-TGF-β1, anti-$\alpha_4$-integrin, anti-$\alpha_4\beta_7$-integrin, anti-connective tissue growth factor, anti-platelet-derived growth factor, anti-plasminogen activator inhibitor-1, or anti-insulin-like growth factor-binding protein antibody. In some embodiments, the antibody is humanized. In some embodiments, the antibody is a chimeric antibody. One or more of these antibodies or antigen binding fragments may be specifically excluded from an embodiment.

In some embodiments, the antibody comprises an anti-TNF-α antibody. In some embodiments, the antibody comprises an anti-IL-1 antibody. In some embodiments, the antibody comprises an anti-IL-5 antibody. In some embodiments, the antibody comprises an anti-IL-6 antibody. In some embodiments, the antibody comprises an anti-IL-6R antibody. In some embodiments, the antibody comprises an anti-IL-12 antibody. In some embodiments, the antibody comprises an anti-IL-17A antibody. In some embodiments, the antibody comprises an anti-IL-18 antibody. In some embodiments, the antibody comprises an anti-IFN-γ antibody. In some embodiments, the antibody comprises an anti-GM-CSF antibody. In some embodiments, the antibody comprises an anti-CD3 antibody. In some embodiments, the antibody comprises an anti-CD20 antibody. In some embodiments, the antibody comprises an anti-VLA-4 antibody. In some embodiments, the antibody comprises an anti-VLA-5 antibody. In some embodiments, the antibody comprises an anti-VCAM-1 antibody. In some embodiments, the antibody comprises an anti-TGF-β1 antibody. In some embodiments, the antibody comprises an anti-$\alpha_4$-integrin antibody. In some embodiments, the antibody comprises an anti-$\alpha_4\beta_7$-integrin antibody. In some embodiments, the antibody comprises an anti-connective tissue growth factor antibody. In some embodiments, the antibody comprises an anti-platelet-derived growth factor antibody. In some embodiments, the antibody comprises an anti-plasminogen activator inhibitor-1 antibody. In some embodiments, the antibody comprises an anti-insulin-like growth factor-binding protein antibody.

In some embodiments, the anti-inflammatory agent comprises an anti-inflammatory cytokine polypeptide. In some embodiments, the cytokine polypeptide comprises a polypeptide from IL-4, IL-1ra, IL-5, IL-10, IL-11, IL-23, IL-35, IL-36ra, IL-37, interferon-0, TGF-β1, TNF receptor I, and TNF receptor II. In some embodiments, the cytokine polypeptide derived from a human cytokine polypeptide. In some embodiments, the cytokine polypeptide derived from a non-human cytokine polypeptide. In some embodiments, the cytokine polypeptide derived from a mouse, dog, horse, pig, or goat cytokine polypeptide. In some embodiments, the cytokine polypeptide comprises an effector region from one or more of IL-4, IL-1ra, IL-5, IL-10, IL-11, IL-23, IL-35, IL-36ra, IL-37, interferon-0, TGF-β1, TNF receptor I, and TNF receptor II. In some embodiments, the cytokine polypeptide comprises a polypeptide from IL-4. In some embodiments, the cytokine polypeptide comprises a polypeptide from IL-1ra. In some embodiments, the cytokine polypeptide comprises a polypeptide from IL-5. In some embodiments, the cytokine polypeptide comprises a polypeptide from IL-10. In some embodiments, the cytokine polypeptide comprises a polypeptide from IL-11. In some embodiments, the cytokine polypeptide comprises a polypeptide from IL-23, IL-35. In some embodiments, the cytokine polypeptide comprises a polypeptide from IL-36ra. In some embodiments, the cytokine polypeptide comprises a polypeptide from IL-37. In some embodiments, the cytokine polypeptide comprises a polypeptide from interferon-β. In some embodiments, the cytokine polypeptide comprises a polypeptide from TGF-β1. In some embodiments, the cytokine polypeptide comprises a polypeptide from TNF receptor I. In some embodiments, the cytokine polypeptide comprises a polypeptide from TNF receptor II. One or more of these anti-inflammatory polypeptides may be specifically excluded from an embodiment. In some embodiments, the cytokine polypeptide is a human cytokine polypeptide or derived from a human cytokine polypeptide.

In some embodiments, the cytokine polypeptide comprises a polypeptide of SEQ ID NO:18-44 or a fragment thereof or a polypeptide with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity (or any derivable range therein) to a polypeptide having an amino acid sequence of one of SEQ ID NO:18-44 or a fragment thereof. In some embodiments, the anti-inflammatory agent comprises a polypeptide of SEQ ID NO:58 or 59, or fragments thereof or a polypeptide with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity (or any derivable range therein) to a polypeptide having an amino acid sequence of one of SEQ ID NO:58 or 59, or a fragment thereof.

In some embodiments, the anti-inflammatory agent comprises a polypeptide from CD200. In some embodiments, the CD200 polypeptide comprises the extracellular domain of CD200. CD200 (UniProt identifier 054901) is a type-I transmembrane protein that can exert immunosuppressive functions through interaction with its receptor, CD200R1. When cleaved from the surface of the cell, the soluble extracellular domain of CD200 can still bind to and activate CD200R. Embodiments of the disclosure relate to polypeptides comprising at least or at most the extracellular portion of CD200 and a serum protein, such as serum albumin. The polypeptides are useful in the method embodiments of the disclosure. Further embodiments relate to a polypeptide comprising at least or at most the extracellular portion of CD200, serum albumin, and an ECM-affinity polypeptide.

In some embodiments, the ECM-affinity peptide comprises a collagen binding domain. In some embodiments, the polypeptide comprises a collagen binding domain from decorin or von Willebrand factor (VWF). In some embodiments, the ECM-affinity peptide comprises a peptide from placenta growth factor-2 (PlGF-2) or CXCL-12γ. In some embodiments, the ECM-affinity peptide comprises a peptide that is at least 85% identical to one of SEQ ID NOS: 1-17, 47, or 52 or a peptide that is at least 85% identical to a fragment of one of SEQ ID NOS: 1-17, 47, or 52. In some embodiments, the ECM-affinity peptide comprises a peptide that has at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity (or any derivable range therein) with a peptide having an amino acid sequence of one of SEQ ID NOS: 1-17, 47, or 52 or a peptide that has at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity (or any derivable range therein) with a fragment of a peptide having an amino acid sequence of one of SEQ ID NOS: 1-17, 47, or 52.

In some embodiments, the anti-inflammatory agent operatively linked to an extracellular matrix (ECM)-affinity peptide further comprises a serum protein operatively linked to the peptide or agent. In some embodiments, the serum protein is operatively linked to the peptide. In some embodiments, the serum protein is operatively linked to the peptide through a peptide bond. In some embodiments, the serum protein comprises albumin. In some embodiments, the anti-inflammatory agent is amino-proximal to the serum protein. In some embodiments, the anti-inflammatory agent is carboxy-proximal to the serum protein. In some embodiments, the ECM-affinity peptide is amino-proximal to the anti-inflammatory agent. In some embodiments, the ECM-affinity peptide is carboxy-proximal to the anti-inflammatory agent. In some embodiments, the serum protein is amino-proximal to the ECM-affinity peptide. In some embodiments, the serum protein is carboxy-proximal to the ECM-affinity peptide.

A first region is carboxy-proximal to a second region when the first region is attached to the carboxy terminus of the second region. There may be further intervening amino acid residues between the first and second regions. Thus, the regions need not be immediately adjacent, unless specifically specified as not having intervening amino acid residues. The term "amino-proximal" is similarly defined in that a first region is amino-proximal to a second region when the first region is attached to the amino terminus of the second region. Similarly, there may be further intervening amino acid residues between the first and second regions unless stated otherwise. In some embodiments, the composition comprises a collagen binding domain amino-amino proximal to a serum albumin protein, and an IL-10 polypeptide carboxy proximal to the serum albumin protein.

In some embodiments, the peptide is covalently linked to the anti-inflammatory agent and/or other molecules, such as a serum protein. In some embodiments, the peptide is crosslinked to the anti-inflammatory agent through a bifunctional linker. Linkers, such as amino acid or peptidomimetic sequences may be inserted between the peptide and/or antibody sequence. In an embodiment, a fynomer domain is joined to a Heavy (H) chain or Light (L) chain immediately after the last amino acid at the amino($NH_2$)-terminus or the carboxy(C)-terminus of the Heavy (H) chain or the Light (L) chain. Linkers may have one or more properties that include a flexible conformation, an inability to form an ordered secondary structure or a hydrophobic or charged character which could promote or interact with either domain. Examples of amino acids typically found in flexible protein regions may include Gly, Asn and Ser. For example, a suitable peptide linker may be GGGSGGGS (SEQ ID NO:48) or (GGGS)n (SEQ ID NO:49), wherein n=1, 2, 3, 4, 5, 6, 7, 8, 9, or 10 (or any range derivable therein). Other near neutral amino acids, such as Thr and Ala, may also be used in the linker sequence. The length of the linker sequence may vary without significantly affecting the function or activity of the fusion protein (see, e.g., U.S. Pat. No. 6,087,329). In a particular aspect, a peptide and an antibody heavy or light chain are joined by a peptide sequence having from about 1 to 25 amino acid residues. Examples of linkers may also include chemical moieties and conjugating agents, such as sulfo-succinimidyl derivatives (sulfo-SMCC, sulfo-SMPB), disuccinimidyl suberate (DSS), disuccinimidyl glutarate (DSG) and disuccinimidyl tartrate (DST). Examples of linkers further comprise a linear carbon chain, such as CN (where N=1-100 carbon atoms, e.g., N=2, 3, 4, 5, 6, 7, 8, 9, or 10). In some embodiments, the linker can be a dipeptide linker, such as a valine-citrulline (val-cit), a phenylalanine-lysine (phe-lys) linker, or maleimidocapronic-valine-citrulline-p-aminobenzyloxycarbonyl (vc) linker. In some embodiments, the linker is sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its sulfo-NHS ester is reactive toward primary amines (as found in lysine and the protein or peptide N-terminus). Further, the linker may be maleimidocaproyl (mc). In some embodiments, the peptide is linked to the anti-inflammatory agent through a peptide bond. The peptide may be linked to the amino or carboxy terminus of the anti-inflammatory agent. In some embodiments, the peptide is linked to the heavy chain of an anti-inflammatory antibody. In some embodiments, the peptide is linked to the light chain of an anti-inflammatory antibody. In some embodiments, the ratio of peptide to the anti-inflammatory agent is about 1:1 to 5:1. In some embodiments, the ratio of peptide to the anti-inflammatory agent is about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, or 20:1 (or any derivable range therein). One or more of these linkers may be specifically excluded from an embodiment.

In some embodiments, the composition further comprises a second anti-inflammatory agent operatively linked to an extracellular matrix (ECM)-affinity peptide. In some embodiments, the composition further comprises a third, fourth, fifth, or sixth anti-inflammatory agent operatively linked to an extracellular matrix (ECM)-affinity peptide.

In some embodiments, the autoimmune or inflammatory condition comprises inflammatory bowel disease, idiopathic pulmonary fibrosis, multiple sclerosis, type 1 diabetes, Crohn's disease, psoriasis, acute inflammation, chronic inflammation, neuroinflammation, arthritis, rheumatoid arthritis, fibrosis, infection, allergy, inflammatory therapy-related adverse events, and -related inflammatory illness. One or more of these conditions may be specifically excluded from an embodiment.

In some embodiments, the composition is administered systemically. In some embodiments, the composition is administered by intravenous injection. In some embodiments, the composition is administered locally. In some embodiments, the composition is administered to or adjacent to a site of inflammation.

In some embodiments, the administered dose of the composition comprising the anti-inflammatory agent operatively linked to the peptide is less than the minimum effective dose of the anti-inflammatory agent administered without the peptide. In some embodiments, the administered dose of the composition comprising the anti-inflammatory agent operatively linked to the peptide is less than the minimum effective dose of the anti-inflammatory agent administered without the peptide by the same route of administration. In some embodiments, the administered dose of the anti-inflammatory agent operatively linked to the peptide is at least 10% less than the minimum effective dose of the anti-inflammatory agent administered without the peptide. In some embodiments, the administered dose of the anti-inflammatory agent operatively linked to the peptide is at least 10, 15, 20, 25, 30, 35, 40, 45, 50, 55, 60, 65, or 70% less (or any range derivable therein) than the minimum effective dose of the anti-inflammatory agent administered without the peptide.

In some embodiments, the subject has been previously treated with an anti-inflammatory agent, anti-inflammatory therapy, or autoimmune therapy. In some embodiments, the subject has been determined to be non-responsive to the previous treatment. In some embodiments, the subject has not been treated previously for the inflammatory or autoimmune disease. In some embodiments, the method further comprises administration of an additional inflammatory or autoimmune therapy. In some embodiments, the method further comprises administration of a second anti-inflammatory agent operatively linked to an extracellular matrix (ECM)-affinity peptide.

The term "cytokine polypeptide" as used herein refers to a polypeptide, which is cytokine or a receptor binding domain thereof and retains at a portion of cytokine activity.

The terms "protein", "polypeptide" and "peptide" are used interchangeably herein when referring to a gene product comprising a polymer of amino acids.

The terms "subject," "mammal," and "patient" are used interchangeably. In some embodiments, the subject is a mammal. In some embodiments, the subject is a human. In some embodiments, the subject is a mouse, rat, rabbit, dog, donkey, or a laboratory test animal such as fruit fly, zebrafish, etc.

It is contemplated that the methods and compositions include exclusion of any of the embodiments described herein.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." Is is specifically contemplated that x, y, or z may be specifically excluded from an embodiment.

Throughout this application, the term "about" is used according to its plain and ordinary meaning in the area of cell biology to indicate that a value includes the standard deviation of error for the device or method being employed to determine the value.

The term "comprising," which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary of Invention, Detailed Description of the Embodiments, Claims, and description of Figure Legends.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-B. CBP-conjugation provided collagen affinity to αTNF. (A) WT-αTNF and CBP-αTNF analyzed by MALDI-TOF MS. Abscissa is mass to charge ratio (m/z) and ordinate is intensity of doubly charged ions. (B) WT-αTNF and CBP-αTNF binding affinities to collagen types I, II, and III are analyzed by ELISA (n=3, mean+SD).

FIG. 2A-D. CBP-αTNF accumulated in the inflamed paw. Arthritis (CAIA) was induced selectively in right hind paw by passive immunization of anti-collagen antibodies, followed by subcutaneous injection of LPS at right hind footpad and PBS at left hind footpad. On the following day of LPS injection, Cy7 labeled CBP-αTNF and Cy7 labeled WT-αTNF were intravenously injected into naïve and CAIA mice. Representative images of accumulation in arthritic or non-arthritic paws of mice injected with CBP-αTNF (A) and WT-αTNF (B). (C) Changes in radiant efficiency ratio of arthritic paw (right hind) to non-arthritic paw (left hind) in naïve and CAIA mice (n=3-4, mean±SD). (D) Representative histology images of joints in CBP-αTNF-injected CAIA mouse (left, H&E staining; right, immunohistochemistry staining against anti-rat IgG).

FIG. 3A-B. CBP-αTNF suppressed arthritis development more effectively than WT-αTNF. Arthritis was induced by passive immunization of anti-collagen antibodies, followed by intraperitoneal injection of LPS. On the day of LPS injection, control IgG, WT-αTNF, or CBP-αTNF was injected intravenously into the arthritis mice. (A) Arthritis scores represent the mean+SE from six mice. * $P<0.05$, compared with control (Dunnett's multiple comparison test). # $P<0.05$, compared with the scores on day 8 of each treatment group (Tukey's multiple comparison test). (B) Representative H&E image of joints on day 8 in each treatment group. The severity of synovial hyperplasia and bone resorption was scored 0 to 4 as described in Materials and Method. Statistical analysis was performed using the Dunnett's multiple comparison test for the difference between control and the αTNF treatment groups.

FIG. 4A-B. Subcutaneous injection of CBP-αTNF also accumulated in the arthritic paw and suppressed arthritis development. (A) Arthritis was induced selectively in right hind paw by passive immunization of anti-collagen antibodies, followed by subcutaneous injection of LPS at right hind footpad and PBS at left hind footpad. On the following day of LPS injection, Cy7 labeled CBP-αTNF was subcutaneously injected at the back of the mouse. Representative images of accumulation in arthritic or non-arthritic paws of mice injected with CBP-αTNF (indicated by arrows). (B) Arthritis was induced in all paws by passive immunization of anti-collagen antibodies, followed by intraperitoneal injection of LPS. On the day of LPS injection, control IgG, WT-αTNF, or CBP-αTNF was subcutaneously injected. Arthritis scores represent the mean+SE from five mice. # P<0.05, compared with the scores on day 8 of each group (Tukey's multiple comparison test).

FIG. 5A-B. Effect of local injection on arthritis development. Arthritis was induced by passive immunization of anti-collagen antibodies, followed by intraperitoneal injection of LPS. On the day of LPS injection, (A) Cy7 labeled $PlGF-2_{123-144}$-αTNF and Cy7 labeled WT-αTNF or (B) control IgG, WT-αTNF, and $PlGF-2_{123-144}$-αTNF were injected subcutaneously into left hind paw of the arthritis mice. (A) Representative images of retention in the injected site of mice with WT-αTNF and $PlGF-2_{123-144}$-αTNF. (B) Arthritis scores represent the mean±SE from eight mice. # P<0.05, compared with the scores on day 6 of each group (Tukey's multiple comparison test).

FIG. 6A-E. A3-IL4 accumulated in spinal cord and reduced EAE score. Affinity of A3-IL4 against collagen type III (A) and affinity between IL-4 and A3-IL4 protein against IL-4Ra (B) were measured by ELISA. Graph with [concentrations] vs [signals] is shown (n=4). EAE was induced by subcutaneous injection of $MOG_{35-55}$/CFA emulsion, followed by intraperitoneal injections of PTX on the day of immunization and the following day. On day 14 post-immunization, DyLight 800-labeled A3-IL4, A3 protein (C) or Cy7 labeled CBP-αTNF (D) was intravenously injected into naive or EAE mice. Spinal cord was harvested 4 hours after the injection and fluorescent intensity was measured. (E) From day 14 after the EAE immunization, normal form IL-4 or A3-IL4 was injected intravenously every other day. Disease scores of EAE represent the mean±SE (n=3-5).

FIG. 7A-C. Localization of A3 protein and CBP-conjugate in inflamed tissues of other inflammatory disease models. (A) DyLight 800-labeled A3 protein, or Cy7 labeled CBP-αTNF was intravenously injected into $IL-10^{-/-}$×$TLR-4^{-/-}$ (DKO) mice that spontaneously developed or non-developed IBD, or normal (C57BL/6) mice. Colon was harvested 4 hours after the injection, and was provided for fluorescent imaging (upper) and histological analyses (lower). Colon of IBD-developed mouse injected Cy7 labeled CBP-αTNF was stained with H&E and periodic acid-Schiff (PAS). In addition, the injected antibody was detected by immunohistochemistry (IHC) against anti-rat IgG. (B) Cy7 labeled CBP-αTGF or Cy7 labeled αTGF was intravenously injected into naïve mice or bleomycin-induced pulmonary fibrosis model 7 days after the bleomycin instillation. Lung was harvested 4 hours after the fluorescence injection, then fluorescent intensity was measured. (C) DyLight 800-labeled A3 protein was intravenously injected into type I diabetes (T1D) spontaneously developed mouse, cyclophosphamide-induced T1D mouse, and non-diabetic mouse. Pancreas was harvested 15 minutes after the fluorescence injection, then fluorescent intensity was measured.

FIG. 8A-D. Albumin fusion to IL-10 provided FcRn binding and resulted in LN accumulation. (A) SDS-PAGE analysis for wt IL-10 and SA-IL-10. (B) Binding analysis of SA-IL-10 to FcRn. (C) Splenocytes (i) or single cells from the popliteal LN (ii) were incubated with SA, SA-IL-10 or CBD-SA-IL-10 for 30 min on ice. Shown in (i) for each cell type (x axis) is, from left to right, a bar representing the % binding (y-axis) for SA, SA-IL-10, and CBD-SA-IL-10. Shown in (ii) for each cell type (x axis) is, from left to right, a bar representing the % binding (y-axis) for SA and SA-IL-10, respectively. Binding of each protein to immune cells was detected by co-staining with an anti-SA antibody and antibodies for specific markers of each immune cell population. (D) Immunofluorescence images of the popliteal LN after intravenous injection of DyLight594-labeled wt IL-10 or SA-IL-10. T cells and high endothelial venules (HEVs) were respectively stained with anti-CD3 or anti-PNAd antibodies.

FIG. 9A-B. Albumin fusion to IL-10 provided prolonged blood circulation, and CBD fusion improved biodistribution to the inflamed joint. (A) wt IL-10, SA-IL-10, or CBD-SA-IL-10 (each equivalent to 35 μg of IL-10) were administered to BALB/c mice via tail vein injection. Serum was collected at the indicated time points. The serum concentration of IL-10 was measured by ELISA (mean±SEM; n=5). Plasma half-lives of IL-10 were calculated using two-phase exponential decay: MFI $(t)=Ae^{-\alpha t}+Be^{-\beta t}$. $t_{1/2,\ \alpha}$, fast clearance half-life; $t_{1/2,\ \beta}$, slow clearance half-life. Area under curve (AUC) was analyzed by Graphpad Prism. (B) Arthritis (CAIA) was induced selectively in the right hind paw by passive immunization of anti-collagen antibodies, followed by subcutaneous injection of LPS at right hind footpad (defined as Day 3). On the day following LPS injection, DyLight800-labeled wt IL-10, SA-IL-10 or CBD-SA-IL-10 were intravenously injected in the CAIA mice. Four hours after injection, indicated organs were harvested and analyzed using an IVIS imaging system. (mean±SEM; n=4). Statistical analyses were done using analysis of variance (ANOVA) with Tukey's test. *P<0.05; **P<0.01. Shown in (B) for each organ (x axis) is, from left to right, a bar representing the % distribution (y-axis) for wt IL-10, SA-IL-10, and CBD-SA-IL-10, respectively.

FIG. 10A-D. Albumin-fused IL-10 suppressed arthritis development more effectively than wt IL-10. (A) Arthritis (CAIA) was induced by passive immunization with anti-collagen antibodies, followed by intraperitoneal injection of LPS. On the day of LPS injection, PBS, wt IL-10, SA-IL-10 or CBD-SA-IL-10 (equivalent to 43.5 μg of IL-10) was injected intravenously into the arthritic mice. Arthritis scores represent the mean+SEM from 7 mice. (B) Comparison of therapeutic effects of wt IL-10 and CBD-SA-IL-10 with αTNF-α antibody in CAIA mice immunized with high dose (1.5 mg/mouse) of anti-collagen antibodies. Arthritis scores represent the mean+SEM from 6-7 mice. (C) Representative H&E histological image of joints on day 13 in each treatment group. Scale bar, 500 μm. The severity of synovial hyperplasia and bone resorption was scored 0 to 4 as described in Materials and Methods. (D) Effect of administration routes on therapeutic effects of SA-IL-10 and CBD-SA-IL-10. Arthritis scores represent the mean+SEM from 6-7 mice. Statistical analyses were done using analysis of variance (ANOVA) with Tukey's test. *P<0.05; P<0.01; *P<0.001; ****P<0.0001.

FIG. 11A-D. Albumin-fused IL-10 showed improved therapeutic effect on established arthritis. DBA/1J male mice were subcutaneously injected with bovine collagen/CFA emulsion in the tail base. After three weeks, bovine collagen/IFA emulsion was further injected as a boost. When arthritis scores become 2-4 (defined as Day 0), mice were intravenously injected with PBS, SA-IL-10, or CBD-SA-IL-10 (each equivalent to 43.5 μg of IL-10), or with 200 μg of anti-TNF-α antibody. In (A), the same treatments were additionally injected to the mice on Day 3. (A and B) Arthritis scores represent the mean+SEM from 9 mice. (C and D) Representative H&E histological image of joints on day 16. Scale bars, 500 μm. The severity of synovial hyperplasia and bone resorption was scored 0 to 4 as described in Materials and Methods. Statistical analyses were done using analysis of variance (ANOVA) with Tukey's test for (A and B) and a two-tailed Student's t-test for (C and D). *P<0.05; P<0.01; *P<0.001.

FIG. 12A-F. Albumin-fused IL-10 accumulated within and suppressed Th17 activation in LNs. Arthritis (CAIA) was induced by passive immunization of anti-collagen antibodies, followed by intraperitoneal injection of LPS (defined as Day 3). On the day LPS injection, wt IL-10, SA-IL-10 or CBD-SA-IL-10 were intravenously injected into the arthritic mice. IL-10 levels and Th17-relating cytokines in LNs were measured using ELISA. (A) Comparison of IL-10 levels 4 hr after injection of each protein. (B) Pharmacokinetics of wt IL-10 or SA-IL-10 in LNs after intravenous injection. (mean±SEM; n=4) (C) AUC of wt IL-10 and SA-IL-10 in various LNs. Th17-relating cytokine levels in joint-draining (popliteal) LN (D) and a non-draining (cervical) LN (E). (F) GM-CSF levels in the popliteal LN. (mean±SEM; n=7) Statistical analyses were done using analysis of variance (ANOVA) with Tukey's test. *P<0.05; P<0.01; *P<0.001; ****P<0.0001; ns; not significant.

FIG. 13A-C. Albumin-fused IL-10 suppressed inflammatory responses within the paws. Arthritis (CAIA) was induced by passive immunization of anti-collagen antibodies, followed by intraperitoneal injection of LPS. On the day of LPS injection (defined as Day 3), PBS, wt IL-10, SA-IL-10 or CBD-SA-IL-10 were intravenously injected into the arthritic mice. (A) Single cells were extracted from the hind paws on day 11, followed by flow cytometric analysis. Graphs depict the frequency of $CD45^+$ cells, B cells ($B220^+$ cells within $CD45^+$ lymphocytes), dendritic cells ($CD11c^+$ cells within $CD45^+$ lymphocytes), monocytes ($CD11b^+$ cells within $CD45^+$ lymphocytes), granulocytic MDSC/neutrophils ($Ly6G^+$ $Ly6C^+$ $CD11b^+$ $CD45^+$), monocytic MDSC ($Ly6G^-$ $Ly6C^+$ $CD11b^+$ $CD45^+$), macrophages ($F4/80^+$ $CD11b^+$ $CD45^+$), M2 macrophages ($CD206^+$ $F4/80^+$ $CD11b^+$ $CD45^+$), and M1 macrophages (MHC $F4/80^+$ $CD11b^+$ $CD45^+$). (mean±SEM; n=7) (B) Cytokine levels in hind paws on day 11. (n=5-7) (C) Representative H&E images of joints on day 14 in each treatment group. Scale bars, 500 μm. The severity of synovial hyperplasia and bone resorption was scored 0 to 4 as described in Materials and Methods. (mean±SEM; n=6-7). Statistical analyses were done using analysis of variance (ANOVA) with Tukey's test except for % $CD11c^+$ in (A). For analysis of % $CD11c^+$ in (A), Kruskal-Wallis test followed by Dunn's multiple comparison test was employed. *P<0.05; P<0.01; *P<0.001; ****P<0.0001.

FIG. 14A-B. CBD-conjugation provided collagen affinity to IL-10. (A) SDS-PAGE analysis for CBD-SA-IL-10. (B) Binding analysis of CBD-SA-IL-10 to type I or type III collagens and FcRn.

FIG. 18A-D. IL-4 retains activity after fusion of SA. (a) Wt IL-4 and SA-IL-4 were analyzed by SDS-PAGE under reducing and non-reducing conditions with Coomassie blue staining. (b) SA-IL-4 binding to freshly isolated immune cells from LN and spleen, measured by flow cytometry. (c) Wt IL-4 and SA-IL-4 activity assay. Phosphorylation of STATE in the T cells was analyzed by flow cytometry after culturing T cells in vitro with indicated concentrations of wt IL-4 or SA-IL-4. (d) IL-17 concentration secreted under Th17 differentiation conditions in the presence of wt IL-4 or SA-IL-4, measured by ELISA. Data are mean±SEM. Two experimental replicates. Statistical analyses were performed using one-way ANOVA with Tukey's test. **P<0.01.

FIG. 19A-H. SA fusion to IL-4 increased the amount of IL-4 in the secondary lymphoid organs after intravenous injection. (a) Binding affinity of SA-IL-4 to FcRn measured by SPR. (b) Plasma concentration of intravenously injected wt IL-4 or SA-IL-4. Wt IL-4 10 (n=4) or equimolar SA-IL-4 (n=3) was injected intravenously to naïve mice. Blood was collected after 1 min to 24 hr, and the plasma concentration of IL-4 was measured by ELISA. (c-d) Amount of IL-4 in the (c) brachial and lumbar LNs and (d) spleen over time. 40 μg of wt IL-4 or equimolar SA-IL-4 was injected intravenously to naïve mice. LNs and spleen were harvested, and IL-4 amount was tested by ELISA (n=5). (e) SA(P573K)-IL-4 amount in the LNs and spleen was measured 1 hr after injection. Wt IL-4 and SA-IL-4 data from (c-d) are represented. (f-g) Immunofluorescence images of the lumbar LN, 1 hr after intravenous injection of DyLight594-labeled IL-4 or SA-IL-4. T cells and high endothelial venules (HEVs) were respectively stained by anti-CD3 or anti-PNAd antibodies. Scale bars represent (g) 200 μm and (h) 100 μm. Data are mean±SEM. Two experimental replicates. Statistical analyses were performed using one-way ANOVA with Tukey's test. **P<0.01.

FIG. 20A-D. SA-IL-4 prevents EAE disease progression and development in the acute phase. (a) Disease progression with (b) disease incidence and (c) body weight change in C57BL/6 myelin oligodendrocyte glycoprotein $(MOG)_{35-55}$ experimental autoimmune encephalomyelitis (EAE) mice injected every other day for 10 days from day 8 after immunization with phosphate-buffered saline (PBS) intraperitoneally (i.p.), wt IL-4 10 μg i.p., or SA-IL-4 10 μg molar equivalent i.p or subcutaneously (s.c.), or dosed with FTY720 1 mg/kg by oral administration. n=7 per group. (d) Representative histology of spinal cord. Myelin expression was detected by immunohistochemistry with anti-myelin basic protein antibody (brown). Arrows indicate demyelination. Graph represents % of mice showing demyelination in each treatment group by blinded pathology analysis. Two experimental replicates. Data are mean±SEM. Statistical analyses were performed using one-way ANOVA with Tukey's test. **P<0.01.

FIG. 21A-H. SA-IL-4 treatment inhibits leukocyte infiltration to the spinal cord and induces immune suppressive cells in the draining LN. Mice were injected with wt IL-4, SA-IL-4, or PBS i.p. or SA-IL-4 s.c. every other day for 10 days from day 8 after immunization, or FTY720 1 mg/kg body weight was administered orally every day from day 8 after immunization. 17 days after immunization, cells from the draining LN and spinal cord were isolated and analyzed by flow cytometry. (a-b) The frequencies of (a) CD45+ leukocytes and (b) RoR□t+ Th17 cells within live cells in the spinal cord. (c-g) In the lumbar draining LN (dLN), frequencies of (c) Ly6G+Ly6C+G-MDSCs within CD11b+ CD45+ cells, (d) Ly6G-Ly6C+M-MDSCs within CD11b+ CD45+ cells, (e) RoR□t+Th17 cells within CD4+CD3+ T cells, (f) CD86+M1 macrophages within F4/80+CD11b+ macrophages, (g) CD206+M2 macrophages within F4/80+ CD11b+ macrophages, and (h) B220+B cells within CD11b+CD45+ cells were analyzed. Data are mean±SEM. The experiment was performed once. Statistical analyses were performed using one-way ANOVA with Tukey's test. *P<0.05, **P<0.01.

FIG. 22A-P. SA-IL-4 treatment activates the PD-1/PD-L1 axis and decreases integrin and cytokine expression in T cells. $MOG_{35-55}$-induced EAE mice were injected with PBS, wt IL-4 or SA-IL-4 s.c. on days 8, 10 and 12 after immunization. The spinal cord and spleen were isolated on day 13 and (a-i) immune cells were analyzed. Frequencies of (a) $Tetramer^+$ (recognizing $MOG_{35-55}$) cells within $CD4^+$ T cells in the spinal cord. In the spleen, (b) $\alpha L\beta 2$ $integrin^+$ cells within $Tetramer^+$ $CD4^+$ T cells, (c) a4131 $integrin^+$ cells within $Tetramer^+$ $CD4^+$ T cells, (d) $\alpha L\beta 2$ integrin cells within $CD8^+$ T cells, and (e) $\alpha 4\beta 1$ integrin cells within $CD8^+$ T cells, are shown. (f) Mean fluorescence intensity (MFI) of PD-1 of central memory (CM) $CD44^+CD62L^+CD4^+$ T cells, (g) MFI of PD-1 of CM $CD44^+CD62L^+CD8^+$ T cells, (h) MFI of PD-L1 of $Ly6C^+Ly6G^-CD11b^+$ M-MDSC, (i) frequency of $PD\text{-}L1^+$ of $Ly6C^+Ly6G^-CD11b^+$ M-MDSC, (j) MFI of PD-L1 of $Ly6C^+Ly6G^+CD11b^+$ G-MDSC, (k) frequency of $PD\text{-}L1^+$ of $Ly6C^+Ly6G^+CD11b^+$ G-MDSC, (1) frequency of $IL\text{-}23R^+$ cells within $Tetramer^+$ $CD4^+$ T cells. (m-n) Splenocytes were cultured in vitro in the presence of MOG protein for 3 days. (m) IL-17A, (n) IFNγ, (o) GM-CSF concentrations in the culture media were analyzed by ELISA. (p) Splenocytes were cultured in vitro in the presence of $MOG_{35-55}$ peptide for 6 h. Cytokine expression within $CD4^+$ T cells was characterized by flow cytometry. Data are mean±SEM. The experiment was performed once. Statistical analyses were performed using one-way ANOVA with Tukey's test. *P<0.05, **P<0.01.

FIG. 23A-K. SA-IL-4 treatment in the chronic phase of EAE decreases the clinical score and prevents immune cell infiltration to the spinal cord. EAE was induced in C57BL/6 mice using $MOG_{35-55}$. PBS, wt IL-4 or SA-IL-4 was injected i.p. every other day for 10 days from day 21 after immunization. (a) Disease progression and (b) body weight change are shown (n=6). (c-d) PBS, wt IL-4 or SA-IL-4 was injected s.c. every other day for 12 days from day 21 after immunization. (c) Disease progression and (d) body weight change are shown (n=8 for PBS and SA-IL-4; n=7 for other treatment groups). (e-h) On day 34, the spinal cord and spleen were collected and immune cells were analyzed by flow cytometry. Graphs represent frequencies of (e) CD45+ cells within live cells in spinal cord, (f) $CD4^+CD3^+CD45^+$ T cells within live cells in spinal cord, (g) $Tetramer^+$ (recognizing $MOG_{35-55}$) $ROR\gamma t^+CD4^+$ Th17 cells within live cells in spinal cord, (h) $IL\text{-}23R^+$ cells within $Tetramer^+CD4^+$ cells in spleen. (i j) Splenocytes were cultured in vitro in the presence of MOG protein for 3 days. (i) IL-17A, (j) GM-CSF concentrations in the culture media were analyzed by ELISA. (k) Splenocytes were cultured in vitro in the presence of $MOG_{35-55}$ peptide for 6 h. Cytokine expression within $CD4^+$ T cells was characterized by flow cytometry. The experiment was performed once. Data are mean±SEM. Statistical analyses were performed using one-way ANOVA with Tukey's test. *P<0.05, **P<0.01.

FIG. 28A-B. SA-IL-4 did not affect the number of macrophages and dendritic cells in the spinal cord and draining LN. Mice were injected with wt IL-4, SA-IL-4, or PBS i.p. or SA-IL-4 s.c. every other day for 10 days from day 8 after immunization. FTY720 1 mg/kg body weight was administered orally every day from day 8 after immunization. 17 days after immunization, cells from the draining LN (dLN) and spinal cord were isolated and analyzed by flow cytometry. The frequencies of (a) $F4/80^+$ macrophage within $CD11b^+$ cells, and (b) $CD11b^+$ $CD11c^+$ DCs within $CD45^+$ cells were analyzed. Data are mean±SEM. The experiment was performed once. Statistical analyses were performed using one-way ANOVA with Tukey's test.

FIG. 29A-O. Blood and organ analysis of SA-IL-4 revealed SA-IL-4 is safe. Toxicity analysis of SA-IL-4. 10 μg of wt IL-4 or equimolar SA-IL-4 was injected i.v. to naïve mice. After 2 days, (a-i) serum was tested using a biochemistry analyzer and (j-m) blood was tested using a hematology analyzer. Lung water content was determined by weighing the lungs before and after lyophilization. Data are mean±SEM. The experiment was performed once. Statistical analyses were performed using one-way ANOVA with Tukey's test.

DETAILED DESCRIPTION

Figure 13A:
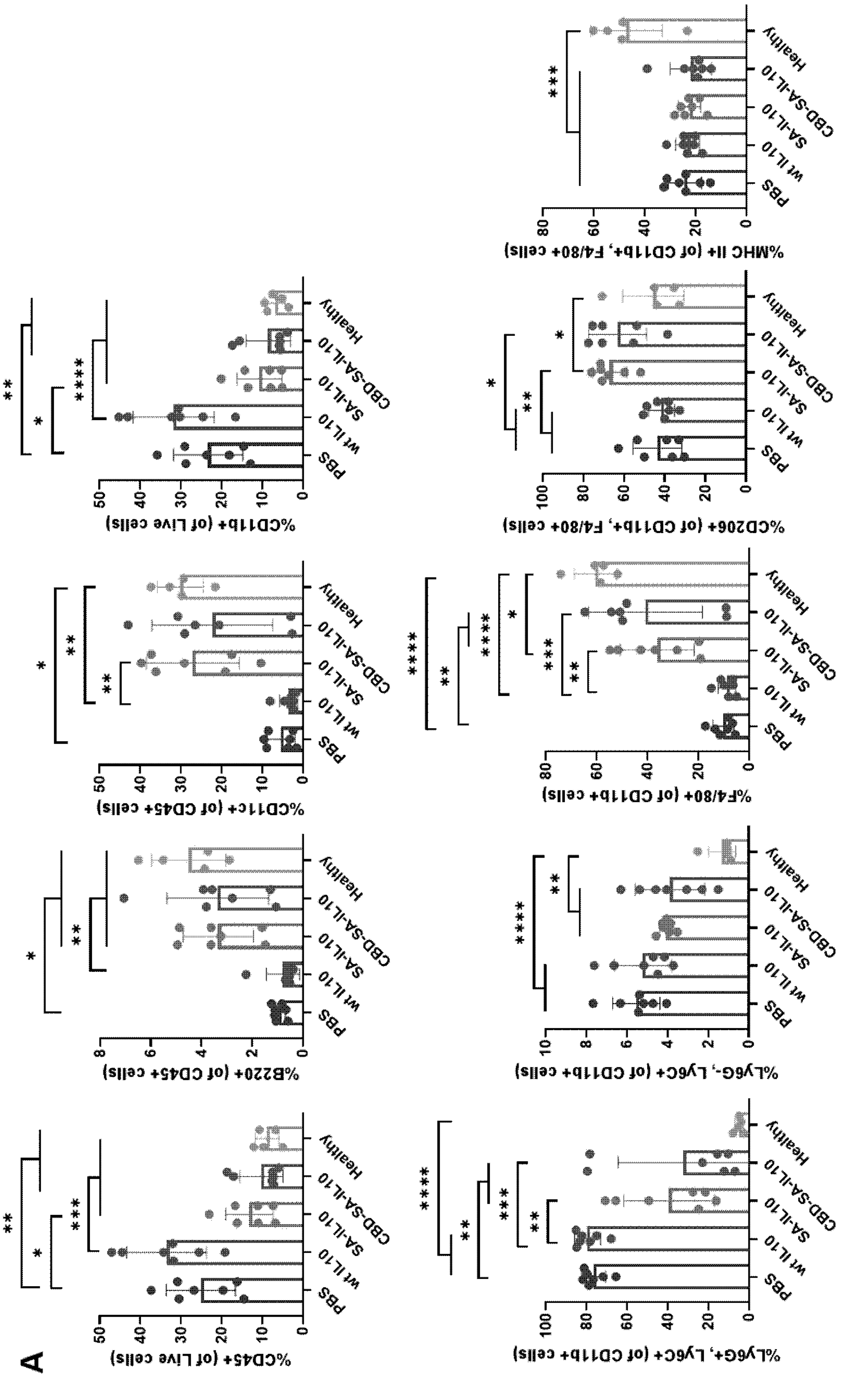

Enhancing therapeutic efficacy of drugs for inflammatory and autoimmune diseases is of huge demand. One possible approach is that targeting anti-inflammatory drugs to inflamed area. Collagens are not accessible in most tissues due to the low permeability of the vasculature, yet are exposed to the bloodstream in the inflamed area due to the hyperpermeability of the vasculature. This disclosure describes ECM-binding anti-inflammatory agents conjugated to ECM-affinity peptides. One such peptide is a collagen-binding peptide (CBP). CBP-conjugation provided collagen affinity to anti-TNFα antibody (αTNF). CBP-αTNF accumulated in inflamed areas of the collagen antibody-induced arthritis model (Example 1). Arthritis development was significantly suppressed by CBP-αTNF compared with the unmodified antibody. Moreover, collagen-binding domain derived from von Willebrand factor (vWF) A3 domain fusion to interleukin (IL)-4 (A3-IL4) enabled it to be detectable in the spinal cord of the experimental autoimmune encephalomyelitis (EAE), a model for multiple sclerosis, following intravenous administration (Example 1). A3-IL4 reduced the clinical symptoms of EAE whereas normal IL-4 did not. Collagen-binding proteins were detectable in the inflamed tissues of the spontaneous inflammatory bowel disease, bleomycin-induced pulmonary fibrosis, and type I diabetes models. Taken together, collagen-affinity enables the anti-inflammatory drugs to target inflamed areas, demonstrating a novel clinically translational approach to treat inflammatory and autoimmune diseases.

III. Anti-inflammatory Agents

A. Antibodies

Aspects of the disclosure relate to anti-inflammatory antibodies or fragments thereof. The term "antibody" refers to an intact immunoglobulin of any isotype, or a fragment thereof that can compete with the intact antibody for specific binding to the target antigen, and includes chimeric, humanized, fully human, and bispecific antibodies. As used herein, the terms "antibody" or "immunoglobulin" are used interchangeably and refer to any of several classes of structurally related proteins that function as part of the immune response of an animal, including IgG, IgD, IgE, IgA, IgM, and related proteins, as well as polypeptides comprising antibody CDR domains that retain antigen-binding activity.

The term "antigen" refers to a molecule or a portion of a molecule capable of being bound by a selective binding agent, such as an antibody. An antigen may possess one or more epitopes that are capable of interacting with different antibodies.

The term "epitope" includes any region or portion of molecule capable eliciting an immune response by binding to an immunoglobulin or to a T-cell receptor. Epitope determinants may include chemically active surface groups such as amino acids, sugar side chains, phosphoryl or sulfonyl groups, and may have specific three-dimensional structural characteristics and/or specific charge characteristics. Generally, antibodies specific for a particular target antigen will preferentially recognize an epitope on the target antigen within a complex mixture.

The epitope regions of a given polypeptide can be identified using many different epitope mapping techniques are well known in the art, including: x-ray crystallography, nuclear magnetic resonance spectroscopy, site-directed mutagenesis mapping, protein display arrays, see, e.g., Epitope Mapping Protocols, (Johan Rockberg and Johan Nilvebrant, Ed., 2018) Humana Press, New York, N.Y. Such techniques are known in the art and described in, e.g., U.S. Pat. No. 4,708,871; Geysen et al. Proc. Natl. Acad. Sci. USA 81:3998-4002 (1984); Geysen et al. Proc. Natl. Acad. Sci. USA 82:178-182 (1985); Geysen et al. Molec. Immunol. 23:709-715 (1986 See, e.g., Epitope Mapping Protocols, supra. Additionally, antigenic regions of proteins can also be predicted and identified using standard antigenicity and hydropathy plots.

An intact antibody is generally composed of two full-length heavy chains and two full-length light chains, but in some instances may include fewer chains, such as antibodies naturally occurring in camelids that may comprise only heavy chains. Antibodies as disclosed herein may be derived solely from a single source or may be "chimeric," that is, different portions of the antibody may be derived from two different antibodies. For example, the variable or CDR regions may be derived from a rat or murine source, while the constant region is derived from a different animal source, such as a human. The antibodies or binding fragments may be produced in hybridomas, by recombinant DNA techniques, or by enzymatic or chemical cleavage of intact antibodies. Unless otherwise indicated, the term "antibody" includes derivatives, variants, fragments, and muteins thereof, examples of which are described below (Sela-Culang et al. Front Immunol. 2013; 4: 302; 2013)

The term "light chain" includes a full-length light chain and fragments thereof having sufficient variable region sequence to confer binding specificity. A full-length light chain has a molecular weight of around 25,000 Daltons and includes a variable region domain (abbreviated herein as VL), and a constant region domain (abbreviated herein as CL). There are two classifications of light chains, identified as kappa (κ) and lambda (k). The term "VL fragment" means a fragment of the light chain of a monoclonal antibody that includes all or part of the light chain variable region, including CDRs. A VL fragment can further include light chain constant region sequences. The variable region domain of the light chain is at the amino-terminus of the polypeptide.

The term "heavy chain" includes a full-length heavy chain and fragments thereof having sufficient variable region sequence to confer binding specificity. A full-length heavy chain has a molecular weight of around 50,000 Daltons and includes a variable region domain (abbreviated herein as VH), and three constant region domains (abbreviated herein as CH1, CH2, and CH3). The term "VH fragment" means a fragment of the heavy chain of a monoclonal antibody that includes all or part of the heavy chain variable region, including CDRs. A VH fragment can further include heavy chain constant region sequences. The number of heavy chain constant region domains will depend on the isotype. The VH domain is at the amino-terminus of the polypeptide, and the CH domains are at the carboxy-terminus, with the CH3 being closest to the —COOH end. The isotype of an antibody can be IgM, IgD, IgG, IgA, or IgE and is defined by the heavy chains present of which there are five classifications: mu (μ), delta (δ), gamma (γ), alpha (α), or epsilon (ε) chains, respectively. IgG has several subtypes, including, but not limited to, IgG1, IgG2, IgG3, and IgG4. IgM subtypes include IgM1 and IgM2. IgA subtypes include IgA1 and IgA2.

Antibodies can be whole immunoglobulins of any isotype or classification, chimeric antibodies, or hybrid antibodies with specificity to two or more antigens. They may also be fragments (e.g., F(ab')2, Fab', Fab, Fv, and the like), including hybrid fragments. An immunoglobulin also includes natural, synthetic, or genetically engineered proteins that act like an antibody by binding to specific antigens to form a complex. The term antibody includes genetically engineered or otherwise modified forms of immunoglobulins, such as the following:

The term "monomer" means an antibody containing only one Ig unit. Monomers are the basic functional units of antibodies. The term "dimer" means an antibody containing two Ig units attached to one another via constant domains of the antibody heavy chains (the Fc, or fragment crystallizable, region). The complex may be stabilized by a joining (J) chain protein. The term "multimer" means an antibody containing more than two Ig units attached to one another via constant domains of the antibody heavy chains (the Fc region). The complex may be stabilized by a joining (J) chain protein.

The term "bivalent antibody" means an antibody that comprises two antigen-binding sites. The two binding sites may have the same antigen specificities or they may be bispecific, meaning the two antigen-binding sites have different antigen specificities.

Bispecific antibodies are a class of antibodies that have two paratopes with different binding sites for two or more distinct epitopes. In some embodiments, bispecific antibodies can be biparatopic, wherein a bispecific antibody may specifically recognize a different epitope from the same antigen. In some embodiments, bispecific antibodies can be constructed from a pair of different single domain antibodies termed "nanobodies". Single domain antibodies are sourced and modified from cartilaginous fish and camelids. Nanobodies can be joined together by a linker using techniques typical to a person skilled in the art; such methods for selection and joining of nanobodies are described in PCT Publication No. WO2015044386A1, No. WO2010037838A2, and Bever et al., Anal Chem. 86:7875-7882 (2014), each of which are specifically incorporated herein by reference in their entirety.

Bispecific antibodies can be constructed as: a whole IgG, Fab'2, Fab'PEG, a diabody, or alternatively as scFv. Diabodies and scFvs can be constructed without an Fc region, using only variable domains, potentially reducing the effects of anti-idiotypic reaction. Bispecific antibodies may be produced by a variety of methods including, but not limited to, fusion of hybridomas or linking of Fab' fragments. See, e.g., Songsivilai and Lachmann, Clin. Exp. Immunol. 79:315-321 (1990); Kostelny et al., J. Immunol. 148:1547-1553 (1992), each of which are specifically incorporated by reference in their entirety.

In certain aspects, the antigen-binding domain may be multispecific or heterospecific by multimerizing with VH and VL region pairs that bind a different antigen. For example, the antibody may bind to, or interact with, (a) a cell surface antigen, (b) an Fc receptor on the surface of an effector cell, or (c) at least one other component. Accordingly, aspects may include, but are not limited to, bispecific, trispecific, tetraspecific, and other multispecific antibodies or antigen-binding fragments thereof that are directed to epitopes and to other targets, such as Fc receptors on effector cells.

In some embodiments, multispecific antibodies can be used and directly linked via a short flexible polypeptide chain, using routine methods known in the art. One such example is diabodies that are bivalent, bispecific antibodies in which the VH and VL domains are expressed on a single polypeptide chain, and utilize a linker that is too short to allow for pairing between domains on the same chain, thereby forcing the domains to pair with complementary domains of another chain creating two antigen binding sites. The linker functionality is applicable for embodiments of triabodies, tetrabodies, and higher order antibody multimers. (see, e.g., Hollinger et al., Proc Natl. Acad. Sci. USA 90:6444-6448 (1993); Polijak et al., Structure 2:1121-1123 (1994); Todorovska et al., J. Immunol. Methods 248:47-66 (2001)).

Bispecific diabodies, as opposed to bispecific whole antibodies, may also be advantageous because they can be readily constructed and expressed in *E. coli*. Diabodies (and other polypeptides such as antibody fragments) of appropriate binding specificities can be readily selected using phage display (WO94/13804) from libraries. If one arm of the diabody is kept constant, for instance, with a specificity directed against a protein, then a library can be made where the other arm is varied and an antibody of appropriate specificity selected. Bispecific whole antibodies may be made by alternative engineering methods as described in Ridgeway et al., (Protein Eng., 9:616-621, 1996) and Krah et al., (N Biotechnol. 39:167-173, 2017), each of which is hereby incorporated by reference in their entirety.

Heteroconjugate antibodies are composed of two covalently linked monoclonal antibodies with different specificities. See, e.g., U.S. Pat. No. 6,010,902, incorporated herein by reference in its entirety.

The part of the Fv fragment of an antibody molecule that binds with high specificity to the epitope of the antigen is referred to herein as the "paratope." The paratope consists of the amino acid residues that make contact with the epitope of an antigen to facilitate antigen recognition. Each of the two Fv fragments of an antibody is composed of the two variable domains, VH and VL, in dimerized configuration. The primary structure of each of the variable domains includes three hypervariable loops separated by, and flanked by, Framework Regions (FR). The hypervariable loops are the regions of highest primary sequences variability among the antibody molecules from any mammal. The term hypervariable loop is sometimes used interchangeably with the term "Complementarity Determining Region (CDR)." The length of the hypervariable loops (or CDRs) varies between antibody molecules. The framework regions of all antibody molecules from a given mammal have high primary sequence similarity/consensus. The consensus of framework regions can be used by one skilled in the art to identify both the framework regions and the hypervariable loops (or CDRs) which are interspersed among the framework regions. The hypervariable loops are given identifying names which distinguish their position within the polypeptide, and on which domain they occur. CDRs in the VL domain are identified as L1, L2, and L3, with L1 occurring at the most distal end and L3 occurring closest to the CL domain. The CDRs may also be given the names CDR-1, CDR-2, and CDR-3. The L3 (CDR-3) is generally the region of highest variability among all antibody molecules produced by a given organism. The CDRs are regions of the polypeptide chain arranged linearly in the primary structure, and separated from each other by Framework Regions. The amino terminal (N-terminal) end of the VL chain is named FR1. The region identified as FR2 occurs between L1 and L2 hypervariable loops. FR3 occurs between L2 and L3 hypervariable loops, and the FR4 region is closest to the CL domain. This structure and nomenclature is repeated for the VH chain, which includes three CDRs identified as H1, H2 and H3. The majority of amino acid residues in the variable domains, or Fv fragments (VH and VL), are part of the framework regions (approximately 85%). The three dimensional, or tertiary, structure of an antibody molecule is such that the framework regions are more internal to the molecule and provide the majority of the structure, with the CDRs on the external surface of the molecule.

Several methods have been developed and can be used by one skilled in the art to identify the exact amino acids that constitute each of these regions. This can be done using any of a number of multiple sequence alignment methods and algorithms, which identify the conserved amino acid residues that make up the framework regions, therefore identifying the CDRs that may vary in length but are located between framework regions. Three commonly used methods have been developed for identification of the CDRs of antibodies: Kabat (as described in T. T. Wu and E. A. Kabat, "AN ANALYSIS OF THE SEQUENCES OF THE VARIABLE REGIONS OF BENCE JONES PROTEINS AND MYELOMA LIGHT CHAINS AND THEIR IMPLICATIONS FOR ANTIBODY COMPLEMENTARITY," *J Exp Med*, vol. 132, no. 2, pp. 211-250, August 1970); Chothia (as described in C. Chothia et al., "Conformations of immunoglobulin hypervariable regions," *Nature*, vol. 342, no. 6252, pp. 877-883, December 1989); and IMGT (as described in M.-P. Lefranc et al., "IMGT unique numbering for immunoglobulin and T cell receptor variable domains and Ig superfamily V-like domains," *Developmental & Comparative Immunology*, vol. 27, no. 1, pp. 55-77, January 2003). These methods each include unique numbering systems for the identification of the amino acid residues that constitute the variable regions. In most antibody molecules, the amino acid residues that actually contact the epitope of the antigen occur in the CDRs, although in some cases, residues within the framework regions contribute to antigen binding.

One skilled in the art can use any of several methods to determine the paratope of an antibody. These methods include:

1) Computational predictions of the tertiary structure of the antibody/epitope binding interactions based on the chemical nature of the amino acid sequence of the antibody variable region and composition of the epitope.
2) Hydrogen-deuterium exchange and mass spectroscopy
3) Polypeptide fragmentation and peptide mapping approaches in which one generates multiple overlapping peptide fragments from the full length of the polypeptide and evaluates the binding affinity of these peptides for the epitope.
4) Antibody Phage Display Library analysis in which the antibody Fab fragment encoding genes of the mammal are expressed by bacteriophage in such a way as to be incorporated into the coat of the phage. This population of Fab expressing phage are then allowed to interact with the antigen which has been immobilized or may be expressed in by a different exogenous expression system. Non-binding Fab fragments are washed away, thereby leaving only the specific binding Fab fragments attached to the antigen. The binding Fab fragments can be readily isolated and the genes which encode them determined. This approach can also be used for smaller regions of the Fab fragment including Fv fragments or specific VH and VL domains as appropriate.

In certain aspects, affinity matured antibodies are enhanced with one or more modifications in one or more CDRs thereof that result in an improvement in the affinity of the antibody for a target antigen as compared to a parent antibody that does not possess those alteration(s). Certain affinity matured antibodies will have nanomolar or picomolar affinities for the target antigen. Affinity matured antibodies are produced by procedures known in the art, e.g., Marks et al., Bio/Technology 10:779 (1992) describes affinity maturation by VH and VL domain shuffling, random mutagenesis of CDR and/or framework residues employed in phage display is described by Rajpal et al., PNAS. 24: 8466-8471 (2005) and Thie et al., Methods Mol Biol. 525:309-22 (2009) in conjugation with computation methods as demonstrated in Tiller et al., Front. Immunol. 8:986 (2017).

Chimeric immunoglobulins are the products of fused genes derived from different species; "humanized" chimeras generally have the framework region (FR) from human immunoglobulins and one or more CDRs are from a non-human source.

In certain aspects, portions of the heavy and/or light chain are identical or homologous to corresponding sequences from another particular species or belonging to a particular antibody class or subclass, while the remainder of the chain(s) is identical or homologous to corresponding sequences in antibodies derived from another species or belonging to another antibody class or subclass, as well as fragments of such antibodies, so long as they exhibit the desired biological activity. U.S. Pat. No. 4,816,567; and Morrison et al., Proc. Natl. Acad. Sci. USA 81:6851 (1984). For methods relating to chimeric antibodies, see, e.g., U.S. Pat. No. 4,816,567; and Morrison et al., Proc. Natl. Acad.

Sci. USA 81:6851-6855 (1985), each of which are specifically incorporated herein by reference in their entirety. CDR grafting is described, for example, in U.S. Pat. Nos. 6,180,370, 5,693,762, 5,693,761, 5,585,089, and 5,530,101, which are all hereby incorporated by reference for all purposes.

In some embodiments, minimizing the antibody polypeptide sequence from the non-human species optimizes chimeric antibody function and reduces immunogenicity. Specific amino acid residues from non-antigen recognizing regions of the non-human antibody are modified to be homologous to corresponding residues in a human antibody or isotype. One example is the "CDR-grafted" antibody, in which an antibody comprises one or more CDRs from a particular species or belonging to a specific antibody class or subclass, while the remainder of the antibody chain(s) is identical or homologous to a corresponding sequence in antibodies derived from another species or belonging to another antibody class or subclass. For use in humans, the V region composed of CDR1, CDR2, and partial CDR3 for both the light and heavy chain variance region from a non-human immunoglobulin, are grafted with a human antibody framework region, replacing the naturally occurring antigen receptors of the human antibody with the non-human CDRs. In some instances, corresponding non-human residues replace framework region residues of the human immunoglobulin. Furthermore, humanized antibodies may comprise residues that are not found in the recipient antibody or in the donor antibody to further refine performance. The humanized antibody may also comprise at least a portion of an immunoglobulin constant region (Fc), typically that of a human immunoglobulin. See, e.g., Jones et al., Nature 321:522 (1986); Riechmann et al., Nature 332:323 (1988); Presta, Curr. Op. Struct. Biol. 2:593 (1992); Vaswani and Hamilton, Ann. Allergy, Asthma and Immunol. 1:105 (1998); Harris, Biochem. Soc. Transactions 23; 1035 (1995); Hurle and Gross, Curr. Op. Biotech. 5:428 (1994); Verhoeyen et al., Science 239:1534-36 (1988).

Intrabodies are intracellularly localized immunoglobulins that bind to intracellular antigens as opposed to secreted antibodies, which bind antigens in the extracellular space.

Polyclonal antibody preparations typically include different antibodies against different determinants (epitopes). In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

Monoclonal antibodies or "mAb" refer to an antibody obtained from a population of homogeneous antibodies from an exclusive parental cell, e.g., the population is identical except for naturally occurring mutations that may be present in minor amounts. Each monoclonal antibody is directed against a single antigenic determinant.

1. Functional Antibody Fragments and Antigen-Binding Fragments a. Antigen-Binding Fragments Certain aspects relate to antibody fragments, such as antibody fragments that bind to and/or neutralize inflammatory mediators. The term functional antibody fragment includes antigen-binding fragments of an antibody that retain the ability to specifically bind to an antigen. These fragments are constituted of various arrangements of the variable region heavy chain (VH) and/or light chain (VL); and in some embodiments, include constant region heavy chain 1 (CH1) and light chain (CL). In some embodiments, they lack the Fc region constituted of heavy chain 2 (CH2) and 3 (CH3) domains. Embodiments of antigen binding fragments and the modifications thereof may include: (i) the Fab fragment type constituted with the VL, VH, CL, and CH1 domains; (ii) the Fd fragment type constituted with the VH and CH1 domains; (iii) the Fv fragment type constituted with the VH and VL domains; (iv) the single domain fragment type, dAb, (Ward, 1989; McCafferty et al., 1990; Holt et al., 2003) constituted with a single VH or VL domain; (v) isolated complementarity determining region (CDR) regions. Such terms are described, for example, in Harlow and Lane, Antibodies: A Laboratory Manual, Cold Spring Harbor Laboratory, N Y (1989); Molec. Biology and Biotechnology: A Comprehensive Desk Reference (Myers, R. A. (ed.), New York: VCH Publisher, Inc.); Huston et al., Cell Biophysics, 22:189-224 (1993); Pluckthun and Skerra, Meth. Enzymol., 178:497-515 (1989) and in Day, E. D., Advanced Immunochemistry, 2d ed., Wiley-Liss, Inc. New York, N.Y. (1990); Antibodies, 4:259-277 (2015). The citations in this paragraph are all incorporated by reference.

Antigen-binding fragments also include fragments of an antibody that retain exactly, at least, or at most 1, 2, or 3 complementarity determining regions (CDRs) from a light chain variable region. Fusions of CDR-containing sequences to an Fc region (or a CH2 or CH3 region thereof) are included within the scope of this definition including, for example, scFv fused, directly or indirectly, to an Fc region are included herein.

The term Fab fragment means a monovalent antigen-binding fragment of an antibody containing the VL, VH, CL and CH1 domains. The term Fab' fragment means a monovalent antigen-binding fragment of a monoclonal antibody that is larger than a Fab fragment. For example, a Fab' fragment includes the VL, VH, CL and CH1 domains and all or part of the hinge region. The term F(ab')2 fragment means a bivalent antigen-binding fragment of a monoclonal antibody comprising two Fab' fragments linked by a disulfide bridge at the hinge region. An F(ab')2 fragment includes, for example, all or part of the two VH and VL domains, and can further include all or part of the two CL and CH1 domains.

The term Fd fragment means a fragment of the heavy chain of a monoclonal antibody, which includes all or part of the VH, including the CDRs. An Fd fragment can further include CH1 region sequences.

The term Fv fragment means a monovalent antigen-binding fragment of a monoclonal antibody, including all or part of the VL and VH, and absent of the CL and CH1 domains. The VL and VH include, for example, the CDRs. Single-chain antibodies (sFv or scFv) are Fv molecules in which the VL and VH regions have been connected by a flexible linker to form a single polypeptide chain, which forms an antigen-binding fragment. Single chain antibodies are discussed in detail in International Patent Application Publication No. WO 88/01649 and U.S. Pat. Nos. 4,946,778 and 5,260,203, the disclosures of which are herein incorporated by reference. The term (scFv)2 means bivalent or bispecific sFv polypeptide chains that include oligomerization domains at their C-termini, separated from the sFv by a hinge region (Pack et al. 1992). The oligomerization domain comprises self-associating a-helices, e.g., leucine zippers, which can be further stabilized by additional disulfide bonds. (scFv)2 fragments are also known as "miniantibodies" or "minibodies."

A single domain antibody is an antigen-binding fragment containing only a VH or the VL domain. In some instances, two or more VH regions are covalently joined with a peptide linker to create a bivalent domain antibody. The two VH regions of a bivalent domain antibody may target the same or different antigens.

b. Fragment Crystallizable Region, Fc

An Fc region contains two heavy chain fragments comprising the CH2 and CH3 domains of an antibody. The two heavy chain fragments are held together by two or more disulfide bonds and by hydrophobic interactions of the CH3 domains. The term "Fc polypeptide" as used herein includes native and mutein forms of polypeptides derived from the Fc region of an antibody. Truncated forms of such polypeptides containing the hinge region that promotes dimerization are included.

2. Polypeptides with Antibody CDRs & Scaffolding Domains that Display the CDRs

Antigen-binding peptide scaffolds, such as complementarity-determining regions (CDRs), are used to generate protein-binding molecules in accordance with the embodiments. Generally, a person skilled in the art can determine the type of protein scaffold on which to graft at least one of the CDRs. It is known that scaffolds, optimally, must meet a number of criteria such as: good phylogenetic conservation; known three-dimensional structure; small size; few or no post-transcriptional modifications; and/or be easy to produce, express, and purify. Skerra, J Mol Recognit, 13:167-87 (2000).

The protein scaffolds can be sourced from, but not limited to: fibronectin type III FN3 domain (known as "monobodies"), fibronectin type III domain 10, lipocalin, anticalin, Z-domain of protein A of *Staphylococcus aureus*, thioredoxin A or proteins with a repeated motif such as the "ankyrin repeat", the "armadillo repeat", the "leucine-rich repeat" and the "tetratricopeptide repeat". Such proteins are described in US Patent Publication Nos. 2010/0285564, 2006/0058510, 2006/0088908, 2005/0106660, and PCT Publication No. WO2006/056464, each of which are specifically incorporated herein by reference in their entirety. Scaffolds derived from toxins from scorpions, insects, plants, mollusks, etc., and the protein inhibiters of neuronal NO synthase (PIN) may also be used.

B. Cytokines

Cytokines are a group of proteins that cells release upon excitation (only very few cytokines are expressed on cell membranes). Cytokines produced by cells can affect target cells nearby or through blood circulation at very low concentration. They have broad functions on promoting growth, differentiation, and activation of target cells. Many cytokines can target immune cells and play a role in immune response. Based on structural and functional differences, cytokines may be broadly divided into chemokines, interleukins, growth factors, transforming growth factors, colony stimulating factors, tumor necrosis factors, and interferons.

The following cytokines may be used as anti-inflammatory agents in methods and compositions of the disclosure. While exemplary sequences are provided below, equivalent or homologous proteins known in the art may also be used.

Human IL-1ra:
(SEQ ID NO: 18)
RPSGRKSSKMQAFRIWDVNQKTFYLRNNQLVAGYLQGPNVNLEEKIDVVPIEPHALF
LGIHGGKMCLSCVKSGDETRLQLEAVNITDLSENRKQDKRFAFIRSDSGPTTSFESAA
CPGW FLCTAMEADQPVSLTNMPDEGVMVTKFYFQ EDE.

Mouse IL-1ra:
(SEQ ID NO: 19)
RPSGKRPCKMQAFRIWDTNQKTFYLRNNQLIAGYLQGPNIKLEEKIDMVPIDLHSVFL
GIHGGKLCLSCAKSGDDIKLQLEEVNITDLSKNKEEDKRFTFIRSEKGPTTSFESAACP
GWFLCTTLEADRPVSLTNTPEEPLIVTKFYFQEDQ Human IL-4:
(SEQ ID NO: 20)
HKCDITLQEIIKTLNSLTEQKTLCTELTVTDIFAASKNTTEKETFCRAATVLRQFYSHH
EKDTRCLGATAQQFHRHKQLIRFLKRLDRNLWGLAGLNSCPVKEANQSTLENFLER
LKTIMREKYSKCSS.

Mouse IL-4:
(SEQ ID NO: 21)
HIHGCDKNHLREIIGILNEVTGEGTPCTEMDVPNVLTATKNTTESELVCRASKVLRIF
YLKHGKTPCLKKNSSVLMELQRLFRAFRCLDSSISCTMNESKSTSLKDFLESLKSIMQ
MDYS Human IL-5:
(SEQ ID NO: 22)
IPTEIPTSALVKETLALLSTHRTLLIANETLRIPVPVHKNHQLCTEEIFQGIGTLESQTVQ
GGTVERLFKNLSLIKKYIDGQKKKCGEERRRVNQFLDYLQEFLGVNINTEWIIES.

Mouse IL-5:
(SEQ ID NO: 23)
EIPMSTVVKETLTQLSAHRALLTSNETMRLPVPTHKNHQLCIGEIFQGLDILKNQTVR
GGTVEMLFQNLSLIKKYIDRQKEKCGEERRRTRQFLDYLQEFLGVMSTEWAMEG.

-continued

Human IL-10:

(SEQ ID NO: 24)
SPGQGTQSENSCTHFPGNLPNMLRDLRDAFSRVKTFFQMKDQLDNLLLKESLLEDFK

GYLGCQALSEMIQFYLEEVMPQAENQDPDIKAHVNSLGENLKTLRLRLRRCHRFLPC

ENKSKAVEQVKNAFNKLQEKGIYKAMSEFDIFINYIEAYMTMKIRN.

Mouse IL-10:

(SEQ ID NO: 25)
LGCQALSEMIQFYLVEVNIPQAEKHGPEIKEHLNSLGQKLKTLRMRLRRCHRFLPCEN

KSKAVEQVKSDFNKLEDQGVYKAMNEFDIFINCIEAYMMIKMKS.

Human IL-11:

(SEQ ID NO: 26)
PGPPPGPPRVSPDPRAELDSTVLLTRSLLADTRQLAAQLRDKFPADGDHNLDSLPTLA

MSAGALGALQLPGVLTRLRADLLSYLRHVQWLRRAGGSSLKTLEPELGTLQARLDR

LLRRLQLLMSRLALPQPPPDPPAPPLAPPSSAWGGIRAAHAILGGLHLTLDWAVRGL

LLLKTRL.

Mouse IL-11:

(SEQ ID NO: 27)
MPGPPAGSPRVSSDPRADLDSAVLLTRSLLADTRQLAAQMRDKFPADGDHSLDSLPT

LAMSAGTLGSLQLPGVLTRLRVDLMSYLRHVQWLRRAGGPSLKTLEPELGALQARL

ERLLRRLQLLMSRLALPQAAPDQPVIPLGPPASAWGSIRAAHAILGGLHLTLDWAVR

GLLLLKTRL.

Human IL-23; p19 Subunit:

(SEQ ID NO: 28)
RAVPGGSSPAWTQCQQLSQKLCTLAWSAHPLVGHMDLREEGDEETTNDVPHIQCGD

GCDPQGLRDNSQFCLQRIHQGLIFYEKLLGSDIFTGEPSLLPDSPVGQLHASLLGLSQL

LQPEGHHWETQQIPSLSPSQPWQRLLLRFKILRSLQAFVAVAARVFAHGAATLSP.

p40 Subunit:

(SEQ ID NO: 29)
IWELKKDVYVVELDWYPDAPGEMVVLTCDTPEEDGITWTLDQSSEVLGSGKTLTIQ

VKEFGDAGQYTCHKGGEVLSHSLLLLHKKEDGIWSTDILKDQKEPKNKTFLRCEAK

NYSGRFTCWWLTTISTDLTFSVKSSRGSSDPQGVTCGAATLSAERVRGDNKEYEYSV

ECQEDSACPAAEESLPIEVMVDAVHKLKYENYTSSFFIRDIIKPDPPKNLQLKPLKNSR

QVEVSWEYPDTWSTPHSYFSLTFCVQVQGKSKREKKDRVFTDKTSATVICRKNASIS

VRAQDRYYSSSWSEWASVPCS.

Human IL-35; p35 Subunit:

(SEQ ID NO: 30)
RNLPVATPDPGMFPCLHHSQNLLRAVSNMLQKARQTLEFYPCTSEEIDHEDITKDKT

STVEACLPLELTKNESCLNSRETSFITNGSCLASRKTSFMMALCLSSIYEDLKMYQVE

FKTMNAKLLMDPKRQIFLDQNMLAVIDELMQALNFNSETVPQKSSLEEPDFYKTKIK

LCILLHAFRIRAVTIDRVMSYLNAS;

Ebi3 subunit:

(SEQ ID NO: 31)
RKGPPAALTLPRVQCRASRYPIAVDCSWTLPPAPNSTSPVSFIATYRLGMAARGHSW

PCLQQTPTSTSCTITDVQLFSMAPYVLNVTAVHPWGSSSSFVPFITEHIIKPDPPEGVRL

SPLAERQLQVQWEPPGSWPFPEIFSLKYWIRYKRQGAARFHRVGPTEATSFILRAVRP

RARYYVQVAAQDLTDYGELSDWSLPATATMSLGK.

Mouse IL-35; p35 Subunit:

(SEQ ID NO: 32)
RVIPVSGPARCLSQSRNLLKTTDDMVKTAREKLKHYSCTAEDIDHEDITRDQTSTLKT

-continued

CLPLELHKNESCLATRETSSTTRGSCLPPQKTSLMMTLCLGSIYEDLKMYQTEFQAIN

AALQNHNHQQIILDKGMLVAIDELMQSLNHNGETLRQKPPVGEADPYRVKMKLCIL

LHAFSTRVVTINRVMGYLSSA;

Ebi3 subunit:

(SEQ ID NO: 33)
ALVALSQPRVQCHASRYPVAVDCSWTPLQAPNSTRSTSFIATYRLGVATQQQSQPCL

QRSPQASRCTIPDVHLFSTVPYMLNVTAVHPGGASSSLLAFVAERIIKPDPPEGVRLRT

AGQRLQVLWHPPASWPFPDIFSLKYRLRYRRRGASHFRQVGPTEATTFTLRNSKPHA

KYCIQVSAQDLTDYGKPSDWSLPGQVESAPHKP.

Human IL-36ra:

(SEQ ID NO: 34)
VLSGALCFRMKDSALKVLYLHNNQLLAGGLHAGKVIKGEEISVVPNRWLDASLSPVI

LGVQGGSQCLSCGVGQEPTLTLEPVNIMELYLGAKESKSFTFYRRDMGLTSSFESAA

YPGWFLCTVPEADQPVRLTQLPENGGWNAPITDFYFQQCD.

Mouse IL-36ra:

(SEQ ID NO: 35)
VLSGALCFRMKDSALKVLYLHNNQLLAGGLHAEKVIKGEEISVVPNRALDASLSPVI

LGVQGGSQCLSCGTEKGPILKLEPVNIMELYLGAKESKSFTFYRRDMGLTSSFESAAY

PGWFLCTSPEADQPVRLTQIPEDPAWDAPITDFYFQQCD.

Human IL-37:

(SEQ ID NO: 36)
VHTSPKVKNLNPKKFSIHDQDHKVLVLDSGNLIAVPDKNYIRPEIFFALASSLSSASAE

KGSPILLGVSKGEFCLYCDKDKGQSHPSLQLKKEKLMKLAAQKESARRPFIFYRAQV

GSWNMLESAAHPGWFICTSCNCNEPVGVTDKFENRKHIEFSFQPVCKAEMSPSEVSD.

Mouse IL-37:

(SEQ ID NO: 37)
VPSSAKVNARAPEKFSIRDQDQKVLVLSDETLIAVPNKPYTVPETFFVLASHTSSSHE

GSPILLAVSKGELCLCCDKDEEQSKPSLQLKKNELMKLATQKEKVRLPFVFYRAQVG

SCCTLESAAHPGWFVCTSRNSGAPVEVTDTSGEGKLMEFSFQQVSETEMSPSEVSI.

Human interferon-β:

(SEQ ID NO: 38)
SYNLLGFLQRSSNFQCQKLLWQLNGRLEYCLKDRMNFDIPEEIKQLQQFQKEDAALT

IYEMLQNIFAIFRQDSSSTGWNETIVENLLANVYHQINHLKTVLEEKLEKEDFTRGKL

MSSLHLKRYYGRILHYLKAKEYSHCAWTIVRVEILRNFYFINRLTGYLRN.

Mouse interferon-β:

(SEQ ID NO: 39)
INYKQLQLQERTNIRKCQELLEQLNGKINLTYRADFKIPMEMTEKMQKSYTAFAIQE

MLQNVFLVFRNNFSSTGWNETIVVRLLDELHQQTVFLKTVLEEKQEERLTWEMSST

ALHLKSYYWRVQRYLKLMKYNSYAWMVVRAEIFRNFLIIRRLTRNFQN.

Human TGF-β1:

(SEQ ID NO: 40)
ALDTNYCFSSTEKNCCVRQLYIDFRKDLGWKWIHEPKGYHANFCLGPCPYIWSLDT

QYSKVLALYNQHNPGASAAPCCVPQALEPLPIVYYVGRKPKVEQLSNMIVRSCKCS.

Mouse TGF-β1:

(SEQ ID NO: 41)
ALDTNYCFSSTEKNCCVRQLYIDFRKDLGWKWIHEPKGYHANFCLGPCPYIWSLDT

QYSKVLALYNQHNPGASASPCCVPQALEPLPIVYYVGRKPKVEQLSNMIVRSCKCS.

Human TNF receptor I:

(SEQ ID NO: 42)
DSVCPQGKYIHPQNNSICCTKCHKGTYLYNDCPGPGQDTDCRECESGSFTASENHLR

HCLSCSKCRKEMGQVEISSCTVDRDTVCGCRKNQYRHYWSENLFQCFNCSLCLNGT

-continued

VHLSCQEKQNTVCTCHAGFFLRENECVSCSNCKKSLECTKLCLPQIEN.

Human TNF receptor II:

(SEQ ID NO: 43)

LPAQVAFTPYAPEPGSTCRLREYYDQTAQMCCSKCSPGQHAKVFCTKTSDTVCDSC

EDSTYTQLWNWVPECLSCGSRCSSDQVETQACTREQNRICTCRPGWYCALSKQEGC

RLCAPLRKCRPGFGVARPGTETSDVVCKPCAPGTFSNTTSSTDICRPHQICNVVAIPG

NASMDAVCTSTSPTRSMAPGAVHLPQPVSTRSQHTQPTPEPSTAPSTSFLLPMGPSPP

AEGSTGDFALPVGLIVGVTALGLLIIGVVNCVIIVITQVKKKPLCLQREAKVPHLPADK

ARGTQGPEQQHLLITAPSSSSSSLESSASALDRRAPTRNQPQAPGVEASGAGEARAST

GSSDSSPGGHGTQVNVTCIVNVCSSSDHSSQCSSQASSTMGDTDSSPSESPKDEQVPF

SKEECAFRSQLETPETLLGSTEEKPLPLGVPDAGMKPS.

Mouse TNF receptor II:

(SEQ ID NO: 44)

VPAQVVLTPYKPEPGYECQISQEYYDRKAQMCCAKCPPGQYVKHFCNKTSDTVCAD

CEASMYTQVWNQFRTCLSCSSSCTTDQVEIRACTKQQNRVCACEAGRYCALKTHSG

SCRQCMRLSKCGPGFGVASSRAPNGNVLCKACAPGTFSDTTSSTDVCRPHRICSILAI

PGNASTDAVCAPESPTLSAIPRTLYVSQPEPTRSQPLDQEPGPSQTPSILTSLGSTPIIEQ

STKGG.

C. CD200

Embodiments of the disclosure relate to polypeptides and compositions comprising the anti-inflammatory agent, CD200. Exemplary CD200 polypeptide amino acid sequences are shown below:

Mouse CD200 extracellular domain is represented by the following sequence:

(SEQ ID NO: 58)

QVEVVTQDERKALHTTASLRCSLKTSQEPLIVTWQKKKAVSPENMVTYSK

THGVVIQPAYKDRINVTELGLWNSSITFWNTTLEDEGCYMCLFNTFGSQK

VSGTACLTLYVQPIVHLHYNYFEDHLNITCSATARPAPAISWKGTGTGIE

NSTESHFHSNGTTSVTSILRVKDPKTQVGKEVICQVLYLGNVIDYKQSLD

KG.

Mouse CD200-MSA fusion protein (linker is underlined):

(SEQ ID NO: 66)

QVEVVTQDERKALHTTASLRCSLKTSQEPLIVTWQKKKAVSPENMVTYSK

THGVVIQPAYKDRINVTELGLWNSSITFWNTTLEDEGCYMCLFNTFGSQK

VSGTACLTLYVQPIVHLHYNYFEDHLNITCSATARPAPAISWKGTGTGIE

NSTESHFHSNGTTSVTSILRVKDPKTQVGKEVICQVLYLGNVIDYKQSLD

KGGGGSGGGSEAHKSEIAHRYNDLGEQHFKGLVLIAFSQYLQKCSYDEHA

KLVQEVTDFAKTCVADESAANCDKSLHTLFGDKLCAIPNLRENYGELADC

CTKQEPERNECFLQHKDDNPSLPPFERPEAEAMCTSFKENPTTFMGHYLH

EVARRHPYFYAPELLYYAEQYNEILTQCCAEADKESCLTPKLDGVKEKAL

VSSVRQRMKCSSMQKFGERAFKAWAVARLSQTFPNADFAEITKLATDLTK

VNKECCHGDLLECADDRAELAKYMCENQATISSKLQTCCDKPLLKKAHCL

-continued

SEVEHDTMPADLPAIAADFVEDQEVCKNYAEAKDVFLGTFLYEYSRRHPD

YSVSLLLRLAKKYEATLEKCCAEANPPACYGTVLAEFQPLVEEPKNLVKT

NCDLYEKLGEYGFQNAILVRYTQKAPQVSTPTLVEAARNLGRVGTKCCTL

PEDQRLPCVEDYLSAILNRVCLLHEKTPVSEHVTKCCSGSLVERRPCFSA

LTVDETYVPKEFKAETFTFHSDICTLPEKEKQIKKQTALAELVKHKPKAT

AEQLKTVMDDFAQFLDTCCKAADKDTCFSTEGPNLVTRCKDALA

Human CD200 extracellular domain (UniProt identifier P41217) is represented by the following sequence:

(SEQ ID NO: 59)

QVQVVTQDEREQLYTPASLKCSLQNAQEALIVTWQKKKAVSPENNIVTFS

ENHGVVIQPAYKDKINITQLGLQNSTITFWNITLEDEGCYMCLFNTFGFG

KISGTACLTVYVQPIVSLHYKFSEDHLNITCSATARPAPMVFWKVPRSGI

ENSTVTLSHPNGTTSVTSILHIKDPKNQVGKEVICQVLHLGTVTDFKQTV

NKG.

An exemplary Human CD200 (lower case)-human serum albumin (upper case) fusion protein (linker is uppercase and underlined) is represented by the following:

(SEQ ID NO: 61)

qvqvvtqdereqlytpaslkcslqnaqealivtwqkkkavspenmvtfse nhgvviqpaykdkinitqlglqnstitfwnitledegcymclfntfgfgk isgtacltvyvqpivslhykfsedhlnitcsatarpapmvfwkvprsgie nstvtlshpngttsvtsilhikdpknqvgkevicqvlhlgtvtdfkqtyn kgGGGSGGGSDAHKSEVAHRFKDLGEENFKALVLIAFAQYLQQCPFEDHV

KLVNEVTEFAKTCVADESAENCDKSLHTLFGDKLCTVATLRETYGEMADC

-continued

CAKQEPERNECFLQHKDDNPNLPRLVRPEVDVMCTAFHDNEETFLKKYLY
EIARRHPYFYAPELLFFAKRYKAAFTECCQAADKAACLLPKLDELRDEGK
ASSAKQRLKCASLQKFGERAFKAWAVARLSQRFPKAEFAEVSKLVTDLTK
VHTECCHGDLLECADDRADLAKYICENQDSISSKLKECCEKPLLEKSHCI
AEVENDEMPADLPSLAADFVESKDVCKNYAEAKDVFLGMFLYEYARRHPD
YSVVLLLRLAKTYETTLEKCCAAADPHECYAKVFDEFKPLVEEPQNLIKQ
NCELFEQLGEYKFQNALLVRYTKKVPQVSTPTLVEVSRNLGKVGSKCCKH
PEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKAT
KEQLKAVMDDFAAFVEKCCKADDKETCFAEEGKKLVAASQAALGL

Mouse CD200 (lower case)-CBD fusion protein (upper case) (linker is uppercase and underlined) is represented by the following:

(SEQ ID NO: 62)
qvevvtqderkalhttaslrcslktsqeplivtwqkkkavspenmvtysk
thgvviqpaykdrinvtelglwnssitfwnttledegcymclfntfgsqk
vsgtacltlyvqpivhlhynyfedhlnitcsatarpapaiswkgtgtgie
nsteshfhsngttsvtsilrvkdpktqvgkevicqvlylgnvidykqsld
kgGGGSGGGSCSQPLDVILLLDGSSSFPASYFDEMKSFAKAFISKANIGP
RLTQVSVLQYGSITTIDVPWNVVPEKAHLLSLVDVMQREGGPSQIGDALG
FAVRYLTSEMHGARPGASKAVVILVTDVSVDSVDAAADAARSNRVTVFPI
GIGDRYDAAQLRILAGPAGDSNVVKLQRIEDLPTMVTLGNSFLHKLCSGF
VRI.

Human CD200 (lower case)-CBD fusion protein (upper case) (linker is uppercase and underlined) is represented by the following:

(SEQ ID NO: 63)
qvqvvtqdereqlytpaslkcslqnaqealivtwqkkkayspenmvtfse
nhgvviqpaykdkinitqlglqnstitfwnitledegcymclfntfgfgk
isgtacltvyvqpivslhykfsedhlnitcsatarpapmvfwkvprsgie
nstvtlshpngttsvtsilhikdpknqvgkevicqvlhlgtvtdfkqtyn
kgGGGSGGGSCSQPLDVILLLDGSSSFPASYFDEMKSFAKAFISKANIGP
RLTQVSVLQYGSITTIDVPWNVVPEKAHLLSLVDVMQREGGPSQIGDALG
FAVRYLTSEMEIGARPGASKAVVILVTDVSVDSVDAAADAARSNRVTVFP
IGIGDRYDAAQLRILAGPAGDSNVVKLQRIEDLPTMVTLGNSFLHKLCSG
FVRI.

Mouse CD200 (uppercase)-mouse serum albumin (lowercase)-CBD (italic underline uppercase) fusion protein is represented by the following (linkers are uppercase and underlined):

(SEQ ID NO: 64)
QVEVVTQDERKALHTTASLRCSLKTSQEPLIVTWQKKKAVSPENMVTYSK
THGVVIQPAYKDRINVTELGLWNSSITFWNTTLEDEGCYMCLFNTFGSQK
VSGTACLTLYVQPIVHLHYNYFEDHLNITCSATARPAPAISWKGTGTGIE
NSTESHFHSNGTTSVTSILRVKDPKTQVGKEVICQVLYLGNVIDYKQSLD
KGGGGSGGGSeahkseiahryndlgeqhfkglvliafsqylqkcsydeha
klvqevtdfaktcvadesaancdkslhtlfgdklcaipnlrenygeladc
ctkqepernecflqhkddnpslppferpeaeamctsfkenpttfmghylh
evarrhpyfyapellyyaeqyneiltqccaeadkescltpkldgykekal
vssyrqrmkcssmqkfgerafkawavarlsqtfpnadfaeitklatdltk
ynkecchgdllecaddraelakymcenqatissklqtccdkpllkkahcl
sevehdtmpadlpaiaadfvedqeycknyaeakdvflgtflyeysrrhpd
ysysllllrlakkyeatlekccaeanppacygtvlaefqplyeepknlvkt
ncdlyeklgeygfqnailvrytqkapqvstptlveaarnlgrvgtkcctl
pedqrlpcvedylsailnrvcllhektpvsehvtkccsgslverrpcfsa
ltvdetyvpkefkaetftfhsdictlpekekqikkqtalaelvkhkpkat
aeqlktvmddfaqfldtcckaadkdtcfstegpnlvtrckdalaGGGSGG
GS*CSQPLDVILLLDGSSSFPASYFDEMKSFAKAFISKANIGPRLTQVSVL*
*QYGSITTIDVPWNVVPEKAHLLSLVDVMQREGGPSQIGDALGFAVRYLTS*
*EMHGARPGASKAVVILVTDVSVDSVDAAADAARSNRVTVFPIGIGDRYDA*
*AQLRILAGPAGDSNVVKLQRIEDLPTMVTLGNSFLHKLCSGFVRI*.

Human CD200 (uppercase)-human serum albumin (lowercase)-CBD (italic underline uppercase) fusion protein is represented by the following (linkers are uppercase and underlined):

(SEQ ID NO: 65)
QVQVVTQDEREQLYTPASLKCSLQNAQEALIVTWQKKKAVSPENMVTFSE
NHGVVIQPAYKDKINITQLGLQNSTITFWNITLEDEGCYMCLFNTFGFGK
ISGTACLTVYVQPIVSLHYKFSEDHLNITCSATARPAPMVFWKVPRSGIE
NSTVTLSHPNGTTSVTSILHIKDPKNQVGKEVICQVLHLGTVTDFKQTVN
KGGGGSGGGSdahksevahrfkdlgeenfkalvliafaqylqqcpfedhv
klvnevtefaktcvadesaencdkslhtlfgdklavatlretygemadcc
akqepernecflqhkddnpnlprlvrpevdvmctafhdneetflkkylye
iarrhpyfyapellffakrykaafteccqaadkaacllpkldelrdegka
ssakqrlkcaslqkfgerafkawavarlsqrfpkaefaevsklvtdltkv
htecchgdllecaddradlakyicenqdsissklkeccekpllekshcia
evendempadlpslaadfveskdvcknyaeakdvflgmflyeyarrhpdy
svvlllrlaktyettlekccaaadphecyakvfdefkplveepqnlikqn
celfeqlgeykfqnallvrytkkvpqvstptivevsrnlgkvgskcckhp
eakrmpcaedylsvvlnqlcvlhektpvsdrvtkccteslvnrrpcfsal
evdetyvpkefnaetftfhadictlsekerqikkqtalvelvkhkpkatk
eqlkavmddfaafvekcckaddketcfaeegkklvaasqaalglGGGSGG
GS*CSQPLDVILLLDGSSSFPASYFDEMKSFAKAFISKANIGPRLTQVSVL*
*QYGSITTIDVPWNVVPEKAHLTSLVDVMQREGGPSQIGDALGFAVRYLTS*

-continued

*EMHGARPGASKAVVILVTDVSVDSVDAAADAARSNRVTVFPIGIGDRYDA*

*AQLRILAGPAGDSNVVKLQRIEDLPTMVTLGNSFLHKLCSGFVRI.*

IV. ECM-Affinity Peptides

Collagen is an extracellular matrix (ECM)-protein that regulates a variety of cellular biological functions, such as proliferation, differentiation, and adhesion in both normal and tumor tissue (Ricard-Blum, Cold Spring Harb Perspect Biol 3:a004978, 2011). Collagen is the most abundant protein in the mammalian body and exists in almost all tissues in one or more of 28 isoforms (Ricard-Blum, Cold Spring Harb Perspect Biol 3:a004978, 2011). The blood vessel sub-endothelial space is rich in collagen. Because of its insolubility under physiological conditions, collagen barely exists within the blood (Dubois et al., Blood 107: 3902-06, 2006; Bergmeier and Hynes, Cold Spring Harb Perspect Biol 4:a005132, 2012). Tumor vasculature is reported to be permeable due to an abnormal structure (Nagy et al., British journal of cancer 100:865, 2009). Thus, with its leaky vasculature, collagen is exposed in the tumor (Liang et al., Journal of controlled release 209:101-109, 2015; Liang et al., Sci Rep 6:18205, 2016; Yasunaga et al., Bioconjugate Chemistry 22:1776-83, 2011; Xu et al. The Journal of cell biology 154:1069-80, 2001; Swartz and Lund, Nat Rev Cancer 12:210-19). Also, tumor tissue contains increased amounts of collagen compared to normal tissues (Zhou et al. J Cancer 8:1466-76, 2017; Provenzano et al. BMC Med 6:11, 2008).

von Willebrand factor (vWF) is a blood coagulation factor and binds to both type I and type III collagen, and the adhesion receptor GPIb on blood platelets (Lenting et al., Journal of thrombosis and haemostasis:JTH 10:2428-37, 2012; Shahidi Advances in experimental medicine and biology 906:285-306, 2017). When injured, collagen beneath endothelial cells is exposed to blood plasma, and vWF-collagen binding initiates the thrombosis cascade (Shahidi Advances in experimental medicine and biology 906:285-306, 2017; Wu et al. Blood 99:3623-28, 2002). The vWF A domain has the highest affinity against collagen among reported non-bacterial origin proteins/peptides (Addi et al., Tissue Engineering Part B: Reviews, 2016). Particularly within the A domain, the A3 domain of vWF has been reported as a collagen binding domain (CBD) (Ribba et al. Thrombosis and Haemostasis 86:848-54, 2001). As described above, the inventors contemplated that a fusion protein with the vWF A3 CBD may achieve targeted cytokine immunotherapy even when injected systemically due to exposure of collagen via the leaky tumor vasculature.

In some embodiments, the ECM-affinity peptide comprises a collagen binding domain from decorin. In some embodiments, the ECM-affinity peptide comprises a decorin peptide such as LRELHLNNNC (SEQ ID NO:1), which is derived from bovine or LRELHLDNNC (SEQ ID NO:2), which is derived from human.

In some embodiments, the ECM-peptide comprises a peptide fragment from human decorin, which is represented by the following amino acid sequence:

(SEQ ID NO: 3)
CGPFQQRGLFDFMLEDEASGIGPEVPDDRDFEPSLGPVCPFRCQCHLRVV

QCSDLGLDKVPKDLPPDTTLLDLQNNKITEIKDGDFKNLKNLHALILVNN

-continued

KISKVSPGAFTPLVKLERLYLSKNQLKELPEKMPKTLQELRAHENEITKV

RKVTFNGLNQMIVIELGTNPLKSSGIENGAFQGMKKLSYIRIADTNITSI

PQGLPPSLTELHLDGNKISRVDAASLKGLNNLAKLGLSFNSISAVDNGSL

ANTPHLRELHLDNNKLTRVPGGLAEHKYIQVVYLHNNNISVVGSSDFCPP

GHNTKKASYSGVSLFSNPVQYWEIQPSTFRCVYVRS AIQLGNYK.

In some embodiments, the ECM-peptide comprises a peptide fragment from vWF. In some embodiments, the ECM-peptide comprises vWF A1 derived from human sequence, residues 1237-1458 (474-695 of mature VWF) or a fragment thereof, which is represented by the amino acid sequence (SEQ ID NO: 4)
CQEPGGLVVPPTDAPVSPTTLYVEDISEPPLHDFYCSRLLDLVFLLDGSS

RLSEAEFEVLKAFVVDMMERLRISQKWVRVAVVEYHDGSHAYIGLKDRKR

PSELRRIASQVKYAGSQVASTSEVLKYTLFQIFSKIDRPEASRITLLLMA

SQEPQRMSRNFVRYVQGLKKKKVIVIPVGI GPHANLKQIRLIEKQAPEN

K AFVLSSVDELEQQRDEIVSYLC.

In some embodiments, the ECM-peptide comprises all or a fragment of vWF A3, which is represented by the following amino acid sequences:

(SEQ ID NO: 5)
CSQPLDVILLLDGSSSFPASYFDEMKSFAKAFISKANIGPRLTQVSVLQY

GSITTIDVPWNVVPEKAHLLSLVDVMQREGGPSQIGDALGFAVRYLTSEM

HGARPGASKAVVILVTDVSVDSVDAAADAARSNRVTVFPIGIGDRYDAAQ

LRILAGPAGDSNVVKLQRIEDLPTMVTLGNSFLHKLCSGFVRICTG and (SEQ ID NO: 47)
CSQPLDVILLLDGSSSFPASYFDEMKSFAKAFISKANIGPRLTQVSVLQY

GSITTIDVPWNVVPEKAHLLSLVDVMQREGGPSQIGDALGFAVRYLTSEM

HGARPGASKAVVILVTDVSVDSVDAAADAARSNRVTVFPIGIGDRYDAAQ

LRILAGPAGDSNVVKLQRIEDLPTMVTLGNSFLHKLCSGFVRI.

In some embodiments, the ECM-peptide comprises all or a fragment of vWF A3, which is represented by the following amino acid sequences:

(SEQ ID NO: 52)
CSQPLDVVLLLDGSSSLPESSFDKMKSFAKAFISKANIGPHLTQVSVIQY

GSINTIDVPWNVVQEKAHLQSLVDLMQQEGGPSQIGDALAFAVRYVTSQI

HGARPGASKAVVIIIMDTSLDPVDTAADAARSNRVAVFPVGVGDRYDEAQ

LRILAGPGASSNVVKLQQVEDLSTMATLGNSFFHKLCSGFSGV.

In some embodiments, the ECM-affinity peptide is a peptide from von Willebrand factor (vWF). The sequence of human vWF comprises the following:

(SEQ ID NO: 6)
MIPARFAGVLLALALILPGTLCAEGTRGRSSTARCSLFGSDFVNTFDGSM

-continued

YSFAGYCSYLLAGGCQKRSFSIIGDFQNGKRVSLSVYLGEFFDIHLFVNG

TVTQGDQRVSMPYASKGLYLETEAGYYKLSGEAYGFVARIDGSGNFQVLL

SDRYFNKTCGLCGNFNIFAEDDFMTQEGTLTSDPYDFANSWALSSGEQWC

ERASPPSSSCNISSGEMQKGLWEQCQLLKSTSVFARCHPLVDPEPFVALC

EKTLCECAGGLECACPALLEYARTCAQEGMVLYGWTDHSACSPVCPAGME

YRQCVSPCARTCQSLHINEMCQERCVDGCSCPEGQLLDEGLCVESTECPC

VHSGKRYPPGTSLSRDCNTCICRNSQWICSNEECPGECLVTGQSHFKSFD

NRYFTFSGICQYLLARDCQDHSFSIVIETVQCADDRDAVCTRSVTVRLPG

LHNSLVKLKHGAGVAMDGQDVQLPLLKGDLRIQHTVTASVRLSYGEDLQM

DWDGRGRLLVKLSPVYAGKTCGLCGNYNGNQGDDFLTPSGLAEPRVEDFG

NAWKLHGDCQDLQKQHSDPCALNPRMTRFSEEACAVLTSPTFEACHRAVS

PLPYLRNCRYDVCSCSDGRECLCGALASYAAACAGRGVRVAWREPGRCEL

NCPKGQVYLQCGTPCNLTCRSLSYPDEECNEACLEGCFCPPGLYMDERGD

CVPKAQCPCYYDGEIFQPEDIFSDHHTMCYCEDGFMHCTMSGVPGSLLPD

AVLSSPLSHRSKRSLSCRPPMVKLVCPADNLRAEGLECTKTCQNYDLECM

SMGCVSGCLCPPGMVRHENRCVALERCPCFHQGKEYAPGETVKIGCNTCV

CRDRKWNCTDHVCDATCSTIGMAHYLTFDGLKYLFPGECQYVLVQDYCGS

NPGTFRILVGNKGCSHPSVKCKKRVTILVEGGEIELFDGEVNVKRPMKDE

THFEVVESGRYIILLLGKALSVVWDRHLSISVVLKQTYQEKVCGLCGNED

GIQNNDLTSSNLQVEEDPVDFGNSWKVSSQCADTRKVPLDSSPATCHNNI

MKQTMVDSSCRILTSDVFQDCNKLVDPEPYLDVCIYDTCSCESIGDCACF

CDTIAAYAHVCAQHGKVVTWRTATLCPQSCEERNLRENGYECEWRYNSCA

PACQVTCQHPEPLACPVQCVEGCHAHCPPGKILDELLQTCVDPEDCPVCE

VAGRRFASGKKVTLNPSDPEHCQICHCDVVNLTCEACQEPGGLVVPPTDA

PVSPTTLYVEDISEPPLHDFYCSRLLDLVFLLDGSSRLSEAEFEVLKAFV

VDMMERLRISQKWVRVAVVEYHDGSHAYIGLKDRKRPSELRRIASQVKYA

GSQVASTSEVLKYTLFQIFSKIDRPEASRITLLLMASQEPQRMSRNFVRY

VQGLKKKKVIVIPVGIGPHANLKQIRLIEKQAPENKAFVLSSVDELEQQR

DEIVSYLCDLAPEAPPPTLPPDMAQVTVGPGLLGVSTLGPKRNSMVLDVA

FVLEGSDKIGEADENRSKEEMEEVIQRMDVGQDSIHVTVLQYSYMVTVEY

PFSEAQSKGDILQRVREIRYQGGNRTNTGLALRYLSDHSFLVSQGDREQA

PNLVYMVTGNPASDEIKRLPGDIQVVPIGVGPNANVQELERIGWPNAPIL

IQDFETLPREAPDLVLQRCCSGEGLQIPTLSPAPDCSQPLDVILLLDGSS

SFPASYFDEMKSFAKAFISKANIGPRLTQVSVLQYGSITTIDVPWNVVPE

KAHLLSLVDVMQREGGPSQIGDALGFAVRYLTSEMHGARPGASKAVVILV

TDVSVDSVDAAADAARSNRVTVFPIGIGDRYDAAQLRILAGPAGDSNVVK

LQRIEDLPTMVTLGNSFLHKLCSGFVRICMDEDGNEKRPGDVWTLPDQCH

TVTCQPDGQTLLKSHRVNCDRGLRPSCPNSQSPVKVEETCGCRWTCPCVC

TGSSTRHIVTFDGQNFKLTGSCSYVLFQNKEQDLEVILHNGACSPGARQG

CMKSIEVKHSALSVELHSDMEVTVNGRLVSVPYVGGNMEVNVYGAIMHEV

RFNHLGHIFTFTPQNNEFQLQLSPKTFASKTYGLCGICDENGANDFMLRD

-continued

GTVTTDWKTLVQEWTVQRPGQTCQPILEEQCLVPDSSHCQVLLLPLFAEC

HKVLAPATFYAICQQDSCHQEQVCEVIASYAHLCRTNGVCVDWRTPDFCA

MSCPPSLVYNHCEHGCPRHCDGNVSSCGDHPSEGCFCPPDKVMLEGSCVP

EEACTQCIGEDGVQHQFLEAWVPDHQPCQICTCLSGRKVNCTTQPCPTAK

APTCGLCEVARLRQNADQCCPEYECVCDPVSCDLPPVPHCERGLQPTLTN

PGECRPNFTCACRKEECKRVSPPSCPPHRLPTLRKTQCCDEYECACNCVN

STVSCPLGYLASTATNDCGCTTTTCLPDKVCVHRSTIYPVGQFWEEGCDV

CTCTDMEDAVMGLRVAQCSQKPCEDSCRSGFTYVLHEGECCGRCLPSACE

VVTGSPRGDSQSSWKSVGSQWASPENPCLINECVRVKEEVFIQQRNVSCP

QLEVPVCPSGFQLSCKTSACCPSCRCERMEACMLNGTVIGPGKTVMIDVC

TTCRCMVQVGVISGFKLECRKTTCNPCPLGYKEENNTGECCGRCLPTACT

IQLRGGQIMTLKRDETLQDGCDTHFCKVNERGEYFWEKRVTGCPPFDEHK

CLAEGGKIMKIPGTCCDTCEEPECNDITARLQYVKVGSCKSEVEVDIHYC

QGKCASKAMYSIDINDVQDQCSCCSPTRTEPMQVALHCTNGSVVYHEVLN

AMECKCSPRKCSK.

In some embodiments, the peptide is from the vWF A3 domain. The vWF A3 domain is derived from the human sequence, residues 1670-1874 (907-1111 of mature vWF) and has the following sequence:

(SEQ ID NO: 7)

CSGEGLQIPTLSPAPDCSQPLDVILLLDGSSSFPASYFDEMKSFAKAFIS

KANIGPRLTQVSVLQYGSITTIDVPWNVVPEKAHLLSLVDVMQREGGPSQ

IGDALGFAVRYLTSEMHGARPGASKAVVILVTDVSVDSVDAAADAARSNR

VTVFPIGIGDRYDAAQLRILAGPAGDSNVVKLQRIEDLPTMVTLGNSFLH

KLCSG.

In some embodiments, the ECM-affinity peptide comprises a peptide from PlGF-2. PlGF-2 has the following sequence:

(SEQ ID NO: 8)

MPVMRLFPCFLQLLAGLALPAVPPQQWALSAGNGSSEVEVVPFQEVWGRS

YCRALERLVDVVSEYPSEVEHMFSPSCVSLLRCTGCCGDENLHCVPVETA

NVTMQLLKIRSGDRPSYVELTFSQHVRCECRPLREKMKPERRRPKGRGKR

RREKQRPTDCHLCGDAVPRR.

Exemplary PlGF-2 ECM affinity peptides include:

(SEQ ID NO: 9)

RRRPKGRGKRRREKQRPTDCHLCGDAVPRR;

(SEQ ID NO: 10)

RRRPKGRGKRRREKQRPTDCHL;

(SEQ ID NO: 11)

RRPKGRGKRRREKQRPTD;

(SEQ ID NO: 12)

RRRPKGRGKRRREKQ;

-continued (SEQ ID NO: 13)
GKRRREKQ;

(SEQ ID NO: 14)
RRRPKGRG;
and (SEQ ID NO: 15)
RRKTKGKRKRSRNSQTEEPHP.

In some embodiments, the ECM-affinity peptide is a peptide from CXCL-12γ. The sequence of CXCL-12γ is the following: CXCL-12γ: KPVSLSYRCPCRFFESHVARANVKHLKILNTPNCALQIVARLKNNNRQVCIDPKLKW IQEYLEKALNKGRREEKVGKKEKIGKKKRQKKRKAAQKRKN (SEQ ID NO:16). An exemplary peptide includes all or part of SEQ ID NO:12 and the following peptide:

(SEQ ID NO: 17)
GRREEKVGKKEKIGKKKRQKKRKAAQKRKN.

The ECM-affinity peptide may be a peptide with 75, 76, 77, 78, 79, 80, 81, 82, 83, 84, 85, 86, 87, 88, 89, 90, 91, 92, 93, 94, 95, 96, 97, 98, 99, or 100% identity (or any derivable range therein) to an ECM or CBD peptide or fragment of the peptides described above.

A linker sequence may be included in the anti-inflammatory agent-peptide construction. For example, a linker having at least, at most, or exactly 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids (or any derivable range therein) may separate that antibody and the peptide.

The ECM-affinity peptides of the disclosure may have affinity to one or more components of the extracellular matrix such as fibronectin, collagen, (collagen type I, collagen type III, and/or collagen type IV) tenascin C, fibrinogen, and fibrin. In certain aspects the ECM-affinity peptide has an affinity for collagen. And in other aspects the ECM-affinity peptide does not bind fibronectin.

In some embodiments, the ECM-affinity peptides and/or anti-inflammatory agent of the disclosure is further linked to a serum protein. Serum proteins include, for example, albumin, globulin, and fibrinogen. Globulins include alpha 1 globulins, alpha 2 globulins, beta globulins, and gamma globulins. The albumin may be mouse, human, bovine, or any other homologous albumin protein. In some embodiments, the albumin comprises human serum albumin, which is encoded by the ALB gene, and exemplified by the following amino acid sequence:

(SEQ ID NO: 45)
kwvtfisllflfssaysrgvfrrdahksevahrfkdlgeenfkalvliaf
aqylqqcpfedhvklvnevtefaktcvadesaencdkslhtlfgdklctv
atlretygemadccakqepernecflqhkddnpnlprlvrpevdvmctaf
hdneetflkkylyeiarrhpyfyapellffakrykaafteccqaadkaac
llpkldelrdegkassakqrlkcaslqkfgerafkawavarlsqrfpkae
faevsklvtdltkvhtecchgdllecaddradlakyicenqdsissklke -continued ccekpllekshciaevendempadlpslaadfveskdvcknyaeakdvfl
gmflyeyarrhpdysvvlllrlaktyettlekccaaadphecyakvfdef
lcplveepqnlikqncelfeqlgeykfqnallvrytkkvpqvstptlvev
srnlgkvgskcckhpeakrmpcaedylsvvlnqlcvlhektpvsdrvtkc
cteslvnrrpcfsalevdetyvpkefnaetftfhadictlsekerqikkq
talvelvkhkpkatkeqlkavmddfaafvekcckaddketcfaeegkklv
aasqaalgl.

In some embodiments, serum albumin comprises a polypeptide having the following sequence:

(SEQ ID NO: 60)
DAHKSEVAHRFKDLGEENFKALVLIAFAQYLQQCPFEDHVKLVNEVTEFA
KTCVADESAENCDKSLHTLFGDKLCTVATLRETYGEMADCCAKQEPERNE
CFLQHKDDNPNLPRLVRPEVDVMCTAFHDNEETFLKKYLYEIARRHPYFY
APELLFFAKRYKAAFTECCQAADKAACLLPKLDELRDEGKASSAKQRLKC
ASLQKFGERAFKAWAVARLSQRFPKAEFAEVSKLVTDLTKVHTECCHGDL
LECADDRADLAKYICENQDSISSKLKECCEKPLLEKSHCIAEVENDEMPA
DLPSLAADFVESKDVCKNYAEAKDVFLGMFLYEYARRHPDYSVVLLLRLA
KTYETTLEKCCAAADPHECYAKVFDEFKPLVEEPQNLIKQNCELFEQLGE
YKFQNALLVRYTKKVPQVSTPTLVEVSRNLGKVGSKCCKHPEAKRMPCAE
DYLSVVLNQLCVLHEKTPVSDRVTKCCTESLVNRRPCFSALEVDETYVPK
EFNAETFTFHADICTLSEKERQIKKQTALVELVKHKPKATKEQLKAVMDD
FAAFVEKCCKADDKETCFAEEGKKLVAASQAALGL

In some embodiments, the albumin comprises mouse albumin having the following sequence:

(SEQ ID NO: 46)
eahkseiahryndlgeqhfkglvliafsqylqkcsydehaklyqevtdfa
ktcvadesaancdkslhtlfgdklcaipnlrenygeladcctkqeperne
cflqhkddnpslppferpeaeamctsfkenpttfmghylhevarrhpyfy
apellyyaeqyneiltqccaeadkescltpkldgvkekalvssvrqrmkc
ssmqkfgerafkawavarlsqtfpnadfaeitklatdltkvnkecchgdl
lecaddraelakymcenqatissklqtccdkpllkkahclsevehdtmpa
dlpaiaadfvedqevcknyaeakdvflgtflyeysrrhpdysvslllrla
kkyeatlekccaeanppacygtvlaefqplveepknlvktncdlyeklge
ygfqnailvrytqkapqvstptlveaarnlgrvgtkcctlpedqrlpcve
dylsailnrycllhektpvsehytkccsgslverrpcfsaltvdetyvpk
efkaetftfhsdictlpekekqikkqtalaelvkhkpkataeqlktvmdd
faqfldtcckaadkdtcfstegpnlvtrckdala.

Related embodiments comprise a vWF A3 (uppercase) linked through a glycine serine peptide linker (italic uppercase and underlined) with mouse serum albumin (MSA) (lowercase is MSA):

(SEQ ID NO: 50)

CSQPLDVILLLDGSSSFPASYFDEMKSFAKAFISKANIGPRLTQVSVLQY
GSITTIDVPWNVVPEKAHLLSLVDVMQREGGPSQIGDALGFAVRYLTSEM
HGARPGASKAVVILVTDVSVDSVDAAADAARSNRVTVFPIGIGDRYDAAQ
LRILAGPAGDSNVVKLQRIEDLPTMVTLGNSFLHKLCSGFVRI*GGGSGGG*
*S*eahkseiahryndlgeqhfkglvliafsqylqkcsydehaklvqevtdf
aktcvadesaancdkslhtlfgdklcaipnlrenygeladcctkqepern
ecflqhkddnpslppferpeaeamctsfkenpttfmghylhevarrhpyf
yapellyyaeqyneiltqccaeadkescltpkldgvkekalvssvrqrmk
cssmqkfgerafkawavarlsqtfpnadfaeitklatdltkvnkecchgd
llecaddraelakymcenqatissklqtccdkpllkkahclsevehdtmp
adlpaiaadfvedqevcknyaeakdvflgtflyeysrrhpdysyslllrl
akkyeatlekccaeanppacygtvlaefqplfeepknlvktncdlyeklg
eygfqnailvrytqkapqvstptlveaarnlgrvgtkcctlpedqrlpcv
edylsailnrvcllhektpvsehvtkccsgslverrpcfsaltvdetyyp
kefkaetftfhsdictlpekekqikkqtalaelvkhkpkataeqlktvmd
dfaqfldtcckaadkdtcfstegpnlvtrckdala.

Further related embodiments comprise a vWF A3 (uppercase) linked through a glycine serine peptide linker (italic uppercase and underlined) with mouse serum albumin (MSA) (lowercase is MSA): vWF A3 (uppercase) linked through a glycine serine peptide linker (italic uppercase and underlined) with human serum albumin (HSA) (lowercase is HSA):

(SEQ ID NO: 51)

CSQPLDVILLLDGSSSFPASYFDEMKSFAKAFISKANIGPRLTQVSVLQY
GSITTIDVPWNVVPEKAHLLSLVDVMQREGGPSQIGDALGFAVRYLTSEM
HGARPGASKAVVILVTDVSVDSVDAAADAARSNRVTVFPIGIGDRYDAAQ
LRILAGPAGDSNVVKLQRIEDLPTMVTLGNSFLHKLCSGFVRI*GGGSGGG*
*S*kwvtfisllflfssaysrgvfrrdahksevahrfkdlgeenflcalvli
afaqylqqcpfedhvklvnevtefaktcvadesaencdkslhtlfgdklc
tvatlretygemadccakqepernecflqhkddnpnlprlvrpevdvmct
afhdneetflkkylyeiarrhpyfyapellffakrykaafteccqaadka
acllpkldelrdegkassakqrlkcaslqkfgerafkawavarlsqrfpk
aefaevsklvtdltkvhtecchgdllecaddradlakyicenqdsisskl
keccekpllekshciaevendempadlpslaadfveskdvcknyaeakdv
flgmflyeyarrhpdysvvlllrlaktyettlekccaaadphecyakvfd
efkplveepqnlikqncelfeqlgeykfqnallvrytkkvpqvstptlve
vsrnlgkvgskcckhpeakrmpcaedylsvvlnqlcvlhektpvsdrvtk
ccteslvnrrpcfsalevdetyvpkefnaetftfhadictlsekerqikk
qtalvelvkhkpkatkeqlkavmddfaafvekcckaddketcfaeegkkl
vaasqaalgl.

V. Proteinaceous Compositions

The polypeptides or polynucleotides of the disclosure, such as the ECM-affinity peptide, serum protein, or cytokine polypeptide, may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more variant amino acids or nucleic acid substitutions or be at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% similar, identical, or homologous with at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids or nucleic acids, or any range derivable therein, of SEQ ID NOs:1-66.

The polypeptides or polynucleotides of the disclosure, such as the ECM-affinity peptide, serum protein, or cytokine polypeptide, may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO:1-66.

In some embodiments, a polypeptide of the disclosure may comprise amino acids 1 to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 (or any derivable range therein) of SEQ ID NOs:1-66.

In some embodiments, a polypeptide of the disclosure, such as the ECM-affinity peptide, serum protein, or cytokine polypeptide, may comprise at least, at most, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 (or any derivable range therein) contiguous amino acids of SEQ ID NOs:1-66.

In some embodiments, the polypeptide, such as the ECM-affinity peptide, serum protein, or cytokine polypeptide, may comprise at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 (or any derivable range therein) contiguous amino acids of SEQ ID NOs:1-66 that are at least, at most, or exactly 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% similar, identical, or homologous with any one of SEQ ID NOS:1-66.

A polypeptide of the disclosure, such as an ECM-affinity peptide, serum protein, or cytokine polypeptide, may be at least, at most, or exactly 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% (or any range derivable therein) similar, identical, or homologous with one of SEQ ID NOS:1-66.

In some aspects there is a nucleic acid molecule or polypeptide starting at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 of any of SEQ ID NOS:1-66 and comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 contiguous nucleotides or amino acids of any of SEQ ID NOS:1-66.

The polypeptides and nucleic acids of the disclosure may include at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 substitutions (or any range derivable therein).

The substitution may be at amino acid position or nucleic acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 of one of SEQ ID NO:1-66. One or more of these substitutions may be specifically excluded from an embodiment.

Peptides, polypeptides, and proteins of the disclosure, such as the ECM-affinity peptide, serum protein, or cytokine polypeptide, having at least, having at least, or having 70, 75, 80, 85, 90, 91, 92, 93, 94, 95, 96, 97, 98, 99, 100% identity to any one of SEQ ID NO:1-66 includes a fragment or segment starting at amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 (or any range derivable therein) and ending at amino acid 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, or 205 (or any range derivable therein).

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa. One or more of these substitutions may be specifically excluded from an embodiment.

Proteins may be recombinant, or synthesized in vitro. Alternatively, a non-recombinant or recombinant protein may be isolated from bacteria. It is also contemplated that bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids.

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity. Structures such as, for example, an enzymatic catalytic domain or interaction components may have amino acid substituted to maintain such function. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In other embodiments, alteration of the function of a polypeptide is intended by introducing one or more substitutions. For example, certain amino acids may be substituted for other amino acids in a protein structure with the intent to modify the interactive binding capacity of interaction components. Structures such as, for example, protein interaction domains, nucleic acid interaction domains, and catalytic sites may have amino acids substituted to alter such function. Since it is the interactive capacity and nature of a protein that defines that protein's biological functional activity, certain amino acid substitutions can be made in a protein sequence, and in its underlying DNA coding sequence, and nevertheless produce a protein with different properties. It is thus contemplated by the inventors that various changes may be made in the DNA sequences of genes with appreciable alteration of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

VI. Nucleic Acids

In certain embodiments, the current disclosure concerns recombinant polynucleotides encoding the proteins, polypeptides, and peptides of the invention, such as ECM-affinity peptide operatively linked to anti-inflammatory agents and/or other molecules. Therefore, certain embodiments relate to nucleotides encoding for an ECM-affinity polypeptide and/or an ECM-affinity polypeptide or fragment thereof fused to an anti-inflammatory agent or fragment thereof.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs (or any range derivable therein), including all values and ranges there between, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein.

In particular embodiments, the invention concerns isolated nucleic acid segments and recombinant vectors incorporating nucleic acid sequences that encode a polypeptide or peptide of the disclosure. The term "recombinant" may be used in conjunction with a polynucleotide or polypeptide and generally refers to a polypeptide or polynucleotide produced and/or manipulated in vitro or that is a replication product of such a molecule.

In other embodiments, the invention concerns isolated nucleic acid segments and recombinant vectors incorporating nucleic acid sequences that encode a polypeptide or peptide of the disclosure.

The nucleic acid segments used in the current disclosure can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, the current disclosure provides polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence of this disclosure using the methods described herein (e.g., BLAST analysis using standard parameters).

The disclosure also contemplates the use of polynucleotides which are complementary to all the above described polynucleotides.

A. Vectors

Polypeptides of the disclosure may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). In addition to encoding a polypeptide of the disclosure, the vector can encode other polypeptide sequences such as a one or more other bacterial peptide, a tag, or an immunogenicity enhancing peptide. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

B. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

C. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988; Macejak and Sarnow, 1991). IRES elements can be linked to heterologous open reading frames. Multiple open reading frames can be transcribed together, each separated by an IRES, creating polycistronic messages. Multiple genes can be efficiently expressed using a single promoter/enhancer to transcribe a single message (see U.S. Pat. Nos. 5,925,565 and 5,935,819, herein incorporated by reference).

D. Selectable and Screenable Markers

In certain embodiments of the invention, cells containing a nucleic acid construct of the current disclosure may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

E. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org).

F. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL□ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

VII. Combination Therapy

The compositions and related methods of the present disclosure, particularly administration of and ECM-affinity peptide operatively linked to an anti-inflammatory agent and/or other molecules may also be used in combination with the administration of additional therapies such as the additional therapeutics described herein or in combination with other traditional therapeutics known in the art for the treatment of autoimmune or inflammatory conditions.

The therapeutic compositions and treatments disclosed herein may precede, be co-current with and/or follow another treatment or agent by intervals ranging from minutes to weeks. In embodiments where agents are applied separately to a cell, tissue or organism, one would generally ensure that a significant period of time did not expire between the time of each delivery, such that the therapeutic agents would still be able to exert an advantageously combined effect on the cell, tissue or organism. For example, in such instances, it is contemplated that one may contact the cell, tissue or organism with two, three, four or more agents or treatments substantially simultaneously (i.e., within less than about a minute). In other aspects, one or more therapeutic agents or treatments may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering another therapeutic agent or treatment.

Various combination regimens of the therapeutic agents and treatments may be employed. Non-limiting examples of such combinations are shown below, wherein a therapeutic agent such as a composition disclosed herein is "A" and a second agent, such as an additional agent or therapy described herein or known in the art is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

In some embodiments, more than one course of therapy may be employed. It is contemplated that multiple courses may be implemented.

VIII. Therapeutic Methods

The compositions of the disclosure may be used for in vivo, in vitro, or ex vivo administration. The route of administration of the composition may be, for example, intracutaneous, subcutaneous, intravenous, local, topical, and intraperitoneal administrations.

The autoimmune condition or inflammatory condition amenable for treatment may include, but not be limited to conditions such as diabetes (e.g. type 1 diabetes), graft rejection, arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and systemic juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), and adult onset diabetes mellitus (Type II diabetes) and autoimmune diabetes. Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), experimental autoimmune encephalomyelitis, myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, graft versus host disease, contact hypersensitivity, asthmatic airway hyperreaction, and endometriosis.

IX. Pharmaceutical Compositions and Methods

In some embodiments, pharmaceutical compositions are administered to a subject. Different aspects involve administering an effective amount of a composition to a subject. In some embodiments, a composition comprising an anti-inflammatory agent may be administered to the subject or patient to treat inflammation and/or autoimmunity. Additionally, such compounds can be administered in combination with an additional treatment.

Compositions can be formulated for parenteral administration, e.g., formulated for injection via the intravenous, transcatheter injection, intraarterial injection, intramuscular, subcutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified. The preparation of such formulations will be known to those of skill in the art in light of the present disclosure. Other routes of administration include intratumoral, peri-tumoral, intralymphatic, injection into inflamed tissue, or into lymph nodes. In some embodiments, the administration is systemic.

Other routes of administration are also contemplated. For example, the constructs and agents may be administered in association with a carrier. In some embodiments, the carrier is a nanoparticle or microparticle.

Particles can have a structure of variable dimension and known variously as a microsphere, microparticle, nanoparticle, nanosphere, or liposome. Such particulate formulations can be formed by covalent or non-covalent coupling of the construct to the particle. By "particle," "microparticle," "bead," "microsphere," and grammatical equivalents herein is meant small discrete particles that are administrable to a subject. In certain embodiments, the particles are substantially spherical in shape. The term "substantially spherical," as used herein, means that the shape of the particles does not deviate from a sphere by more than about 10%. The particles typically consist of a substantially spherical core and optionally one or more layers. The core may vary in size and composition. In addition to the core, the particle may have one or more layers to provide functionalities appropriate for the applications of interest. The thicknesses of layers, if present, may vary depending on the needs of the specific applications. For example, layers may impart useful optical properties.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. The pharmaceutically acceptable salts can be synthesized from the parent compound which contains a basic or acidic moiety by conventional chemical methods.

Some variation in dosage will necessarily occur depending on the condition of the subject. The person responsible for administration will, in any event, determine the appropriate dose for the individual subject. An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the effects desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

Typically, for a human adult (weighing approximately 70 kilograms), from about 0.1 mg to about 3000 mg (including all values and ranges there between), or from about 5 mg to about 1000 mg (including all values and ranges there between), or from about 10 mg to about 100 mg (including all values and ranges there between), of a compound are administered. It is understood that these dosage ranges are by way of example only, and that administration can be adjusted depending on the factors known to the skilled artisan.

In certain embodiments, a subject is administered about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or μg/kg or micrograms/kg/minute or mg/kg/min or micrograms/kg/hour or mg/kg/hour, or μM or mM of an agent discussed herein. Any range derivable therein is contemplated.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of a condition. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of the condition (or any range derivable therein). The patient may be treated for 1, 2, 3, 4, 5, 6, 7, 8, 9, 10 or more days (or any range derivable therein) or until symptoms of the condition have disappeared or been reduced or after 6, 12, 18, or 24 hours or 1, 2, 3, 4, or 5 days after symptoms of an infection have disappeared or been reduced.

X. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Engineering of Collagen-Binding Modification Enhanced the Efficacy of anti-inflammatory agents A. Results 1. CBP-Conjugation Provided Collagen Affinity to Anti-TNFα Antibody (αTNF)

After mixing anti-TNFα antibody (αTNF) with sulfosuccinimidyl-4-(N-maleimidomethyl) cyclohexane-1-carboxylate (sulfo-SMCC), the CBP was cross-linked covalently to the antibody. Up to 5 CBPs were bound to the antibody as calculated by matrix-assisted laser desorption/ionization-time-of-flight (MALDI-TOF) mass spectrometry (FIG. 1A). To examine the capacities of CBP-conjugated αTNF (CBP-αTNF) to bind collagens, the binding activities of CBP-αTNF and unmodified αTNF (WT-αTNF) against types I, II, and III collagen were determined by ELISA. CBP-αTNF bound to all tested types of collagen, whereas WT-αTNF binding signal to collagen was at undetectable level (FIG. 1B).

2. CBP-Conjugation Enabled αTNF to Localize in the Inflamed Paw of the Arthritis Model Localization of CBP-αTNF in the inflamed paw of the collagen antibody-induced arthritis (CAIA) model through binding to endogenous collagen was determined by in vivo bio-distribution analysis. Arthritis was induced selectively in right hind paw by passive immunization of anti-collagen antibodies, followed by subcutaneous injection of LPS at right hind footpad. The local LPS injection induced severe arthritis at the right hind paw compared with the other paws. On the following day of LPS injection, fluorescence labeled CBP-αTNF and WT-αTNF was intravenously injected into the CAIA and naïve mice. Fluorescence level in whole body was measured before the antibody injection and at 0.5, 1, 2, 4, 6, 24, and 48 hours after the injection. The fluorescence level in right hind arthritic paw of the CAIA mice injected with CBP-αTNF and WT-αTNF increased immediately after the injection, whereas that of naïve mice was almost the same in both arthritic and non-arthritic paws (FIGS. 2A and 2B). The ratio of the level in arthritic paw to non-arthritic paw was higher in mice injected with CBP-αTNF than WT-αTNF (FIG. 2C). The injected CBP-αTNF was detected in the synovium and pannus, the principal inflamed area of arthritis by the immunohistochemistry (FIG. 2D). These data indicate that CBD-αTNF preferentially localizes to the inflamed tissue (i.e. arthritic paw) after systemic injection, more than its unmodified form.

3. CBP-Conjugation Enhanced the Efficacy of αTNF in the Arthritis Model

The inventors next examined the anti-inflammatory efficacy of CBP-αTNF in the CAIA model. Arthritis was induced in all paws by passive immunization of anti-collagen antibodies, followed by intraperitoneal injection of LPS. On the day of LPS injection, control IgG, WT-αTNF, or CBP-αTNF was intravenously injected. Arthritis score was increased in control mice and the score was reduced by WT-αTNF and CBP-αTNF (FIG. 3A). The score reduction in CBP-αTNF-treated mice was significantly greater than WT-αTNF-treated mice. The histological observation revealed that the joint destruction was significantly suppressed by CBP-αTNF (FIG. 3B). The inventors further investigated whether CBP-αTNF could show the efficacy by injection via subcutaneous route. Similar tendency in the accumulation and the inhibitory efficacy was observed even in subcutaneous injection of CBP-αTNF (FIG. 4). These data indicate that CBP modification of αTNF provides superior anti-inflammatory efficacy to its unmodified form.

4. Local Injection of ECM-Binding αTNF had a Robust Effect on Arthritis Development To assess the therapeutic potency of localized therapy, the inventors conjugated αTNF with promiscuous ECM-binding peptide derived from placenta growth factor 2 (specifically, PlGF-$2_{123-144}$) in the same manner as CBP conjugation described previously (32, 33). PlGF-$2_{123-144}$ peptide binds to multiple ECM proteins with high affinity, thus it retains at injection site. PlGF-$2_{123-144}$-conjugated αTNF (PlGF-$2_{123-144}$-αTNF) injected at left hind footpad of CAIA mice retained at the injection site, whereas the signal from WT-αTNF rapidly reduced after the injection (FIG. 5A). To compare the efficacy, control IgG, WT-αTNF, or PlGF-$2_{123-144}$-αTNF was injected subcutaneously at left hind footpad of CAIA mice. Arthritis score was increased in both right and left hind limbs in control IgG-treated mice. WT-αTNF did not suppress the score in this treatment regimen. PlGF-$2_{123-144}$-αTNF, however, suppressed arthritis development almost completely in the treated paw (left) even at 100-times lower dose than WT-αTNF. Interestingly, PlGF-$2_{123-144}$-αTNF did not suppress the arthritis development in the untreated paw (right), indicating its localized efficacy (FIG. 5B). These data suggest that accumulation of drug in inflammatory site is crucial to suppress inflammation and maximize the efficacy of anti-inflammatory drugs.

5. CBD Protein Derived from the vWF A3 Domain can Target Inflamed Spinal Cord in the Experimental Autoimmune Encephalomyelitis (EAE) Model IL-4 is a cytokine that induces differentiation of naïve helper T cells (Th0) to Th2 cells. Application of IL-4 to the central nerve system by intrathecal or intranasal administration has been reported to ameliorate clinical signs and axonal morphology in experimental autoimmune encephalomyelitis (EAE) model, a mouse model for multiple sclerosis. Thus, to achieve EAE targeting of IL-4 from intravenously injection, which is clinically relevant injection route, the inventors synthesized vWF A3 domain-fused IL-4 (A3-IL4) protein. A3-IL4 bound to collagen III with a dissociation constant (Kd) of 28.6 nM (FIG. 6A). vWF A3 domain-fusion to IL-4 did not abolish the binding affinity against its receptor, IL-4Ra (FIG. 6B). Next, localization of the vWF A3 domain protein in the inflamed spinal cord of EAE model through binding to endogenous collagen was determined by fluorescence imaging. On day 14 post-immunization when the target tissues were inflamed, fluorescence-labeled A3 or A3-IL4 was intravenously injected into the naïve and EAE mice. A3 and A3-IL4 were detected in spinal cord of EAE mice, but not in that of a naïve mouse (FIG. 6C). The inventors next examined the therapeutic effect of A3-IL4 on EAE symptoms. From day 14 post-immunization when the first EAE symptoms appeared, PBS, normal form IL-4, and A3-IL4 were intravenously injected every other day. A3-IL4 reduced the mean disease score whereas normal IL-4 did not show any therapeutic effect (FIG. 6E).

6. A3 Protein and CBP-Conjugate can Also Target Inflamed Tissues of Other Inflammatory Disease Models To explore whether the collagen-binding engineering has versatile application for inflammatory diseases, localization of the A3 protein and CBP-conjugated antibody was determined in the inflamed tissues of the spontaneous inflammatory bowel disease (IBD), bleomycin-induced idiopathic pulmonary fibrosis (IPF), and type I diabetes (T1D) models by fluorescence imaging. When the target tissue was inflamed, fluorescence-labeled A3, CBP-αTNF, or CBP-conjugated anti-TGF-β antibody (CBP-αTGF) was intravenously injected to EAE, IBD, IPF, and T1D models, and fluorescent level in the target tissues was determined. A3 was detected in the colon of IBD-developed mice, and pancreas of spontaneous T1D and cyclophosphamide-induced T1D mice, but not in that of healthy mice (FIGS. 7A and 7C). Similarly, CBP-αTNF was detected in the spinal cord of EAE model, and the colon of IBD-developed mice, but not in that of healthy mice (FIGS. 6D and 7A). Histopathological analysis revealed that CBP-αTNF was localized in colonic lamina propria of the IBD model, where there were infiltrating cells (FIG. 7A). Also, CBP-αTGF was detected in the lung of IPF model, whereas unmodified antibody did not (FIG. 7B). These results suggest that installing collagen affinity to antibody and cytokine enables them to target inflamed tissues.

B. Discussion

In this study, it was demonstrated that installing collagen-binding affinity to anti-inflammatory antibody enhances its retention in the inflamed tissue and its therapeutic potency. Intravenously and subcutaneously injected CBP-αTNF was accumulated in the inflamed paw of CAIA model. Also, CBP conjugation to antibody enabled it to be detected in multiple inflammatory sites of EAE, IBD, and IPF models. This suggests that collagen affinity can target inflamed sites and is widely applicable to various inflammatory diseases. This is because collagen is universally and abundantly present around the vasculature, but is exposed to the blood stream only when hyper permeability of vasculature occurs in inflammatory tissue. Thus, collagen affinity as a drug delivery method is neither tissue, molecular expression, nor disease specific approach, rather general inflammation specific approach. More importantly, CBP-αTNF reduced arthritis score more effectively than unmodified αTNF in CAIA model. αTNF for inflammatory diseases such as RA and IBD does not show complete response in most patients and can have significant side effects (6-10). Therefore, CBP-αTNF holds translational potential to achieve advanced therapy for inflammation and autoimmune diseases.

To assess whether other collagen-binding protein can also target the site of inflammation after systemic injection, the inventors used the vWF A3 domain recombinant protein. A3-IL4 accumulated in the spinal cord and reduced disease scores in EAE model, whereas normal form of IL-4 did not. Targeting neuronal IL-4 signaling is expected to be a new therapeutic strategy to halt disability progression in multiple sclerosis (34). Although intrathecal or intranasal route is proposed for the IL-4 treatment to pass through blood brain barrier, this Example demonstrates that providing collagen-binding ability to IL-4 enabled to reduce clinical signs in EAE model even via intravenous route. It also shows A3 protein accumulation in the inflamed tissue of IBD and T1D models. The inventors used CAIA model for autoantibody-induced acute inflammation, EAE model for autoimmune-mediated chronic inflammation, IBD model for spontaneous developed inflammation, IPF model for fibrosis accompanied by inflammation, and T1D for spontaneously developed T-cell mediated autoimmune disease, as principal inflammatory models. These data suggest that collagen-binding antibodies and cytokines are able to achieve efficient antibody and cytokine therapy in multiple inflammatory diseases through accumulating in the site of inflammation.

This example shows that local injection of PlGF-2123-144-αTNF retained at injection site and showed strong therapeutic efficacy at a low dose. However, PlGF-2123-144-αTNF therapy is effective only when locally injected due to its promiscuous ECM affinity. The main translational advantage of collagen binding approach for inflammation-targeted therapy is that it can target inflammatory site from systemic delivery route. For clinical translation of collagen binding anti-inflammatory drugs, an advantage lies in the use of the A3 domain from vWF or the CBP from decorin is that both naturally exists in the human body, limiting the possibility of immune system recognition. Also, the CBP can be conjugated to antibodies with a simple chemical reaction. The advantage of this feature is in simplicity in production, in that it is possible to work with antibodies for which production has already been optimized. The inventors have shown that CBP was able to conjugate both anti-TNFα and anti-TGFβ antibodies in this example. The CBP conjugation synthesis reaction for antibodies can be done in only 90 minutes, using chemistry that is analogous to PEGylation of proteins. The same reaction is used in antibody-drug conjugates, such as in the production of trastuzumab emtansine (35, 36). As to A3-IL4, given that cytokines are small molecules and are generally easy to produce, the inventors chose to recombinantly fuse rather than to conjugate the A3 with IL-4. These features may facilitate development of collagen binding-drug therapy to overcome the barriers to clinical translation.

In conclusion, it was found that installing collagen affinity to antibody and cytokine enables them to target inflammatory sites. Moreover, collagen-binding anti-inflammatory drugs showed high therapeutic efficacy compared with their unmodified forms. This simple approach of an engineered collagen-binding drug may hold potential for clinical translation as an inflammation-targeted therapeutic.

C. Materials and Methods

1. Synthesis of CBP-Conjugated Antibodies

Rat anti-mouse TNF-α antibody (clone XT3.11, BioXcell) was incubated with 20 eq. of sulfo-succinimidyl 4-(N-maleimidomethyl) cyclohexane-1-carboxylate (sulfo-SMCC) for 30 min at room temperature. Excess sulfo-SMCC was removed using a Zeba spin desalting column (Thermo Fisher Scientific). 30 eq. of collagen-binding sequence peptide derived from decorion (CBP, LRELHLNNNC) was then added and reacted for 1 hour at room temperature for conjugation to the thiol moiety on the C residue. The peptide had been synthesized with >95% purity by Genscript.

2. Production and Purification of Recombinant vWF A3 Domain and A3-Fused IL-4 Proteins The sequence encoding for the human vWF A3 domain residues Cys1670-Gly1874 (907-1111 of mature vWF), and the human vWF A3 domain and mouse IL-4 fusion protein were synthesized and subcloned into the mammalian expression vector pcDNA3.1(+) by Genscript. A sequence encoding for 6 His was added at the N-terminus for further purification of the recombinant protein. Suspension-adapted HEK-293F cells were routinely maintained in serum-free FreeStyle 293 Expression Medium (Gibco). On the day of transfection, cells were inoculated into fresh medium at a density of $1\times10^6$ cells/ml. 2 μg/ml plasmid DNA, 2 μg/ml linear 25 kDa polyethylenimine (Polysciences), and OptiPRO SFM media (4% final concentration, Thermo Fisher) were sequentially added. The culture flask was agitated by orbital shaking at 135 rpm at 37° C. in the presence of 5% $CO_2$. 6 days after transfection, the cell culture medium was collected by centrifugation and filtered through a 0.22 μm filter. Culture media was loaded into a HisTrap HP 5 ml column (GE Healthcare), using an AKTA pure 25 (GE Healthcare). After washing of the column with wash buffer (20 mM imidazole, 20 mM $NaH_2PO_4$, 0.5 M NaCl, pH 7.4), protein was eluted with a gradient of 500 mM imidazole (in 20 mM $NaH_2PO_4$, 0.5 M NaCl, pH 7.4). The elusion solution was further purified with size exclusion chromatography using a HiLoad Superdex 200PG column (GE healthcare). All purification steps were carried out at 4° C. The expression of A3 and A3-IL-4 was determined by western blotting using anti-His tag antibody (BioLegend) and the proteins were verified as >90% pure by SDS-PAGE.

3. Detection of CBP-αTNF or A3-IL4 Binding to Collagen Proteins

The measurement is performed as described previously (32). 96-well ELISA plates (Greiner Bio One) were coated with types I, II, and III human collagen (10 μg/mL each in PBS, Millipore Sigma) for overnight at 37° C., followed by blocking with 1% BSA in PBS with 0.05% Tween 20 (PBS-T) for 1 hour at room temperature. Then, wells were washed with PBS-T and further incubated with 1 μM CBP-αTNF, 1 μM unmodified αTNF, or 0-740 nM A3-IL4 for 1 hour at room temperature. After 3 washes with PBS-T, antibody was detected by HRP-conjugated antibody against rat IgG, incubated 1 hour at room temperature (Jackson ImmunoResearch). A3-IL4 was detected by specific antibody against mouse IL-4 (R&D Systems). After washes, bound proteins were detected with tetramethylbenzidine substrate by measurement of the absorbance at 450 nm with subtraction of the absorbance at 570 nm.

4. Detection of A3-IL4 Binding to its Receptor

The measurement is performed as described previously (32). 96-well ELISA plates (Greiner Bio One) were coated with recombinant mouse IL-4Ra protein (10 μg/mL each in PBS, R&D Systems) for overnight at 37° C., followed by blocking with 1% BSA in PBS with PBS-T for 1 hour at room temperature. Then, wells were washed with PBS-T and further incubated with 0-740 nM A3-IL4 or IL-4 for 1 hour at room temperature. After 3 washes with PBS-T, IL-4 was detected by specific antibody against mouse IL-4 (R&D Systems). After washes, bound proteins were detected with tetramethylbenzidine substrate by measurement of the absorbance at 450 nm with subtraction of the absorbance at 570 nm.

5. MALDI-TOF MS

Antibodies were analyzed by MALDI-TOF MS (Bruker Ultraflextreme MALDI TOF/TOF). All spectra were collected with acquisition software Bruker flexControl™ and processed with analysis software Bruker flexAnalysis™. First, a saturated solution of the matrix, α-cyano-4-hydroxycinnamic acid (Sigma-Aldrich), was prepared in 50:50 acetonitrile:1% TFA in water as a solvent. The analyte in PBS (5 μL, 0.1 mg/mL) and the matrix solution (25 μL) were then mixed, and 1 μL of that mixture was deposited on the MTP 384 ground steel target plate. The drop was allowed to dry in a nitrogen gas flow, which resulted in the formation of uniform sample/matrix co-precipitate. All samples were analyzed using high mass linear positive mode method with 2500 laser shots at the laser intensity of 75%. The measurements were externally calibrated at three points with a mix of carbonic anhydrase, phosphorylase B, and bovine serum albumin.

6. In Vivo Bio-Distribution Study

Anti-TNFα antibody (clone XT3.11, BioXcell) and anti-TGF-β antibody (clone 1D11.16.8, BioXcell) were incubated with 8 eq. of $SM(PEG)_{24}$ (Thermo Fisher Scientific) for 30 min at room temperature. Excess $SM(PEG)_{24}$ was removed using a Zeba spin desalting column (Thermo Fisher Scientific). 30 eq Cy7-labeled CBP ([Cy7]LRELHLNNNC [COOH]) was then added and reacted for 30 min at room temperature for conjugation to the thiol moiety on the C residue. The peptide had been synthesized with >95% purity by Genscript. Unreacted dye was removed by dialysis against PBS. As to CBP-unconjugated antibodies, αTNF and αTGF were labeled using sulfo-Cy7 NHS ester (Lumiprobe) according to the manufacture's instruction. A3 and A3-IL4 were labeled using DyLight 800 NHS ester (Thermo Fisher Scientific) according to the manufacture's instruction. When the target tissue of the model mice was inflamed, 10 to 100 μg of Cy7 labeled WT-αTNF, WT-αTGF, CBP-αTNF and CBP-αTGF, or DyLight 800 labeled A3 and A3-IL4 were intravenously injected. Mice organs were harvested and imaged with the Xenogen IVIS Imaging System 100 (Xenogen) under the following conditions: f/stop: 2; optical filter excitation 745 nm; excitation 800 nm; exposure time: 5 sec; small binning.

7. Mouse Collagen Antibody-Induced Arthritis (CAIA) Model

Arthritis was induced in female Balb/c mice (7 weeks of age) by intraperitoneal injection of anti-collagen antibody cocktail (1.5 mg/mouse, Chondrex) on day −3, followed by intraperitoneal injection of LPS (50 μg/mouse, Chondrex) on day 0. On the day of LPS injection, mice were injected intravenously or subcutaneously at back with control IgG (200 μg/mouse), WT-αTNF (200 μg/mouse), or CBP-αTNF (200 μg/mouse); or injected subcutaneously at left hind footpad with control IgG (100 μg/mouse), WT-αTNF (100 μg/mouse), or PlGF-2123-144-αTNF (1 μg/mouse). Joint swelling was scored everyday as described elsewhere (31). On day 8, hind paws were fixed in 10% neutral formalin (Sigma-Aldrich), decalcified in Decalcifer II (Leica), and then provided to histological analysis.

8. Experimental Autoimmune Encephalomyelitis (EAE) Model

EAE was induced in female C57BL/6 mice (13 weeks of age) by immunization with an emulsion of $MOG_{35-55}$ in complete Freund's adjuvant (200 μg/mouse, Hooke Laboratories) on day 0, followed by administration of pertussis toxin in PBS (100 ng/mouse) on the day of immunization and the following day. On day 14 post-immunization when the EAE symptoms appeared, treatment of recombinant mouse IL-4 (Peprotech) at 1 μg/mouse or A3-IL4 at 1 μg/mouse (equivalent to 0.4 μg/mouse on a molar basis) was started and repeated every other day. Individual mice were scored daily for disease severity on the basis of the following scale: 0, no clinical disease; 0.5, tail weakness; 1, tail paralysis; 2, hindlimb weakness; 3, hindlimb paralysis; 3.5, forelimb weakness; 4, forelimb paralysis; or 5, moribund or death.

9. Spontaneous Colitis Model of Inflammatory Bowel Disease (IBD)

IL-$10^{-/-}$×TLR-$4^{-/-}$ (DKO) mice were kindly provided by Cathyn Nagler (The University of Chicago). The DKO mice develop colitis spontaneously and exhibit a high incidence of rectal prolapses. At 29 weeks of age when the first sign of rectal prolapse appeared, the mice were used as IBD-developed mice for imaging analysis. As a control of non-developed IBD, DKO mice at 16 weeks of age and genetic background strain (C57BL/6) mice were used.

10. Bleomycin-Induced Idiopathic Pulmonary Fibrosis (IPF) Model

Pulmonary fibrosis accompanied by inflammation were induced in female C57BL/6 mice (9 weeks of age) by an intranasal instillation of 100 μg/mouse of bleomycin (Sigma-Aldrich) in saline. On day 7 after the bleomycin administration when the lung was inflamed, the mice were used for imaging analysis.

11. NOD Mouse Model of Type I Diabetes (T1D)

Nonobese diabetic (NOD) mice is known as a spontaneous model of T-cell mediated autoimmune insulin-dependent diabetes mellitus (37, 38). Cyclophosphamide can promote the onset of diabetes in NOD mice (39). For imaging analysis, Balb/c mouse was used as a non-diabetic control, naturally developed diabetic NOD mouse, and diabetic mouse accelerated by intraperitoneal injection of cyclophosphamide (Sigma-Aldrich) at 300 mg/kg. Blood glucose level was used as an index of diabetes development.

12. Histological Analyses and Immunohistochemistry

Paraffin-embedded joint tissues from CAIA mice and colon from IBD-developed mice were sliced at 5 μm thickness and stained with H&E and/or PAS for pathological analysis. The severity of synovial hyperplasia and bone resorption for the arthritis model was scored by three-grade evaluation (0-2) according to the previously reported criteria with slight modifications as follows: 0, normal to minimal infiltration of pannus in cartilage and subchondral bone of marginal zone; 1, mild to moderate infiltration of marginal zone with minor cortical and medullary bone destruction; 2, severe infiltration associated with total or near total destruction of joint architecture. The scores in both hind paws were summed up for each mouse (score per mouse total, 0-4).

Immunohistostaining was performed according to standard procedures. Briefly, the sections were incubated in 0.3% $H_2O_2$ for 20 min, blocked with PBS-buffered 1% BSA for 1 hour, and incubated overnight at 4° C. with HRP-conjugated anti-rat IgG (Jackson ImmunoResearch) for 1 hour at room temperature and visualized with diaminobenzidine.

13. Statistical Analysis

Statistical analyses were performed using GraphPad Prism software, and $P<0.05$ was considered statistically significant. Changes in arthritis scores over time were assessed by repeated-measurement two-way ANOVA, and when interactions were considered significant, data were assessed using Dunnett's multiple comparison test at each time point of measurement. To compare the efficacy of CBP-αTNF with WT-αTNF, the data on day 8 were analyzed again via Tukey's multiple comparison test. For histological scores in the CAIA model, Dunnett's multiple comparison test was used to compare the difference between the control IgG-injected group and the αTNF treatment groups.

D. References

The following references and the publications referred to throughout the specification, to the extent that they provide exemplary procedural or other details supplementary to those set forth herein, are specifically incorporated herein by reference.

1. Moreland L W, Schiff M H, Baumgartner S W, Tindall E A, Fleischmann R M, Bulpitt K J, et al. Etanercept therapy in rheumatoid arthritis. A randomized, controlled trial. Ann Intern Med. 1999; 130(6):478-86.
2. Maini R, St Clair E W, Breedveld F, Furst D, Kalden J, Weisman M, et al. Infliximab (chimeric anti-tumour necrosis factor alpha monoclonal antibody) versus placebo in rheumatoid arthritis patients receiving concomitant methotrexate: a randomised phase III trial. ATTRACT Study Group. Lancet. 1999; 354(9194):1932-9.
3. Sandborn W J, Hanauer S B, Katz S, Safdi M, Wolf D G, Baerg R D, et al. Etanercept for active Crohn's disease: a randomized, double-blind, placebo-controlled trial. Gastroenterology. 2001; 121(5):1088-94.
4. Weinblatt M E, Keystone E C, Furst D E, Moreland L W, Weisman M H, Birbara C A, et al. Adalimumab, a fully human anti-tumor necrosis factor alpha monoclonal antibody, for the treatment of rheumatoid arthritis in patients taking concomitant methotrexate: the ARMADA trial. Arthritis Rheum. 2003; 48(1):35-45.
5. Jarnerot G, Hertervig E, Friis-Liby I, Blomquist L, Karlen P, Granno C, et al. Infliximab as rescue therapy in severe to moderately severe ulcerative colitis: a randomized, placebo-controlled study. Gastroenterology. 2005; 128(7): 1805-11.
6. Bongartz T, Sutton A J, Sweeting M J, Buchan I, Matteson E L, Montori V. Anti-TNF antibody therapy in rheumatoid arthritis and the risk of serious infections and malignancies: systematic review and meta-analysis of rare harmful effects in randomized controlled trials. JAMA. 2006; 295(19):2275-85.
7. Dixon W G, Hyrich K L, Watson K D, Lunt M, Galloway J, Ustianowski A, et al. Drug-specific risk of tuberculosis in patients with rheumatoid arthritis treated with anti-TNF therapy: results from the British Society for Rheumatology Biologics Register (BSRBR). Ann Rheum Dis. 2010; 69(3):522-8.
8. Bellis E, Scire C A, Carrara G, Adinolfi A, Batticciotto A, Bortoluzzi A, et al. Ultrasound-detected tenosynovitis independently associates with patient-reported flare in patients with rheumatoid arthritis in clinical remission: results from the observational study STARTER of the Italian Society for Rheumatology. Rheumatology (Oxford). 2016; 55(10):1826-36.
9. Lisbona M P, Solano A, Ares J, Almirall M, Salman-Monte T C, Maymo J. ACR/EULAR Definitions of Remission Are Associated with Lower Residual Inflammatory Activity Compared with DAS28 Remission on Hand MRI in Rheumatoid Arthritis. J Rheumatol. 2016; 43 (9):1631-6.
10. Vreju F A, Filippucci E, Gutierrez M, Di Geso L, Ciapetti A, Ciurea M E, et al. Subclinical ultrasound synovitis in a particular joint is associated with ultrasound evidence of bone erosions in that same joint in rheumatoid patients in clinical remission. Clin Exp Rheumatol. 2016; 34(4):673-8.
11. Maeda H, Wu J, Sawa T, Matsumura Y, Hori K. Tumor vascular permeability and the EPR effect in macromolecular therapeutics: a review. J Control Release. 2000; 65(1-2):271-84.

12. Fang J, Nakamura H, Maeda H. The EPR effect: Unique features of tumor blood vessels for drug delivery, factors involved, and limitations and augmentation of the effect. Adv Drug Deliv Rev. 2011; 63(3):136-51.
13. Matsumura Y, Maeda H. A new concept for macromolecular therapeutics in cancer chemotherapy: mechanism of tumoritropic accumulation of proteins and the antitumor agent smancs. Cancer Res. 1986; 46(12 Pt 1):6387-92.
14. Nehoff H, Parayath N N, Domanovitch L, Taurin S, Greish K. Nanomedicine for drug targeting: strategies beyond the enhanced permeability and retention effect. Int J Nanomedicine. 2014; 9:2539-55.
15. Rahman M, Akhter S, Ahmad J, Ahmad M Z, Beg S, Ahmad F J. Nanomedicine-based drug targeting for psoriasis: potentials and emerging trends in nanoscale pharmacotherapy. Expert Opin Drug Deliv. 2015; 12(4):635-52.
16. Maeda H. Polymer therapeutics and the EPR effect. J Drug Target. 2017; 25(9-10):781-5.
17. McDonald D M. Angiogenesis and remodeling of airway vasculature in chronic inflammation. Am J Respir Crit Care Med. 2001; 164(10 Pt 2): S39-45.
18. Ricard-Blum S. The collagen family. Cold Spring Harb Perspect Biol. 2011; 3(1):a004978.
19. Dubois C, Panicot-Dubois L, Merrill-Skoloff G, Furie B, Furie B C. Glycoprotein VI-dependent and -independent pathways of thrombus formation in vivo. Blood. 2006; 107(10):3902-6.
20. Bergmeier W, Hynes R O. Extracellular matrix proteins in hemostasis and thrombosis. Cold Spring Harb Perspect Biol. 2012; 4(2):a005132.
21. Wynn T A. Cellular and molecular mechanisms of fibrosis. J Pathol. 2008; 214(2):199-210.
22. Addi C, Murschel F, De Crescenzo G. Design and Use of Chimeric Proteins Containing a Collagen-Binding Domain for Wound Healing and Bone Regeneration. Tissue Eng Part B Rev. 2017; 23(2):163-82.
23. Svensson L, Heinegard D, Oldberg A. Decorin-binding sites for collagen type I are mainly located in leucine-rich repeats 4-5. J Biol Chem. 1995; 270(35):20712-6.
24. Nareyeck G, Seidler D G, Troyer D, Rauterberg J, Kresse H, Schonherr E. Differential interactions of decorin and decorin mutants with type I and type VI collagens. Eur J Biochem. 2004; 271(16):3389-98.
25. Bidanset D J, Guidry C, Rosenberg L C, Choi H U, Timpl R, Hook M. Binding of the proteoglycan decorin to collagen type VI. J Biol Chem. 1992; 267(8):5250-6.
26. Kalamaj ski S, Aspberg A, Oldberg A. The decorin sequence SYIRIADTNIT binds collagen type I. J Biol Chem. 2007; 282(22):16062-7.
27. Federico S, Pierce B F, Piluso S, Wischke C, Lendlein A, Neffe A T. Design of Decorin-Based Peptides That Bind to Collagen I and their Potential as Adhesion Moieties in Biomaterials. Angew Chem Int Ed Engl. 2015; 54(37): 10980-4.
28. Lenting P J, Casari C, Christophe O D, Denis C V. von Willebrand factor: the old, the new and the unknown. J Thromb Haemost. 2012; 10(12):2428-37.
29. Shahidi M. Thrombosis and von Willebrand Factor. Adv Exp Med Biol. 2017; 906:285-306.
30. Wu D, Vanhoorelbeke K, Cauwenberghs N, Meiring M, Depraetere H, Kotze H F, et al. Inhibition of the von Willebrand (VWF)-collagen interaction by an antihuman VWF monoclonal antibody results in abolition of in vivo arterial platelet thrombus formation in baboons. Blood. 2002; 99(10):3623-8.
31. Ribba A S, Loisel I, Lavergne J M, Juhan-Vague I, Obert B, Cherel G, et al. Ser968Thr mutation within the A3 domain of von Willebrand factor (VWF) in two related patients leads to a defective binding of VWF to collagen. Thromb Haemost. 2001; 86(3):848-54.
32. Ishihara J, Fukunaga K, Ishihara A, Larsson H M, Potin L, Hosseinchi P, et al. Matrix-binding checkpoint immunotherapies enhance antitumor efficacy and reduce adverse events. Sci Transl Med. 2017; 9(415).
33. Martino M M, Briquez P S, Guc E, Tortelli F, Kilarski W W, Metzger S, et al. Growth factors engineered for super-affinity to the extracellular matrix enhance tissue healing. Science. 2014; 343(6173):885-8.
34. Vogelaar C F, Mandal S, Lerch S, Birkner K, Birkenstock J, Buhler U, et al. Fast direct neuronal signaling via the IL-4 receptor as therapeutic target in neuroinflammation. Sci Transl Med. 2018; 10(430).
35. Lambert J M, Chari R V. Ado-trastuzumab Emtansine (T-DM1): an antibody-drug conjugate (ADC) for HER2-positive breast cancer. J Med Chem. 2014; 57(16):6949-64.
36. Peters C, Brown S. Antibody-drug conjugates as novel anti-cancer chemotherapeutics. Biosci Rep. 2015; 35(4): e00225.
37. Castano L, Eisenbarth G S. Type-I diabetes: a chronic autoimmune disease of human, mouse, and rat. Annu Rev Immunol. 1990; 8:647-79.
38. Bach J F. Insulin-dependent diabetes mellitus as an autoimmune disease. Endocr Rev. 1994; 15(4):516-42.
39. Charlton B, Bacelj A, Slattery R M, Mandel T E. Cyclophosphamide-induced diabetes in NOD/WEHI mice. Evidence for suppression in spontaneous autoimmune diabetes mellitus. Diabetes. 1989; 38(4):441-7.

Example 2: Enhanced Lymph Node Trafficking of Engineered IL-10 Suppresses Murine Models of Rheumatoid Arthritis Rheumatoid arthritis (RA) is a major autoimmune disease. Although clinical trials using interleukin-10 (IL-10) have been performed as a potential treatment of RA, its therapeutic effects have been limited, potentially due to insufficient residence in lymphoid organs, where antigen recognition primarily occurs. Here, the inventors engineered IL-10 as a fusion with serum albumin (SA) without and with fusion of a collagen binding domain (CBD). SA-IL-10 and CBD-SA-IL-10 exhibited longer circulation times than unmodified IL-10 after intravenous injection; moreover, SA fusion led to enhanced lymph node (LN) accumulation compared with unmodified IL-10. Intravenous SA-IL-10 and CBD-SA-IL-10 treatment restored immune cell composition in the paws to a normal status, elevated the frequency of suppressive M2 macrophages, and protected joint morphology. Intravenous SA-IL-10 and CBD-SA-IL-10 showed similar efficacy as treatment with an anti-TNF-α antibody. SA fusion to IL-10 is a simple but effective engineering strategy to achieve LN accumulation and control of RA.

Rheumatoid arthritis (RA) is an autoimmune disease that is currently controlled through treatment with inhibitors of inflammatory pathways. Pathological features of RA are synovitis and joint destruction, which cause severe pain and joint dysfunction (1, 2). Although the causal antigen for RA has not been fully elucidated, collagen recognition by immune cells plays a key role. During progression of RA, autoantigen-specific T cells, especially Th17 cells, are activated and produce inflammatory cytokines including IL-17.

Inflammatory cytokines, such as TNF-α and IL-6, in the joint induce activation of macrophages and neutrophils as mediators of the inflammatory response. These inflammatory cells infiltrate the joints and cause various inflammatory responses including activation of osteoclasts that destroy the bones in the joint (3). The current strategy for RA treatment is symptomatic, and considering that many inflammatory cytokines are involved RA progression, various biological therapeutics, such as antibodies or soluble receptors for TNF-α, have been developed and approved for clinical use (4).

As another type of biological therapeutic, administration of anti-inflammatory cytokines has been studied for treatment of RA to induce systemic suppression of inflammation or tolerance. IL-10 is one such anti-inflammatory cytokine (5-7), and various attempts have been performed to explore IL-10-based autoimmune disease therapeutics (6-8). However, the therapeutic effect of IL-10 in autoimmune disease is still controversial, possibly because of its short circulating half-life and its uncontrolled biodistribution after systemic administration (8).

In the present study, the inventors engineered IL-10 by fusion of serum albumin (SA) to provide prolonged blood circulation and by fusion of a collagen binding domain (CBD) to provide binding affinity to the inflamed site where the permeability of blood vessels is enhanced and extracellular matrix proteins including collagens are exposed to proteins from the blood (16, 17). Thus, the inventors reasoned that CBD-fusion to SA would add inflammatory site targeting to the SA-fused cytokine. By doing this, the inventors sought to explore if enhanced blood circulation and disease site vasculature targeting synergizes to improve IL-10's therapeutic effects on RA. However, the inventors made the observation that SA fusion to IL-10 not only enhanced circulation time but also accumulation in the lymph nodes (LNs). Here, suppression effects of arthritis by engineered IL-10 were evaluated using a passive collagen antibody-induced arthritis (CAIA) model and an active CIA model in the mouse. The inventors found that CBD fusion enhanced accumulation in the inflamed paw and moreover that SA fusion to IL-10 enhanced trafficking of IL-10 into LNs after intravenous injection. SA-fused IL-10 significantly improved the anti-inflammatory effects of IL-10 in the two murine RA models and functioned similarly to TNF-α blockade.

A. Albumin-Fused IL-10 Binds to FcRn and APCs and Accumulates within the LNs

Figure 14A:
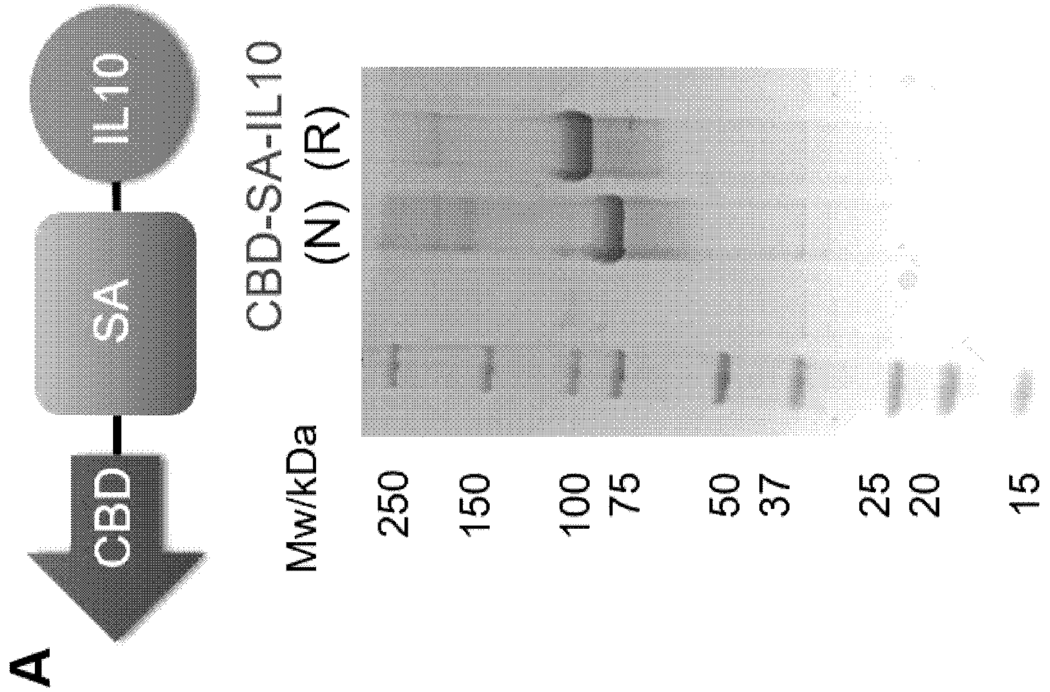

Wild type (wt) mouse IL-10, SA-fused mouse IL-10, and CBD-SA-fused IL-10 were recombinantly expressed, and the molecular weights of the fusion proteins were correspondingly higher than for wt IL-10 as determined by SDS-PAGE; in addition, most of the SA-IL-10 and CBD-SA-IL-10 existed as a monomer under non-reducing conditions (FIGS. 8A and 14A). Surface plasmon resonance (SPR) analysis revealed that SA-IL-10 and CBD-SA-IL-10 bind to neonatal Fc receptor (FcRn) with micromolar order of $K_d$ (FIGS. 8B and 14B). In addition, CBD-SA-IL-10 was shown to bind type I and type III collagens with nanomolar order of $K_d$ (FIG. 14B). The binding ability of these proteins to splenocytes and single cells isolated from the popliteal LN was further evaluated by flow cytometry (FIG. 8C). SA-fused IL-10 exhibited high binding to macrophages and dendritic cells in both splenocytes and LN-derived cells. After intravenous administration of fluorescently-labeled SA-IL-10, significantly higher fluorescence signals were observed within the popliteal LN compared with wt IL-10 (FIG. 8D). Interestingly, higher fluorescence signals were located surrounding high endothelial venules (HEVs), where antigen presenting cells (APCs) reside (18).

B. Albumin-Fused IL-10 Shows Prolonged Blood Circulation, and CBD Fusion Leads to Accumulation in the Inflamed Paw SA is known to demonstrate long circulation via FcRn-mediated recycling on vascular endothelial cells (19, 20). As expected, SA-IL-10 showed significantly prolonged blood circulation compared with wt IL-10; CBD-SA-IL-10 had also comparable circulation as SA-IL-10 (FIG. 9A). FIG. 9B represents the fluorescence signals from major organs of mice intravenously injected with DyLight800-labeled proteins. Reflecting their long circulation properties, SA-IL-10 and CBD-SA-IL-10 showed higher signals in the heart, lungs and spleen than that of wt IL-10. In addition, significantly higher signal was detected from the inflamed paw of mice treated with CBD-SA-IL-10 than wt IL-10, whereas the non-inflamed paw exhibited fluorescence that was not significantly different between wt IL-10 and CBD-SA-IL-10, indicating the inflammation targeting capability of CBD-SA-IL-10 through collagen affinity, as reported in previous studies in other contexts (16, 21).

C. Albumin-Fused IL-10 Suppresses the Development of Arthritis

The therapeutic effects of engineered IL-10 in the passive collagen antibody-induced arthritis (CAIA) model were evaluated (FIG. 10). Intravenous injection of SA-IL-10 or CBD-SA-IL-10 significantly suppressed the development of arthritis, whereas PBS- or wt IL-10-injected mice exhibited severe inflammation in the paws (FIG. 10A). The therapeutic effect of CBD-SA-IL-10 was compared with treatment with anti-TNF-α antibody (αTNF-α), a mouse model of a clinically used antibody drug for treatment of RA, where CBD-SA-IL-10 induced comparable suppression of CAIA as αTNF-α (FIG. 10B). Histological analysis revealed that both CBD-SA-IL-10 and αTNF-α suppressed joint destruction compared with PBS- or wt IL-10 treatment (FIG. 10C). Histological scores also significantly decreased due to treatment with CBD-SA-IL-10 and αTNF-α (FIG. 10C). The effect of the administration route on therapeutic efficacy was also investigated, comparing intravenous, local (footpad), and subcutaneous (at a distant site, mid-back) administration (FIG. 10D). Footpad injection of CBD-SA-IL-10 induced a relatively high suppression effect on CAIA compared with the results of its intravenous injection shown in FIG. 10A and FIG. 10B, suggesting retention of CBD-SA-IL-10 at the inflamed paws via collagen affinity (FIG. 8B). Strikingly, SA-IL-10 showed quite high suppression effects on CAIA by all of the administration routes tested (FIG. 10D).

As a second arthritis model, the active collagen-induced arthritis (CIA) model was used for evaluation of CBD-SA-IL-10 and SA-IL-10 on RA treatment. CBD-SA-IL-10 significantly suppressed the increase of clinical scores compared with PBS-treated CIA mice (FIG. 11A), and its therapeutic effect was comparable with αTNF-α treatment. Histology of the joints and histological scores also revealed suppression of arthritis establishment by CBD-SA-IL-10 (FIG. 11B). Importantly, 5 out of 10 mice treated with CBD-SA-IL-10 showed a score of 1 or less, suggesting a high therapeutic effect of CBD-SA-IL-10. Without the CBD domain, a single injection of SA-IL-10 to CIA mice induced significant suppression of establishment of arthritis compared with PBS (FIG. 11C). Most mice treated with PBS showed severe inflammation at the paws as indicated by histology and the histological score (FIG. 11D). In contrast, SA-IL-10-treated mice exhibited almost identical status in the paw as naïve mice, and most mice showed a histological score of 1 or less. Taken together, these results indicate the highly suppressive effect of inflammation by local or intravenous administration of CBD-SA-IL-10 and by even subcutaneous administration of SA-IL-10.

D. Albumin-Fused IL-10 Reduces Immune Activity after Accumulation within LNs

SA-fused IL-10 showed micromolar affinity to FcRn (FIG. 8B) and accumulation within LNs after intravenous injection (FIG. 8D). Next, the amounts of IL-10 and its pharmacokinetics in the LNs were quantitatively evaluated (FIG. 12A-C). After intravenous injection of wt IL-10, SA-IL-10, or CBD-SA-IL-10 within CAIA mice, IL-10 concentrations in the LNs at various time points were detected using ELISA. SA-IL-10 showed significantly higher IL-10 signals in the joint-draining (popliteal) LN, the mesenteric LN and relatively high signals in a non-draining (cervical) LN compared with wt IL-10 and CBD-SA-IL-10 at 4 hr after injection, and CBD-SA-IL-10 showed higher accumulation than wt IL-10 (FIG. 12A). SA-IL-10-injected mice also showed a peak for IL-10 concentration at around 1 hour after injection (FIG. 12B) and 5-10 times higher AUC than wt IL-10 in the LNs (FIG. 12C). These data indicate that SA-IL-10 immediately accumulated within LNs after intravenous injection and showed higher retention in the LNs compared with wt IL-10.

Figure 15A:
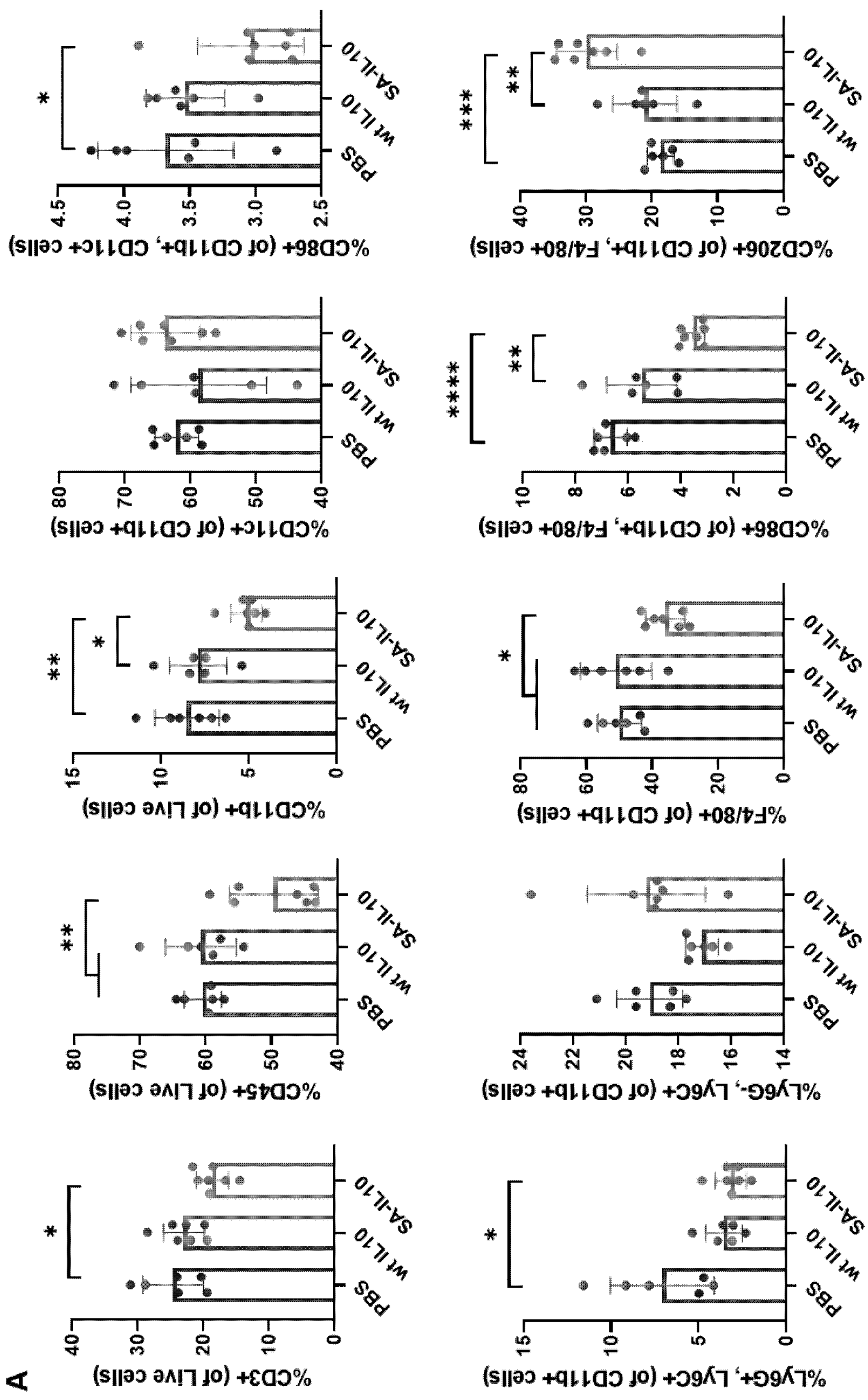
FIG. 15A-B. Effect of albumin-fused IL-10 on immune cell populations in the spleen (A) and LNs (B). Arthritis (CAIA) was induced by passive immunization of anti-collagen antibodies, followed by intraperitoneal injection of LPS (defined as Day 3). On Day 3 and Day 6, PBS, wt IL-10, or SA-IL-10 were intravenously injected to mice. Single cells were extracted from the spleen and the popliteal LN on the day following the last injection, followed by flow cytometric analysis. Graphs depict the frequency of $CD3^+$ T cells within live cells, $CD45^+$ lymphocytes within live cells, $CD11b^+$ cells within live cells, $CD11c^+$ cells within $CD11b^+$ cells, $CD86^+$ cells within $CD11c^+$ cells, granulocytic MDSC/neutrophils ($Ly6G^+$ $Ly6C^+$ within $CD11b^+$ cells), monocytic MDSC ($Ly6G^-$ $Ly6C^+$ within $CD11b^+$ cells), macrophages ($F4/80^+$ within $CD11b^+$ cells), $CD86^+$ cells within macrophages, and M2 macrophages ($CD206^+$ $F4/80^+$ within $CD11b^+$ cells. (mean±SEM; n=6-7) Statistical analyses were done using analysis of variance (ANOVA) with Tukey's test except for the following graphs. For analysis of % $CD11c^+$ within $CD11b^+$ cells in (A) and % $Ly6G^+$, $Ly6C^+$ within $CD11b^+$ cells in (B), Kruskal-Wallis test followed by Dunn's multiple comparison test was employed.*P<0.05; P<0.01; *P<0.001; ****P<0.0001.
Figure 15B:
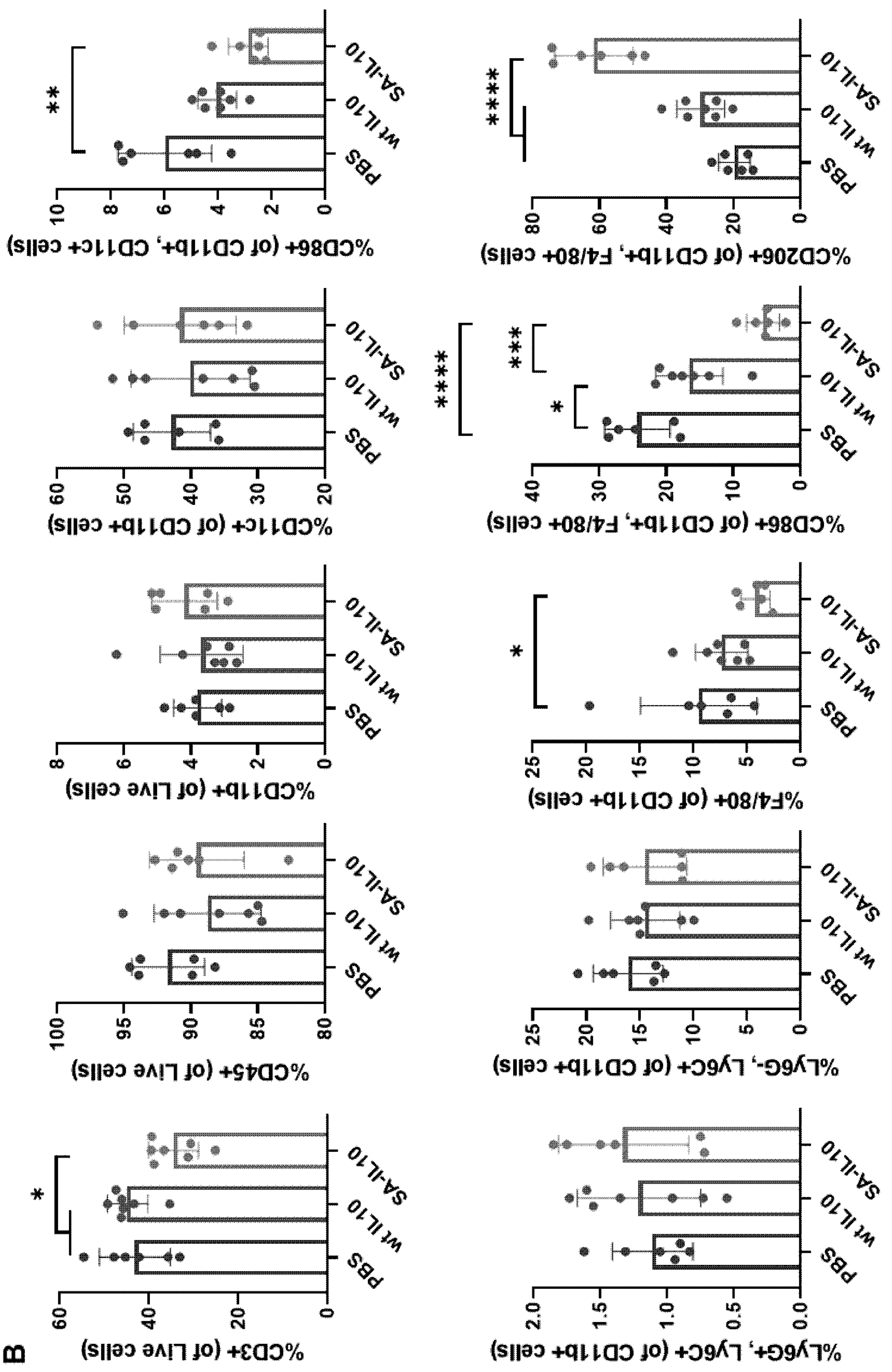

High concentrations and AUC of SA-IL-10 in the LNs may affect the phenotypes of various immune cells in LNs and other secondary lymphoid organs. Therefore, immune cell populations in the spleen and popliteal LN were analyzed by flow cytometry (FIG. 15). Intravenous injection of SA-IL-10 induced a significant decrease in the frequency of $CD3^+$ T cells and $CD45^+$ lymphocytes in the spleen (FIG. 15A). In addition, the frequencies of $CD86^+$ dendritic cells, granulocytic myeloid-derived suppressor cells (G-MDSCs), and $CD86^+$ M1 macrophages decreased and that of $CD206^+$ M2 macrophages increased after injection of SA-IL-10 compared with PBS or wt IL-10. A similar tendency was observed within the popliteal LNs (FIG. 15B). These data suggest that SA-IL-10 suppressed the activity of APCs and simultaneously activated immunosuppressive M2 macrophages. Deactivation of APCs in the LNs, and high accumulation of IL-10 might suppress the activity of Th17 cells, which play a crucial role in the development of RA (22, 23). The inventors measured Th17-relating cytokines (IL-17, IL-6 and TGF-β) in the LNs in the joint-draining (popliteal) and a non-draining (cervical) LN: compared to treatment with wt IL-10, IL-17 was statistically reduced in the popliteal LN after treatment by SA-IL-10, but not statistically by CBD-SA-IL-10, and levels in the cervical LN were not statistically reduced by either IL-10 variant (FIGS. 12D and 12E). Treatment by SA-IL-10 reduced the concentration of GM-CSF in the popliteal LN, whereas wt IL-10 did not (FIG. 12F).

E. Albumin-Fused IL-10 Suppresses Inflammatory Responses in the Paws

Figure 16A:
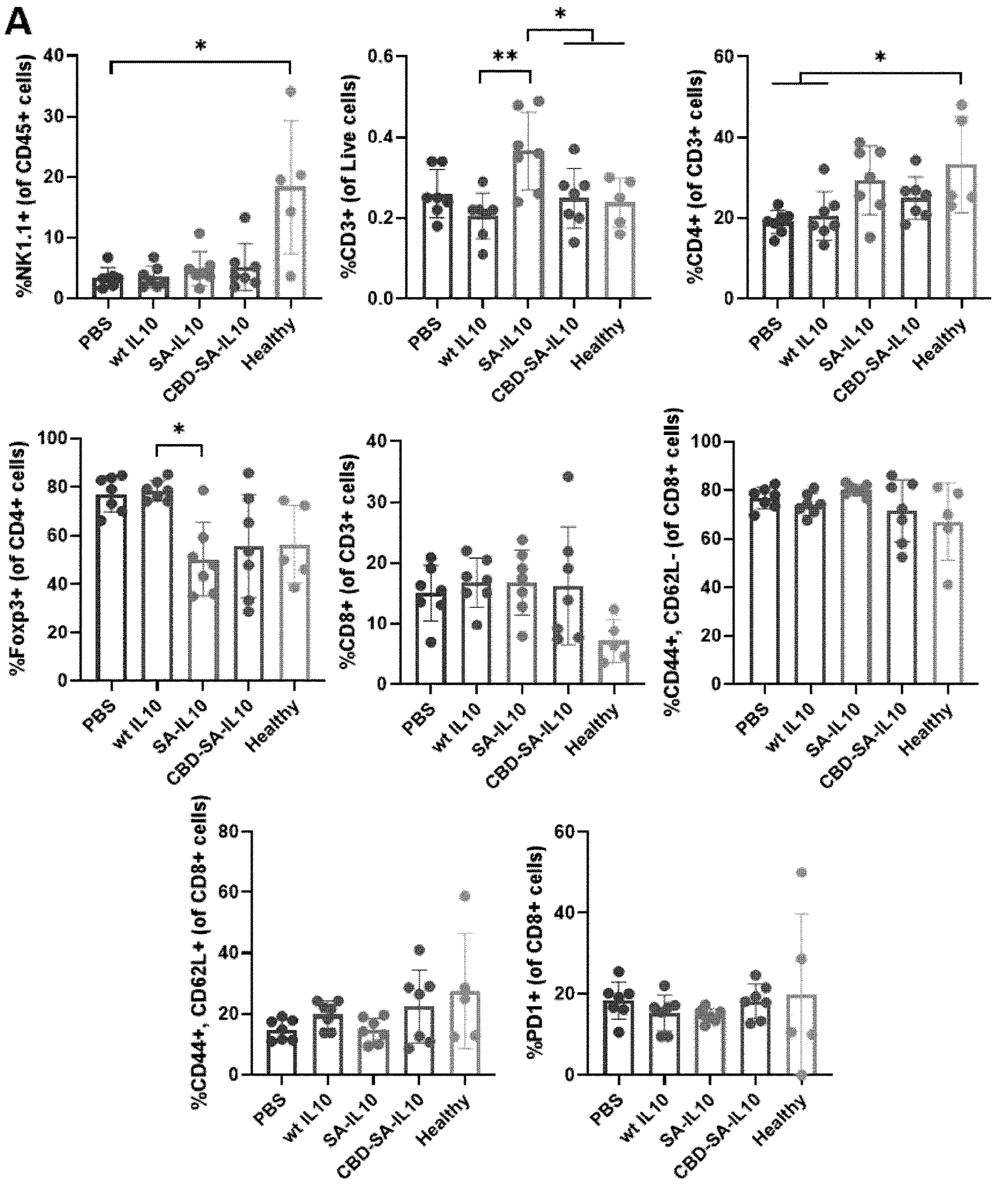
FIG. 16A-B. Effect of albumin-fused IL-10 on T cell populations in paws and blood. Arthritis (CAIA) was induced by passive immunization of anti-collagen antibodies, followed by intraperitoneal injection of LPS (defined as Day 3). On the day of LPS injection, PBS, wt IL-10, SA-IL-10 or CBD-SA-IL-10 were intravenously injected to mice. (A) Single cells were extracted from the hind paws on day 11, followed by flow cytometric analysis. Graphs depict the frequency of $NK1.1^+$ $CD3^-$ NK cells within $CD45^+$ lymphocytes, $CD3^+$ T cells within $CD45^+$ lymphocytes, $CD3^+$ $CD4^+$ T cells within $CD45^+$ lymphocytes, Treg ($Foxp3^+$ $CD25^+$) of $CD3^+$ $CD4^+$ T cells, $CD3^+$ $CD8^+$ T cells within $CD45^+$ lymphocytes, effector memory T cells ($CD62L^-$ $CD44^+$) of $CD3^+$ $CD8^+$ T cells, central memory T cells ($CD62L^+$ $CD44^+$) of $CD3^+$ $CD8^+$ T cells, $PD\text{-}1^+$ cells of $CD3^+$ $CD8^+$ T cells. (B) Lymphocytes were extracted from blood on day 11, followed by flow cytometric analysis. Graphs depict the frequency of $CD3^+$ T cells within $CD45^+$ lymphocytes, $CD3^+$ $CD4^+$ T cells within $CD45^+$ lymphocytes, Treg ($Foxp3^+$ $CD25^+$) of $CD3^+$ $CD4^+$ T cells, $CD3^+$ $CD8^+$ T cells within $CD45^+$ lymphocytes. (mean±SEM; n=5-7) Statistical analyses were done using analysis of variance (ANOVA) with Tukey's test except for the following graphs: for analysis of % $NK1.1^+$ within $CD45^+$ cells, % $Foxp3^+$ within $CD4^+$ cells, % $CD44^+/CD62L^-$ within $CD8^+$ cells, % $CD44^+/CD62L^+$ within $CD8^+$ cells and % $PD\text{-}1^+$ within $CD8^+$ cells in (A), Kruskal-Wallis test followed by Dunn's multiple comparison test was employed. *P<0.05; P<0.01; *P<0.001.
Figure 16B:
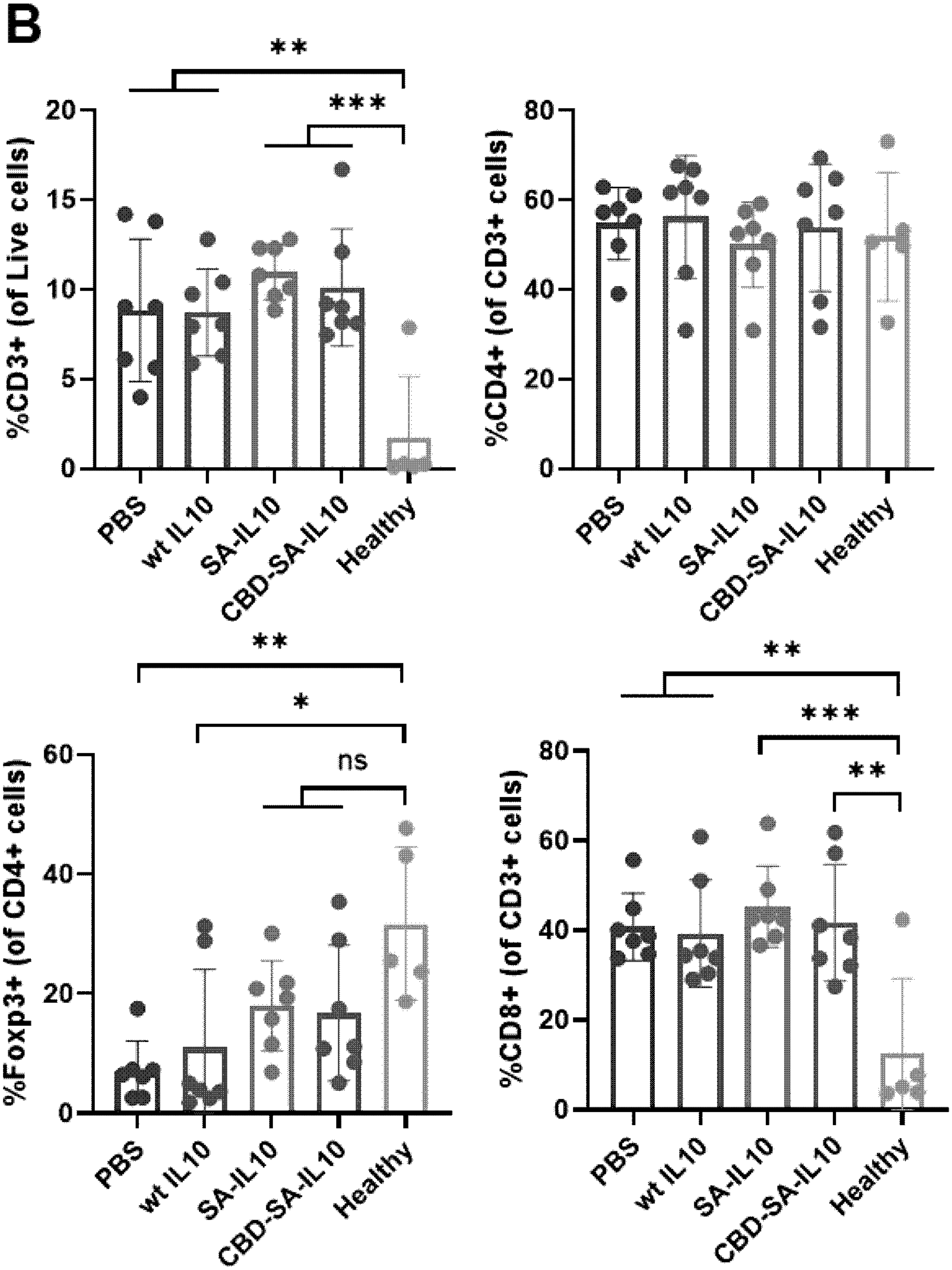

Next, immune cell populations in the hind paws were analyzed using flow cytometry (FIG. 13A). After intravenous injection of SA-IL-10 or CBD-SA-IL-10, frequencies of $CD45^+$ immune cells were significantly decreased compared with PBS- or wt IL-10-treated groups. Within $CD45^+$ cells, the frequencies of B cells and dendritic cells became comparable to levels in healthy mice, and $CD11b^+$ cells were remarkably decreased to the level of healthy mice as well. Among $CD11b^+$ cells, the G-MDSC population was reduced, and the macrophage frequency was recovered to the level of healthy mice. In addition, the frequency of $CD206^+$ M2 macrophages was significantly increased by injection of SA-IL-10 compared with PBS or wt IL-10 treatment, even exceeding that of healthy mice. The analysis of T cell populations in the paws revealed that SA-IL-10 suppressed the change in CD4+ cells and $Foxp3^+$ Treg in CAIA mice (FIG. 16A). Furthermore, SA-IL-10 suppressed a decrease of the Treg frequency in the blood (FIG. 16B). Reflecting these changes in immune cell populations, various inflammatory cytokines in the paws were significantly decreased by intravenous injection of SA-IL-10 or CBD-SA-IL-10, which levels were comparable with those in healthy mice (FIG. 13B). From histological analysis, intravenous administration of SA-IL-10 significantly suppressed the inflammatory responses in the paws compared with PBS-treated mice and reduced joint pathology (FIG. 13C).

F. Albumin-Fused IL-10 Shows No Toxicity after Injection

Figure 17A:
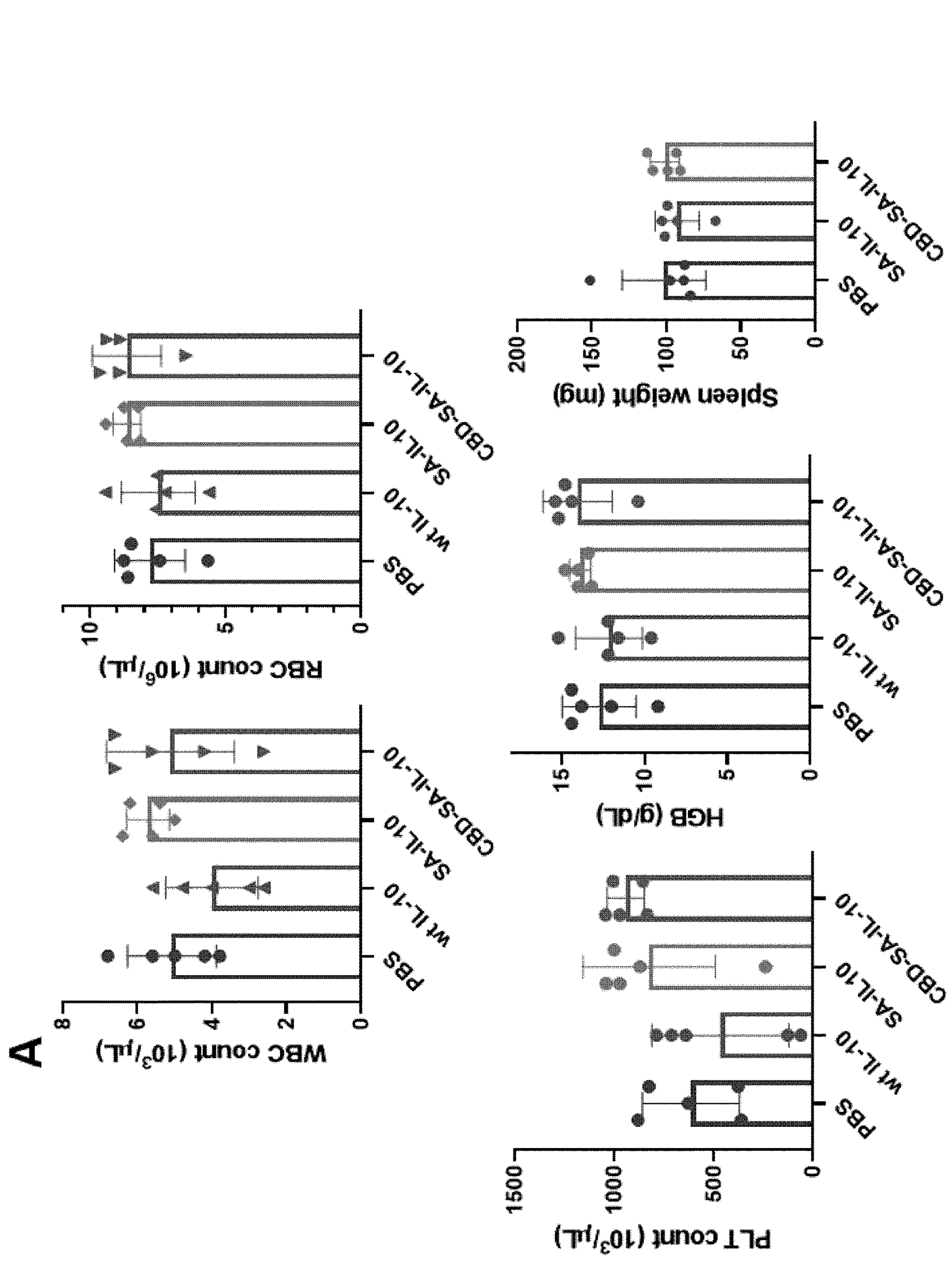
FIG. 17A-B. Safety assessments of albumin-fused IL-10. wt IL-10, SA-IL-10, or CBD-SA-IL-10 were intravenously injected to healthy BALB/c mice. (A) Two days after injection, white blood cell counts, red blood cell counts, platelet counts, the concentration of hemoglobin in blood and the weight of spleen were assessed. (B) The concentrations of alanine transaminase (ALT), amylase, blood urea nitrogen (BUN), serum calcium, creatine kinase (CK), $CO_2$, total bilirubin (TBli) and total proteins in serum were assessed using biochemistry analyzer. (mean±SEM; n=5) Statistical analyses were done using analysis of variance (ANOVA) with Tukey's test. *P<0.05; **P<0.01.
Figure 17B:
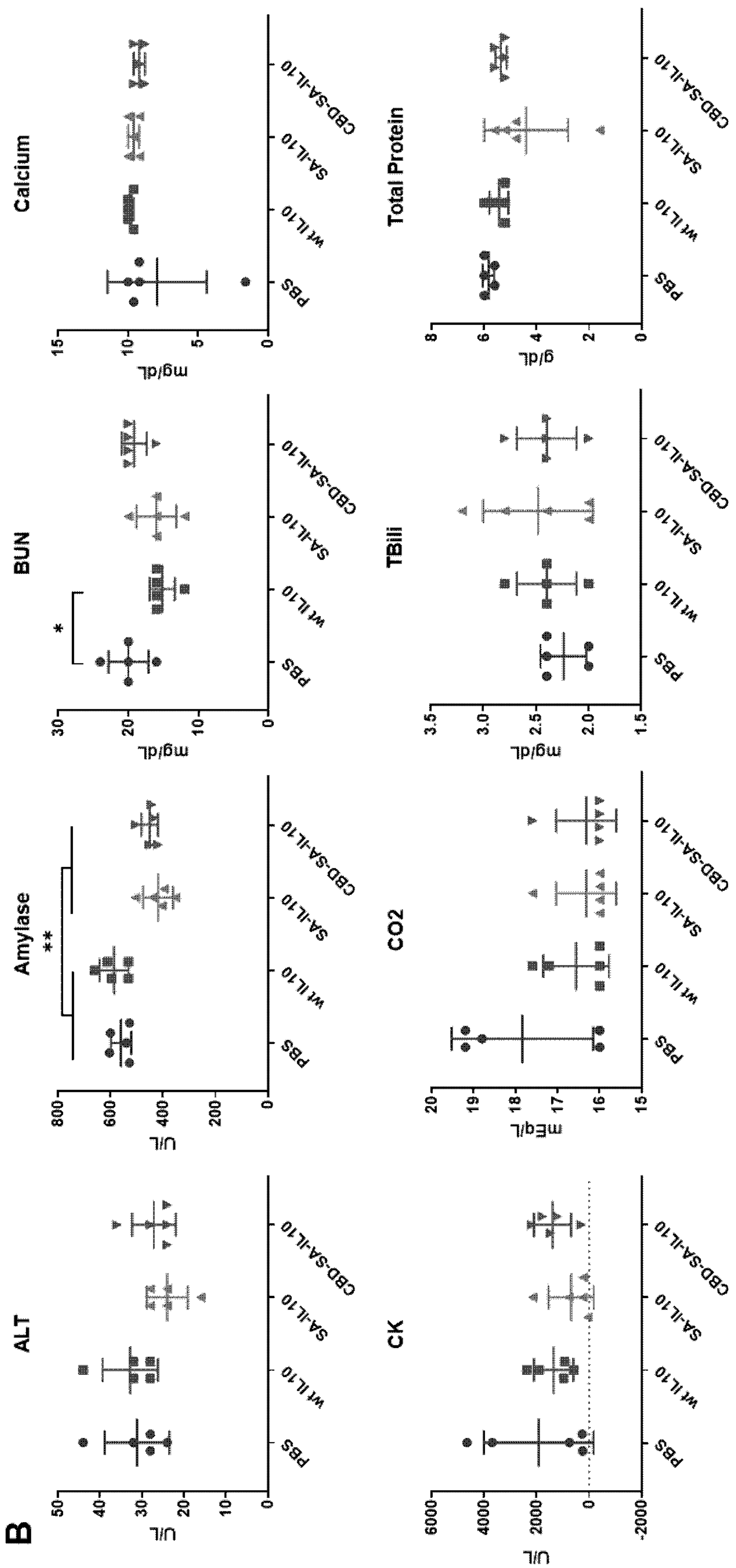

Finally, safety assessments were performed to investigate whether engineered IL-10 demonstrates any adverse effects. Representative blood parameters measured by a hematology analyzer and spleen weights did not show any significant changes among the treatment groups (FIG. 17A). Various biochemical markers in serum were also investigated using a biochemistry analyzer (FIG. 17B). For the engineered IL-10-treated groups, most markers, except for amylase (which was not increased, rather slightly decreased), showed similar levels compared with PBS-treated group, indicating that engineered IL-10 possesses high safety after systemic administration.

G. Discussion

Current treatment for RA is based on symptomatic therapy by relieving pain, controlling synovitis and suppressing joint injury. Antibody drugs or competitive soluble receptors that neutralize inflammatory cytokines, especially TNF-α, have provided high therapeutic efficacy for patients with RA (4). These biotherapeutics mainly act at the inflamed joints to capture the inflammatory cytokines. However, these inhibitory drugs are known to increase the risk of infection, because their targets are pleiotropic in immune function and these drugs are repeatedly administered to provide their anti-inflammatory effect at disease site (24-27). In addition, administration of antibody drugs can also cause the induction of neutralizing anti-drug antibodies, which decreases therapeutic efficiency (28). Therefore, development of an alternative approach with a structurally different molecular class and with a different immuno-suppressive molecular mechanism such as tolerance is desired.

Here, the inventors explore a novel approach to treat RA through enhanced lymph node trafficking using engineered IL-10, which is a representative anti-inflammatory cytokine and modulates the phenotypes of RA-relating immune cells toward immunosuppressive states. Clinical trials using recombinant IL-10 have been already performed to treat autoimmune diseases including RA (6-8, 29). One of the drawbacks of IL-10 is its short half-life in the blood (8). Here, the inventors genetically fused SA to IL-10 to extend its retention in the blood and moreover in the secondary lymphoid organs. Furthermore, to enhance binding at inflammatory sites, where the microvasculature is hyperpermeable, the inventors genetically fused a CBD derived from the blood protein von Willebrand Factor (16, 17). The inventors evaluated both SA-IL-10 and CBD-SA-IL-10, in comparison to wt IL-10, for amelioration of arthritis in two models. CAIA is a macrophage- and neutrophil-mediated acute RA model, whereas CIA is a T cell-, and especially Th17-mediated RA model. Given that RA is a heterogeneous disease in the clinic and the models complement each other, it is encouraging to show and SA-fused IL-10 suppresses disease severity in both models. SA fusion to IL-10 is crucial for obtaining a marked therapeutic effect, which was comparable to treatment with αTNF-α antibody, a common therapy in the clinic. Additionally, to the inventors' best knowledge, this study is the first to show a therapeutic effect of IL-10 in the CAIA model.

SA fusion to IL-10 resulted in enhanced accumulation within LNs after intravenous injection and kept high IL-10 concentrations in the LNs for prolonged durations compared with wt IL-10 (FIG. 12A). So far, LN trafficking of SA or albumin-binding nanoparticles has been mainly achieved by intradermal or subcutaneous administration, where the LN is accessed via the afferent lymphatic vessel downstream of the collecting lymphatics at the injection site (30-33). In the context of a biodistribution study of an inflammatory cytokines, one paper showed high localization of human SA-fused IL-2 after intravenous injection into spleen, liver and LNs, where IL-2 receptor-expressing T cells exist, but the precise mechanism for this high localization has not been elucidated (34). Here, the inventors reveal enhanced trafficking of SA-fused IL-10 into LNs after intravenous injection, where the SA enters the LN via the blood vasculature. CBD-SA-IL-10 showed lesser accumulation in the LNs than SA-IL-10, perhaps due to binding to collagen in other tissues. Both SA-IL-10 and CBD-SA-IL-10 exhibited high binding affinity (micromolar $K_d$, as expected) to FcRn (FIGS. 8B and 14B), which provides prolonged blood circulation properties to both proteins via recycling mediated via FcRn expressed in vascular endothelial cells (FIG. 9A). Recycling via transcytosis (from the basal side back to the lumenal side) of IgG via FcRn is a well-established phenomenon, whereas the same phenomenon for SA has been more recently reported (19, 20). Here, in the LN, molecular transport would seem to be in the other direction, from the lumenal to the basal side. Interestingly, histological analysis revealed the accumulation of SA-IL-10 surrounding the HEVs of the LNs (FIG. 8D). Further experiments are required to reveal a more detailed mechanism of enhanced LN accumulation and the relationship with FcRn, such as LN accumulation analysis using mutated SA-fused IL-10 to abrogate FcRn binding.

SA-IL-10 shows high binding to APCs (FIG. 8B). After accumulation within the LNs, SA-IL-10 molecules are taken up by APCs resident within the LNs, leading to the suppression of dendritic cell and M1 macrophage activities and the induction of M2 macrophages (FIG. 15). M2 macrophages can change the differentiation fate of Th0 cells to Treg cells in the LNs (35). Furthermore, the immunosuppressive environment by high concentrations of IL-10 in the LN may cause the further polarization of macrophages to M2 phenotype and the suppression of Th17 differentiation (36, 37), resulting in the decrease of IL-17, GM-CSF or other cytokines in the LNs that the inventors observed (FIGS. 12D and 12F). GM-CSF is a cytokine that is a marker for pathogenic Th17, and its inhibitory antibody is currently being tested in clinical trials (38). Thus, the decrease of GM-CSF by SA-IL-10 treatment indicates decreased immuno-activation in the joint-draining LN. Th17 cells reportedly express IL-10 receptor, and IL-10 binding suppresses IL-17 expression and secretion (14, 36). Because Th17 cell antigen recognition primarily occurs in the lymphoid tissue, SA-IL-10 may bind to Th17 cells directly to suppress the IL-17 pathway. These changes in LNs also suppressed the infiltration of immune cells, especially G-MDSC and macrophages, into the paws (FIG. 13A) and also induced an increase of M2 macrophages (FIG. 13A), resulting in the decrease of inflammatory cytokines (FIG. 13B) and the suppression of joint inflammation (FIGS. 10, 11, and 13C).

SA-IL-10 induced high anti-inflammatory responses after administration by any of the routes tested, namely intravenous, subcutaneous (at a distant site) or footpad (local) injections, suggesting that SA-IL-10 can enter the LNs systemically after uptake by a local injection-site draining lymphatics and transit through the lymphatics back into the systemic circulation via the thoracic duct. The high therapeutic effect by subcutaneous injection suggests a particular clinical benefit of SA-IL-10. Intravenous CBD-SA-IL-10 also shows suppression effects on the development of CAIA and CIA that are comparable to anti-TNF-α antibody, which is the current standard biological therapeutic for RA. However, the therapeutic effects of CBD-SA-IL-10 are lower than that observed with SA-IL-10, which corresponds to lower LN trafficking of CBD-SA-IL-10 (FIG. 12A). CBD-SA-IL-10 might bind to collagens in inflamed tissues after permeation there, which causes the accumulation to inflamed paws (FIG. 9B), but such collagen affinity may interfere the LN trafficking of CBD-SA-IL-10 (16, 39). Therefore, SA-fusion is a simple but effective way for preparation of engineered cytokines to achieve enhanced LN trafficking.

In this study, SA-fusion to IL-10 achieved increased persistence within the LNs, where autoimmunity-relating immune recognition develops and persists. As a result, SA-IL-10 suppressed the main inflammatory pathway of RA progression, yet without inhibition of a pleiotropic inflammatory cytokine such as TNF-α. In addition, SA-IL-10 did not show any remarkable toxicities in preliminary safety assessments (FIG. 17). SA-IL-10 exhibited marked therapeutic effects in both CIA and CAIA models. Therefore, the data suggest the potential of SA-IL-10 for clinical application in suppression of RA, and the inventors' findings more broadly suggest the ability to modulate immunity through systemic tolerogenic manipulation of the LNs in other autoimmune and inflammatory diseases.

H. Amino Acid Sequences for Mouse Wt IL-10, SA-IL-10 and CBD-SA-IL-10

```
Mouse wt IL-10
                                        (SEQ ID NO: 53)
RGQYSREDNNCTHFPVGQSHMLLELRTAFSQVKTFFQTKDQLD

NILLTDSLMQDFKGYLGCQALSEMIQFYLVEVMPQAEKHGPEIK

EHLNSLGEKLKTLRMRLRRCHRFLPCENKSKAVEQVKSDFNKL

QDQGVYKAMNEFDIFINCIEAYMMIKMKSHHHHHH

Mouse serum albumin and mouse IL-10 fusion protein
                                        (SEQ ID NO: 54)
EAHKSEIAHRYNDLGEQHFKGLVLIAFSQYLQKCSYDEHAKLVQ

EVTDFAKTCVADESAANCDKSLHTLFGDKLCAIPNLRENYGELA

DCCTKQEPERNECFLQHKDDNPSLPPFERPEAEAMCTSFKENPTT

FMGHYLHEVARRHPYFYAPELLYYAEQYNEILTQCCAEADKES

CLTPKLDGVKEKALVSSVRQRMKCSSMQKFGERAFKAWAVAR

LSQTFPNADFAEITKLATDLTKVNKECCHGDLLECADDRAELAK

YMCENQATISSKLQTCCDKPLLKKAHCLSEVEHDTMPADLPAIA

ADFVEDQEVCKNYAEAKDVFLGTFLYEYSRRHPDYSVSLLLRLA
```

-continued

```
KKYEATLEKCCAEANPPACYGTVLAEFQPLVEEPKNLVKTNCDL

YEKLGEYGFQNAILVRYTQKAPQVSTPTLVEAARNLGRVGTKC

CTLPEDQRLPCVEDYLSAILNRVCLLHEKTPVSEHVTKCCSGSLV

ERRPCFSALTVDETYVPKEFKAETFTFHSDICTLPEKEKQIKKQTA

LAELVKHKPKATAEQLKTVMDDFAQFLDTCCKAADKDTCFSTE

GPNLVTRCKDALAGGGSGGGSSRGQYSREDNNCTHFPVGQSHM

LLELRTAFSQVKTFFQTKDQLDNILLTDSLMQDFKGYLGCQALS

EMIQFYLVEVMPQAEKHGPEIKEHLNSLGEKLKTLRMRLRRCHR

FLPCENKSKAVEQVKSDFNKLQDQGVYKAMNEFDIFINCIEAYM

MIKMKSHHHHHH

Human VWF A3 domain (CBD), mouse serum albumin and
mouse IL-10 fusion protein
                                        (SEQ ID NO: 55)
CSQPLDVVLLLDGSSSLPESSFDKMKSFAKAFISKANIGPHLTQVS

VIQYGSINTIDVPWNVVQEKAHLQSLVDLMQQEGGPSQIGDALA

FAVRYVTSQIHGARPGASKAVVIIIMDTSLDPVDTAADAARSNR

VAVFPVGVGDRYDEAQLRILAGPGASSNVVKLQQVEDLSTMAT

LGNSFFHKLCSGFSGVGGGSGGGSEAHKSEIAHRYNDLGEQHFK

GLVLIAFSQYLQKCSYDEHAKLVQEVTDFAKTCVADESAANCD

KSLHTLFGDKLCAIPNLRENYGELADCCTKQEPERNECFLQHKD

DNPSLPPFERPEAEAMCTSFKENPTTFMGHYLHEVARRHPYFYA

PELLYYAEQYNEILTQCCAEADKESCLTPKLDGVKEKALVSSVR

QRMKCSSMQKFGERAFKAWAVARLSQTFPNADFAEITKLATDL

TKVNKECCHGDLLECADDRAELAKYMCENQATISSKLQTCCDK

PLLKKAHCLSEVEHDTMPADLPAIAADFVEDQEVCKNYAEAKD

VFLGTFLYEYSRRHPDYSVSLLLRLAKKYEATLEKCCAEANPPA

CYGTVLAEFQPLVEEPKNLVKTNCDLYEKLGEYGFQNAILVRYT

QKAPQVSTPTLVEAARNLGRVGTKCCTLPEDQRLPCVEDYLSAI

LNRVCLLHEKTPVSEHVTKCCSGSLVERRPCFSALTVDETYVPK

EFKAETFTFHSDICTLPEKEKQIKKQTALAELVKHKPKATAEQLK

TVMDDFAQFLDTCCKAADKDTCFSTEGPNLVTRCKDALAGGGS

GGGSSRGQYSREDNNCTHFPVGQSHMLLELRTAFSQVKTFFQTK

DQLDNILLTDSLMQDFKGYLGCQALSEMIQFYLVEVMPQAEKH

GPEIKEHLNSLGEKLKTLRMRLRRCHRFLPCENKSKAVEQVKSD

FNKLQDQGVYKAMNEFDIFINCIEAYMMIKMKSHHHHHH
```

I. Materials and Methods

1. Study Design

This study was designed to test the strategy of targeting anti-inflammatory cytokines to LNs through engineered affinity for FcRn. Specifically, the inventors tested whether LN targeting of the anti-inflammatory cytokine IL-10 by serum albumin fusion is superior to nontargeted wt IL-10 and currently available anti-inflammatory antibody therapeutics (αTNF-α) in mouse models of RA. To evaluate the efficacy of wt IL-10, SA-IL-10 and anti-TNF-α antibody, the inventors scored arthritic symptoms and joint histology in both the passive CAIA model and the active CIA model. The inventors also measured biodistribution and LN trafficking, immune responses within LNs and paws, and various aspects of toxicity after treatment. Statistical methods were not used to predetermine necessary sample size, but sample sizes were chosen on the basis of estimates from pilot experiments so that appropriate statistical tests could yield statistically significant results. Production of wt IL-10, SA-IL-10 and CBD-SA-IL-10 was performed by multiple individuals to ensure reproducibility. All experiments were replicated at least twice. For animal studies, mice were randomized into treatment groups within a cage immediately before the first drug injection and treated in the same manner. The n values used to calculate statistics are indicated in the figure legends. Drug administration and pathological analyses were performed in a blinded fashion. Statistical methods are described in the "Statistical Analysis" section.

2. Production and Purification of Recombinant Proteins

The sequences encoding for the mouse serum albumin without pro-peptide (25 to 608 amino acids of whole serum albumin), mouse IL-10, human VWF A3 domain residues Cys1670-Gly1874 (907-1111 of mature VWF, referred to herein as CBD), and a $(GGGS)_2$ linker were synthesized and subcloned into the mammalian expression vector pcDNA3.1 (+) by Genscript. A sequence encoding for 6 His was added at the C-terminus for further purification of the recombinant protein. Suspension-adapted HEK-293F cells were routinely maintained in serum-free FreeStyle 293 Expression Medium (Gibco). On the day of transfection, cells were inoculated into fresh medium at a density of $1\times10^6$ cells/mL. 2 μg/mL plasmid DNA, 2 μg/mL linear 25 kDa polyethylenimine (Polysciences), and OptiPRO SFM media (4% final concentration, Thermo Fisher) were sequentially added. The culture flask was agitated by orbital shaking at 135 rpm at 37° C. in the presence of 5% $CO_2$. Seven days after transfection, the cell culture medium was collected by centrifugation and filtered through a 0.22 μm filter. Culture media was loaded into a HisTrap HP 5 mL column (GE Healthcare), using an AKTA pure 25 (GE Healthcare). After washing the column with wash buffer (20 mM $NaH_2PO_4$, 0.5 M NaCl, pH 8.0), protein was eluted with a gradient of 500 mM imidazole (in 20 mM $NaH_2PO_4$, 0.5 M NaCl, pH 8.0). The protein was further purified with size exclusion chromatography using a HiLoad Superdex 200PG column (GE Healthcare) using PBS as an eluent. All purification steps were carried out at 4° C. The expression of the proteins was verified as >90% pure by SDS-PAGE. Purified proteins were tested for endotoxin via HEK-Blue TLR4 reporter cell line and endotoxin levels were confirmed to be less than 0.01 EU/mL. Protein concentration was determined through absorbance at 280 nm using NanoDrop (Thermo Scientific).

3. Detection of Binding to Collagens and FcRn

SPR measurements were carried out with Biacore X100 instrument. In collagen binding experiments, recombinant human type I or type III collagen (Millipore Sigma) were immobilized on a CMS sensor chip by standard amine coupling method (~1500 resonance units (RUs)) and blocked with ethanolamine. A reference cell was also blocked with ethanolamine. Binding assays were carried out at room temperature and the $K_d$ values of the CBD-SA-IL-10 were determined by fitting 1:1 Langmuir binding model to the data using BIAevaluation software (GE Healthcare). In FcRn binding experiments, recombinant mouse FcRn (Acro Biosystems) was immobilized via amine coupling on a C1 chip (GE Healthcare) for ~200 RU according to the manufacturer's instructions. SA-IL-10 or CBD-SA-IL-10 was flowed at decreasing concentrations in the running buffer (0.01 M monobasic anhydrous sodium phosphate, pH 5.8, 0.15 M NaCl) at 30 μL/min at room temperature. The sensor chip was regenerated with PBS, pH 7.4 for every cycle. Specific binding of SA-fused proteins to FcRn was calculated by comparison to a non-functionalized channel used as a reference. The $K_d$ values of the SA-IL-10 and CBD-SA-IL-10 were determined by fitting 1:1 Langmuir binding model to the data using BIAevaluation software (GE Healthcare).

4. Mice

BALB/c female mice at 7 wk of age and DBA/1J male mice at 8 wk of age were obtained from the Jackson Laboratory. Experiments were performed with approval from the Institutional Animal Care and Use Committee of the University of Chicago.

5. Binding of the Proteins to Splenocytes or LN-Derived Cells

Single-cell suspensions were obtained by gently disrupting the spleen and popliteal LN through a 70-μm cell strainer. Red blood cells were lysed with ACK lysing buffer (Quality Biological) for splenocytes. Cells were counted and re-suspended in RPMI-1640 supplemented with 10% FBS and 1% penicillin/streptomycin (all from Life Technologies). $1\times10^5$ cells/well were seeded in a 96 well microplate and were incubated with 2 μg/100 μL of SA, SA-IL-10 or CBD-SA-IL-10 for 30 min on ice. After 4-times washing by PBS, cells were further incubated with anti-mouse albumin antibodies (abcam) for 20 min on ice. After 3-times washing by PBS, cells were incubated with 1 μg/mL AlexaFluor 647-labeled anti-Rabbit IgG (Jackson ImmunoResearch), anti-B220 (RA3-6B2, BioLegend), anti-CD3 (145-2C11, BD Biosciences), anti-CD4 (RM4-5, BD Biosciences), anti-CD8 (53-6.7, BD Biosciences), anti-CD11c (HL3, BD Biosciences), anti-CD45 (30-F11, BD Biosciences) and anti-F4/80 (T45-2342, BD Biosciences) antibodies for 20 min on ice. Cells were analyzed by flow cytometry as described below.

6. Plasma Pharmacokinetics of the Proteins

IL-10, SA-IL-10 or CBD-SA-IL-10 (equivalent to 35 μg of IL-10) was injected intravenously into female BALB/c mice. Blood samples were collected in protein-low binding tubes at 1, 5, 10, and 30 min, and 1, 4, 8 and 24 hr after injection, followed by overnight incubation at 4° C. IL-10 concentrations in serum were measured by IL-10 Mouse Uncoated ELISA kit (Invitrogen) according to the manufacturer's protocol. Exponential two-phase decay ($Y=Ae^{-\alpha t}+Be^{-\beta t}$) fitting was used to calculate the half-life. Fast clearance half-life, $t_{1/2,\alpha}$; slow clearance half-life, $t_{1/2,\beta}$. Data were analyzed using Prism software (v8, GraphPad).

7. CAIA Model

Arthritis was induced in female BALB/c mice by intraperitoneal injection of anti-collagen antibody cocktail (1.0 mg/mouse, Chondrex) on day 0, followed by intraperitoneal injection of LPS (25 μg/mouse, Chondrex) on day 3. Only for FIG. 3B-C, 1.5 mg/mouse of anti-collagen antibody cocktail was injected. On the day 3, mice were intravenously, subcutaneously (mid-back), or via footpad injected with PBS, wt IL-10, SA-IL-10, CBD-SA-IL-10 (each equivalent to 43.5 μg of IL-10), or 200 μg of Rat anti-mouse TNF-α antibody (clone XT3.11, Bio X Cell) before LPS injection. Joint swelling was scored every day according to the manufacture's protocol (Chondrex). On the last day of scoring, the hind paws were fixed in 10% neutral formalin (Sigma-Aldrich), decalcified in Decalcifer II (Leica), and then provided for histological analysis. Paraffin-embedded paws were sliced at 5 μm thickness and stained with H&E. The images were scanned with a Pannoramic digital slide scanner and analyzed using a Pannoramic Viewer software. The severity of synovial hyperplasia and bone resorption for the arthritis model was scored by three-grade evaluation (0-2) according to the previously reported criteria with slight modifications as follows: 0, normal to minimal infiltration of pannus in cartilage and subchondral bone of marginal zone; 1, mild to moderate infiltration of marginal zone with minor cortical and medullary bone destruction; 2, severe infiltration associated with total or near total destruction of joint architecture. The scores in both hind paws were summed for each mouse (score per mouse total, 0-4). The histopathological analyses were performed in a blinded fashion.

8. CIA Model

Male DBA/1J mice (8 wk old) were immunized by subcutaneous injection at the base of the tail with bovine collagen/complete Freund's adjuvant (CFA) emulsion (Hooke Kit, Hooke Laboratories). Three weeks later, a booster injection of bovine collagen/incomplete Freund's adjuvant (IFA) emulsion (Hooke Kit, Hooke Laboratories) was performed. After the booster injection, mice were inspected every day, and joint swelling was scored according to the manufacture's protocol (Hooke Laboratories). When showing total score of 2-4 (defined as Day 0), mice were intravenously injected with PBS, SA-IL-10, CBD-SA-IL-10 (each equivalent to 43.5 μg of IL-10), or 200 μg of Rat anti-mouse TNF-α antibody (clone XT3.11, Bio X Cell). On the last day of scoring, hind paws were collected and histological analyses were employed as described above.

9. In Vivo Bio-Distribution Study

To make fluorescently labeled protein, wt IL-10, SA-IL-10 and CBD-SA-IL-10 were incubated with 8-fold molar excess of using DyLight 800 NHS ester (Thermo Fisher) for 1 hr at room temperature, and unreacted dye was removed by a Zebaspin spin column (Thermo Fisher) according to the manufacturer's instruction. BALB/c mice were intraperitoneal injected by anti-collagen antibody cocktail (1.0 mg/mouse) on day 0, subsequently 10 μg of LPS was injected to right hind paw on day 3. The following day, 20 μg of DyLight 800-labeled proteins were intravenously injected. After 4 hr, organs harvested from the disease model were imaged with the Xenogen IVIS Imaging System 100 (Xenogen) under the following conditions: f/stop: 2; optical filter excitation 745 nm; excitation 800 nm; exposure time: 5 sec; small binning. Each organ was weighed to normalize the fluorescence signal from each organ.

10. LN Microscopy

BALB/c mice were intravenously injected with DyLight594-labeled wt IL-10 (43.5 μg) or SA-IL-10 labeled with equimolar amounts of dye. 24 hr after injection, popliteal LNs were harvested and frozen in dry ice with optimal cutting temperature (OCT) compound. Tissue slices (10 μm) were obtained by cryo-sectioning. The tissues were fixed with 2% paraformaldehyde in PBS for 15 min at room temperature. After washing with PBS-T, the tissues were blocked with 2% BSA in PBS-T for 1 hr at room temperature. The tissues were stained with anti-mouse CD3 antibody (1:100, 145-2C11, BioLegend) or anti-mouse peripheral node addressin (PNAd) antibody (1:200, MECA79, BioLegend) and Alexa Fluor 488 donkey anti-rat (1:400, Jackson ImmunoResearch). The tissues were washed three times and then covered with ProLong gold antifade mountant with 4',6-diamidino-2-phenylindole (DAPI; Thermo Fisher Scientific). An IX83 microscope (Olympus) was used for imaging with 10× magnification for CD3 staining, and a Leica SP8 3D Laser Scanning Confocal microscope with 20× magnification for PNAd staining. Images were processed using ImageJ software (NIH).

11. LN Pharmacokinetics wt IL-10, SA-IL-10 or CBD-SA-IL-10 (each equivalent to 35 μg of IL-10) was injected intravenously into CAIA mice. Popliteal, mesenteric, cervical LNs were collected at 30 min, and 1, 4, 8 and 24 hr after injection, and were subsequently homogenized using Lysing Matrix D and Fast-Prep-24 5G (MP Biomedical) for 40 s at 5000 beats/min in T-PER tissue protein extraction reagent (Thermo Scientific) with cOmplete™ proteinase inhibitor cocktail (Roche). After homogenization, samples were incubated overnight at 4° C. Samples were centrifuged (5000 g, 5 min), and the total protein concentration and IL-10 concentration were analyzed using a BCA assay kit (Thermo Fisher) and IL-10 Mouse Uncoated ELISA kit (Invitrogen), respectively. Simultaneously, cytokine levels in the LN extract were measured using Mouse Uncoated ELISA kit (Invitrogen) or Ready-SET-Go! ELISA kits (eBioscience) according to the manufacturer's protocol. For detection of GM-CSF, wt IL-10 or SA-IL-10 (each equivalent to 35 μg of IL-10) was injected intravenously twice with a 3 day interval into CAIA mice. The day following the last injection, popliteal LNs were collected for detection of GM-CSF.

12. Flow Cytometry

CAIA mice were intravenously injected with PBS, wt IL-10, SA-IL-10 or CBD-SA-IL-10 (each equivalent to 43.5 μg of IL-10). Eight days after, blood and hind paws were harvested. Red blood cells in blood were lysed with ACK lysing buffer (Quality Biological), followed by antibody staining for flow cytometry. Paws were digested in Dulbecco's Modified Eagle Medium (DMEM) supplemented with 2% FBS, 2 mg/mL collagenase D and 40 μg/mL DNase I (Roche) for 60 min at 37° C. Single-cell suspensions were obtained by gently disrupting through a 70-μm cell strainer. Antibodies against the following molecules were used: anti-mouse CD3 (145-2C11, BD Biosciences), CD4 (RM4-5, BD Biosciences), anti-mouse CD8a (53-6.7, BD Biosciences), anti-mouse CD25 (PC61, BD Biosciences), anti-mouse CD45 (30-F11, BD Biosciences), CD44 (IM7, BD Biosciences), CD62L (MEL-14, BD Biosciences), PD-1 (29F.1A12, BD Biosciences), NK1.1 (PK136, BD Biosciences), Foxp3 (MF23, BD Biosciences), F4/80 (T45-2342, BD Biosciences), MEW II (M5/114.15.2, BioLegend), CD206 (C068C2, BioLegend), Ly6G (1A8, BioLegend), Ly6C (HK1.4, BioLegend), CD11b (M1/70, BioLegend), CD11c (HL3, BD Biosciences), B220 (RA3-6B2, BioLegend). Fixable live/dead cell discrimination was performed using Fixable Viability Dye eFluor 455 (eBioscience) according to the manufacturer's instructions. Staining was carried out on ice for 20 min if not indicated otherwise, and intracellular staining was performed using the Foxp3 staining kit according to manufacturer's instructions (BioLegend). Following a washing step, cells were stained with specific antibodies for 20 min on ice prior to fixation. All flow cytometric analyses were done using a Fortessa (BD Biosciences) flow cytometer and analyzed using FlowJo software (Tree Star).

13. Safety Assessments

BALB/c mice were intravenously injected with PBS, wt IL-10, SA-IL-10 or CBD-SA-IL-10 (each equivalent to 43.5 μg of IL-10). Two days after injection, blood samples collected from mice were analyzed using a COULTER Ac•T 5diff CP hematology analyzer (Beckman Coulter) according to the manufacturer's instructions. Spleen weight was also measured. Serum samples collected from protein-injected mice were analyzed using Biochemistry Analyzer (Alfa Wassermann Diagnostic Technologies) according to the manufacturer's instructions.

14. Statistical Analysis

Statistically significant differences between experimental groups were determined using Prism software (v8, GraphPad). Where one-way ANOVA followed by Tukey's HSD post hoc test was used, variance between groups was found to be similar by Brown-Forsythe test. For non-parametric data, Kruskal-Wallis test followed by Dunn's multiple comparison test was used. For single comparisons, a two-tailed Student's t-test was used. The symbols *, , * and **** indicate P values less than 0.05, 0.01, 0.001 and 0.0001 respectively; ns, not significant.

J. References

The following references and the publications referred to throughout the specification, to the extent that they provide exemplary procedural or other details supplementary to those set forth herein, are specifically incorporated herein by reference.

1. G. S. Firestein, Evolving concepts of rheumatoid arthritis. *Nature* 423, 356-361 (2003).
2. I. B. McInnes, G. Schett, The pathogenesis of rheumatoid arthritis. *N. Engl. J. Med.* 365, 2205-2219 (2011).
3. Q. Guo, Y. Wang, D. Xu, J. Nossent, N. J. Pavlos, J. Xu, Rheumatoid arthritis: pathological mechanisms and modern pharmacologic therapies. *Bone Res.* 6, 15 (2018).
4. M. E. Weinblatt, E. C. Keystone, D. E. Furst, L. W. Moreland, M. H. Weisman, C. A. Birbara, L. A. Teoh, S. A. Fischkoff, E. K. Chartash, Adalimumab, a fully human anti-tumor necrosis factor alpha monoclonal antibody, for the treatment of rheumatoid arthritis in patients taking concomitant methotrexate: The ARMADA trial. *Arthritis Rheum.* 48, 35-45 (2003).
5. K. N. Couper, D. G. Blount, E. M. Riley, IL-10: The master regulator of immunity to infection. *J. Immunol.* 180, 5771-5777 (2008).
6. K. Asadullah, W. Sterry, H. D. Volk, Interleukin-10 therapy-review of a new approach. *Pharmacol. Rev.* 55, 241-269 (2003).
7. W. Ouyang, A. O'Garra, IL-10 family cytokines IL-10 and IL-22: from basic science to clinical translation. *Immunity* 50, 871-891 (2019).
8. A. Saxena, S. Khosraviani, S. Noel, D. Mohan, T. Donner, A. R. Hamad, Interleukin-10 paradox: A potent immunoregulatory cytokine that has been difficult to harness for immunotherapy. *Cytokine* 74, 27-34 (2015).
9. H. M. Alvarez, O. Y. So, S. Hsieh, N. Shinsky-Bjorde, H. Ma, Y. Song, Y. Pang, M. Marian, E. Escandón, Effects of PEGylation and immune complex formation on the pharmacokinetics and biodistribution of recombinant interleukin 10 in mice. *Drug Metab. Dispos.* 40, 360-373 (2012).
10. K. Schwager, M. Kaspar, F. Bootz, R. Marcolongo, E. Paresce, D. Neri, E. Trachsel, Preclinical characterization of DEKAVIL (F8-IL10), a novel clinical-stage immunocytokine which inhibits the progression of collagen-induced arthritis. *Arthritis Res. Ther.* 11, R142 (2009).
11. F. Doll, K. Schwager, T. Hemmerle, D. Neri, Murine analogues of etanercept and of F8-IL10 inhibit the progression of collagen-induced arthritis in the mouse. *Arthritis Res. Ther.* 15, R138 (2013).
12. S. T. G. Bruijnen, D. M. S. H. Chandrupatla, L. Giovanonni, D. Neri, D. J. Vugts, M. C. Huisman, O. S. Hoekstra, R. J. P. Musters, A. A. Lammertsma, G. A. M. S. van Dongen, G. Jansen, C. F. M. Molthoff, C. J. van der Laken, F8-IL10: a new potential antirheumatic drug evaluated by a PET-guided translational approach. *Mol. Pharm.* 16, 273-281 (2019).
13. B. Ruffell, D. Chang-Strachan, V. Chan, A. Rosenbusch, C. M. Ho, N. Pryer, D. Daniel, E. S. Hwang, H. S. Rugo, Macrophage IL10 blocks $CD8^+$ T cell-dependent responses to chemotherapy by suppressing IL-12 expression in intratumoral dendritic cells. *Cancer Cell* 26, 623-637 (2014).
14. S. Huber, N. Gagliani, E. Esplugues, W. O'Connor, Jr., F. J. Huber, A. Chaudhry, M. Kamanaka, Y. Kobayashi, C. J. Booth, A. Y. Rudensky, M. G. Roncarolo, M. Battaglia, R. A. Flavell, Th17 cells express interleukin-10 receptor and are controlled by $Foxp3^-$ and $Foxp3^+$ regulatory $CD4^+$ T cells in an interleukin-10-dependent manner. *Immunity* 34, 554-565 (2011).
15. S. K. Mittal, K. J. Cho, S. Ishido, P. A. Roche, Interleukin 10 (IL-10)-mediated immunosuppression: MARCH-I induction regulates antigen presentation by macrophages but not dendritic cells. *J. Biol. Chem.* 290, 27158-27167 (2015).
16. J. Ishihara, A. Ishihara, K. Sasaki, S. S. Lee, J. M. Williford, M. Yasui, H. Abe, L. Potin, P. Hosseinchi, K. Fukunaga, M. M. Raczy, L. T. Gray, A. Mansurov, K. Katsumata, M. Fukayama, S. J. Kron, M. A. Swartz, J. A. Hubbell, Targeted antibody and cytokine cancer immunotherapies through collagen affinity. *Sci. Transl. Med.* 11, eaau3259 (2019).
17. K. Sasaki, J. Ishihara, A. Ishihara, R. Miura, A. Mansurov, K. Fukunaga, J. A. Hubbell, Engineered collagen-binding serum albumin as a drug conjugate carrier for cancer therapy. *Sci. Adv.* 5, eaaw6081 (2019).
18. M. Miyasaka, T. Tanaka, Lymphocyte trafficking across high endothelial venules: dogmas and enigmas. *Nat. Rev. Immunol.* 4, 360-370 (2004).
19. M. Pyzik, T. Rath, T. T. Kuo, S. Win, K. Baker, J. J. Hubbard, R. Grenha, A. Gandhi, T. D. Kramer, A. R. Mezo, Z. S. Taylor, K. McDonnell, V. Nienaber, J. T. Andersen, A. Mizoguchi, L. Blumberg, S. Purohit, S. D. Jones, G. Christianson, W. I. Lencer, I. Sandlie, N. Kaplowitz, D. C. Roopenian, R. S. Blumberg, Hepatic FcRn regulates albumin homeostasis and susceptibility to liver injury. *Proc. Natl. Acad. Sci. USA* 114, E2862-E2871 (2017).
20. M. Pyzik, K. M. K. Sand, J. J. Hubbard, J. T. Andersen, I. Sandlie, R. S. Blumberg, The neonatal Fc receptor (FcRn): a misnomer? *Front. Immunol.* 10, 1540 (2019).
21. K. Katsumata, J. Ishihara, A. Mansurov, A. Ishihara, M. M. Raczy, E. Yuba, J. A. Hubbell, Targeting inflammatory sites through collagen affinity enhances the therapeutic efficacy of anti-inflammatory antibodies. *Sci. Adv.* 5, eaay1971 (2019)
22. S. Kotake, T. Yago, T. Kobashigawa, Y. Nanke, The plasticity of Th17 cells in the pathogenesis of rheumatoid arthritis. *J. Clin. Med.* 6, E67 (2017).
23. J. P. van Hamburg, S. W. Tas, Molecular mechanisms underpinning T helper 17 cell heterogeneity and functions in rheumatoid arthritis. *J. Autoimmun.* 87, 69-81 (2018).
24. Y. C. Chiang, L. N. Kuo, Y. H. Yen, C. H. Tang, H. Y. Chen, Infection risk in patients with rheumatoid arthritis treated with etanercept or adalimumab. *Comput. Methods Programs Biomed.* 116, 319-327 (2016).
25. C. Downey, Serious infection during etanercept, infliximab and adalimumab therapy for rheumatoid arthritis: A literature review. *Int. J. Rheum. Dis.* 19, 536-550 (2016).
26. J. D. Reid, B. Bressler, J. English, A case of adalimumab-induced pneumonitis in a 45-year-old man with Crohn's disease. *Can. Respir. J.* 18, 262-264 (2011).
27. J. Zalevsky, A. K. Chamberlain, H. M. Horton, S. Karki, I. W. Leung, T. J. Sproule, G. A. Lazar, D. C. Roopenian, J. R. Desjarlais. Enhanced antibody half-life improves in vivo activity. *Nat. Biotechnol.* 28, 157-159 (2010).
28. I. Cludts, F. R. Spinelli, F. Morello, J. Hockley, G. Valesini, M. Wadhwa, Anti-therapeutic antibodies and their clinical impact in patients treated with the TNF antagonist adalimumab. *Cytokine* 96, 16-23 (2017).
29. X. Wang, K. Wong, W. Ouyang, S. Rutz, Targeting IL-10 family cytokines for the treatment of human diseases. *Cold Spring Harb. Perspect. Biol.* 11, a028548 (2019).
30. H. Liu, K. D. Moynihan, Y. Zheng, G. L. Szeto, A. V. Li, B. Huang, D. S. Van Egeren, C. Park, D. J. Irvine, Structure-based programming of lymph-node targeting in molecular vaccines. *Nature* 507, 519-522 (2014).
31. P. Wang, P. Zhao, S. Dong, T. Xu, X. He, M. Chen, An albumin-binding polypeptide both targets cytotoxic T lymphocyte vaccines to lymph nodes and boosts vaccine presentation by dendritic cells. *Theranostics* 8, 223-236 (2018).
32. G. Zhu, G. M. Lynn, O. Jacobson, K. Chen, Y. Liu, H. Zhang, Y. Ma, F. Zhang, R. Tian, Q. Ni, S. Cheng, Z. Wang, N. Lu, B. C. Yung, Z. Wang, L. Lang, X. Fu, A. Jin, I. D. Weiss, H. Vishwasrao, G. Niu, H. Shroff, D. M. Klinman, R. A. Seder, X. Chen, Albumin/vaccine nanocomplexes that assemble in vivo for combination cancer immunotherapy. *Nat. Commun.* 8, 1954 (2017).
33. K. Vandoorne, Y. Addadi, M. Neeman, Visualizing vascular permeability and lymphatic drainage using labeled serum albumin. *Angiogenesis* 13, 75-85 (2010).
34. Z. Yao, W. Dai, J. Perry, M. W. Brechbiel, C. Sung, Effect of albumin fusion on the biodistribution of interleukin-2. Cancer *Immunol. Immunother.* 53, 404-410 (2004).
35. J. Li, H. C. Hsu, J. D. Mountz, The dynamic duo-inflammatory M1 macrophages and Th17 cells in rheumatic diseases. *J. Orthop. Rheumatol.* 1, 4 (2013).
36. B. Guo, IL-10 modulates Th17 pathogenicity during autoimmune diseases. *J. Clin. Cell Immunol.* 7, 400 (2016).
37. Y. Degboé, B. Rauwel, M. Baron, J. F. Boyer, A. Ruyssen-Witrand, A. Constantin, J. L. Davignon, Polarization of rheumatoid macrophages by TNF targeting through an IL-10/STAT3 mechanism. *Front. Immunol.* 10, 3 (2019).
38. A. B. Avci, E. Feist, G. R. Burmester, Tagering GM-CSF in rheumatoid arthritis. *Clin. Exp. Rheumatol.* 34, S39-S44 (2016).
S. Schwager, M. Detmar, Inflammation and lymphatic function. *Front. Immunol.* 10, 308 (2019).

Example 3: Prolonged Residence of Albumin-Fused IL-4 in the Secondary Lymphoid Organs Via FcRn Ameliorates Experimental Autoimmune Encephalomyelitis Multiple sclerosis (MS) is a common and severe demyelinating autoimmune disease of the central nervous system. Although interleukin (IL)-4 suppresses development of pathology in a murine MS model, experimental autoimmune encephalomyelitis (EAE), IL-4 has not been clinically translated. Here, the inventors have engineered a fusion protein of serum albumin (SA) and IL-4 (SA-IL-4) to target secondary lymphoid organs (SLOs), where antigen-specific T cell priming primarily occurs. SA-IL-4 showed greater accumulation and residence time in lymph nodes (LNs) and spleen compared to wild-type (wt) IL-4 via neonatal Fc receptor (FcRn) binding. Subcutaneous administration of SA-IL-4 prevented EAE disease development in all mice and demonstrated higher therapeutic efficacy compared to FTY720 and wt IL-4. SA-IL-4 prevented immune cell infiltration into the spinal cord, facilitating maintenance of spinal cord structure and resulting neurological function. SA-IL-4 decreased integrin expression in antigen-reactive $CD4^+$ T cells, indicating impaired cell migration capability. SA-IL-4 increased the number of and programmed death ligand-1 expression on granulocyte-like myeloid-derived suppressor cells, a key EAE disease suppressor, in the spinal cord-draining LN (dLN). SA-IL-4 decreased the number of Th17 cells, a pathogenic cell population for EAE disease. In the chronic phase of EAE, SA-IL-4 also showed marked therapeutic effects, accompanied by inhibition of immune cell infiltration into the spinal cord and complete abrogation of immune response to the myelin antigen in the spleen. Engineered SA-IL-4 demonstrates translational promise for MS as both a preventative and therapeutic treatment via accumulation in SLOs.

Multiple sclerosis (MS) is a potentially disabling autoimmune disease that affects millions globally. Autoreactive immune cells home to the central nervous system (CNS) and cause demyelination and consequently focal damage to white matter(1). Lymphocytes and macrophages that have infiltrated into the CNS cause axonal damage. Recent studies have shown that Th17 cells, activated in the secondary lymphoid organs (SLOs), migrate to the spinal cord and brain and play a crucial role in the disease development and severity of MS (20). Thus, inhibition of lymphocyte migration to the CNS and inducing an immune-suppressive microenvironment in the SLOs would provide an effective therapy for MS. FTY720 and anti-integrin a4 antibody are used in the clinic to inhibit lymphocyte migration (3,4). Experimental autoimmune encephalomyelitis (EAE) is a widely accepted murine model of MS, reflecting many features of disease progression and developmental mechanism, including lymphocyte migration to the CNS and demyelination.

A. SA-IL-4 Binds to Immune Cells and Inhibits Th17 Differentiation

The inventors have recombinantly expressed wild-type (wt) mouse IL-4 and mouse SA-fused mouse IL-4 (FIG. 18A). SDS-PAGE revealed that the molecular size was increased by SA fusion to IL-4. When added to freshly isolated immune cells from LN and spleen, SA-IL4 preferentially bound to antigen presenting cells (APCs), such as macrophages and dendritic cells (DCs) in vitro, compared to other immune cells (FIG. 18B).

IL-4 receptor is expressed on T cells when stimulated (12). SA-IL-4 induced downstream phosphorylation of STATE in T cells with 32 times higher EC50 than wt IL-4. This suggests that wt IL-4 is more active than SA-IL-4 in vitro (FIG. 18C). The inventors found that both wt IL-4 and SA-IL-4 inhibit Th17 differentiation of naïve $CD4^+$ T cells cultured in Th17 cell differentiation media (FIG. 18D). Taken together, the results demonstrate that the inventors successfully made functionally active SA-IL-4 fusion protein.

Figure 24:
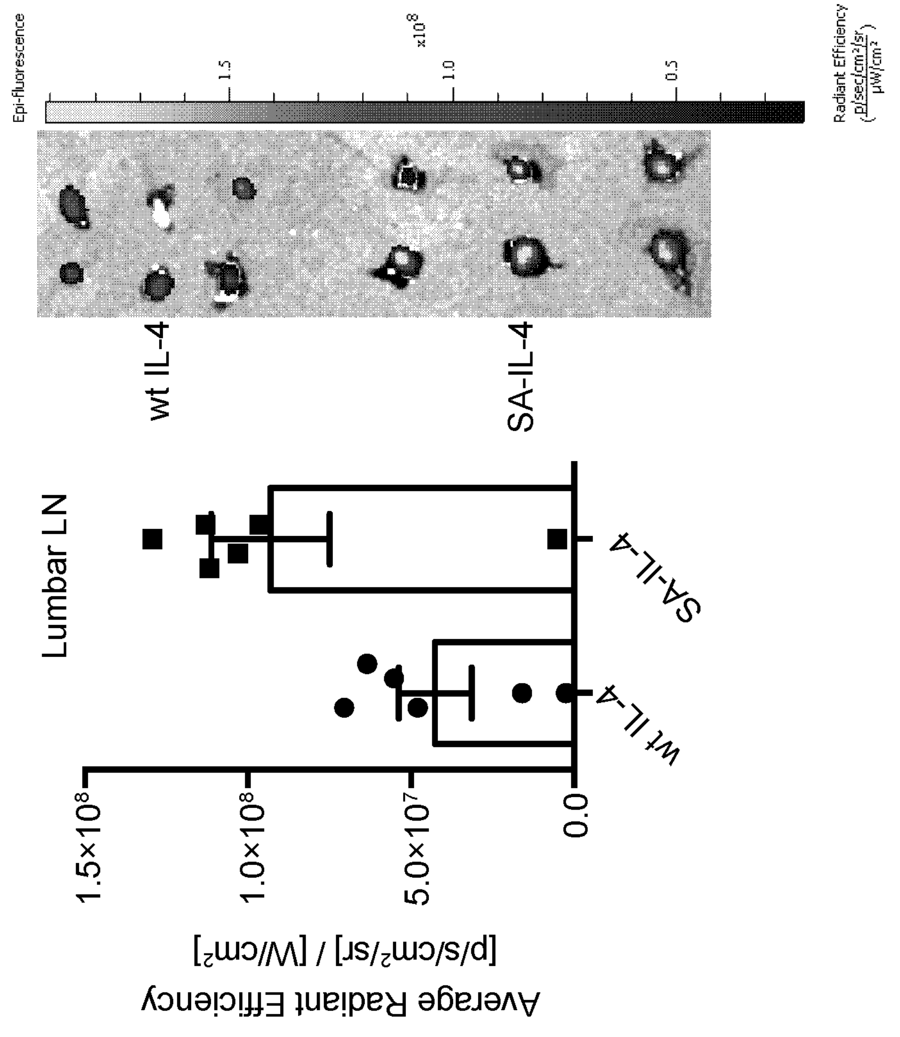
FIG. 24. Injected SA-IL-4 accumulates in the LN more than wt IL-4, analyzed by IVIS. Biodistribution analysis of DyLight 800-labeled wt IL-4 and SA-IL-4 in the LN. 10 μg of wt IL-4 or SA-IL-4 with an equal amount of fluorescence was injected i.v. 4 hr after injection, the lumbar LN was harvested and imaged by an IVIS in vivo imaging system (n=6). Data are mean±SEM. The experiment was performed once. Statistical analyses were performed using Student's t-test.
Figure 25:
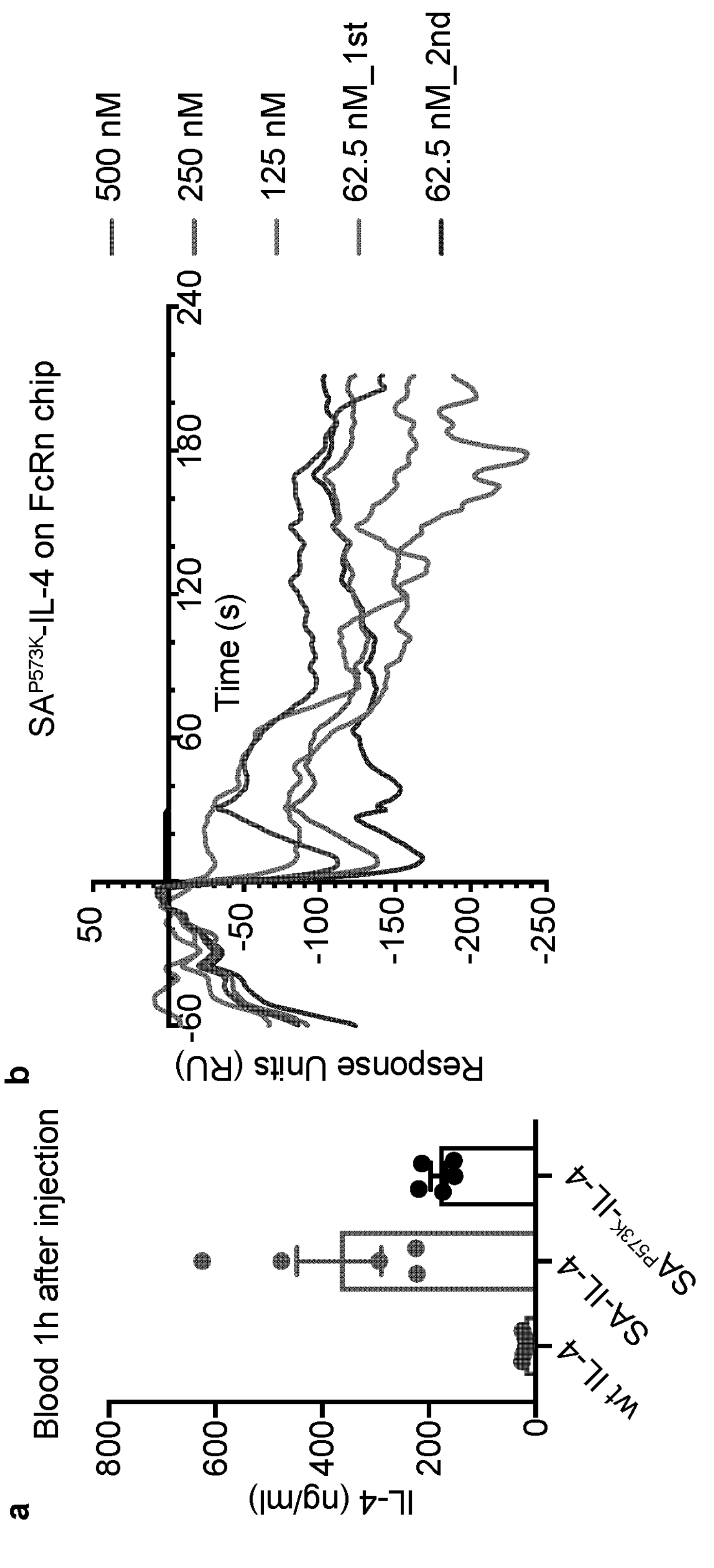
FIG. 25A-B. SA(P573K) mutation to SA-IL-4 decreases blood concentration and abolished FcRn binding. Mice were injected with 40 μg of wt IL-4, SA-IL-4, or SA(P573K)-IL-4 i.v. After 1 hr, blood was collected and IL-4 concentration in the plasma was determined by ELISA. Data are mean±SEM. (b) Binding affinity of SA(P573K)-IL-4 and FcRn measured by SPR. The binding affinity could not be determined. 1*st* and 2*nd* mean the 62.5 nM concentration was tested twice to validate the variability. Two experimental replicates.

SA-IL-4 increases blood half-life and persistence in the SLOs, both in LNs and spleen Surface plasmon resonance (SPR) analysis showed that SA-IL-4 binds to FcRn with a dissociation constant (KD) of 385 nM (FIG. 19A). Plasma half-life after intravenous (i.v.) injection of SA-IL-4 was extended remarkably in contrast to wt IL-4, which was cleared from plasma within a few minutes (FIG. 19B). The inventors next tested if i.v.-injected SA-IL-4 accumulates in the spleen and LN using naïve mice. SA-IL-4 substantially increased the amount of IL-4 in both the lumbar and brachial LNs and in the spleen after i.v. injection (FIG. 2*cd*). Fluorescence-based biodistribution analysis also showed enhanced SA-IL-4 accumulation in the lumbar LN compared to wt IL-4 (FIG. 24). To test the involvement of FcRn in SA-IL-4 accumulation in the LN, the inventors made a P573K point mutation of SA in the fusion to IL-4, which abolishes FcRn binding (FIG. 25A) (13). The SA(P573K) mutation decreased the IL-4 amount in the LN compared to SA-IL-4, down to a similar level as wt IL-4 (FIG. 19E). SA(P573K)-IL-4 has a longer blood half-life compared to wt IL-4 due to an increase in molecular size, but shorter than SA-IL-4 due to impaired FcRn binding (FIG. 25B). Taken together, these data suggest that SA trafficking to the LN requires FcRn binding.

After i.v. injection of SA-IL-4, histology of the LN showed an increased signal of SA-IL-4 in the lumbar LN compared to wt IL-4. SA-IL-4 localized especially to the subcapsular space, without co-localizing with $CD3^+$ T cells (FIG. 19G). Higher magnification revealed that SA-IL-4 partially co-localized with high endothelial venues, which are indicated by peripheral node addressin$^+$ (PNAd$^+$) cells (FIG. 19H). The SA(P573K)-IL-4 amount in the spleen was lower than with SA-IL-4 (FIG. 19F). Taken together, the inventors have shown that SA fusion to IL-4 increases persistence of IL-4 within the LN and spleen through FcRn binding.

Figure 20D:
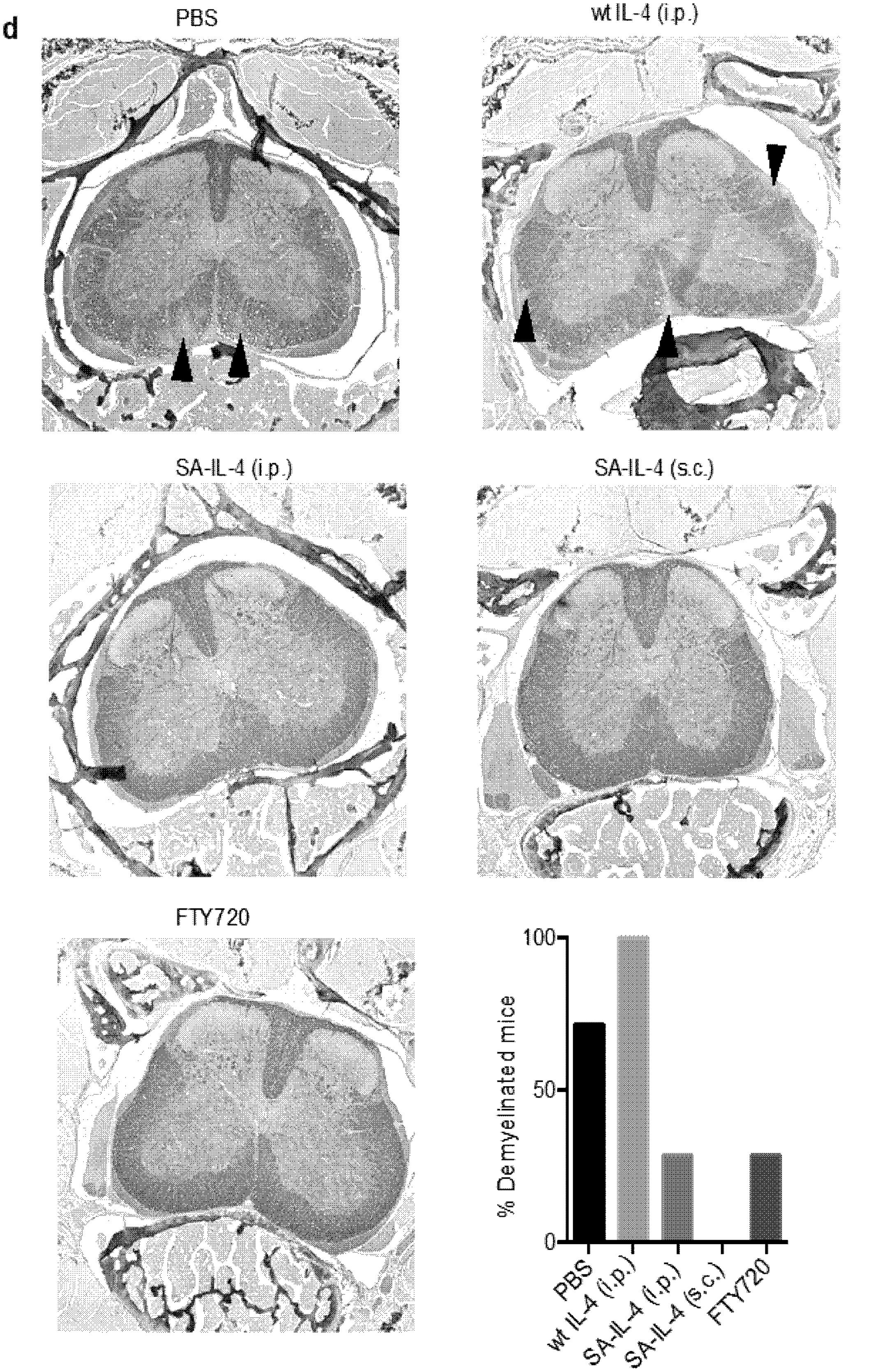
Figure 26:
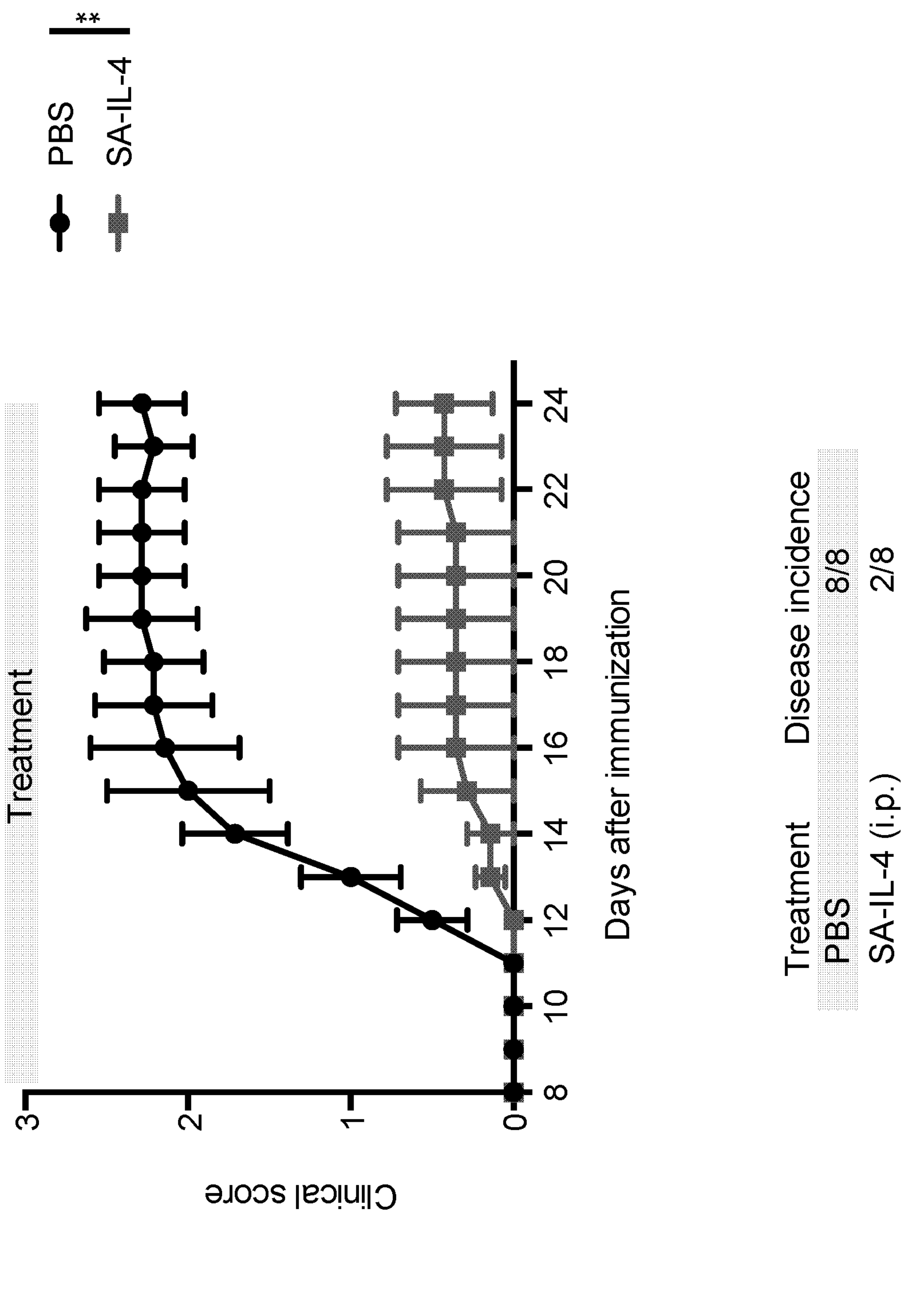
FIG. 26. Long-term treatment of SA-IL-4 suppresses EAE disease development and progression. Disease progression in C57BL/6 $MOG_{35-55}$ EAE mice injected i.p. every other day for 16 days from day 8 after immunization with PBS or SA-IL-4 (10 μg on an IL-4 basis) (n=8). The number of mice that developed EAE per total mice in each treatment group is indicated. Mice were monitored until day 24. Data are mean±SEM. Two experimental replicates. Statistical analyses were performed using Student's t-test. **P<0.01.
Figure 27:
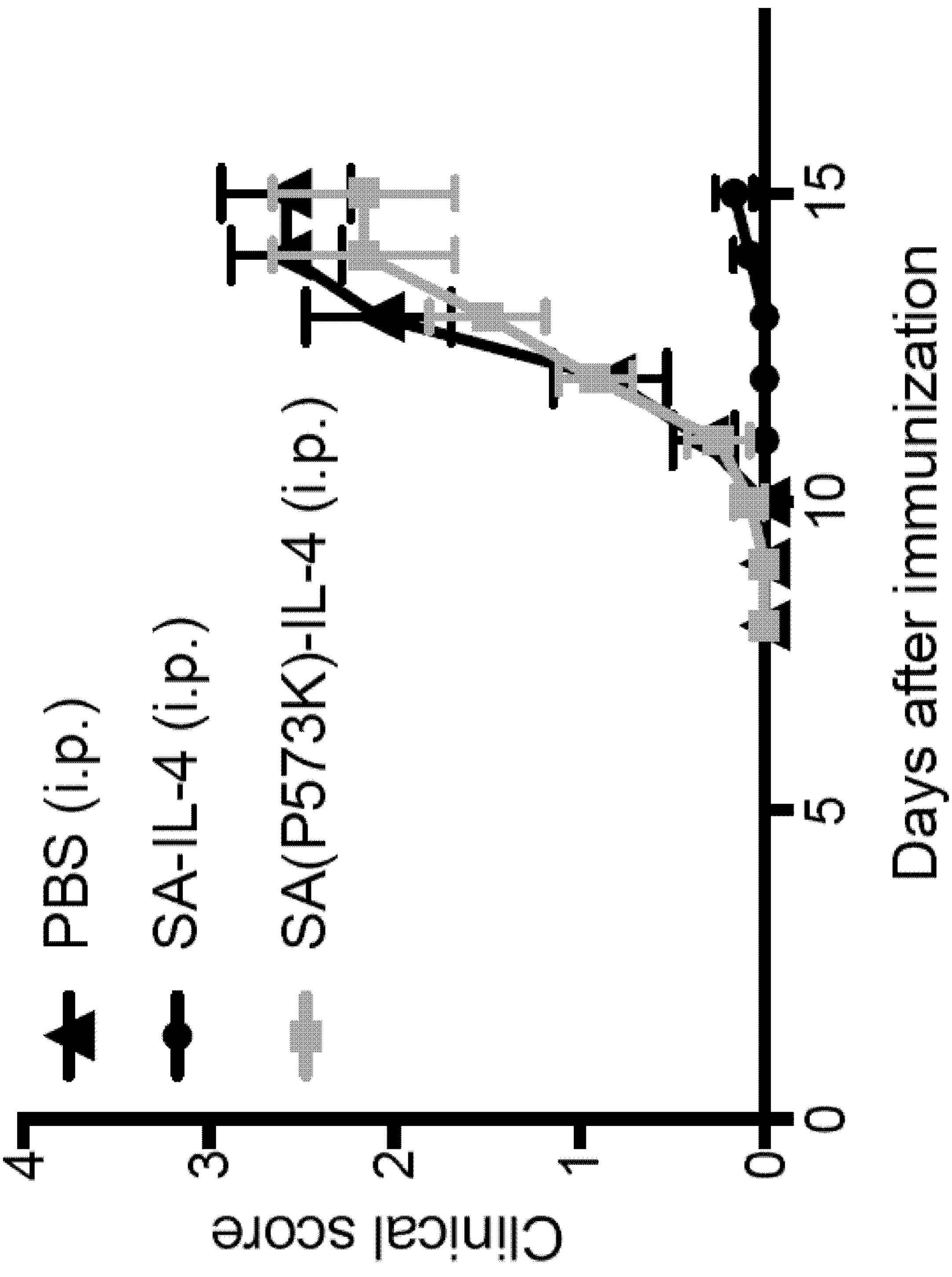
FIG. 27, FcRn binding is crucial for SA-IL-4 to suppresses EAE disease development and progression. Disease progression in C57BL/6 $MOG_{35-55}$ EAE mice injected i.p. every other day from day 8 after immunization with PBS or SA-IL-4 (10 μg on an IL-4 basis) (n=6). Data are mean±SEM. Two experimental replicates. Statistical analyses were performed using Student's t-test. **P<0.01.
Figure 30A:
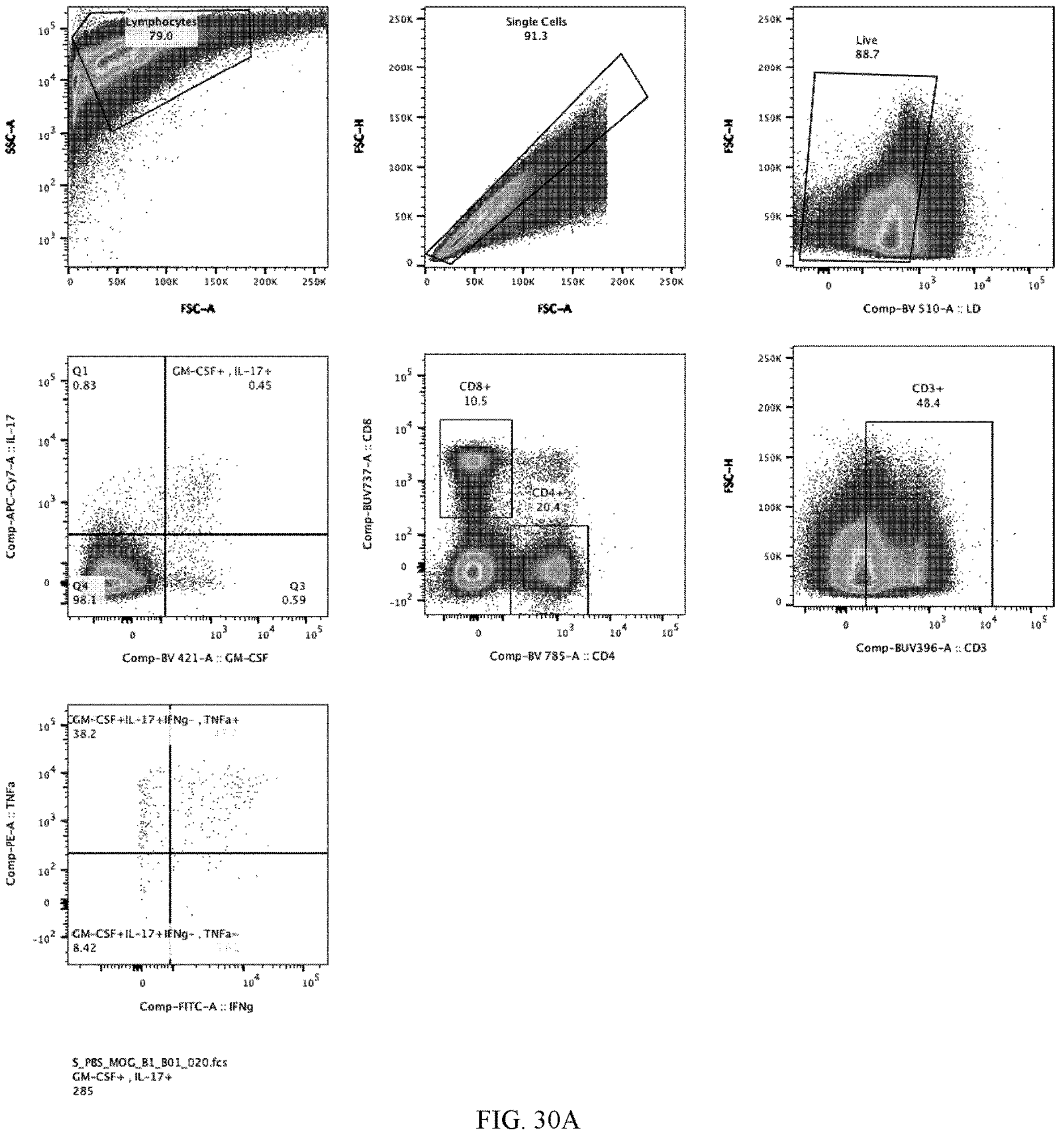
FIG. 30A-D. Gating strategy for flow cytometry. (A) Re-stimulation (cytokine expression). (B) Integrin expression. (C) MDSCs. (D) $CD45^+$ and T cells.
Figure 30B:
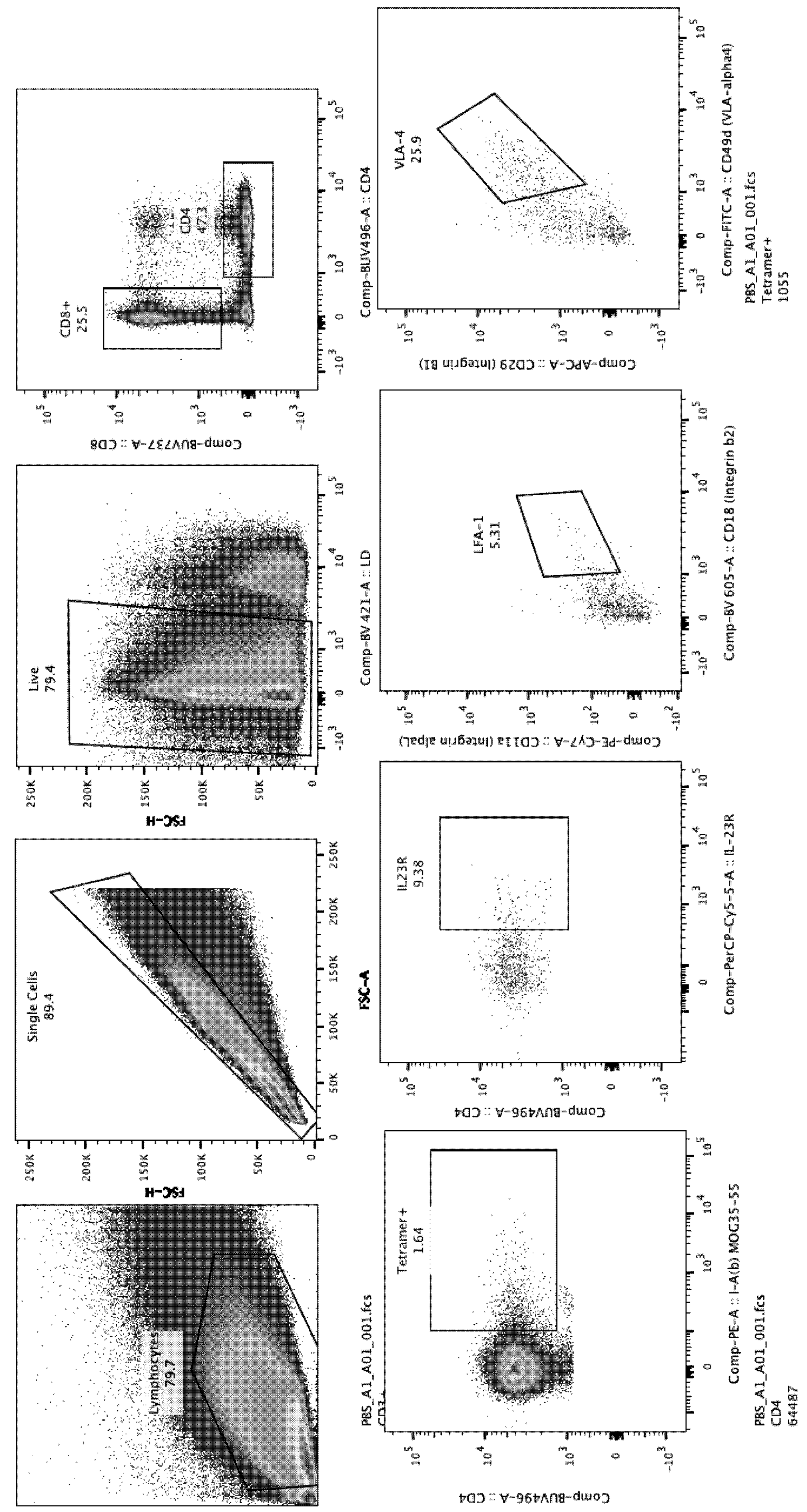
Figure 30C:
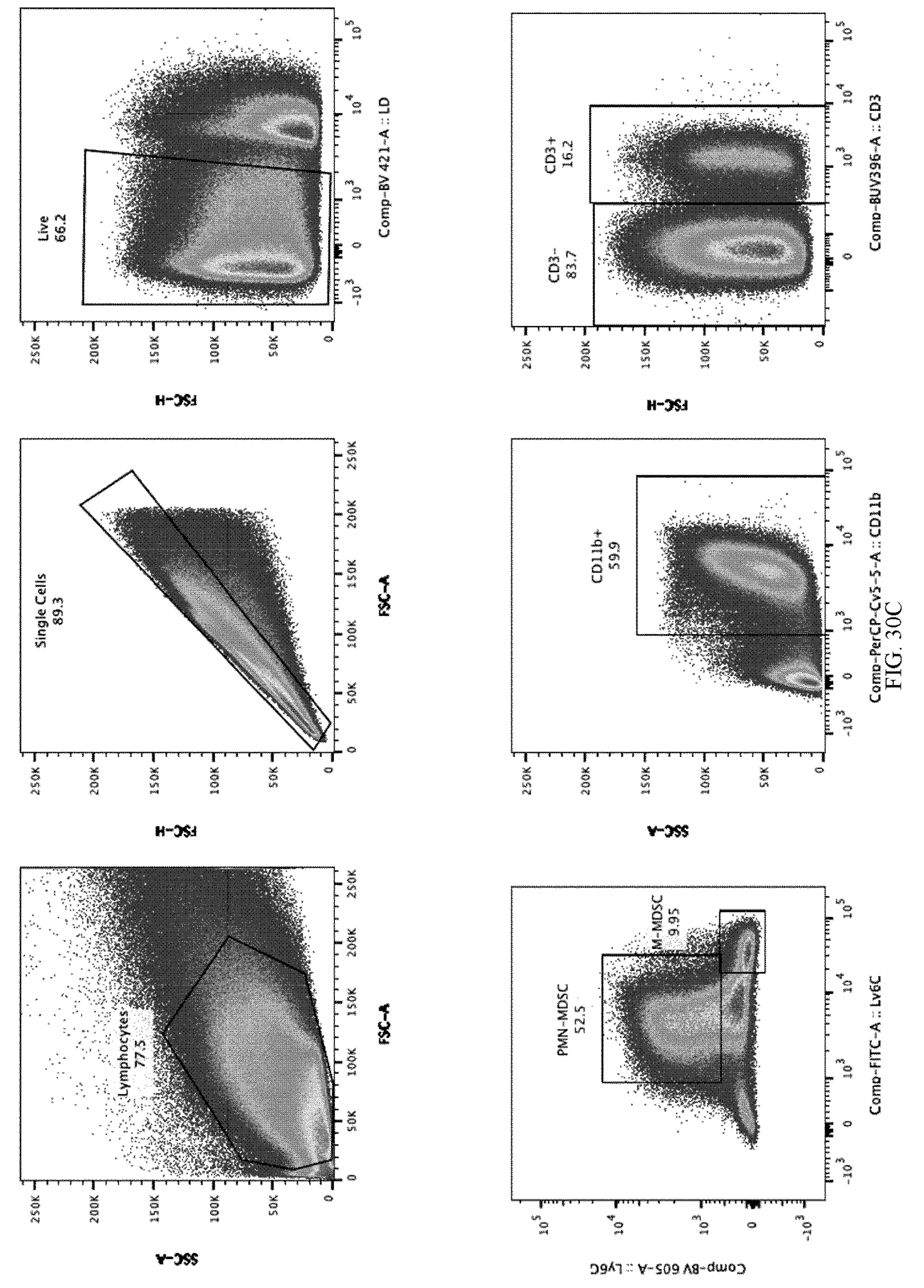
Figure 30D:
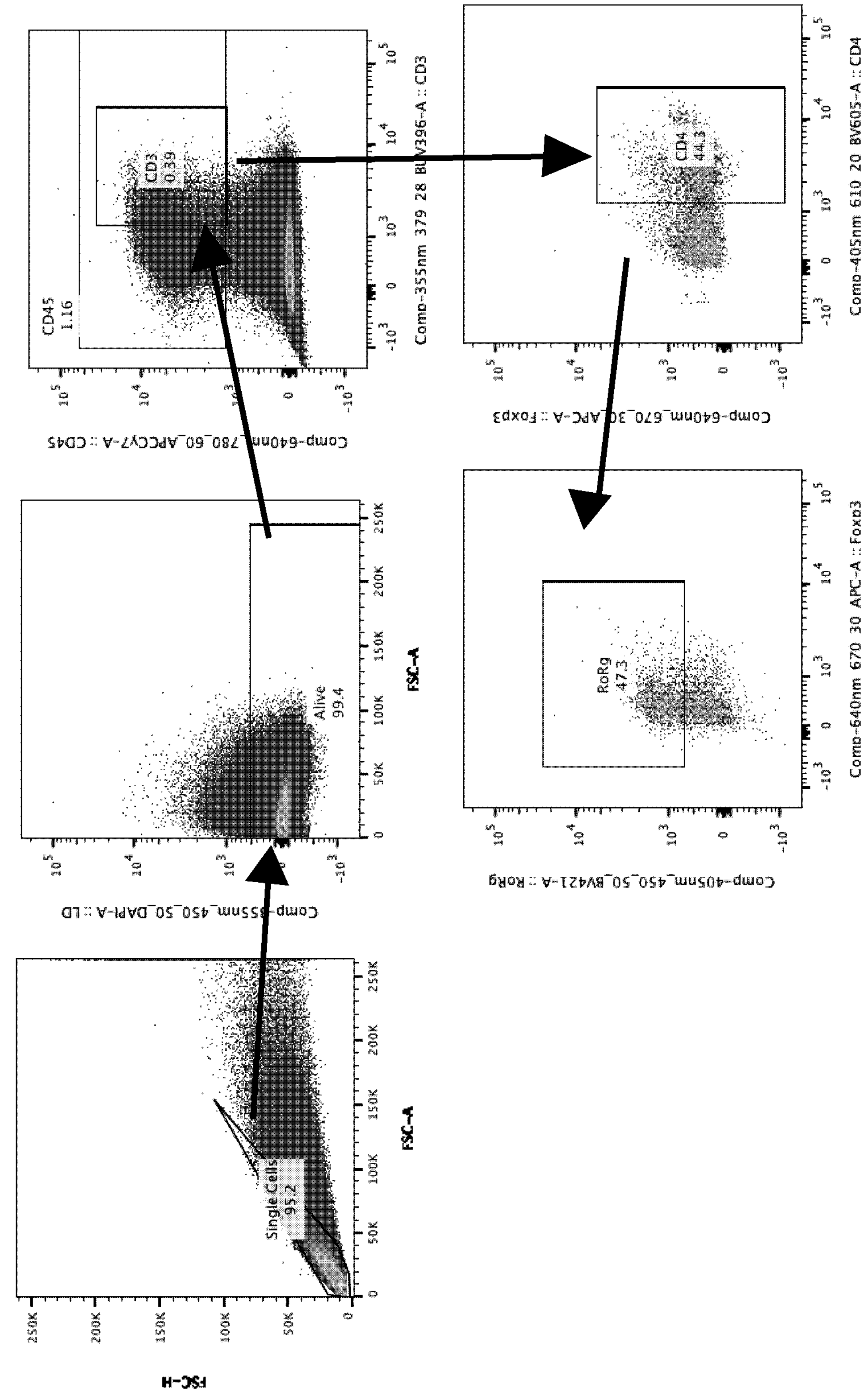

B. SA-IL-4 Treatment Strongly Suppresses EAE Disease Development in Prophylactic Treatment The inventors next treated myelin oligodendrocyte glycoprotein (MOG) antigen-induced EAE with SA-IL-4 in the acute phase of EAE (FIG. 20). SA-IL-4 was injected subcutaneously (s.c.) or intraperitoneally (i.p.). The inventors chose s.c. injection because it is clinically convenient and drug is absorbed slowly from the injection site. Injection i.p. was done as a surrogate for i.v. because the tail becomes flaccid in mice that have developed EAE, and tail vein injection thus becomes difficult. The inventors further compared the therapeutic effect of SA-IL-4 with FTY720, a clinically approved drug (fingolimod) for treating MS that sequesters lymphocytes in the LNs and prevents them from reacting with autoantigens in target tissues (3). Subcutaneous injection of SA-IL-4 completely suppressed disease development in all mice (FIG. 20A,B). SA-IL-4 injected i.p. and FTY720 prevented EAE development in 4 of 7 mice and suppressed disease severity in the rest. Wt IL-4 treatment did not show EAE clinical score suppression compared to the PBS treated group, all of which mice developed disease. Using body weight changes as a clinal indicator of health, mice treated with PBS and wt IL-4 were observed to markedly lose weight (FIG. 20C). Mice injected s.c. with SA-IL-4 gained their weight more than all other groups, indicating good health. The i.p. SA-IL-4 group gained weight on average, while FTY720 treated mice maintained their body weight. The inventors next analyzed demyelination of the spinal cord, which is the main morphological manifestation of EAE disease (FIG. 20D). Importantly, mice injected s.c. with SA-IL-4 did not have any detectable demyelination, demonstrating prevention of damage in the spinal cord. All wt IL-4-treated mice showed demyelination. The inventors then monitored mice long-term, until day 24, where SA-IL-4 i.p. injection inhibited disease development and progression (FIG. 26). Importantly, SA(P573K)-IL-4 did not suppress disease score (FIG. 27). These data suggest that SA fusion to IL-4 strongly improves the therapeutic effects of IL-4 on EAE disease suppression.

C. SA-IL-4 Treatment Suppresses Immune Cell Infiltration into the Spinal Cord and Induces an Immune-Suppressive Environment in the dLN The inventors next analyzed immune cells in the spinal cord and dLN after treatment. Strikingly, s.c. injection of SA-IL-4 significantly suppressed immune cell infiltration into the CNS; very few $CD45^+$ immune cells were detected within the spinal cord (FIG. 21A). Hence, Th17 cells in the spinal cord were barely detectable in the s.c. SA-IL4 treatment group (FIG. 21B). I.p. injection of SA-IL-4 suppressed immune cell infiltration in 4 of 7 mice, which corresponds to the incidence of EAE disease in that group. FTY720 administration also suppressed immune cell infiltration into the spinal cord, as expected. Wt IL-4 did not show any effects on immune cell infiltration, including Th17, into the spinal cord compared to PBS treatment.

The inventors then analyzed immune cells in the lumbar dLN. SA-IL-4 increased granulocyte-like myeloid-derived suppressor cells (G-MDSCs), but reduced monocyte-like MDSCs (M-MDSCs) (FIG. 21C,D). The frequency of Th17 cells within $CD4^+$ T cells in the dLN was also reduced by SA-IL-4 treatment (both i.p. and s.c.), compared to FTY720 treatment (FIG. 21E). FTY720 treatment trended to increase Th17 cell frequency in the dLN compared to PBS group, probably because FTY720 inhibits lymphocyte egress from LNs. SA-IL-4 treatment reduced the frequency of M1 macrophages and increased M2 macrophages in the dLN (FIG. 21F). Wt IL-4 did not decrease the frequency of M1 macrophages but increased M2 macrophages. The frequency of macrophages within $CD11b^+$ cells was maintained (FIG. 28A), as well as the frequency of DCs within $CD45^+$ cells (supplementary FIG. 4*b*). B cells reportedly promote induction of EAE by facilitating reactivation of T cells (14). SA-IL-4 (s.c.) decreased the frequency of B cells compared to both PBS and FTY720 treatment groups (FIG. 21H). Taken together, these data demonstrate that SA-IL-4 treatment generates an immunosuppressive environment in dLN and prevents immune cell infiltration into the spinal cord.

D. SA-IL-4 Treatment Decreases IL-17-Related Cytokine and Integrin Expression on Antigen-Reacting $CD4^+$ T Cells The inventors next analyzed the molecular mechanisms of decreased immune cell infiltration in the spinal cord and of the complete EAE disease prevention by s.c. injection of SA-IL-4. The inventors found that the number of $MOG_{35-55}$-reacting T cells in the dLN was maintained in all treatment groups, suggesting that SA-IL-4 does not change antigen recognition (FIG. 22A). Thus, the inventors hypothesized that SA-IL-4 changes T cell functionality. The inventors first tested the migratory ability of T cells. Expression levels of $\alpha L\beta 2$ and $\alpha 4\beta 1$ integrins, crucial adhesion molecules for lymphocytes migration (15), are reportedly decreased by IL-4 (16). The inventors found that SA-IL-4 treatment significantly decreased $\alpha L\beta 2$ integrin expression on $MOG_{35-55}$-reacting $CD4^+$ T cells, but not on total $CD8^+$ T cells (FIG. 22B-E). Expression of $\alpha 4\beta 1$ integrin was not significantly changed on $MOG_{35-55}$-reacting $CD4^+$ T cells, neither on total $CD8^+$ T cells. Because $\alpha L\beta 2$ integrin is indispensable for Th17 cell infiltration into the spinal cord (15), this suggests that down-regulation of integrin expression is one of the mechanisms by which SA-IL-4 decreases lymphocyte migration to the spinal cord.

The inventors then tested PD-1 expression on T cells and PD-L1 expression on MDSCs (FIG. 22F-K), as PD-1 and PD-L1 association suppresses T cell activation (17). Strikingly, SA-IL-4 but not wt IL-4 increased the expression of PD-1 on both central memory $CD4^+$ T cells and central memory $CD8^+$ T cells (FIG. 22F,G). Moreover, SA-IL-4 but not wt IL-4 increased the expression levels of PD-L1 and the frequency of PD-L1-expressing cells on both M-MDSCs and G-MDSCs (FIG. 22H-K). These data suggest T cell suppression may be induced through MDSCs and the PD-1/PD-L1 axis.

The inventors next analyzed Th17-related protein expression. IL-23 is a crucial cytokine for Th17 functionality. IL-4 reportedly binds to APCs and silences IL-23 and concordant Th17 differentiation (18). The inventors found that SA-IL-4 treatment decreases the frequency of $IL\text{-}23R^+$ cells within the $MOG_{35-55}$-reactive T cell repertoire (FIG. 22L).

Next, the inventors re-stimulated splenocytes with MOG protein (FIG. 22M,N). ELISA of culture supernatant revealed a decrease in IL-17A expression with SA-IL-4 treatment, but not wt IL-4 treatment, compared to PBS (FIG. 22M). The reduction in IL-17 expression implies a decreased number and/or level of activity of $MOG_{35-55}$-reactive Th17 cells in the SA-IL-4 treated group. The IFNγ concentration was maintained, suggesting little effect of SA-IL-4 on Th1 cells (FIG. 22N). SA-IL-4 trended toward a decreased level of GM-CSF, a reportedly pathogenic cytokine for EAE (19) (FIG. 22O). The inventors then tested cytokine expression within T cells by flow cytometry after $MOG_{35-55}$ peptide re-stimulation of splenocytes (FIG. 22P). The inventors analyzed GM-CSF, IL-17, IFNγ and TNFα, all pathogenic cytokines for EAE. SA-IL-4 decreased the frequency of cytokine-expressing cells within the $CD4^+$ T cell compartment, compared to other treatments. These results strongly suggest that Th17 cells in the SA-IL-4-treated mice are fewer and less pathogenic compared to other treatment groups. Taken together, these data suggest that SA-IL-4 modulates multiple immune cell responses in the SLOs and suppresses EAE disease development through preventing immune cell infiltration, especially T cell infiltration, into the spinal cord.

E. SA-IL-4 Recovers Paralysis Due to EAE in the Chronic Phase

To determine if SA-IL-4 has a therapeutic effect in the chronic phase of EAE, the inventors designed an experiment involving treating mice that had already reached a stage of severe paralysis. The inventors began i.p. injection of IL-4 from day 21 after induction (FIG. 23A,B). Strikingly, SA-IL-4 but not wt IL-4 demonstrated therapeutic efficacy even when administered at this late time point. SA-IL-4-but not wt IL-4-treated mice gained weight, indicating disease recovery. The inventors next tested the effect of SA-IL-4 in the chronic phase via s.c. injection, and compared with oral FTY720 therapy (FIG. 23C,D). As a result, SA-IL-4-treated mice trended toward a decrease of the clinical score compared to other treatment groups. Mice receiving SA-IL-4 gained weight compared to other groups. FTY720- and wt IL-4-treated mice did not gain weight compared to PBS-treated mice.

The inventors then tested immune cell infiltration into the spinal cord at day 34 after induction by flow cytometry (FIG. 23E-G). SA-IL-4 and FTY720 treatment decreased the number of spinal cord infiltrated immune cells, including $CD4^+$ T cells and $MOG_{35-55}$-reactive Th17 cells, compared to PBS and wt IL-4 treatment. SA-IL-4 decreased IL-23R expressing cells within $MOG_{35-55}$-reactive $CD4^+$ T cells in the spleen compared to other treatment groups (FIG. 23H). Finally, splenocyte re-stimulation with MOG protein was performed. ELISA of the culture supernatant revealed decreased IL-17A and GM-CSF concentrations in the SA- IL-4 treatment group, but not after wt IL-4 and FTY720 treatment, compared to PBS (FIG. 23I,J). Flow cytometric analysis after $MOG_{35-55}$ peptide re-stimulation showed that SA-IL-4 decreased the frequency of cytokine-expressing cells within the $CD4^+$ T cell compartment compared to other treatments. (FIG. 23K). Taken together, these results suggest that SA-IL-4 treatment has a potent therapeutic effect on the EAE chronic phase.

F. SA-IL-4 Did not Show Marked Toxicity after Systemic Injection

To test if SA-IL-4 exhibits any adverse effects, the inventors analyzed serum using a biochemistry analyzer and blood using a hematology analyzer (FIG. 29). SA-IL-4 treatment did not increase organ damage markers nor change blood cell counts (FIG. 29A-M). SA-IL-4 and wt IL-4 induced splenomegaly (FIG. 29N). Wt IL-4 induced pulmonary edema, indicated by water content increase in the lung, whereas SA-IL-4 did not (FIG. 29N). These evidence suggests that SA-IL-4 is safe after systemic administration.

Although a number of treatments for MS are currently available in the clinic, the disease remains poorly addressed. Some effective therapies, such as with FTY720 (fingolimod) and anti-α4 integrin (natalizumab) inhibit effector lymphocyte infiltration into the diseased tissue, which is associated with risk of immune-related adverse events (20). IFNβ functions by multiple mechanisms, including reduction of lymphocyte migration into the CNS (21). Although IFNβ is not as effective as fingolimod (22), IFNβ is employed clinically to modulate pathology in MS (23). Here, the inventors seek to explore a therapy that could sculpt the immune response away from the Th17 pathway that is known to be involved in the pathology of the disease, toward a more tolerogenic phenotype using IL-4, without adverse effects. Here, the inventors utilized a molecular engineering approach to target IL-4 to the SLOs to ameliorate the underlying autoimmune response to myelin antigens.

In this study, s.c. injection of SA-IL-4 prevented the development of EAE in all mice tested. Strikingly, SA-IL-4 strongly reduced lymphocyte infiltration into the spinal cord with treatment at both early and late time points. Analysis of the dLN revealed that SA-IL-4 increased M2 macrophage and G-MDSCs, as well as decreased Th17 cells. However, wt IL-4 also increased the number of M2 macrophages, suggesting that the IL-4-mediated suppression of inflammatory macrophages is insufficient to control EAE under these experimental conditions.

IL-4 reportedly maintains and increases the immunosuppressive character of MDSCs (24). G-MDSCs are a crucial population that suppresses EAE development (17). G-MDSCs express PD-L1 to induce functional suppression of T cells. On the other hand, M-MDSCs were decreased by SA-IL-4 treatment. The role of M-MDSCs on EAE is controversial, and a pathogenic effect has been reported (25). Interestingly, SA-IL-4 but not wt IL-4 enhanced expression of PD-L1 on both G- and M-MDSCs in the SLOs. Simultaneously, SA-IL-4 but not wt IL-4 enhanced expression of PD-1 on both $CD4^+$ and $CD8^+$ central memory T cells in the SLOs. The inventors suppose that this PD-1/PD-L1 induction effect is the mechanism through which MDSCs in the SA-IL-4 treated mice suppress pathogenic T cells, and the observation of this phenomenon in the SLOs attests to the value of the SLO-targeting capability conferred by SA fusion.

Th17 cells play a crucial role in EAE disease severity and development (26). SA-IL-4 treatment reduced the frequency of Th17 cells in the dLN, compared to FTY720 treatment. IL-4 directly inhibits naïve T cell differentiation into Th17 cells, as the inventors have shown in FIG. 18D. Additionally, there is a possible Th17 inhibition pathway mediated through APCs. IL-23 is expressed by APCs (26) and generates pathogenic Th17 cells and induces expression of IL-17 (27). IL-4 reportedly reduces expression of IL-17 through silencing of IL-23 in APCs (18). Thus, it may be that SA-IL-4 acts on APCs to decrease IL-23 expression, thereby blocking generation of pathogenic Th17 cells in the SLOs. This model agrees with the inventors' data that SA-IL-4 decreases $GM\text{-}CSF^+$-mediated T cell pathogenicity, as $GM\text{-}CSF^+$ is a marker for pathogenic Th17 cells.

Additionally, SA-IL-4 treatment resulted in decreased integrin expression in the MOG-reactive $CD4^+$ T cell compartment. Although immunized mice had already mounted an anti-MOG response before treatment, SA-IL-4 was able to prevent the migration of autoimmune cells into the CNS. Therefore SA-IL-4 treatment did not change the number of antigen-reacting T cells, but rather inactivated T cell function. Overall, this data show that SA-IL-4 acts through multiple immune pathways to generate an immunosuppressive environment in the SLOs.

FTY720 is one of the FDA-approved drugs against MS, functioning through induction of lymphocytopenia and thus limiting migration of effector lymphocytes to the CNS disease site. Subcutaneously administered SA-IL-4 showed higher efficacy than FTY720 in this study. This improvement with SA-IL-4 is strong evidence for its potential for clinical translation. FTY720 has the drawback that it cannot be administered to infected patients. Also, among the approved therapies for MS that modulate lymphocyte migration, such as FTY720 and integrin a4 blockade, induction of John Cunningham virus (JCV) activity can lead to progressive multifocal leukoencephalopathy (PML) which can ultimately cause severe adverse events including death. SA-IL-4 decreased integrin expression only on the antigen-reactive $CD4^+$ T cells, but not $CD8^+$ T cells. This suggests that SA-IL-4 has additional migratory inhibitory effects on antigen-reactive $CD4^+$ T cells, which may contribute to inflammation suppression in the spinal cord. The hematology study showed that SA-IL-4 did not induce lymphocytopenia. This may be an additional advantage over approved drugs, as SA-IL-4 is not expected to strongly suppress the immune response against infectious diseases, and thus it may be that SA-IL-4 may be useful for patients who are not amenable to treatment with FTY720. SA-IL-4 likely suppresses autoimmunity through various mechanisms that are not redundant with current therapeutics. In this study, FTY720 did not suppress Th17 development in the dLN, while SA-IL-4 did. Thus, SA-IL-4 may be useful for patients who do not obtain sufficient therapeutic effects with current treatments.

Intradermal or s.c. injections of SA have been well studied to accumulate in the injection site-draining LN (28). Here, the inventors showed that SA-IL-4 accumulates in the LNs after i.v. injection, i.e. from the blood rather than via the afferent lymphatic vessel. Although previously a biodistribution study of SA-fused IL-2 showed spleen, liver and LN accumulation of IL-2 through i.v. injection (29), the molecular mechanism and its localization within LNs were unclear. The histological analysis shows that i.v. injected SA-IL-4 accumulates and co-localizes around high endothelial venules (HEVs) (30). Although IgG transcytosis through FcRn has been well studied, only recently has the transcytosis of albumin through FcRn binding been reported by multiple research groups (31-33). Because FcRn is highly expressed in the LN (34), it is likely that i.v.-injected SA-IL-4 trafficked to the LN by transcytosis. In this study, SA(P573K)-

IL-4 achieved lower amounts of IL-4 in the LN compared to SA-IL-4, similar to wt IL-4. This would suggest that FcRn binding plays an important role in SA-IL-4 transport to the LN from the blood. From the inventors' observation of SA-IL-4 concentrating around the medullary space, where APCs reside, the inventors postulate that SA-IL-4 enters through HEVs and then binds to DCs and macrophages, as the inventors have shown in FIG. 18. SA(P573K)-IL-4 did not suppress disease score in FIG. 27, which indicates that FcRn binding and subsequent increased persistence in the SLO are crucial to suppress EAE disease symptoms. Thus, the inventors believe that the SA-cytokine fusion immunosuppressive molecules function not primarily by extending blood circulation time, rather by extending the recycle time in the SLO, such as the LNs and spleen. Thus, the SA fused cytokine can be collected by one immune cell and recycled by that cell to stimulate another immune cell. As such, blood circulation lifetimes are not directly related to SLO presence lifetimes. The inventors believe that this biological finding can open a new research field of LN molecular trafficking, and further research will clarify the detailed mechanisms.

SA-IL-4 exhibited therapeutic efficacy in the chronic phase of EAE. Nasal or lumbar administration of IL-4 has been previously reported to lead to direct binding of IL-4 to neurons, in attempts to regenerate the nervous system in EAE (9). The therapeutic effect of i.p.-injected SA-IL-4 was comparable to nasally administered wt IL-4 in the previous report. This suggests that SA-IL-4 may also bind to neurons and induce regeneration. Because the blood brain barrier is disrupted in the EAE model, SA-IL-4 may have access to neurons within the spinal cord. It will be interesting to study the direct effect of SA-IL-4 on neural regeneration in future research.

Subcutaneous administration of SA-IL-4 showed higher preventative effect than that of i.p. injection. This route is convenient for clinical translation and generally shows slow release from the tissue. The inventors assume that this slow release was a further contributing factor for suppression of EAE development.

Systemically injected SA-IL-4 did not show obvious toxicity in the blood biochemistry analysis and hematology analysis. Although the inventors have observed splenomegaly, this is typically transient and is not considered as a critical toxicity. Wt IL-4 induced pulmonary edema, which would be more concerning. However, pulmonary edema was not observed with SA-IL-4; this difference may be because of diminished activity of SA-IL-4 on STATE activation. These results indicate a low risk of adverse event induction by SA-IL-4 administration in the clinic.

In conclusion, the engineered SA-IL-4 demonstrated persistence in SLOs through FcRn binding. SA-IL-4 displayed marked therapeutic effects on multiple phases of EAE after systemic injection, and it modulates key immune pathways of EAE, such as decreasing Th17 cells and increasing G-MDSCs and PD-L1 expression by MDSCs in SLOs. SA-IL-4 holds translational potential in both preventative and therapeutic usage through a novel biologic approach utilizing mechanisms that are different from currently approved therapies.

G. Amino Acid Sequence of Wt IL-4 and SA-IL-4

```
Mouse IL- 4
                                        (SEQ ID NO: 56)
MHIHGCDKNHLREIIGILNEVTGEGTPCTEMDVPNVLTATKNTTE

SELVCRASKVLRIFYLKHGKTPCLKKNSSVLMELQRLFRAFRCLD
```

-continued

```
SSISCTMNESKSTSLKDFLESLKSIMQMDYSHHHHHH

Mouse serum albumin and mouse IL-4 fusion protein
                                        (SEQ ID NO: 57)
EAHKSEIAHRYNDLGEQHFKGLVLIAFSQYLQKCSYDEHAKLVQ

EVTDFAKTCVADESAANCDKSLHTLFGDKLCAIPNLRENYGELA

DCCTKQEPERNECFLQHKDDNPSLPPFERPEAEAMCTSFKENPTT

FMGHYLHEVARRHPYFYAPELLYYAEQYNEILTQCCAEADKESC

LTPKLDGVKEKALVSSVRQRMKCSSMQKFGERAFKAWAVARLS

QTFPNADFAEITKLATDLTKVNKECCHGDLLECADDRAELAKYM

CENQATISSKLQTCCDKPLLKKAHCLSEVEHDTMPADLPAIAADF

VEDQEVCKNYAEAKDVFLGTFLYEYSRRHPDYSVSLLLRLAKKY

EATLEKCCAEANPPACYGTVLAEFQPLVEEPKNLVKTNCDLYEK

LGEYGFQNAILVRYTQKAPQVSTPTLVEAARNLGRVGTKCCTLPE

DQRLPCVEDYLSAILNRVCLLHEKTPVSEHVTKCCSGSLVERRPC

FSALTVDETYVPKEFKAETFTFHSDICTLPEKEKQIKKQTALAELV

KHKPKATAEQLKTVMDDFAQFLDTCCKAADKDTCFSTEGPNLVT

RCKDALAGGGGSGGGSMHIHGCDKNHLREIIGILNEVTGEGTPCT

EMDVPNVLTATKNTTESELVCRASKVLRIFYLKHGKTPCLKKNSS

VLMELQRLFRAFRCLDSSISCTMNESKSTSLKDFLESLKSIMQMD

YSHHHHHH
```

H. Materials and Methods

1. Production and Purification of Recombinant Proteins

The sequences encoding for mouse SA without propeptide (25 to 608 amino acids of whole serum albumin), mouse IL-4, and a $(GGGS)_2$ linker were synthesized and subcloned into the mammalian expression vector pcDNA3.1 (+) by Genscript. A sequence encoding for 6 His was added at the C-terminus for further purification of the recombinant protein. The amino acid sequence of the protein is shown in the supplemental table 1. Suspension-adapted HEK-293F cells were routinely maintained in serum-free FreeStyle 293 Expression Medium (Gibco). On the day of transfection, cells were inoculated into fresh medium at a density of $1\times10^6$ cells/ml. 2 μg/ml plasmid DNA, 2 μg/ml linear 25 kDa polyethylenimine (Polysciences), and OptiPRO SFM media (4% final concentration, Thermo Fisher) were sequentially added. The culture flask was agitated by orbital shaking at 135 rpm at 37° C. in the presence of 5% $CO_2$. Seven days after transfection, the cell culture medium was collected by centrifugation and filtered through a 0.22 μm filter. Culture media was loaded into a HisTrap HP 5 ml column (GE Healthcare), using an AKTA pure 25 (GE Healthcare). After washing the column with wash buffer (20 mM $NaH_2PO_4$, 0.5 M NaCl, pH 8.0), protein was eluted with a gradient of 500 mM imidazole (in 20 mM $NaH_2PO_4$, 0.5 M NaCl, pH 8.0). The protein was further purified by size exclusion chromatography using a HiLoad Superdex 200PG column (GE Healthcare) using PBS as an eluent. All purification steps were carried out at 4° C. The expressed proteins were verified as >90% pure by SDS-PAGE. Purified proteins were tested for endotoxin via the HEK-Blue TLR4 reporter cell line, and endotoxin levels were confirmed to be less than 0.01 EU/ml. Protein concentration was determined through absorbance at 280 nm using NanoDrop (Thermo Scientific).

2. Mice

C57BL/6 female mice at 8 weeks of age mice were obtained from the Charles River Laboratories. Mice were housed at the University of Chicago Animal facility for at least 1 week before immunization. All experiments were performed with approval from the Institutional Animal Care and Use Committee of the University of Chicago.

3. Binding of the Proteins to Splenocytes or LN-Derived Cells

Single-cell suspensions were obtained by gently disrupting the spleen or popliteal lymph node through a 70-μm cell strainer. Red blood cells were lysed with ACK lysing buffer (Quality Biological) for splenocytes. Cells were counted and re-suspended in RPMI-1640 supplemented with 10% FBS and 1% penicillin/streptomycin (all from Life Technologies). $1\times10^5$ cells/well were seeded in a 96 well microplate and were incubated with 2 μg/100 μl of SA, SA-IL4 for 30 min on ice. After 4-times washing by PBS, cells were further incubated with Rabbit monoclonal anti-mouse serum albumin antibody (clone EPR20195 abcam) for 20 min on ice. After 3-times washing by PBS, cells were incubated with 1 μg/ml AlexaFluor 647-labeled anti-Rabbit IgG, anti-B220, anti-CD3, anti-CD4, anti-CD8, anti-CD11c, anti-CD45 and anti-F4/80 antibodies for 20 min on ice. Cells were analyzed by flow cytometry as described below.

4. Analysis of STAT6 Phosphorylation by Flow Cytometry

Mouse $CD4^+$ T cells were purified from spleens of C57BL/6 mice using EasySep mouse $CD4^+$ T cell isolation kit (Stem Cell). Purified $CD4^+$ T cells ($10^6$ cells/nil) were activated in six-well plates precoated with 5 μg/ml anti-CD3 antibody(clone 17A2, Bioxcell) and supplemented with soluble 2 μg/ml anti-CD28 antibody (clone 37.51, BioLegend) for 2 days. Culture medium was IMDM (Gibco) containing 10% heat-inactivated FBS, 1% Penicillin/Streptomycin and 50 μM 2-mercaptoethanol (Sigma Aldrich). After 2 days of culture, activated $CD4^+$ T cells were stimulated with 50 ng/ml recombinant murine IL-2 (Peprotech) for 3 hr to induce IL-4Rα expression. After stimulation with IL-2, cells were washed and rested in fresh medium for 3 hr. Cells were then transferred into 96-well plates (50,000 cells/well). Indicated amounts of wt IL-4 or SA-IL-4 were applied to $CD4^+$ T cells for 15 min at 37° C. to induce STAT6 phosphorylation. Cells were fixed immediately using BD Phosflow Lyse/Fix buffer for 10 min at 37° C. and then permeabilized with BD Phosflow Perm Buffer III for 30 min on ice. Cells were stained with AlexaFluor 647 anti-pSTAT6 antibody (Clone J71-773.58.11, BD) recognizing phosphorylation of Tyr641. Staining was performed for 1 hr at room temperature (RT) in the dark. Cells were acquired on BD LSR and data were analyzed using FlowJo (Treestar). Mean fluorescence intensity (MFI) of $pSTAT6^+$ population was plotted against cytokine concentration. Dose-response curve was fitted using Prism (v8, GraphPad).

5. Surface Plasmon Resonance (SPR)

SPR measurements were made with a Biacore X100 SPR system (GE Healthcare). Murine FcRn recombinant protein (Acro Biosystems) was immobilized via amine coupling on a C1 chip (GE Healthcare) for ~200 resonance units (RU) according to the manufacturer's instructions. SA-IL4 was flowed at decreasing concentrations in the running buffer (0.01 M monobasic anhydrous sodium phosphate, pH 5.8, 0.15 M NaCl) at 30 μl/min. The sensor chip was regenerated with PBS, pH 7.4 for every cycle. Specific bindings of SA fusion proteins to FcRn were calculated by comparison to a non-functionalized channel used as a reference. Experimental results were fitted with Langmuir binding kinetics using BIAevaluation software (GE Healthcare).

6. Th17 Cell Differentiation In Vitro in Culture

Naïve $CD4^+$ T cells were isolated from splenocytes using EasySep™ Mouse Naïve $CD4^+$ T Cell Isolation Kit (STEMCELL Technologies) according to the manufacture's instructions. $10^5$ cells were plated in the 96 well plate and cultured for 3 days. As Th17 induction media, IL-17A concentrations in the culture media were measured by IL-17 Ready-Set-Go! Mouse Uncoated ELISA kit (Invitrogen) according to the manufacturer's protocol. Data were analyzed using Prism software (v6, GraphPad).

7. Plasma Pharmacokinetics of the Proteins

Wt IL-4 or SA-IL-4 (equivalent to 10 μg of IL-4) was injected intravenously into female C57BL/6 mice. Blood samples were collected in protein-low binding tubes at 1 min, 10 min, 30 min, 1 hr, 2 hr, 4 hr and 24 hr after injection. IL-4 concentrations in plasma were measured by IL-4 Ready-Set-Go! Mouse Uncoated ELISA kit (Invitrogen) according to the manufacturer's protocol.

8. Lymph Node and Spleen Pharmacokinetics of the Proteins

Wt IL-4, SA-IL-4 or SA(P573K)-IL-4 (equivalent to 40 μg of IL-4) was injected intravenously into healthy C57BL/6 mice. Lumbar and brachial LNs and spleen were collected at 1 hr, 4 hr, and 24 hr after injection, and were subsequently homogenized using Lysing Matrix D and FastPrep-24 5G (MP Biomedical) for 40 s at 5000 beats/min in T-PER tissue protein extraction reagent (Thermo Scientific) with cOmplete™ proteinase inhibitor cocktail (Roche). After homogenization, samples were incubated overnight at 4° C. Samples were centrifuged (5000 g, 5 min), and the total protein concentration and IL-4 concentration were analyzed using a BCA assay kit (Thermo Fisher) and IL-4 Mouse Uncoated ELISA kit (Invitrogen), respectively. Simultaneously, cytokine levels in LN extract were measured using Mouse Uncoated ELISA kit (Invitrogen) or Ready-SET-Go! ELISA kits (eBioscience) according to the manufacturer's protocol.

9. Fluorescence Based IL-4 Detection in the LN

To make fluorescently labeled wt IL-4 and SA-IL-4, proteins were incubated with 8-fold molar excess of using DyLight 800 NHS ester (Thermo Fisher) for 1 hr at RT, and unreacted dye was removed by a Zebaspin spin column (Thermo Fisher) according to the manufacturer's instruction. 10 μg of DyLight 800-labeled wt IL-4 and SA-IL-4 with equivalent fluorescence were injected i.v. to naïve C57BL/6 mice. After 4 hr, the iliac LN was imaged with the Xenogen IVIS Imaging System 100 (Xenogen) under the following conditions: f/stop: 2; optical filter excitation 745 nm; excitation 800 nm; exposure time: 5 sec; small binning.

10. Immunofluorescence

Wt IL-4 and SA-IL-4 were fluorescently labeled with DyLight 594 NHS ester (Thermo Fisher), as described above. 1 hr after i.v. injection of fluorescently-labeled IL-4 (40 μg for wt IL-4 and same fluorescent amount for SA-IL-4), mice were sacrificed. Mouse LNs were harvested and fixed in 2% PFA in PBS overnight and washed with PBS. After overnight incubations in 30% sucrose solutions, LNs were embedded in Optimum Cutting Temperature compound. Then, 5 μm cryosections were cut using a cryostat. Sections were then blocked with 2% BSA in PBS at RT and incubated with the following primary antibodies for 2 hr at RT: 10 μg/ml hamster anti-mouse CD3c antibody (clone: 145-2C11, BioLegend) and 2.5 μg/ml rat anti-mouse PNAd (clone: MECA-79, BioLegend) antibody. After washing with PBS-T, tissues were stained for 1 hr at RT with the following fluorescently-labeled secondary antibodies were used: Alexa Fluor 647 goat anti-hamster (1:400, Jackson ImmunoResearch) and Alexa Fluor 488 donkey anti-rat (1:400, Jackson ImmunoResearch). The tissues were washed three times and then covered with ProLong gold antifade mountant with 4',6-diamidino-2-phenylindole (DAPI; Thermo Fisher Scientific). An IX83 microscope (Olympus) was used for imaging with 10× magnification for CD3 staining, and a Leica SP8 3D Laser Scanning Confocal microscope with 20× magnification for PNAd staining. Images were processed using ImageJ software (NIH).

11. EAE Model

C57BL/6 young female mice aged 9 to 12 wk were immunized subcutaneously at the dorsal flanks with an emulsion of $MOG_{35-55}$ in complete Freund's adjuvant (CFA), followed by intraperitoneal administration of pertussis toxin (PTX) in PBS, first on the day of immunization and then again the following day. $MOG_{35-55}$/CFA Emulsion and PTX were purchased from Hooke Laboratories. Following the first immunization, the severity of EAE was monitored and clinical scores were measured daily from day 8 after immunization. The clinical scores were determined by A.I., M.N. or A.S. based on the Hooke Laboratories criteria under blinding to the treatment grouping. IL-4, SA-IL-4, PBS was administered i.p. or s.c. (in the mouse back) in 100 µl PBS, every other day. FTY720 (1 mg/kg body weight) was administered orally every day.

12. Histology of Spinal Cord

The thoracic and lumbar spines of EAE mice were harvested and cut out at the thoracolumbar junction. Tissues were fixed in 2% PFA overnight. After PBS wash, tissues were decalcified using Decalcifier II (Leica Biosystem) overnight. Then, tissues were embedded in paraffin. After paraffin embedding, blocks were cut into 5 mm sections. After deparaffinization and rehydration, tissue sections were treated with target retrieval solution (S1699, DAKO) and heated in a steamer for 20 min at temperature >95 C°. Tissue sections were incubated with anti-mouse aMBP, abcam ab40390) for 1 hr incubation at RT in a humidity chamber. Following a TBS wash, the tissue sections were incubated with biotinylated anti-rat IgG (10 mg/mL, Vector laboratories) for 30 min at RT. The antigen-antibody binding was detected by Elite kit (PK-6100, Vector Laboratories) and DAB (DAKO, K3468) system. Slides were imaged by EVOS FL Auto (Life Technologies).

13. Flow Cytometry

EAE mice were treated with PBS, wt IL-4, or SA-IL-4 (equivalent to 10 µg of IL-4) every other day, starting 8 days after immunization. Thirteen, 17 or 34 days after immunization, the spinal cord, spleen, and lumbar LNs were harvested. Spinal cord tissues were digested in Dulbecco's Modified Eagle Medium (DMEM) supplemented with 2% FBS, 2 mg/ml collagenase D (Sigma-Aldrich) and 40 µg/ml DNase I (Roche) for 30 min at 37° C. Single-cell suspensions were obtained by gently disrupting through a 70-µm cell strainer. For spleen, red blood cells in blood were lysed with ACK lysing buffer (Quality Biological), followed by antibody staining for flow cytometry. Antibodies against the following molecules were used: anti-mouse CD3c (145-2C11, BD Biosciences), CD4 (RM4-5, BD Biosciences), anti-mouse CD8a (53-6.7, BD Biosciences), anti-mouse CD45 (30-F11, BD Biosciences), CD44 (IM7, BD Biosciences), CD62L (MEL-14, BD Biosciences), F4/80 (T45-2342, BD Biosciences), CD86 (GL1, BD Biosciences), CD206 (C068C2, BioLegend), Ly6G (1A8, BioLegend), Ly6C (HK1.4, BioLegend), CD11b (M1/70, BioLegend), CD11c (HL3, BD Biosciences), B220 (RA3-6B2, BioLegend), PD-1 (29F.1A12, BD Biosciences), PD-L1 (MIH7, BioLegend), IL-23R (O78-1208, BD Biosciences), Integrin integrin at (HIM, BD Biosciences), integrin 132 (M18/2, BD Biosciences), integrin 131 (HMb1-1, BD Biosciences), integrin a4 (R1-2, BD Biosciences), GM-CSF (MP1-22E9, BD Biosciences), IL-17 (TC11-18H10.1, BD Biosciences), IFNγ (XMG1.2, BD Biosciences), TNFα (eBioscience, MP6-XT22), and RoRγt antibody (Q31-378, BD Biosciences). For detection of MOG-recognizing T cells, T-Select I-Ab $MOG_{35-55}$ Tetramer-PE (MBL International Corporation) or $MOG_{38-49}$ Tetramer-PE (NIH Tetramer Core Facility) was used. Fixable live/dead cell discrimination was performed using Fixable Viability Dye eFluor 455 (eBioscience), Live/Dead Fixable Violet (eBioscience), or Live/Dead Fixable Aqua (eBioscience), according to the manufacturer's instructions. Staining was carried out on ice for 20 min. For intracellular staining, Cytofix/Cytoperm (BD Bioscience) was used to fix cells for 20 min at 4° C. For permeabilization, perm/wash buffer (BD Bioscience) was used, and cells were stained in perm/wash buffer for 30 min at 4° C. Following a washing step, cells were stained with specific antibodies for 20 min on ice prior to fixation. All flow cytometric analyses were done using a Fortessa (BD Biosciences) flow cytometer and analyzed using FlowJo software (Tree Star).

14. Re-Stimulation of Splenocytes

Single cell suspensions were created from the dLNs and spleen. For analysis of cytokine production, $5\times10^5$ lymphocytes and $2\times10^6$ splenocytes were plated in a 96 well round bottom plate. Cells were stimulated with 10 µM $MOG_{35-55}$ peptide (Genscript). After 2 hr, GolgiPlug (brefeldin A) and GolgiStop (Monensin) were added per manufacturer's protocol to block secretion of intracellular cytokines. Four hours after addition of GolgiPlug and GolgiStop, cells were stained for flow cytometry. For fixation, Cytofix/Cytoperm (BD Bioscience) was used for 20 min at 4° C. For permeabilization, perm/wash buffer (BD Bioscience) was used, and cells were stained in perm/wash buffer for 30 min at 4° C. For 3 day restimulation, $2.5\times10^5$ lymphocytes or $1\times10^6$ splenocytes were plated in a 96 well round bottom plate. Cells were stimulated with 10 µM $MOG_{35-55}$ (for 6 hr culture followed by flow cytometry) or 100 µg/ml MOG protein (for 72 hr culture) (Anaspec). After 72 hr, supernatant was collected for analysis by ELISA using Ready-Set-Go! Kit (Invitrogen) or LEGEND MAX mouse GM-CSF ELISA kit (BioLegend).

15. Safety Assessments of SA-IL-4

C57BL/6 mice were intravenously injected with PBS, wt IL-4, or SA-IL4 (equivalent to 10 µg of IL-4). Two days after, blood samples collected from mice were analyzed using a COULTER Ac•T 5diff CP hematology analyzer (Beckman Coulter) according to the manufacturer's instructions. Lung and spleen were harvested and weighed. Water content in the lung was determined by weighing before and after overnight lyophilization using a FreeZone 6 Benchtop Freeze Dryer (Labconco). Serum samples collected from PBS, wt IL-4, and SA-IL-4-injected mice were analyzed using a Biochemistry Analyzer (Alfa Wassermann Diagnostic Technologies) according to the manufacturer's instructions.

16. Statistical Analysis

Statistically significant differences between experimental groups were determined using Prism software (v6, GraphPad). Where one-way ANOVA followed by Tukey's HSD post hoc test was used, variance between groups was found to be similar by the Brown-Forsythe test. For single comparisons, a two-tailed Student's t-test was used. The symbols * and ** indicate P values less than 0.05 and 0.01 respectively.

I. References

1. Friese, M. A., Schattling, B. & Fugger, L. Mechanisms of neurodegeneration and axonal dysfunction in multiple sclerosis. Nature reviews. Neurology 10, 225-238 (2014).
2. Ellwardt, E., Walsh, J. T., Kipnis, J. & Zipp, F. Understanding the Role of T Cells in CNS Homeostasis. Trends in immunology 37, 154-165 (2016).
3. Chun, J. & Hartung, H. P. Mechanism of action of oral fingolimod (FTY720) in multiple sclerosis. Clinical neuropharmacology 33, 91-101 (2010).
4. Rice, G. P., Hartung, H. P. & Calabresi, P. A. Anti-alpha4 integrin therapy for multiple sclerosis: mechanisms and rationale. Neurology 64, 1336-1342 (2005).
5. Cooney, L. A., Towery, K., Endres, J. & Fox, D. A. Sensitivity and resistance to regulation by IL-4 during Th17 maturation. Journal of immunology (Baltimore, Md.: 1950) 187, 4440-4450 (2011).
6. Gadani, S. P., Cronk, J. C., Norris, G. T. & Kipnis, J. IL-4 in the brain: a cytokine to remember. Journal of immunology (Baltimore, Md.: 1950) 189, 4213-4219 (2012).
7. Racke, M. K. et al. Cytokine-induced immune deviation as a therapy for inflammatory autoimmune disease. The Journal of experimental medicine 180, 1961-1966 (1994).
8. Butti, E. et al. IL4 gene delivery to the CNS recruits regulatory T cells and induces clinical recovery in mouse models of multiple sclerosis. Gene therapy 15, 504-515 (2008).
9. Vogelaar, C. F. et al. Fast direct neuronal signaling via the IL-4 receptor as therapeutic target in neuroinflammation. Science translational medicine 10 (2018).
10. van Zwam, M. et al. Surgical excision of CNS-draining lymph nodes reduces relapse severity in chronic-relapsing experimental autoimmune encephalomyelitis. The Journal of pathology 217, 543-551 (2009).
11. Dennis, M. S. et al. Albumin binding as a general strategy for improving the pharmacokinetics of proteins. The Journal of biological chemistry 277, 35035-35043 (2002).
12. Liao, W. et al. Priming for T helper type 2 differentiation by interleukin 2-mediated induction of interleukin 4 receptor alpha-chain expression. Nature immunology 9, 1288-1296 (2008).
13. Nilsen, J. et al. Human and mouse albumin bind their respective neonatal Fc receptors differently. Sci Rep 8, 14648-14648 (2018).
14. Pierson, E. R., Stromnes, I. M. & Goverman, J. M. B cells promote induction of experimental autoimmune encephalomyelitis by facilitating reactivation of T cells in the central nervous system. Journal of immunology (Baltimore, Md.: 1950) 192, 929-939 (2014).
15. Rothhammer, V. et al. Th17 lymphocytes traffic to the central nervous system independently of α4 integrin expression during EAE. The Journal of experimental medicine 208, 2465-2476 (2011).
16. Sasaki, K. et al. IL-4 suppresses very late antigen-4 expression which is required for therapeutic Th1 T-cell trafficking into tumors. J Immunother 32, 793-802 (2009).
17. Ioannou, M. et al. Crucial role of granulocytic myeloid-derived suppressor cells in the regulation of central nervous system autoimmune disease. Journal of immunology (Baltimore, Md.: 1950) 188, 1136-1146 (2012).
18. Guenova, E. et al. IL-4 abrogates T(H)17 cell-mediated inflammation by selective silencing of IL-23 in antigen-presenting cells. Proceedings of the National Academy of Sciences of the United States of America 112, 2163-2168 (2015).
19. Lotfi, N. et al. Roles of GM-CSF in the Pathogenesis of Autoimmune Diseases: An Update. Frontiers in immunology 10 (2019).
20. Luna, G. et al. Infection Risks Among Patients With Multiple Sclerosis Treated With Fingolimod, Natalizumab, Rituximab, and Injectable Therapies. JAMA Neurology (2019).
21. De Angelis, F., John, N. A. & Brownlee, W. J. Disease-modifying therapies for multiple sclerosis. BMJ 363, k4674 (2018).
22. Comi, G. et al. Efficacy of fingolimod and interferon beta-1b on cognitive, Mill, and clinical outcomes in relapsing-remitting multiple sclerosis: an 18-month, open-label, rater-blinded, randomised, multicentre study (the GOLDEN study). J Neurol 264, 2436-2449 (2017).
23. Sanford, M. & Lyseng-Williamson, K. A. Subcutaneous recombinant interferon-beta-1a (Rebif(R)): a review of its use in the treatment of relapsing multiple sclerosis. Drugs 71, 1865-1891 (2011).
24. Apolloni, E. et al. Immortalized myeloid suppressor cells trigger apoptosis in antigen-activated T lymphocytes. Journal of immunology (Baltimore, Md.: 1950) 165, 6723-6730 (2000).
25. Crook, K. R. & Liu, P. Role of myeloid-derived suppressor cells in autoimmune disease. World journal of immunology 4, 26-33 (2014).
26. Komiyama, Y. et al. IL-17 Plays an Important Role in the Development of Experimental Autoimmune Encephalomyelitis. The Journal of Immunology 177, 566-573 (2006).
27. Lee, P. W. et al. IL-23R-activated STAT3/STAT4 is essential for Th1/Th17-mediated CNS autoimmunity. JCI Insight 2, e91663 (2017).
28. Liu, H. et al. Structure-based programming of lymph-node targeting in molecular vaccines. Nature 507, 519-522 (2014).
29. Yao, Z., Dai, W., Perry, J., Brechbiel, M. W. & Sung, C. Effect of albumin fusion on the biodistribution of interleukin-2. Cancer Immunol Immunother 53, 404-410 (2004).
30. Miyasaka, M. & Tanaka, T. Lymphocyte trafficking across high endothelial venules: dogmas and enigmas. Nature Reviews Immunology 4, 360-370 (2004).
31. Pyzik, M. et al. Hepatic FcRn regulates albumin homeostasis and susceptibility to liver injury. Proceedings of the National Academy of Sciences of the United States of America 114, E2862-e2871 (2017).
32. Pyzik, M. et al. The Neonatal Fc Receptor (FcRn): A Misnomer? Frontiers in immunology 10 (2019).
33. Hashem, L., Swedrowska, M. & Vllasaliu, D. Intestinal uptake and transport of albumin nanoparticles: potential for oral delivery. Nanomedicine (London, England) 13, 1255-1265 (2018).
34. Fan, Y. Y. et al. Human FcRn Tissue Expression Profile and Half-Life in PBMCs. Biomolecules 9 (2019).

Although certain embodiments have been described above with a certain degree of particularity, or with reference to one or more individual embodiments, those skilled in the art could make numerous alterations to the disclosed embodiments without departing from the scope of this invention. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments. Any reference to a patent publication or other publication is a herein a specific incorporation by reference of the disclosure of that publication. The claims are not to be interpreted as including means-plus- or step-plus-function limitations, unless such a limitation is explicitly recited in a given claim using the phrase(s) “means for” or “step for,” respectively.

The invention claimed is:

1. A method for reducing inflammation in a subject comprising administering to the subject an effective amount of a composition comprising IL-10 linked to a peptide having at least 95% sequence identity to one of SEQ ID NOs: 3, 4, 5, 47, or 52.

2. The method of claim 1, wherein the inflammation comprises an inflammatory condition selected from the group consisting of inflammatory bowel disease, idiopathic pulmonary fibrosis, multiple sclerosis, type 1 diabetes, Crohn's disease, psoriasis, acute inflammation, chronic inflammation, neuroinflammation, and rheumatoid arthritis.

3. The method of claim 1, wherein the composition is administered systemically.

4. The method of claim 3, wherein the composition is administered by intravenous injection.

5. The method of claim 1, wherein the composition is administered locally.

6. The method of claim 5, wherein the composition is administered to or adjacent to a site of inflammation.

7. The method of claim 1, wherein the method further comprises administration of an additional inflammation therapy.

8. The method of claim 1, wherein the IL-10 linked to the peptide having 95% sequence identity to one of SEQ ID NOs: 3, 4, 5, 47, or 52 further comprises a serum protein linked to the peptide or IL-10.

9. The method of claim 8, wherein the serum protein comprises albumin.

10. The method of claim 1, wherein the ratio of peptide having 95% sequence identity to one of SEQ ID NOs: 3, 4, 5, 47, or 52 to the IL-10 is 1:1 to 5:1.

11. The method of claim 2, wherein the inflammatory condition comprises inflammatory bowel disease and wherein the inflammatory bowel disease is selected from Crohn's disease, autoimmune-mediated gastrointestinal diseases, colitis, and autoimmune inflammatory bowel disease.

12. The method of claim 11, wherein the colitis is selected from ulcerative colitis, colitis ulcerosa, microscopic colitis, collagenous colitis, colitis polyposa, necrotizing enterocolitis, and transmural colitis.

13. The method of claim 1, wherein the IL-10 is linked to a peptide having the amino acid sequence of one of SEQ ID NOs: 3, 4, 5, 47, or 52.

14. The method of claim 1, wherein the IL-10 is linked to a peptide having the amino acid sequence of SEQ ID NO:47.

15. The method of claim 1, wherein the IL-10 is linked to a peptide having the amino acid sequence of SEQ ID NO:52.

* * * * *